US008420081B2

(12) United States Patent
Fraunhofer et al.

(10) Patent No.: US 8,420,081 B2
(45) Date of Patent: Apr. 16, 2013

(54) ANTIBODY FORMULATIONS AND METHODS OF MAKING SAME

(75) Inventors: Wolfgang Fraunhofer, Shrewsbury, MA (US); Annika Bartl, Ludwigshafen (DE); Hans-juergen Krause, Grünstadt (DE); Markus Tschoepe, Hessheim (DE); Katharina Kaleta, Ludwigshafen (DE)

(73) Assignee: AbbVie, Inc., North Chicago, IL (US)

( * ) Notice: Subject to any disclaimer, the term of this patent is extended or adjusted under 35 U.S.C. 154(b) by 411 days.

(21) Appl. No.: 12/325,049

(22) Filed: Nov. 28, 2008

(65) Prior Publication Data

US 2009/0291062 A1  Nov. 26, 2009

Related U.S. Application Data

(60) Provisional application No. 61/004,992, filed on Nov. 30, 2007.

(51) Int. Cl.
A61K 39/00 (2006.01)
A61K 39/395 (2006.01)
A61K 38/00 (2006.01)
C07K 16/00 (2006.01)
C07K 16/24 (2006.01)

(52) U.S. Cl.
USPC ............... 424/130.1; 424/145.1; 530/387.1; 530/388.23; 514/1.1

(58) Field of Classification Search .................. None
See application file for complete search history.

(56) References Cited

U.S. PATENT DOCUMENTS

| 4,597,966 A | 7/1986 | Zolton et al. |
| 4,877,608 A | 10/1989 | Lee et al. |
| 5,608,038 A | 3/1997 | Eibl et al. |
| 6,090,382 A | 7/2000 | Salfeld et al. |
| 6,171,586 B1 | 1/2001 | Lam et al. |
| 6,258,562 B1 | 7/2001 | Salfeld et al. |
| 6,436,397 B1 | 8/2002 | Baker et al. |
| 6,485,932 B1 | 11/2002 | McIntosh et al. |
| 6,509,015 B1 | 1/2003 | Salfeld et al. |
| 6,693,173 B2 | 2/2004 | Mamidi et al. |
| 7,070,775 B2 | 7/2006 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,541,031 B2 | 6/2009 | Salfeld et al. |
| 7,588,761 B2 | 9/2009 | Salfeld et al. |
| 7,758,860 B2 | 7/2010 | Warne et al. |
| 2003/0012786 A1 | 1/2003 | Teoh et al. |
| 2003/0143603 A1* | 7/2003 | Giles-Komar et al. ........... 435/6 |
| 2003/0161828 A1 | 8/2003 | Abdelghany et al. |
| 2003/0180287 A1 | 9/2003 | Gombotz et al. |
| 2003/0190316 A1 | 10/2003 | Kakuta et al. |
| 2003/0206898 A1 | 11/2003 | Fischkoff et al. |
| 2003/0219438 A1 | 11/2003 | Salfeld et al. |
| 2003/0235585 A1 | 12/2003 | Fischkoff et al. |
| 2004/0009172 A1 | 1/2004 | Fischkoff et al. |
| 2004/0033228 A1 | 2/2004 | Krause et al. |
| 2004/0038878 A1 | 2/2004 | Tanikawa et al. |
| 2004/0105889 A1 | 6/2004 | Ryde et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0170623 A1 | 9/2004 | Arvinte et al. |
| 2004/0197324 A1 | 10/2004 | Liu et al. |
| 2004/0219142 A1 | 11/2004 | Banerjee et al. |
| 2005/0118163 A1 | 6/2005 | Mizushima et al. |
| 2005/0214278 A1 | 9/2005 | Kakuta et al. |
| 2006/0009385 A1 | 1/2006 | Hoffman et al. |
| 2006/0083741 A1 | 4/2006 | Hoffman et al. |
| 2006/0115472 A1 | 6/2006 | Li et al. |
| 2006/0142549 A1 | 6/2006 | Takeda et al. |
| 2006/0149042 A1* | 7/2006 | Konstantinov et al. ....... 530/412 |
| 2006/0153846 A1 | 7/2006 | Krause et al. |
| 2006/0159653 A1 | 7/2006 | Saito et al. |
| 2006/0182740 A1 | 8/2006 | Yang et al. |

(Continued)

FOREIGN PATENT DOCUMENTS

| EP | 0486526 A1 | 5/1992 |
| EP | 419251 B | 1/1993 |

(Continued)

OTHER PUBLICATIONS

Zhao et al. "Recent U.S. Patents on Protein Drug Formulation: 2000-2007" *Protein Drug Formulation* 2008.
Daugherty et al. "Formulation and Delivery Issues for Monoclonal Antibody Therapeutics," *Advanced Drug Delivery Reviews* 58:686-706 2006.
Liu et al. "Reversible Self-Association Increases the viscosity of a Concentrated Monoclonal Anitbody in Aqueous Solution", *J Pharma Sci*,vol. 94, No. 9, pp. 1928-1940 (2005).
Wang et al. "Opalescence of an IgG1 Monoclonal Antibody Formulation is Mediated by Ionic Strength and Excipients", *BioPharm Internatl*, vol. 22(4) (2009).
Li et al., "Resurrecting Abandoned Proteins with Pure Water: CD and NMR Studies of Protein Fragments Solubilized in Salt-Free Water," biophysj 91:4201-4209 (2006).
Manning et al., "Stability of Protein Pharmaceuticals," Pharm res 6:903-918 (1989).
Shire et al., "Challenges in the Development of High Protein Concentration Formulations," J Pharm Sci 93:1390-1402 (2004).
Tian et al., "Spectroscopic evaluation of the stabilization of humanized monoclonal antibodies in amino acid formulations," Intl J Pharm 355:20-31(2007).
Akers, et al., "Development and Manufacture of Protein Pharmaceuticals (Pharmaceutical Biotechnology)", Chapter 2: "Formulation Development of Protein Dosage Forms", 2002, Kluver Academic/Plenum, pub., New York.
Barrera, et al., "Effects of treatment with a fully human antitumour necrosis factor alpha monoclonal antibody on the local and systemic homeostasis of interleukin 1 and TNFalpha in patients with rheumatoid arthritis," Ann Rheum. Dis. 2001, 60(7):660-669.

(Continued)

*Primary Examiner* — Robert Landsman
*Assistant Examiner* — Bruce D Hissong
(74) *Attorney, Agent, or Firm* — Tara Seshadri; Cristin H. Cowles; McCarter & English, LLP

(57) ABSTRACT

The invention provides an aqueous formulation comprising water and a protein, and methods of making the same. The aqueous formulation of the invention may be a high protein formulation and/or may have low levels of conductivity resulting from the low levels of ionic excipients. Also included in the invention are formulations comprising water and proteins having low osmolality.

135 Claims, 36 Drawing Sheets

U.S. PATENT DOCUMENTS

| | | |
|---|---|---|
| 2006/0210557 A1 | 9/2006 | Luisi et al. |
| 2006/0246073 A1 | 11/2006 | Knight et al. |
| 2006/0269479 A1 | 11/2006 | Colton et al. |
| 2007/0020255 A1 | 1/2007 | Ueno et al. |
| 2007/0036779 A1 | 2/2007 | Bardet et al. |
| 2007/0041905 A1 | 2/2007 | Hoffman et al. |
| 2007/0053906 A1 | 3/2007 | Samaritani et al. |
| 2007/0065440 A1 | 3/2007 | Tomlinson et al. |
| 2007/0071747 A1 | 3/2007 | Hoffman et al. |
| 2007/0081996 A1 | 4/2007 | Hoffman et al. |
| 2007/0122402 A1 | 5/2007 | Bolli et al. |
| 2007/0172475 A1* | 7/2007 | Matheus et al. ............ 424/143.1 |
| 2007/0172897 A1 | 7/2007 | Maksymowych et al. |
| 2007/0184045 A1 | 8/2007 | Doctor et al. |
| 2007/0184050 A1 | 8/2007 | Ishikawa et al. |
| 2007/0190047 A1 | 8/2007 | Brych et al. |
| 2007/0202051 A1* | 8/2007 | Schuschnig .................... 424/45 |
| 2007/0202104 A1 | 8/2007 | Banerjee et al. |
| 2007/0237762 A1 | 10/2007 | Winter |
| 2007/0269463 A1 | 11/2007 | Donavan et al. |
| 2007/0292442 A1 | 12/2007 | Wan et al. |
| 2008/0118496 A1 | 5/2008 | Medich et al. |
| 2008/0131374 A1 | 6/2008 | Medich et al. |
| 2008/0139792 A1 | 6/2008 | Sek et al. |
| 2008/0166348 A1 | 7/2008 | Kupper et al. |
| 2008/0193466 A1 | 8/2008 | Banerjee et al. |
| 2008/0200655 A1 | 8/2008 | Sek et al. |
| 2008/0227136 A1 | 9/2008 | Pla et al. |
| 2008/0311043 A1 | 12/2008 | Hoffman et al. |
| 2008/0311078 A1 | 12/2008 | Gokarn et al. |
| 2009/0017472 A1 | 1/2009 | Stuhlmuller et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0148406 A1 | 6/2009 | Jezek |
| 2009/0148513 A1 | 6/2009 | Fraunhofer et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0129379 A1 | 5/2010 | Carpenter et al. |
| 2010/0160894 A1 | 6/2010 | Julian et al. |
| 2010/0278822 A1 | 11/2010 | Fraunhofer et al. |
| 2011/0054414 A1 | 3/2011 | Shang et al. |
| 2011/0171227 A1 | 7/2011 | Okun et al. |
| 2011/0236391 A1 | 9/2011 | Mahler et al. |
| 2011/0300151 A1 | 12/2011 | Okun et al. |
| 2012/0014956 A1 | 1/2012 | Kupper et al. |

FOREIGN PATENT DOCUMENTS

| | | |
|---|---|---|
| EP | 1174148 A1 | 1/2002 |
| WO | WO-89/11298 A1 | 11/1989 |
| WO | WO-93/08837 A1 | 5/1993 |
| WO | WO 95/03826 | 2/1995 |
| WO | WO 95/03826 | 9/1995 |
| WO | WO 97/04801 | 12/1997 |
| WO | WO 97/45140 | 12/1997 |
| WO | WO 98/42376 | 10/1998 |
| WO | WO 98/44948 | 10/1998 |
| WO | WO 98/56418 | 12/1998 |
| WO | WO-99/37329 A1 | 7/1999 |
| WO | WO 00/67789 | 11/2000 |
| WO | WO 02/13860 | 2/2002 |
| WO | WO-0212502 A2 | 2/2002 |
| WO | WO 02/30463 | 4/2002 |
| WO | WO 02/43695 | 6/2002 |
| WO | WO 02/43750 | 6/2002 |
| WO | WO 02/051979 | 7/2002 |
| WO | WO 02/096457 | 12/2002 |
| WO | WO 03/053471 | 7/2003 |
| WO | WO 04/001007 | 12/2003 |
| WO | WO 2004/016286 | 2/2004 |
| WO | WO 2004/024752 | 3/2004 |
| WO | WO 2004/050059 | 6/2004 |
| WO | WO 2004/055164 | 7/2004 |
| WO | WO 2004/066957 | 8/2004 |
| WO | WO 2004/102184 | 11/2004 |
| WO | WO2005072772 | 8/2005 |
| WO | WO 2006/031560 | 3/2006 |
| WO | WO 2006/138181 | 12/2006 |
| WO | WO 2007/003936 | 1/2007 |
| WO | WO 2007/074880 | 7/2007 |
| WO | WO 2007/095337 | 8/2007 |
| WO | WO 2008/015419 | 2/2008 |
| WO | WO2009015367 | 1/2009 |

OTHER PUBLICATIONS

Harris, et al., "Commercial manufacturing scale formulation and analytical characterization of therapeutic recombinant antibodies", Drug Development Research, 2004, vol. 61, No. 3, p. 137-154.

Hillgren, et al., "Protection mechanism of Tween 80 during freeze-thawing of a model protein," International Journal of Pharmaceutics, 2002, vol. 237: 57-69.

Holt, et al., "Domain antibodies: proteins for therapy," Trends in Biotechnology, 2003, vol. 21(11):484-490.

Wang, et al., "Antibody Structure, Instability, and Formulation," J Pharmaceutical Sci, 2007, 96(1): 1-26.

Wang, et al., "Instability, Stablization, and Formulation of Liquid Protein Pharmaceuticals," Int. J. Pharmaceutics, 1999, 185:129-188.

Adalimumab entry from National Library of Medicine website: www.nlm.nih.gov/cgi/mesh; printed on Sep. 28, 2009.

International Preliminary Examination Report for Application No. PCT/US2008/085066, 2009.

International Search Report for Application No. PCT/US2008/085066, 2009.

* cited by examiner

Figure 15
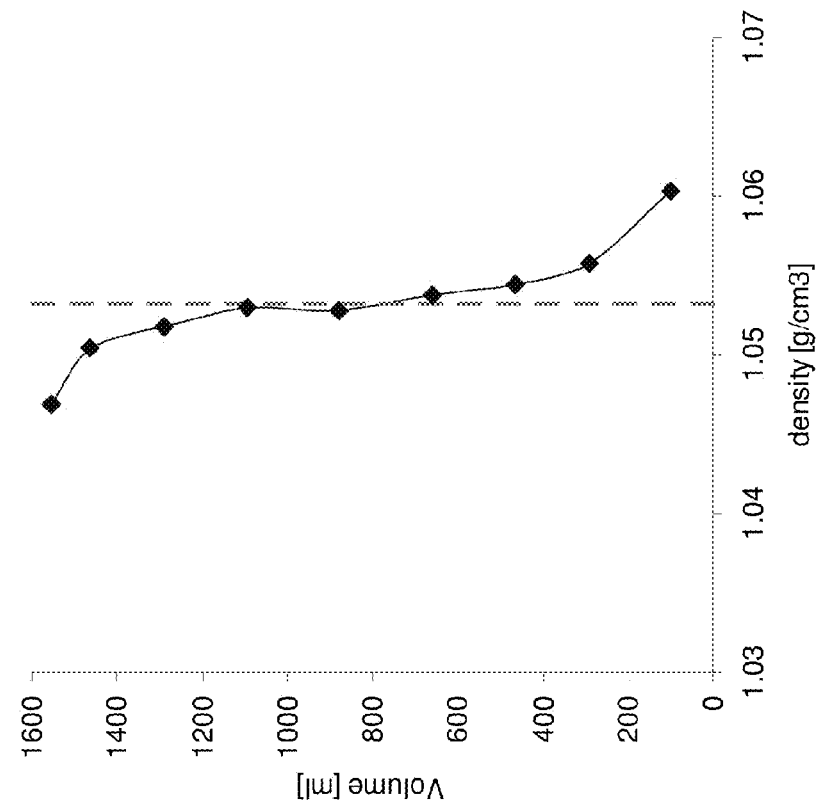
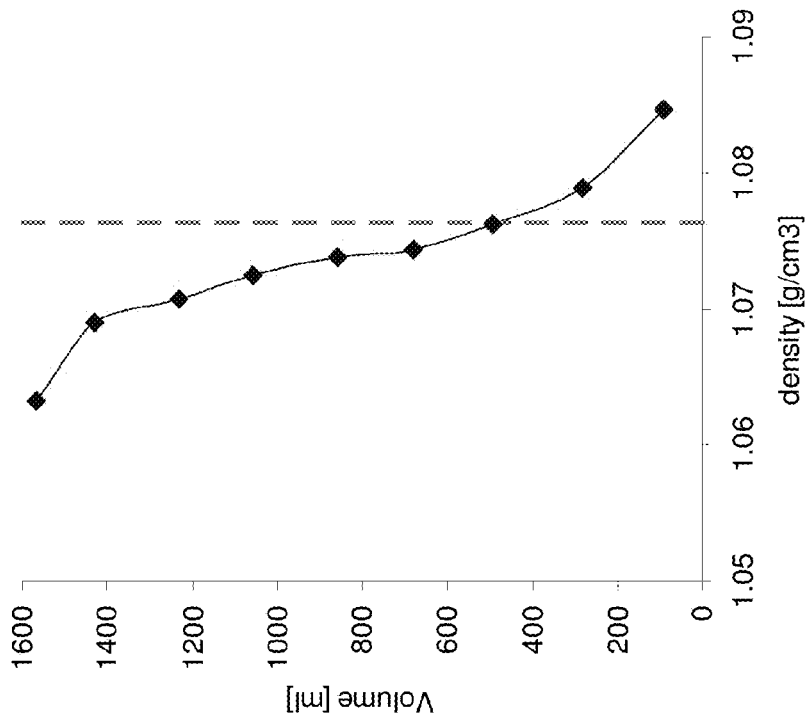

ANTIBODY FORMULATIONS AND METHODS OF MAKING SAME

RELATED APPLICATIONS

This application claims the benefit of priority to U.S. Provisional Appln. No. 61/004,992, filed on Nov. 30, 2007. The contents of the priority application are hereby incorporated by reference.

SEQUENCE LISTING

The instant application contains a Sequence Listing which has been submitted in ASCII format via EFS-Web and is hereby incorporated by reference in its entirety. Said ASCII copy, created on Aug. 3, 2011, is named SeqList and is 3,883 bytes in size.

BACKGROUND OF THE INVENTION

A basic principle of pharmaceutical protein formulations is that certain instabilities must be overcome. Degradation pathways of proteins can be separated into two distinct classes, involving chemical instability and physical instability. Chemical instabilities lead to the modification of the protein through bond formation or cleavage. Examples of chemical instability problems include deamidation, racemization, hydrolysis, oxidation, beta elimination and disulfide exchange. Physical instabilities, on the other hand, do not lead to covalent changes in proteins. Rather, they involve changes in the higher order structure (secondary and above) of proteins. These include denaturation, adsorption to surfaces, aggregation and precipitation (Manning et al., *Pharm. Res.* 6, 903 (1989)).

It is generally accepted that these instabilities, which can have great effect on the commercial viability and efficacy of pharmaceutical protein formulations, can be overcome by including additional molecules in the formulation. Protein stability can be improved by including excipients that interact with the protein in solution to keep the protein stable, soluble and unaggregated. For example, salt compounds and other ionic species are very common additives to protein formulations. They assist in fighting denaturation of proteins by binding to proteins in a non-specific fashion and increasing thermal stability. Salt compounds (e.g., NaCl, KCl) have been used successfully in commercial insulin preparations to fight aggregation and precipitation (ibid. at 911). Amino acids (e.g., histidine, arginine) have been shown to reduce alterations in proteins' secondary structures when used as formulation additives (Tian et al., *Int'l J. Pharm.* 355, 20 (2007)). Other examples of commonly used additives include polyalcohol materials such as glycerol and sugars, and surfactants such as detergents, both nonionic (e.g., Tween, Pluronic) and anionic (sodium dodecyl sulfate). The near universal prevalence of additives in all liquid commercial protein formulations indicates that protein solutions without such compounds may encounter challenges with degradation due to instabilities.

The primary goal of protein formulation is to maintain the stability of a given protein in its native, pharmaceutically active form over prolonged periods of time to guarantee acceptable shelf-life of the pharmaceutical protein drug. Maintaining the stability and solubility of proteins in solution, however, is especially challenging in pharmaceutical formulations where the additives are included into therapeutics. To date, biologic formulations require additional excipients to maintain protein stability. Typically, liquid pharmaceutical formulations contain multiple additives for stability. For example, a liquid formulation for patient self-administration of human growth hormone, Norditropin SimpleXx®, contains the additives mannitol (a sugar alcohol), histidine and poloxamer 188 (a surfactant) to stabilize the hormone.

Pharmaceutical additives need to be soluble, non-toxic and used at particular concentrations that provide stabilizing effects on the specific therapeutic protein. Since the stabilizing effects of additives are protein- and concentration-dependent, each additive being considered for use in a pharmaceutical formulation must be carefully tested to ensure that it does not cause instability or have other negative effects on the chemical or physical make-up of the formulation. Ingredients used to stabilize the protein may cause problems with protein stability over time or with protein stability in changing environments during storage.

Typically, long shelf-life is achieved by storing the protein in frozen from (e.g., at $-80°$ C.) or by subjecting the protein to a lyophilization process, i.e., by storing the protein in lyophilized form, necessitating a reconstitution step immediately before use and thus posing a significant disadvantage with regard to patient convenience. However, freezing a protein formulation for storage may lead to localized high concentrations of proteins and additives, which can create local extremes in pH, degradation and protein aggregation within the formulation. In addition, it is well known to those skilled in the art that freezing and thawing processes often impact protein stability, meaning that even storage of the pharmaceutical protein in frozen form can be associated with the loss of stability due to the freezing and thawing step. Also, the first process step of lyophilization involves freezing, which can negatively impact protein stability. In industry settings, a pharmaceutical protein may be subjected to repeated freeze-thaw processing during Drug Substance manufacturing (holding steps, storage, re-freeze and re-thaw to increase timing and batch size flexibility in Drug Product fill-finishing) and during subsequent Drug Product fill-finishing (lyophilization). Since it is well known that the risk of encountering protein instability phenomena increases with increasing the number of freeze-thaw cycles a pharmaceutical protein encounters, achieving formulation conditions that maintain protein stability over repeated freeze-thaw processes is a challenging task. There is a need in the biopharmaceutical industry for formulations that can be frozen and thawed without creating undesired properties in the formulations, especially gradients of pH, osmolarity, density or protein or excipient concentration.

Often protein-based pharmaceutical products need to be formulated at high concentrations for therapeutic efficacy. Highly concentrated protein formulations are desirable for therapeutic uses since they allow for dosages with smaller volumes, limiting patient discomfort, and are more economically packaged and stored. The development of high protein concentration formulations, however, presents many challenges, including manufacturing, stability, analytical, and, especially for therapeutic proteins, delivery challenges. For example, difficulties with the aggregation, insolubility and degradation of proteins generally increase as protein concentrations in formulations are raised (for review, see Shire, S. J. et al. *J. Pharm. Sci.*, 93, 1390 (2004)). Previously unseen negative effects may be caused by additives that, at lower concentrations of the additives or the protein, provided beneficial effects. The production of high concentration protein formulations may lead to significant problems with opalescence, aggregation and precipitation. In addition to the potential for normative protein aggregation and particulate formation, reversible self-association may occur, which may result in increased viscosity or other properties that complicate delivery by injection. High viscosity also may complicate manufacturing of high protein concentrations by filtration approaches.

Thus, pharmaceutical protein formulations typically carefully balance ingredients and concentrations to enhance protein stability and therapeutic requirements while limiting any negative side-effects. Biologic formulations should include stable protein, even at high concentrations, with specific amounts of excipients reducing potential therapeutic complications, storage issues and overall cost.

As proteins and other biomacromolecules gain increased interest as drug molecules, formulations for delivering such molecules are becoming an important issue. Despite the revolutionary progress in the large-scale manufacturing of proteins for therapeutic use, effective and convenient delivery of these agents in the body remains a major challenge due to their intrinsic physicochemical and biological properties, including poor permeation through biological membranes, large molecular size, short plasma half life, self association, physical and chemical instability, aggregation, adsorption, and immunogenicity.

SUMMARY OF THE INVENTION

The invention is directed towards the surprising findings that proteins formulated in water maintain solubility, as well as stability, even at high concentrations, during long-term liquid storage or other processing steps, such as freeze/thawing and lyophilization.

The present invention relates to methods and compositions for aqueous protein formulations which comprise water and a protein, where the protein is stable without the need for additional agents. Specifically, the methods and compositions of the invention are based on a diafiltration process wherein a first solution containing the protein of interest is diafiltered using water as a diafiltration medium. The process is performed such that there is at least a determined volume exchange, e.g., a five fold volume exchange, with the water. By performing the methods of the invention, the resulting aqueous formulation has a significant decrease in the overall percentage of excipients in comparison to the initial protein solution. For example, 95-99% less excipients are found in the aqueous formulation in comparison to the initial protein solution. Despite the decrease in excipients, the protein remains soluble and retains its biological activity, even at high concentrations. In one aspect, the methods of the invention result in compositions comprising an increase in concentration of the protein while decreasing additional components, such as ionic excipients. As such, the hydrodynamic diameter of the protein in the aqueous formulation is smaller relative to the same protein in a standard buffering solution, such as phosphate buffered saline (PBS).

The formulation of the invention has many advantages over standard buffered formulations. In one aspect, the aqueous formulation comprises high protein concentrations, e.g., 50 to 200 mg/mL or more. Proteins of all sizes may be included in the formulations of the invention, even at increased concentrations. Despite the high concentration of protein, the formulation has minimal aggregation and can be stored using various methods and forms, e.g., freezing, without deleterious effects that might be expected with high protein formulations. Formulations of the invention do not require excipients, such as, for example, surfactants and buffering systems, which are used in traditional formulations to stabilize proteins in solution. As a result of the low level of ionic excipients, the aqueous formulation of the invention has low conductivity, e.g., less than 2 mS/cm. The methods and compositions of the invention also provide aqueous protein formulations having low osmolality, e.g., no greater than 30 mOsmol/kg. In addition, the formulations described herein are preferred over standard formulations because they have decreased immunogenicity due to the lack of additional agents needed for protein stabilization.

The methods and compositions of the invention may be used to provide an aqueous formulation comprising water and any type of protein of interest. In one aspect, the methods and compositions of the invention are used for large proteins, including proteins which are larger than 47 kDa. Antibodies, and fragments thereof, including those used for in vivo and in vitro purposes, are another example of proteins which may be used in the methods and compositions of the invention.

Furthermore, the multiple step purification and concentration processes that are necessary to prepare proteins and peptide formulations often introduce variability in compositions, such that the precise composition of a formulation may vary from lot to lot. Federal regulations require that drug compositions be highly consistent in their formulations regardless of the location of manufacture or lot number. Methods of the invention can be used to create solutions of proteins formulated in water to which buffers and excipients are added back in precise amounts, allowing for the creation of protein formulations with precise concentrations of buffers and/or excipients.

In one embodiment, the invention provides an aqueous formulation comprising a protein and water, wherein the formulation has certain characteristics, such as, but not limited to, low conductivity, e.g., a conductivity of less than about 2.5 mS/cm, a protein concentration of at least about 10 µg/mL, an osmolality of no more than about 30 mOsmol/kg, and/or the protein has a molecular weight ($M_w$) greater than about 47 kDa. In one embodiment, the formulation of the invention has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized, or spray-dried.

In one embodiment, proteins included in the formulation of the invention may have a minimal size, including, for example, a $M_w$ greater than about 47 kDa, a $M_w$ greater than about 57 kDa, a $M_w$ greater than about 100 kDa, a $M_w$ greater than about 150 kDa, a $M_w$ greater than about 200 kDa, or a $M_w$ greater than about 250 kDa.

In one embodiment, the formulation of the invention has a low conductivity, including, for example, a conductivity of less than about 2.5 mS/cm, a conductivity of less than about 2 mS/cm, a conductivity of less than about 1.5 mS/cm, a conductivity of less than about 1 mS/cm, or a conductivity of less than about 0.5 mS/cm.

In one embodiment, proteins included in the formulation of the invention have a given concentration, including, for example, a concentration of at least about 1 mg/mL, at least about 10 mg/mL, at least about 50 mg/mL, at least about 100 mg/mL, at least about 150 mg/mL, at least about 200 mg/mL, or greater than about 200 mg/mL.

In one embodiment, the formulation of the invention has an osmolality of no more than about 15 mOsmol/kg.

In one embodiment, the invention provides an aqueous formulation comprising water and a given concentration of a protein, wherein the protein has a hydrodynamic diameter ($D_h$) which is at least about 50% less than the $D_h$ of the protein in a buffered solution at the given concentration. In one embodiment, the $D_h$ of the protein is at least about 50% less than the $D_h$ of the protein in phosphate buffered saline (PBS) at the given concentration; the $D_h$ of the protein is at least about 60% less than the $D_h$ of the protein in PBS at the given concentration; the $D_h$ of the protein is at least about 70% less than the $D_h$ of the protein in PBS at the given concentration.

In one embodiment, the invention provides an aqueous formulation comprising a protein, such as, but not limited to, an antibody, or an antigen-binding fragment, wherein the protein has a hydrodynamic diameter ($D_h$) of less than about 5 μm. In one embodiment, the protein has a $D_h$ of less than about 3 μm.

Any protein may be used in the methods and compositions of the invention. In one embodiment, the formulation comprises a therapeutic protein. In one embodiment, the formulation comprises an antibody, or an antigen-binding fragment thereof. Types of antibodies, or antigen binding fragments, that may be included in the methods and compositions of the invention include, but are not limited to, a chimeric antibody, a human antibody, a humanized antibody, and a domain antibody (dAb). In one embodiment, the antibody, or antigen-binding fragment thereof, is an anti-TNFa, such as but not limited to adalimumab or golimumab, or an anti-IL-12 antibody, such as but not limited to J695. In addition, the formulation of the invention may also include at least two distinct types of proteins, e.g., adalimumab and J695.

In yet another embodiment of the invention, the formulation may further comprise a non-ionizable excipient. Examples of non-ionizable excipients include, but are not limited to, a sugar alcohol or polyol (e.g., mannitol or sorbitol), a non-ionic surfactant (e.g., polysorbate 80, polysorbate 20, polysorbate 40, polysorbate 60), and/or a sugar (e.g., sucrose). Other non-limiting examples of non-ionizable excipients that may be further included in the formulation of the invention include, but are not limited to, non-trehalose, raffinose, and maltose.

In one embodiment, the formulation does not comprise an agent selected from the group consisting of a tonicity modifier, a stabilizing agent, a surfactant, an anti-oxidant, a cryoprotectant, a bulking agent, a lyroprotectant, a basic component, and an acidic component.

The formulation of the invention may be suitable for any use, including both in vitro and in vivo uses. In one embodiment, the formulation of the invention is suitable for administration to a subject via a mode of administration, including, but not limited to, subcutaneous, intravenous, inhalation, intradermal, transdermal, intraperitoneal, and intramuscular administration. The formulation of the invention may be used in the treatment of a disorder in a subject.

Also included in the invention are devices that may be used to deliver the formulation of the invention. Examples of such devices include, but are not limited to, a syringe, a pen, an implant, a needle-free injection device, an inhalation device, and a patch.

In one embodiment, the formulation of the invention is a pharmaceutical formulation.

The invention also provides a method of preparing an aqueous formulation comprising a protein and water, the method comprising providing the protein in a first solution, and subjecting the first solution to diafiltration using water as a diafiltration medium until at least a five fold volume exchange with the water has been achieved to thereby prepare the aqueous formulation. In one embodiment, the protein in the resulting formulation retains its biological activity.

The invention further provides a method of preparing an aqueous formulation of a protein, the method comprising providing the protein in a first solution; subjecting the first solution to diafiltration using water as a diafiltration medium until at least a five-fold volume exchange with the water has been achieved to thereby prepare a diafiltered protein solution; and concentrating the diafiltered protein solution to thereby prepare the aqueous formulation of the protein. In one embodiment, the protein in the resulting formulation retains its biological activity.

In one embodiment, the concentration of the diafiltered protein solution is achieved via centrifugation.

In one embodiment, the diafiltration medium consists of water.

In one embodiment, the first solution is subjected to diafiltration with water until a volume exchange greater than a five-fold volume exchange is achieved. In one embodiment, the first solution is subjected to diafiltration with water until at least about a six-fold volume exchange is achieved. In one embodiment, the first solution is subjected to diafiltration with water until at least about a seven-fold volume exchange is achieved.

In one embodiment, the aqueous formulation has a final concentration of excipients which is at least about 95% less than the first solution.

In one embodiment, the aqueous formulation has a final concentration of excipients which is at least about 99% less than the first solution.

In one embodiment, the first protein solution is obtained from a mammalian cell expression system and has been purified to remove host cell proteins (HCPs).

In one embodiment, the method of the invention further comprises adding an excipient to the aqueous formulation.

BRIEF DESCRIPTION OF THE DRAWINGS

FIG. 15 shows bottle mapping density data for 250 mg/ml and 200 mg/ml low-ionic Adalimumab solutions after freeze thaw.

DETAILED DESCRIPTION OF THE INVENTION

I. Definitions

Figure 1:
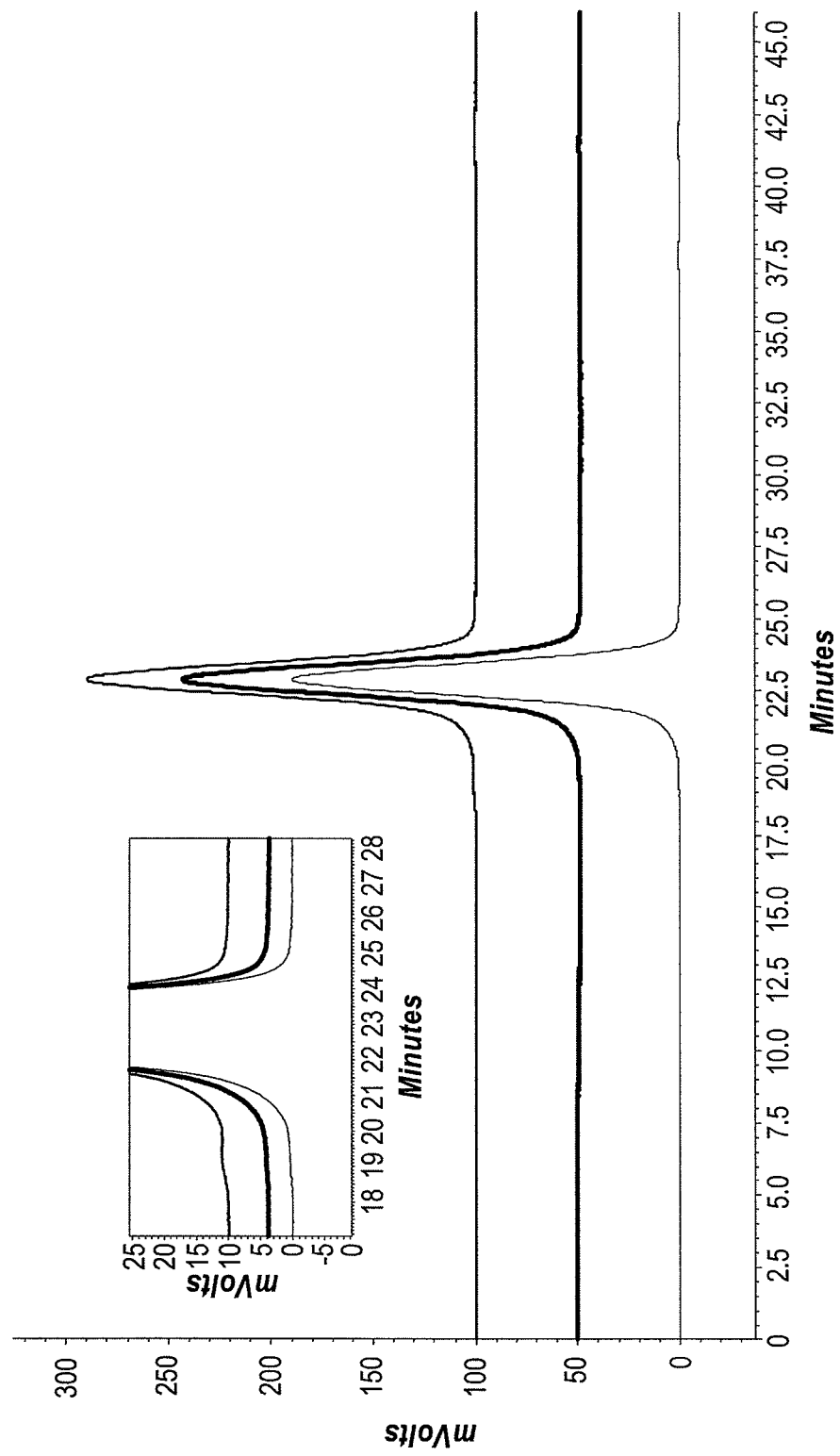
FIG. 1 shows the SEC chromatogram of Adalimumab reference standard AFP04C (bottom line), Adalimumab DS (drug substance before (middle line) and after DF/UF processing (top line).

In order that the present invention may be more readily understood, certain terms are first defined.

As used herein, the term "acidic component" refers to an agent, including a solution, having an acidic pH, i.e., less than 7.0. Examples of acidic components include phosphoric acid, hydrochloric acid, acetic acid, citric acid, oxalic acid, succinic acid, tartaric acid, lactic acid, malic acid, glycolic acid and fumaric acid. In one embodiment, the aqueous formulation of the invention does not include an acidic component.

As used herein, the term "antioxidant" is intended to mean an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, butylated hydroxyanisole, butylated hydroxytoluene, hydrophosphorous acid, monothioglycerol, propyl gallate, methionine, sodium ascorbate, sodium citrate, sodium sulfide, sodium sulfite, sodium bisulfite, sodium formaldehyde sulfoxylate, thioglycolic acid, sodium metabisulfite, EDTA (edetate), penetrate and others known to those of ordinary skill in the art.

The term "aqueous formulation" refers to a solution in which the solvent is water.

As used herein, the term "basic component" refers to an agent which is alkaline, i.e., pH greater than 7.0. Examples of basic components include potassium hydroxide (KOH) and sodium hydroxide (NaOH)

As used herein, the term "bulking agent" is intended to mean a compound used to add bulk to the reconstitutable solid and/or assist in the control of the properties of the formulation during preparation. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

The term "conductivity," as used herein, refers to the ability of an aqueous solution to conduct an electric current between two electrodes. Generally, electrical conductivity or specific conductivity is a measure of a material's ability to conduct an electric current. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter sold, e.g., by Orion Research, Inc. (Beverly, Mass.). The conductivity of a solution may be altered by changing the concentration of ions therein. For example, the concentration of ionic excipients in the solution may be altered in order to achieve the desired conductivity.

The term "cryoprotectants" as used herein generally includes agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations.

As used herein, the terms "ultrafiltration" or "UF" refers to any technique in which a solution or a suspension is subjected to a semi-permeable membrane that retains macromolecules while allowing solvent and small solute molecules to pass through. Ultrafiltration may be used to increase the concentration of macromolecules in a solution or suspension. In a preferred embodiment, ultrafiltration is used to increase the concentration of a protein in water.

As used herein, the term "diafiltration" or "DF" is used to mean a specialized class of filtration in which the retentate is diluted with solvent and re-filtered, to reduce the concentration of soluble permeate components. Diafiltration may or may not lead to an increase in the concentration of retained components, including, for example, proteins. For example, in continuous diafiltration, a solvent is continuously added to the retentate at the same rate as the filtrate is generated. In this case, the retentate volume and the concentration of retained components does not change during the process. On the other hand, in discontinuous or sequential dilution diafiltration, an ultrafiltration step is followed by the addition of solvent to the retentate side; if the volume of solvent added to the retentate side is not equal or greater to the volume of filtrate generated, then the retained components will have a high concentration. Diafiltration may be used to alter the pH, ionic strength, salt composition, buffer composition, or other properties of a solution or suspension of macromolecules.

As used herein, the terms "diafiltration/ultrafiltration" or "DF/UF" refer to any process, technique or combination of techniques that accomplishes ultrafiltration and/or diafiltration, either sequentially or simultaneously.

As used herein, the term "diafiltration step" refers to a total volume exchange during the process of diafiltration.

The term "excipient" refers to an agent that may be added to a formulation to provide a desired consistency, (e.g., altering the bulk properties), to improve stability, and/or to adjust osmolality. Examples of commonly used excipients include, but are not limited to, sugars, polyols, amino acids, surfactants, and polymers. The term "ionic excipient" or "ionizable excipient," as used interchangeably herein, refers to an agent that has a net charge. In one embodiment, the ionic excipient has a net charge under certain formulation conditions, such as pH. Examples of an ionic excipient include, but are not limited to, histidine, arginine, and sodium chloride. The term "non-ionic excipient" or "non-ionizable excipient," as used interchangeably herein, refers to an agent having no net charge. In one embodiment, the non-ionic excipient has no net charge under certain formulation conditions, such as pH. Examples of non-ionic excipients include, but are not limited to, sugars (e.g., sucrose), sugar alcohols (e.g., mannitol), and non-ionic surfactants (e.g., polysorbate 80).

The term "first protein solution" or "first solution" as used herein, refers to the initial protein solution or starting material used in the methods of the invention, i.e., the initial protein solution which is diafiltered into water. In one embodiment, the first protein solution comprises ionic excipients, non-ionic excipients, and/or a buffering system.

The term "hydrodynamic diameter" or "$D_h$" of a particle refers to the diameter of a sphere that has the density of water and the same velocity as the particle. Thus the term "hydrodynamic diameter of a protein" as used herein refers to a size determination for proteins in solution using dynamic light scattering (DLS). A DLS-measuring instrument measures the time-dependent fluctuation in the intensity of light scattered from the proteins in solution at a fixed scattering angle. Protein $D_h$ is determined from the intensity autocorrelation function of the time-dependent fluctuation in intensity. Scattering intensity data are processed using DLS instrument software to determine the value for the hydrodynamic diameter and the size distribution of the scattering molecules, i.e. the protein specimen.

The term "lyoprotectant" as used herein includes agents that provide stability to a protein during water removal during the drying or lyophilisation process, for example, by maintaining the proper conformation of the protein. Examples of lyoprotectants include saccharides, in particular di- or trisaccharides. Cryoprotectants may also provide lyoprotectant effects.

The term "pharmaceutical" as used herein with reference to a composition, e.g., an aqueous formulation, that it is useful for treating a disease or disorder.

The term "protein" is meant to include a sequence of amino acids for which the chain length is sufficient to produce the higher levels of secondary and/or tertiary and/or quaternary structure. This is to distinguish from "peptides" or other small molecular weight drugs that do not have such structure. In one embodiment, the proteins used herein have a molecular weight of at least about 47 kD. Examples of proteins encompassed within the definition used herein include therapeutic proteins. A "therapeutically active protein" or "therapeutic protein" refers to a protein which may be used for therapeutic purposes, i.e., for the treatment of a disorder in a subject. It should be noted that while therapeutic proteins may be used for treatment purposes, the invention is not limited to such use, as said proteins may also be used for in vitro studies. In a preferred embodiment, the therapeutic protein is a fusion protein or an antibody, or antigen-binding portion thereof. In one embodiment, the methods and compositions of the invention comprise at least two distinct proteins, which are defined as two proteins having distinct amino acid sequences. Additional distinct proteins do not include degradation products of a protein.

The phrase "protein is dissolved in water" as used herein refers to a formulation of a protein wherein the protein is dissolved in an aqueous solution in which the amount of small molecules (e.g., buffers, excipients, salts, surfactants) has been reduced by DF/UF processing. Even though the total elimination of small molecules cannot be achieved in an absolute sense by DF/UF processing, the theoretical reduction of excipients achievable by applying DF/UF is sufficiently large to create a formulation of the protein essentially in water exclusively. For example, with 6 volume exchanges in a continuous mode DF/UF protocol, the theoretical reduction of excipients is ~99.8% ($ci=e^{-x}$, with ci being the initial excipient concentration, and x being the number of volume exchanges).

The term "pharmaceutical formulation" refers to preparations which are in such a form as to permit the biological activity of the active ingredients to be effective, and, therefore may be administered to a subject for therapeutic use.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. In one embodiment, the stability of the protein is determined according to the percentage of monomer protein in the solution, with a low percentage of degraded (e.g., fragmented) and/or aggregated protein. For example, an aqueous formulation comprising a stable protein may include at least 95% monomer protein. Alternatively, an aqueous formulation of the invention may include no more than 5% aggregate and/or degraded protein.

The term "stabilizing agent" refers to an excipient that improves or otherwise enhances stability. Stabilizing agents include, but are not limited to, α-lipoic acid, α-tocopherol, ascorbyl palmitate, benzyl alcohol, biotin, bisulfites, boron, butylated hydroxyanisole (BHA), butylated hydroxytoluene (BHT), ascorbic acid and its esters, carotenoids, calcium citrate, acetyl-L-carnitine, chelating agents, chondroitin, chromium, citric acid, coenzyme Q-10, cysteine, cysteine hydrochloride, 3-dehydroshikimic acid (DHS), EDTA (ethylenediaminetetraacetic acid; edetate disodium), ferrous sulfate, folic acid, fumaric acid, alkyl gallates, garlic, glucosamine, grape seed extract, gugul, magnesium, malic acid, metabisulfite, N-acetyl cysteine, niacin, nicotinomide, nettle root, ornithine, propyl gallate, pycnogenol, saw palmetto, selenium, sodium bisulfite, sodium metabisulfite, sodium sulfite, potassium sulfite, tartaric acid, thiosulfates, thioglycerol, thiosorbitol, tocopherol and their esters, e.g., tocopheral acetate, tocopherol succinate, tocotrienal, d-α-tocopherol acetate, vitamin A and its esters, vitamin B and its esters, vitamin C and its esters, vitamin D and its esters, vitamin E and its esters, e.g., vitamin E acetate, zinc, and combinations thereof.

The term "surfactants" generally includes those agents that protect the protein from air/solution interface-induced stresses and solution/surface induced-stresses. For example surfactants may protect the protein from aggregation. Suitable surfactants may include, e.g., polysorbates, polyoxyethylene alkyl ethers such as Brij 35®, or poloxamer such as Tween 20, Tween 80, or poloxamer 188. Preferred detergents are poloxamers, e.g., Poloxamer 188, Poloxamer 407; polyoxyethylene alkyl ethers, e.g., Brij 35®, Cremophor A25, Sympatens ALM/230; and polysorbates/Tweens, e.g., Polysorbate 20, Polysorbate 80, and Poloxamers, e.g., Poloxamer 188, and Tweens, e.g., Tween 20 and Tween 80.

As used herein, the term "tonicity modifier" is intended to mean a compound or compounds that can be used to adjust the tonicity of a liquid formulation. Suitable tonicity modifiers include glycerin, lactose, mannitol, dextrose, sodium chloride, magnesium sulfate, magnesium chloride, sodium sulfate, sorbitol, trehalose, sucrose, raffinose, maltose and others known to those or ordinary skill in the art. In one embodiment, the tonicity of the liquid formulation approximates that of the tonicity of blood or plasma.

The term "water" is intended to mean water that has been purified to remove contaminants, usually by distillation or reverse osmosis, also referred to herein as "pure water". In a preferred embodiment, water used in the methods and compositions of the invention is excipient-free. In one embodiment, water includes sterile water suitable for administration to a subject. In another embodiment, water is meant to include water for injection (WFI). In one embodiment, water refers to distilled water or water which is appropriate for use in in vitro assays. In a preferred embodiment, diafiltration is performed in accordance with the methods of the invention using water alone as the diafiltration medium.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., TNFα, IL-12). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al, (1989) Nature 341:544-546), which consists of a $V_H$ or $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. In one embodiment of the invention, the antibody fragment is selected from the group consisting of a Fab, an Fd, an Fd', a single chain Fv (scFv), an scFv$_a$, and a domain antibody (dAb).

Still further, an antibody or antigen-binding portion thereof may be part of a larger immunoadhesion molecule, formed by covalent or noncovalent association of the antibody or antibody portion with one or more other proteins or peptides. These other proteins or peptides can have functionalities that allow for the purification of antibodies or antigen-binding portions thereof or allow for their association with each other or other molecules. Thus examples of such immunoadhesion molecules include use of the streptavidin core region to make a tetrameric single chain variable fragment (scFv) molecules (Kipriyanov et al. (1995) *Human Antibodies and Hybridomas* 6:93-101) and the use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Two antibody domains are "complementary" where they belong to families of structures which form cognate pairs or groups or are derived from such families and retain this feature. For example, a VH domain and a VL domain of an antibody are complementary; two VH domains are not complementary, and two VL domains are not complementary. Complementary domains may be found in other members of the immunoglobulin superfamily, such as the Vα and Vβ (or gamma and delta) domains of the T-cell receptor.

The term "domain" refers to a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

Variable domains of the invention may be combined to form a group of domains; for example, complementary domains may be combined, such as VH domains being combined with VH domains. Non-complementary domains may also be combined. Domains may be combined in a number of ways, involving linkage of the domains by covalent or non-covalent means.

A "dAb" or "domain antibody" refers to a single antibody variable domain ($V_H$ or $V_L$) polypeptide that specifically binds antigen.

As used herein, the term "antigen binding region" or "antigen binding site" refers to the portion(s) of an antibody molecule, or antigen binding portion thereof, which contains the amino acid residues that interact with an antigen and confers on the antibody its specificity and affinity for the antigen.

The term "epitope" is meant to refer to that portion of any molecule capable of being recognized by and bound by an antibody at one or more of the antibody's antigen binding regions. In the context of the present invention, first and second "epitopes" are understood to be epitopes which are not the same and are not bound by a single monospecific antibody, or antigen-binding portion thereof.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The term "human antibody" refers to antibodies having variable and constant regions corresponding to, or derived from, human germline immunoglobulin sequences as described by, for example, Kabat et al. (See Kabat, et al. (1991) Sequences of Proteins of Immunological Interest, Fifth Edition, U.S. Department of Health and Human Services, NIH Publication No. 91-3242). The human antibodies of the invention, however, may include amino acid residues not encoded by human germline immunoglobulin sequences (e.g., mutations introduced by random or site-specific mutagenesis in vitro or by somatic mutation in vivo), for example in the CDRs and in particular CDR3.

Recombinant human antibodies of the invention have variable regions, and may also include constant regions, derived from human germline immunoglobulin sequences (See Kabat et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis or backmutation or both.

The term "backmutation" refers to a process in which some or all of the somatically mutated amino acids of a human antibody are replaced with the corresponding germline residues from a homologous germline antibody sequence. The heavy and light chain sequences of a human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmuation may occur at any stage of antibody optimization.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

Various aspects of the invention are described in further detail in the following subsections.

II. Methods of Invention

Generally, diafiltration is a technique that uses membranes to remove, replace, or lower the concentration of salts or solvents from solutions containing proteins, peptides, nucleic acids, and other biomolecules. Protein production operations often involve final diafiltration of a protein solution into a formulation buffer once the protein has been purified from impurities resulting from its expression, e.g., host cell proteins. The invention described herein provides a means for obtaining an aqueous formulation by subjecting a protein solution to diafiltration using water alone as a diafiltration solution. Thus, the formulation of the invention is based on using water as a formulation medium during the diafiltration process and does not rely on traditional formulation mediums which include excipients, such as surfactants, used to solubilize and/or stabilize the protein in the final formulation. The invention provides a method for transferring a protein into pure water for use in a stable formulation, wherein the protein remains in solution and is able to be concentrated at high levels without the use of other agents to maintain its stability.

Prior to diafiltration or DF/UF in accordance with the teachings herein, the method includes first providing a protein in a first solution. The protein may be formulated in any first solution, including formulations using techniques that are well established in the art, such as synthetic techniques (e.g., recombinant techniques, peptide synthesis, or a combination thereof). Alternatively, the protein used in the methods and compositions of the invention is isolated from an endogenous source of the protein. The initial protein solution may be obtained using a purification process whereby the protein is purified from a heterogeneous mix of proteins. In one embodiment, the initial protein solution used in the invention is obtained from a purification method whereby proteins, including antibodies, expressed in a mammalian expression system are subjected to numerous chromatography steps which remove host cell proteins (HCPs) from the protein solution. In one embodiment, the first protein solution is obtained from a mammalian cell expression system and has been purified to remove host cell proteins (HCPs). Examples of methods of purification are described in U.S. application Ser. No. 11/732,918 (US 20070292442), incorporated by reference herein. It should be noted that there is no special preparation of the first protein solution required in accordance with the methods of the invention.

Proteins which may be used in the compositions and methods of the invention may be any size, i.e., molecular weight ($M_w$). For example, the protein may have a $M_w$ equal to or greater than about 1 kDa, a $M_w$ equal to or greater than about 10 kDa, a $M_w$ equal to or greater than about 47 kDa, a $M_w$ equal to or greater than about 57 kDa, a $M_w$ equal to or greater than about 100 kDa, a $M_w$ equal to or greater than about 150 kDa, a $M_w$ equal to or greater than about 200 kDa, or a $M_w$ equal to or greater than about 250 kDa. Numbers intermediate to the above recited $M_w$, e.g., 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 153, 153, 154, 155, 156, 157, 158, 159, 160, 161, 162, 163, 164, 165, 166, 167, 168, 169, 170, and so forth, as well as all other numbers recited herein, are also intended to be part of this invention. Ranges of values using a combination of any of the above recited values as upper and/or lower limits are intended to be included in the scope of the invention. For example, proteins used in the invention may range in size from 57 kDa to 250 kDa, from 56 kDa to 242 kDa, from 60 kDa to 270 kDa, and so forth.

The methods of the invention also include diafiltration of a first protein solution that comprises at least two distinct proteins. For example, the protein solution may contain two or more types of antibodies directed to different molecules or different epitopes of the same molecule.

In one embodiment, the protein that is in solution is a therapeutic protein, including, but not limited to, fusion proteins and enzymes. Examples of therapeutic proteins include, but are not limited to, PULMOZYME® (Dornase alfa), REGRANEX® (Becaplermin), ACTIVASE® (Alteplase), ALDURAZYME® (Laronidase), AMEVIVE® (Alefacept), ARANESP® (Darbepoetin alfa), Becaplermin Concentrate, BETASERON® (Interferon beta-1b), BOTOX® (Botulinum Toxin Type A), ELITEK® (Rasburicase), ELSPAR® (Asparaginase), EPOGEN® (Epoetin alfa), ENBREL® (Etanercept), FABRAZYME® (Agalsidase beta), INFERGEN® (Interferon alfacon-1), INTRON® A (Interferon alfa-2a), KINERET® (Anakinra), MYOBLOC® (Botulinum Toxin Type B), NEULASTA® (Pegfilgrastim), NEUMEGA® (Oprelvekin), NEUPOGEN® (Filgrastim), ONTAK® (Denileukin diftitox), PEGASYS® (Peginterferon alfa-2a), PROLEUKIN® (Aldesleukin), PULMOZYME® (Dornase alfa), REBIF® (Interferon beta-1a), REGRANEX® (Becaplermin), RETAVASE® (Reteplase), ROFERON®-A (Interferon alfa-2), TNKase® (Tenecteplase), and XIGRIS® (Drotrecogin alfa), ARCALYS® (Rilonacept), NPlate® (Romiplostim), MIRCERA® (methoxypolyethylene glycol-epoetin beta), CINRYZE® (C1 esterase inhibitor), ELAPRASE® (idursulfase), MYOZYME® (alglucosidase alfa), ORENCIA® (abatacept), NAGLAZYME® (galsulfase), KEPIVANCE® (palifermin) and ACTIMMUNE® (interferon gamma-1b).

The protein used in the invention may also be an antibody, or antigen-binding fragment thereof. Examples of antibodies that may be used in the invention include chimeric antibodies, non-human antibodies, human antibodies, humanized antibodies, and domain antibodies (dAbs). In one embodiment, the antibody, or antigen-binding fragment thereof, is an anti-TNFα and/or an anti-IL-12 antibody (e.g., it may be a dual variable domain (DVD) antibody). Other examples of antibodies, or antigen-binding fragments thereof, which may be used in the methods and compositions of the invention include, but are not limited to, 1D4.7 (anti-IL-12/IL-23 antibody; Abbott Laboratories), 2.5(E)mg1 (anti-IL-18; Abbott Laboratories), 13C5.5 (anti-IL-13 antibody; Abbott Laboratories), J695 (anti-IL-12; Abbott Laboratories), Afelimomab (Fab 2 anti-TNF; Abbott Laboratories), HUMIRA® (adalimumab) Abbott Laboratories), CAMPATH® (Alemtuzumab), CEA-Scan Arcitumomab (fab fragment), ERBITUX® (Cetuximab), HERCEPTIN® (Trastuzumab), MYOSCINT® (Imciromab Pentetate), ProstaScint® (Capromab Pendetide), REMICADE® (Infliximab), ReoPro® (Abciximab), RITUXAN® (Rituximab), SIMULECT® (Basiliximab), SYNAGIS® (Palivizumab), VERLUMA® (Nofetumomab), XOLAIR® (Omalizumab), ZENAPAX® (Daclizumab), ZEVALIN® (Ibritumomab Tiuxetan), ORTHOCLONE OKT®3 (Muromonab-CD3), PANOREX® (Edrecolomab), MYLOTARG® (Gemtuzumab ozogamicin), golimumab (Centocor), CIMZIA® (Certolizumab pegol), SOLIRIS® (Eculizumab), CNTO 1275 (ustekinumab), VECTIBIX® (panitumumab), BEXXAR® (tositumomab and $I^{131}$ tositumomab), an anti-IL-17 antibody Antibody 7 as described in International Application WO 2007/149032 (Cambridge Antibody Technology), the entire contents of which are incorporated by reference herein, the anti-IL-13 antibody CAT-354 (Cambridge Antibody Technology), the anti-human CD4 antibody CE9y4PE (IDEC-151, clenoliximab) (Biogen IDEC/Glaxo Smith Kline), the anti-human CD4 antibody IDEC CE9.1/SB-210396 (keliximab) (Biogen IDEC), the anti-human CD80 antibody IDEC-114 (galiximab) (Biogen IDEC), the anti-Rabies Virus Protein antibody CR4098 (foravirumab), and the anti-human TNF-related apoptosis-inducing ligand receptor 2 (TRAIL-2) antibody HGS-ETR2 (lexatumumab) (Human Genome Sciences, Inc.), and AVASTIN® (bevacizumab).

Techniques for the production of antibodies are provided below.

Polyclonal Antibodies

Polyclonal antibodies generally refer to a mixture of antibodies that are specific to a certain antigen, but bind to different epitopes on said antigen. Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1NCNR$, where R and $R_1$ are different alkyl groups. Methods for making polyclonal antibodies are known in the art, and are described, for example, in *Antibodies: A Laboratory Manual*, Lane and Harlow (1988), incorporated by reference herein.

Monoclonal Antibodies

A "monoclonal antibody" as used herein is intended to refer to a hybridoma-derived antibody (e.g., an antibody secreted by a hybridoma prepared by hybridoma technology, such as the standard Kohler and Milstein hybridoma methodology). For example, the monoclonal antibodies may be made using the hybridoma method first described by Kohler et al., Nature, 256:495 (1975), or may be made by recombinant DNA methods (U.S. Pat. No. 4,816,567). Thus, a hybridoma-derived dual-specificity antibody of the invention is still referred to as a monoclonal antibody although it has antigenic specificity for more than a single antigen.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Antibodies and antibody fragments may also be isolated from yeast and other eukaryotic cells with the use of expression libraries, as described in U.S. Pat. Nos. 6,423,538; 6,696,251; 6,699,658; 6,300,065; 6,399,763; and 6,114,147. Eukaryotic cells may be engineered to express library proteins, including from combinatorial antibody libraries, for display on the cell surface, allowing for selection of particular cells containing library clones for antibodies with affinity to select target molecules. After recovery from an isolated cell, the library clone coding for the antibody of interest can be expressed at high levels from a suitable mammalian cell line.

Additional methods for developing antibodies of interest include cell-free screening using nucleic acid display technology, as described in U.S. Pat. Nos. 7,195,880; 6,951,725; 7,078,197; 7,022,479, 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315. These methods can be used to transcribe a protein in vitro from a nucleic acid in such a way that the protein is physically associated or bound to the nucleic acid from which it originated. By selecting for an expressed protein with a target molecule, the nucleic acid that codes for the protein is also selected. In one variation on cell-free screening techniques, antibody sequences isolated from immune system cells can be isolated and partially randomized polymerase chain reaction mutagenesis techniques to increase antibody diversity. These partially randomized antibody genes are then expressed in a cell-free system, with concurrent physical association created between the nucleic acid and antibody.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting non-human (e.g., rodent) CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some framework (FR) residues are substituted by residues from analogous sites in rodent antibodies. Additional references which describe the humanization process include Sims et al., J. Immunol., 151:2296 (1993); Chothia et al., J. Mol. Biol., 196:901 (1987); Carter et al., Proc. Natl. Acad. Sci. USA, 89:4285 (1992); Presta et al., J. Immunol., 151:2623 (1993); each of which is incorporated by reference herein.

Human Antibodies

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 (1991)).

In one embodiment, the formulation of the invention comprises an antibody, or antigen-binding portion thereof, which binds human TNFα, including, for example, adalimumab (also referred to as Humira, adalimumab, or D2E7; Abbott Laboratories). In one embodiment, the antibody, or antigen-binding fragment thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. Examples and methods for making human, neutralizing antibodies which have a high affinity for human TNFα, including sequences of the antibodies, are described in U.S. Pat. No. 6,090,382 (referred to as D2E7), incorporated by reference herein.

In one embodiment, the human neutralizing, antibody, or an antigen-binding portion thereof, having a high affinity for human TNFα is an isolated human antibody, or an antigen-binding portion thereof, with a light chain variable region (LCVR) having a CDR3 domain comprising the amino acid sequence of SEQ ID NO:3, or modified from SEQ ID NO:3 by a single alanine substitution at position 1, 4, 5, 7 or 8, and with a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11. Preferably, the LCVR further has a CDR2 domain comprising the amino acid sequence of SEQ ID NO:5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO:7 (i.e., the D2E7 VL CDR1) and the HCVR has a CDR1 domain comprising the amino acid sequence of SEQ ID NO:8 (i.e., the D2E7 VH CDR1).

In another embodiment, the human neutralizing, antibody, or an antigen-binding portion thereof, having a high affinity for human TNFα is an isolated human antibody, or an antigen-binding portion thereof, with a light chain variable region (LCVR) comprising the amino acid sequence of SEQ ID NO:1 (i.e., the D2E7 VL) and a heavy chain variable region (HCVR) comprising the amino acid sequence of SEQ ID NO:2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region.

In one embodiment, the formulation of the invention comprises an antibody, or antigen-binding portion thereof, which binds human IL-12, including, for example, the antibody J695 (Abbott Laboratories; also referred to as ABT-874) (U.S. Pat. No. 6,914,128). J695 is a fully human monoclonal antibody designed to target and neutralize interleukin-12 and interleukin-23. In one embodiment, the antibody, or antigen-binding fragment thereof, has the following characteristics: it dissociates from human IL-1α with a $K_D$ of $3 \times 10^{-7}$ M or less; dissociates from human IL-1β with a $K_D$ of $5 \times 10^{-5}$ M or less; and does not bind mouse IL-1α or mouse IL-1β. Examples and methods for making human, neutralizing antibodies which have a high affinity for human IL-12, including sequences of the antibody, are described in U.S. Pat. No. 6,914,128, incorporated by reference herein.

In one embodiment, the formulation of the invention comprises an antibody, or antigen-binding portion thereof, which binds human IL-18, including, for example, the antibody 2.5(E)mg1 (Abbott Bioresearch; also referred to as ABT-325) (see U.S. Patent Application No. 2005/0147610, incorporated by reference herein).

In one embodiment, the formulation of the invention comprises an anti-IL-12/anti-IL-23 antibody, or antigen-binding portion thereof, which is the antibody 1D4.7 (Abbott Laboratories; also referred to as ABT-147) (see WO 2007/005608 A2, published Jan. 11, 2007, incorporated by reference herein).

In one embodiment, the formulation of the invention comprises an anti-IL-13 antibody, or antigen-binding portion thereof, which is the antibody 13C5.5 (Abbott Laboratories; also referred to as ABT-308) (see. PCT/US2007/19660 (WO 08/127,271), incorporated by reference herein).

In one embodiment, the formulation of the invention comprises an antibody, or antigen-binding portion thereof, which is the antibody 7C6, an anti-amyloid β antibody (Abbott Laboratories; see PCT publication WO 07/062,852, incorporated by reference herein).

Bispecific Antibodies

Bispecific antibodies (BsAbs) are antibodies that have binding specificities for at least two different epitopes. Such antibodies can be derived from full length antibodies or antibody fragments (e.g., F(ab')2 bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences.

The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., Methods in Enzymology, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. For example, Fab' fragments recovered from $E.$ $coli$ can be chemically coupled in vitro to form bivalent antibodies. See, Shalaby et al., J. Exp. Med., 175:217-225 (1992).

Various techniques for making and isolating bivalent antibody fragments directly from recombinant cell culture have also been described. For example, bivalent heterodimers have been produced using leucine zippers. Kostelny et al., J. Immunol., 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. USA, 90:6444-6448 (1993) has provided an alternative mechanism for making bispecific/bivalent antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific/bivalent antibody fragments by the use of single-chain Fv (sFv) dimers has also been reported. See Gruber et al., J. Immunol., 152:5368 (1994).

In one embodiment, the formulation of the invention comprises an antibody which is bispecific for IL-1 (including IL-1α and IL-1β). Examples and methods for making bispecific IL-1 antibodies can be found in U.S. Provisional Appln. No. 60/878,165, filed Dec. 29, 2006.

Diafiltration/Ultrafiltration (also generally referred to herein as DF/UF) selectively utilizes permeable (porous) membrane filters to separate the components of solutions and suspensions based on their molecular size. A membrane retains molecules that are larger than the pores of the membrane while smaller molecules such as salts, solvents and water, which are permeable, freely pass through the membrane. The solution retained by the membrane is known as the concentrate or retentate. The solution that passes through the membrane is known as the filtrate or permeate. One parameter for selecting a membrane for concentration is its retention characteristics for the sample to be concentrated. As a general rule, the molecular weight cut-off (MWCO) of the membrane should be ⅓rd to ⅙th the molecular weight of the molecule to be retained. This is to assure complete retention. The closer the MWCO is to that of the sample, the greater the risk for some small product loss during concentration. Examples of membranes that can be used with methods of the invention include Omega™ PES membrane (30 kDa MWCO, i.e. molecules larger than 30 kDa are retained by the membrane and molecules less than 30 kDa are allowed to pass to the filtrate side of the membrane) (Pall Corp., Port Washington, N.Y.); Millex®-GV Syringe Driven Filter Unit, PVDF 0.22 μm (Millipore Corp., Billerica, Mass.); Millex®-GP Syringe Driven Filter Unit, PES 0.22 μm; Sterivex® 0.22 μm Filter Unit (Millipore Corp., Billerica, Mass.); and Vivaspin concentrators (MWCO 10 kDa, PES; MWCO 3 kDa, PES) (Sartorius Corp., Edgewood, N.Y.). In order to prepare a low-ionic protein formulation of the invention, the protein solution (which may be solubilized in a buffered formulation) is subjected to a DF/UF process, whereby water is used as a DF/UF medium. In a preferred embodiment, the DF/UF medium consists of water and does not include any other excipients.

Any water can be used in the DF/UF process of the invention, although a preferred water is purified or deionized water. Types of water known in the art that may be used in the practice of the invention include water for injection (WFI) (e.g., HyPure WFI Quality Water (HyClone), AQUANOVA® WFI (Aqua Nova)), UltraPure™ Water (Invitrogen), and distilled water (Invitrogen; Sigma-Aldrich).

There are two forms of DF/UF, including DF/UF in discontinuous mode and DF/UF in continuous mode. The methods of the invention may be performed according to either mode.

Continuous DF/UF (also referred to as constant volume DF/UF) involves washing out the original buffer salts (or other low molecular weight species) in the retentate (sample or first protein solution) by adding water or a new buffer to the retentate at the same rate as filtrate is being generated. As a result, the retentate volume and product concentration does not change during the DF/UF process. The amount of salt removed is related to the filtrate volume generated, relative to the retentate volume. The filtrate volume generated is usually referred to in terms of "diafiltration volumes". A single diafiltration volume (DV) is the volume of retentate when diafiltration is started. For continuous diafiltration, liquid is added at the same rate as filtrate is generated. When the volume of filtrate collected equals the starting retentate volume, 1 DV has been processed.

Discontinuous DF/UF (examples of which are provided below in the Examples section) includes two different methods, discontinuous sequential DF/UF and volume reduction discontinuous DF/UF. Discontinuous DF/UF by sequential dilution involves first diluting the sample (or first protein solution) with water to a predetermined volume. The diluted sample is then concentrated back to its original volume by UF. Discontinuous DF/UF by volume reduction involves first concentrating the sample to a predetermined volume, then diluting the sample back to its original volume with water or replacement buffer. As with continuous DF/UF, the process is repeated until the level of unwanted solutes, e.g., ionic excipients, are removed.

DF/UF may be performed in accordance with conventional techniques known in the art using water, e.g., WFI, as the DF/UF medium (e.g., Industrial Ultrafiltration Design and Application of Diafiltration Processes, Beaton & Klinkowski, J. Separ. Proc. Technol., 4(2) 1-10 (1983)). Examples of commercially available equipment for performing DF/UF include Millipore Labscale™ TFF System (Millipore), LV Centramate™ Lab Tangential Flow System (Pall Corporation), and the UniFlux System (GE Healthcare).

For example, in a preferred embodiment, the Millipore Labscale™ Tangential Flow Filtration (TFF) system with a 500 mL reservoir is used to perform a method of the invention to produce a diafiltered antibody solution. The DF/UF procedure is performed in a discontinuous manner, with 14 process steps used to produce a high concentration antibody formulation in water. For additional exemplary equipment, solution and water volumes, number of process steps, and other parameters of particular embodiments of the invention, see the Examples section below.

Alternative methods to diafiltration for buffer exchange where a protein is re-formulated into water in accordance with the invention include dialysis and gel filtration, both of which are techniques known to those in the art. Dialysis requires filling a dialysis bag (membrane casing of defined porosity), tying off the bag, and placing the bag in a bath of water. Through diffusion, the concentration of salt in the bag will equilibrate with that in the bath, wherein large molecules, e.g., proteins that cannot diffuse through the bag remain in the bag. The greater the volume of the bath relative to the sample volume in the bags, the lower the equilibration concentration that can be reached. Generally, replacements of the bath water are required to completely remove all of the salt. Gel filtration is a non-adsorptive chromatography technique that separates molecules on the basis of molecular size. In gel filtration, large molecules, e.g., proteins, may be separated from smaller molecules, e.g., salts, by size exclusion.

In a preferred embodiment of the invention, the first protein solution is subjected to a repeated volume exchange with the water, such that an aqueous formulation, which is essentially water and protein, is achieved. The diafiltration step may be performed any number of times, depending on the protein in solution, wherein one diafiltration step equals one total volume exchange. In one embodiment, the diafiltration process is performed 1, 2, 3, 4, 5, 6, 7, 8, 9, or up to as many times are deemed necessary to remove excipients, e.g., salts, from the first protein solution, such that the protein is dissolved essentially in water. A single round or step of diafiltration is achieved when a volume of water has been added to the retentate side that is equal to the starting volume of the protein solution.

In one embodiment, the protein solution is subjected to at least 2 diafiltration steps. In one embodiment, the diafiltration step or volume exchange with water may be repeated at least four times, and preferably at least five times. In one embodiment, the first protein solution is subjected to diafiltration with water until at least a six-fold volume exchange is achieved. In another embodiment, the first protein solution is subjected to diafiltration with water until at least a seven-fold volume exchange is achieved. Ranges intermediate to the above recited numbers, e.g., 4 to 6 or 5 to 7, are also intended to be part of this invention. For example, ranges of values using a combination of any of the above recited values as upper and/or lower limits are intended to be included.

In a preferred embodiment, loss of protein to the filtrate side of an ultrafiltration membrane should be minimized. The risk of protein loss to the filtrate side of a particular membrane varies in relation to the size of the protein relative to the membrane's pore size, and the protein's concentration. With increases in protein concentration, risk of protein loss to the filtrate increases. For a particular membrane pore size, risk of protein loss is greater for a smaller protein that is close in size to the membrane's MWCO than it is for a larger protein. Thus, when performing DF/UF on a smaller protein, it may not be possible to achieve the same reduction in volume, as compared to performing DF/UF on a larger protein using the same membrane, without incurring unacceptable protein losses. In other words, as compared to the ultrafiltration of a solution of a smaller protein using the same equipment and membrane, a solution of a larger protein could be ultrafiltered to a smaller volume, with a concurrent higher concentration of protein in the solution. DF/UF procedures using a particular pore size membrane may require more process steps for a smaller protein than for a larger protein; a greater volume reduction and concentration for a larger protein permits larger volumes of water to be added back, leading to a larger dilution of the remaining buffer or excipient ingredients in the protein solution for that individual process step. Fewer process steps may therefore be needed to achieve a certain reduction in solutes for a larger protein than for a smaller one. A person with skill in the art would be able to calculate the amount of concentration possible with each process step and the number of overall process steps required to achieve a certain reduction in solutes, given the protein size and the pore size of the ultrafiltration device to be used in the procedure.

As a result of the diafiltration methods of the invention, the concentration of solutes in the first protein solution is significantly reduced in the final aqueous formulation comprising essentially water and protein. For example, the aqueous formulation may have a final concentration of excipients which is at least 95% less than the first protein solution, and preferably at least 99% less than the first protein solution. For example, in one embodiment, to dissolve a protein in WFI is a process that creates a theoretical final excipient concentration, reached by constant volume diafiltration with five diafiltration volumes, that is equal or approximate to Ci $e^{-5}$=0.00674, i.e., an approximate 99.3% maximum excipient reduction. In one embodiment, a person with skill in the art may perform 6 volume exchanges during the last step of a commercial DF/UF with constant volume diafiltration, i.e., Ci would be $C_i\ e^{-6}$=0.0025. This would provide an approximate 99.75% maximum theoretical excipient reduction. In another embodiment, a person with skill in the art may use 8 diafiltration volume exchanges to obtain a theoretical ~99.9% maximum excipient reduction.

The term "excipient-free" or "free of excipients" indicates that the formulation is essentially free of excipients. In one embodiment, excipient-free indicates buffer-free, salt-free, sugar-free, amino acid-free, surfactant-free, and/or polyol free. In one embodiment, the term "essentially free of excipients" indicates that the solution or formulation is at least 99% free of excipients. It should be noted, however, that in certain embodiments, a formulation may comprise a certain specified non-ionic excipient, e.g., sucrose or mannitol, and yet the formulation is otherwise excipient free. For example, a formulation may comprise water, a protein, and mannitol, wherein the formulation is otherwise excipient free. In another example, a formulation may comprise water, a protein, and polysorbate 80, wherein the formulation is otherwise excipient free. In yet another example, the formulation may comprise water, a protein, a sorbitol, and polysorbate 80, wherein the formulation is otherwise excipient free.

When water is used for diafiltering a first protein solution in accordance with the methods described herein, ionic excipients will be washed out, and, as a result, the conductivity of the diafiltered aqueous formulation is lower than the first protein solution. If an aqueous solution conducts electricity, then it must contain ions, as found with ionic excipients. A low conductivity measurement is therefore indicative that the aqueous formulation of the invention has significantly reduced excipients, including ionic excipients.

Conductivity of a solution is measured according to methods known in the art. Conductivity meters and cells may be used to determine the conductivity of the aqueous formulation, and should be calibrated to a standard solution before use. Examples of conductivity meters available in the art include MYRON L Digital (Cole Parmer®), Conductometer (Metrohm AG), and Series 3105/3115 Integrated Conductivity Analyzers (Kemotron). In one embodiment, the aqueous formulation has a conductivity of less than 3 mS/cm. In another embodiment, the aqueous formulation has a conductivity of less than 2 mS/cm. In yet another embodiment, the aqueous formulation has a conductivity of less than 1 mS/cm. In one aspect of the invention, the aqueous formulation has a conductivity of less than 0.5 mS/cm. Ranges intermediate to the above recited numbers, e.g., 1 to 3 mS/cm, are also intended to be encompassed by the invention. For example, ranges of values using a combination of any of the above recited values as upper and/or lower limits are intended to be included. In addition, values that fall within the recited numbers are also included in the invention, e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 and so forth.

An important aspect of the invention is that the diafiltered protein solution (solution obtained following the diafiltration process of the first protein solution) can be concentrated. By following this process, it has been discovered that high concentrations of protein are stable in water. Concentration following diafiltration results in an aqueous formulation containing water and an increased protein concentration relative to the first protein solution. Thus, the invention also includes diafiltering a protein solution using water as a diafiltration medium and subsequently concentrating the resulting aqueous solution. Concentration of the diafiltered protein solution may be achieved through means known in the art, including centrifugation. For example, following diafiltration, the water-based diafiltrated protein solution is subjected to a centrifugation process which serves to concentrate the protein via ultrafiltration into a high concentration formulation while maintaining the water-based solution. Means for concentrating a solution via centrifugation with ultrafiltration membranes and/or devices are known in the art, e.g., with Vivaspin centrifugal concentrators (Sartorius Corp. Edgewood, N.Y.).

The methods of the invention provide a means of concentrating a protein at very high levels in water without the need for additional stabilizing agents. The concentration of the protein in the aqueous formulation obtained using the methods of the invention can be any amount in accordance with the desired concentration. For example, the concentration of protein in an aqueous solution made according to the methods herein is at least about 10 µg/mL; at least about 1 mg/mL; at least about 10 mg/mL; at least about 20 mg/mL; at least about 50 mg/mL; at least about 75 mg/mL; at least about 100 mg/mL; at least about 125 mg/mL; at least about 150 mg/mL; at least about 175 mg/mL; at least about 200 mg/mL; at least about 220 mg/mL; at least about 250 mg/mL; at least about 300 mg/mL; or greater than about 300 mg/mL: Ranges intermediate to the above recited concentrations, e.g., at least about 113 mg/mL, at least about 214 mg/mL, and at least about 300 mg/mL, are also intended to be encompassed by the invention. In addition, ranges of values using a combination of any of the above recited values (or values between the ranges described above) as upper and/or lower limits are intended to be included, e.g., 100 to 125 mg/mL, 113 to 125 mg/mL, and 126 to 200 mg/mL or more.

The methods of the invention provide the advantage that the resulting formulation has a low percentage of protein aggregates, despite the high concentration of the aqueous protein formulation. In one embodiment, the aqueous formulations comprising water and a high concentration of a protein, e.g., antibodies, contains less than about 5% protein aggregates, even in the absence of a surfactant or other type of excipient. In one embodiment, the formulation comprises no more than about 7.3% aggregate protein; the formulation comprises no more than about 5% aggregate protein; the formulation comprises no more than about 4% aggregate protein; the formulation comprises no more than about 3% aggregate protein; the formulation comprises no more than about 2% aggregate protein; or the formulation comprising no more than about 1% aggregate protein. In one embodiment, the formulation comprises at least about 92%, at least about 93%, at least about 94%, at least about 95%, at least about 96%, at least about 97%, at least about 98%, or at least about 99% monomer protein. Ranges intermediate to the above recited concentrations, e.g., at least about 98.6%, no more than about 4.2%, are also intended to be part of this invention. In addition, ranges of values using a combination of any of the above recited values as upper and/or lower limits are intended to be included.

Many protein-based pharmaceutical products need to be formulated at high concentrations. For example, antibody-based products increasingly tend to exceed 100 mg/mL in their Drug Product (DP) formulation to achieve appropriate efficacy and meet a typical patient usability requirement of a maximal ~1 mL injection volume. Accordingly, downstream processing steps, such as diafiltration into the final formulation buffer or ultrafiltration to increase the protein concentration, are also conducted at higher concentrations.

Classic thermodynamics predicts that intermolecular interactions can affect the partitioning of small solutes across a dialysis membrane, especially at higher protein concentrations, and models describing non-ideal dialysis equilibrium and the effects of intermolecular interactions are available (Tanford *Physical chemistry or macromolecules*. New York, John Wiley and Sons, Inc., p. 182, 1961; Tester and Modell *Thermodynamics and its applications*, $3^{rd}$ ed. Upper Saddle River, NL, Prentice-Hall, 1997). In the absence of the availability of detailed thermodynamic data in the process development environment, which is necessary to apply these type of models, intermolecular interactions rarely are taken into account during the design of commercial DF/UF operations. Consequently, DP excipient concentrations may differ significantly from the concentration labeled. Several examples of this discrepancy in commercial and development products are published, e.g., chloride being up to 30% lower than labeled in an IL-1 receptor antagonist, histidine being 40% lower than labeled in a PEG-sTNF receptor, and acetate being up to 200% higher than labeled in a fusion conjugate protein (Stoner et al., *J. Pharm. Sci.*, 93, 2332-2342 (2004)). There are several reasons why the actual DP may be different from the composition of the buffer the protein is diafiltered into, including the Donnan effect (Tombs and Peacocke (1974) Oxford; Clarendon Press), non-specific interactions (Arakawa and Timasheff, *Arch. Biochem. Biophys.*, 224, 169-77 (1983); Timasheff, *Annu. Rev. Biophys. Biomol. Struct.*, 22, 67-97 (1993)), and volume exclusion effects. Volume exclusion includes most protein partial specific volumes are between 0.7 and 0.8 mL/g.[5] Thus, for a globular protein at 100 mg/mL, protein molecules occupy approx. 7.5% of the total solution volume. No significant intermolecular interactions assumed, this would translate to a solute molar concentration on the retentate side of the membrane that is 92.5% of the molar concentration on the permeate side of the membrane. This explains why basically all protein solution compositions necessarily change during ultrafiltration processing. For instance, at 40 mg/mL the protein molecules occupy approx. 3% of the total solution volume, and an ultrafiltration step increasing the concentration to 150 mg/mL will necessarily induce molar excipient concentrations to change by more than 8% (as protein at 150 mg/mL accounts for more than 11% of total solution volume). Ranges intermediate to the above recited percentages are also intended to be part of this invention. In addition, ranges of values using a combination of any of the above recited values as upper and/or lower limits are intended to be included.

In accordance with the methods and compositions of the invention, buffer composition changes during DF/UF operations can be circumvented by using pure water as diafiltration medium. By concentrating the protein ~20% more than the concentration desired in the final Bulk DS, excipients could subsequently be added, for instance, via highly concentrated excipient stock solutions. Excipient concentrations and solution pH could then be guaranteed to be identical as labeled.

The aqueous formulation of the invention provides an advantage as a starting material, as it essentially contains no excipient. Any excipient(s) which is added to the formulation following the diafiltration in water can be accurately calculated, i.e., pre-existing concentrations of excipient(s) do not interfere with the calculation. Examples of pharmaceutically acceptable excipients are described in Remington's Pharmaceutical Sciences 16th edition, Osol, A. Ed. (1980), incorporated by reference herein. Thus, another aspect of the invention includes using the aqueous formulation obtained through the methods described herein, for the preparation of a formulation, particularly a pharmaceutical formulation, having known concentrations of excipient(s), including non-ionic excipient(s) or ionic excipient(s). One aspect of the invention includes an additional step where an excipient(s) is added to the aqueous formulation comprising water and protein. Thus, the methods of the invention provide an aqueous formulation which is essentially free of excipients and may be used as a starting material for preparing formulations comprising water, proteins, and specific concentrations of excipients.

In one embodiment, the methods of the invention may be used to add non-ionic excipients, e.g., sugars or non-ionic surfactants, such as polysorbates and poloxamers, to the formulation without changing the characteristics, e.g., protein concentration, hydrodynamic diameter of the protein, conductivity, etc.

Additional characteristics and advantages of aqueous formulations obtained using the above methods are described below in section III. Exemplary protocols for performing the methods of the invention are also described below in the Examples.

III. Formulations of Invention

The invention provide an aqueous formulation comprising a protein and water which has a number of advantages over conventional formulations in the art, including stability of the protein in water without the requirement for additional excipients, increased concentrations of protein without the need for additional excipients to maintain solubility of the protein, and low osmolality. The formulations of the invention also have advantageous storage properties, as the proteins in the formulation remain stable during storage, e.g., stored as a liquid form for more than 3 months at 7° C. or freeze/thaw conditions, even at high protein concentrations and repeated freeze/thaw processing steps. In one embodiment, formulations of the invention include high concentrations of proteins such that the aqueous formulation does not show significant opalescence, aggregation, or precipitation.

The aqueous formulation of the invention does not rely on standard excipients, e.g., a tonicity modifier, a stabilizing agent, a surfactant, an anti-oxidant, a cryoprotectant, a bulking agent, a lyoprotectant, a basic component, and an acidic component. In other embodiments of the invention, the formulation contains water, one or more proteins, and no ionic excipients (e.g., salts, free amino acids).

In certain embodiments, the aqueous formulation of the invention comprises a protein concentration of at least 50 mg/mL and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg, and also have a high protein concentration, e.g., the concentration of the protein is at least 100 mg/mL, and may be as much as 200 mg/mL or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation of the invention is not limited by the protein size and the formulation may include any size range of proteins. Included within the scope of the invention is an aqueous formulation comprising at least 50 mg/mL and as much as 200 mg/mL or more of a protein, which may range in size from 5 kDa to 150 kDa or more. In one embodiment, the protein in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation of the invention may be characterized by the hydrodynamic diameter ($D_h$) of the proteins in solution. The hydrodynamic diameter of the protein in solution may be measured using dynamic light scattering (DLS), which is an established analytical method for determining the $D_h$ of proteins. Typical values for monoclonal antibodies, e.g., IgG, are about 10 nm. Low-ionic formulations, like those described herein, may be characterized in that the $D_h$ of the proteins are notably lower than protein formulations comprising ionic excipients. It has been discovered that the $D_h$ values of antibodies in aqueous formulations made using the DF/UF process using pure water as an exchange medium, are notably lower than the $D_h$ of antibodies in conventional formulations independent of protein concentration. In one embodiment, antibodies in the aqueous formulation of the invention have a $D_h$ of less than 4 nm, or less than 3 nm.

In one embodiment, the $D_h$ of the protein in the aqueous formulation is smaller relative to the $D_h$ of the same protein in a buffered solution, irrespective of protein concentration. Thus, in certain embodiments, protein in an aqueous formulation made in accordance with the methods described herein, will have a $D_h$ which is at least 25% less than the $D_h$ of the protein in a buffered solution at the same given concentration. Examples of buffered solutions include, but are not limited to phosphate buffered saline (PBS). In certain embodiments, proteins in the aqueous formulation of the invention have a $D_h$ that is at least 50% less than the $D_h$ of the protein in PBS in at the given concentration; at least 60% less than the $D_h$ of the protein in PBS at the given concentration; at least 70% less than the $D_h$ of the protein in PBS at the given concentration; or more than 70% less than the $D_h$ of the protein in PBS at the given concentration. Ranges intermediate to the above recited percentages are also intended to be part of this invention, e.g., 55%, 56%, 57%, 64%, 68%, and so forth. In addition, ranges of values using a combination of any of the above recited values as upper and/or lower limits are intended to be included, e.g., 50% to 80%.

Protein aggregation is a common problem in protein solutions, and often results from increased concentration of the protein. The instant invention provides a means for achieving a high concentration, low protein aggregation formulation. Formulations of the invention do not rely on a buffering system and excipients, including surfactants, to keep proteins in the formulation soluble and from aggregating. Formulations of the invention can be advantageous for therapeutic purposes, as they are high in protein concentration and water-based, not relying on other agents to achieve high, stable concentrations of proteins in solution.

The majority of biologic products (including antibodies) are subject to numerous degradative processes which frequently arise from non-enzymatic reactions in solution. These reactions may have a long-term impact on product stability, safety and efficacy. These instabilities can be retarded, if not eliminated, by storage of product at subzero temperatures, thus gaining a tremendous advantage for the manufacturer in terms of flexibility and availability of supplies over the product life-cycle. Although freezing is often the safest and most reliable method of biologics product storage, it has inherent risks. Freezing can induce stress in proteins through cold denaturation, by introducing ice-liquid interfaces, and by freeze-concentration (cryoconcentration) of solutes when the water crystallizes.

Cryoconcentration is a process in which a flat, uncontrolled moving ice front is formed during freezing that excludes solute molecules (small molecules such as sucrose, salts, and other excipients typically used in protein formulation, or macromolecules such as proteins), leading to zones in which proteins may be found at relatively high concentration in the presence of other solutes at concentrations which may potentially lead to local pH or ionic concentration extremes. For most proteins, these conditions can lead to denaturation and in some cases, protein and solute precipitation. Since buffer salts and other solutes are also concentrated under such conditions, these components may reach concentrations high enough to lead to pH and/or redox changes in zones within the frozen mass. The pH shifts observed as a consequence of buffer salt crystallization (e.g., phosphates) in the solutions during freezing can span several pH units, which may impact protein stability.

Concentrated solutes may also lead to a depression of the freezing point to an extent where the solutes may not be frozen at all, and proteins will exist within a solution under these adverse conditions. Often, rapid cooling may be applied to reduce the time period the protein is exposed to these undesired conditions. However, rapid freezing can induce a large-area ice-water interface, whereas slow cooling induces smaller interface areas. For instance, rapid cooling of six model proteins during one freeze/thaw step was shown to reveal a denaturation effect greater than 10 cycles of slow cooling, demonstrating the great destabilization potential of hydrophobic ice surface-induced denaturation.

The aqueous formulation of the invention has advantageous stability and storage properties. Stability of the aqueous formulation is not dependent on the form of storage, and includes, but is not limited to, formulations which are frozen, lyophilized, or spray-dried. Stability can be measured at a selected temperature for a selected time period. In one aspect of the invention, the protein in the aqueous formulations is stable in a liquid form for at least 3 months; at least 4 months, at least 5 months; at least 6 months; at least 12 months.

Ranges intermediate to the above recited time periods are also intended to be part of this invention, e.g., 9 months, and so forth. In addition, ranges of values using a combination of any of the above recited values as upper and/or lower limits are intended to be included. Preferably, the formulation is stable at room temperature (about 30° C.) or at 40° C. for at least 1 month and/or stable at about 2-8° C. for at least 1 year, or more preferably stable at about 2-8° C. for at least 2 years. Furthermore, the formulation is preferably stable following freezing (to, e.g., −80° C.) and thawing of the formulation, hereinafter referred to as a "freeze/thaw cycle."

Stability of a protein can be also be defined as the ability to remain biologically active. A protein "retains its biological activity" in a pharmaceutical formulation, if the protein in a pharmaceutical formulation is biologically active upon administration to a subject. For example, biological activity of an antibody is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding assay).

Stability of a protein in an aqueous formulation may also be defined as the percentage of monomer, aggregate, or fragment, or combinations thereof, of the protein in the formulation. A protein "retains its physical stability" in a formulation if it shows substantially no signs of aggregation, precipitation and/or denaturation upon visual examination of color and/or clarity, or as measured by UV light scattering or by size exclusion chromatography. In one aspect of the invention, a stable aqueous formulation is a formulation having less than about 10%, and preferably less than about 5% of the protein being present as aggregate in the formulation.

Another characteristic of the aqueous formulation of the invention is that, in some instances, diafiltering a protein using water results in an aqueous formulation having improved viscosity features in comparison to the first protein solution (i.e., the viscosity of the diafiltered protein solution is reduced in comparison to the first protein solution.) A person with skill in the art will recognize that multiple methods for measuring viscosity can be used in the preparation of formulations in various embodiments of the invention. For example, kinematic viscosity data (cSt) may be generated using capillaries. In other embodiments, dynamic viscosity data is stated, either alone or with other viscosity data. The dynamic viscosity data may be generated by multiplying the kinematic viscosity data by the density.

In one embodiment, the invention also provides a method for adjusting a certain characteristic, such as the osmolality and/or viscosity, as desired in high protein concentration-water solutions, by adding non-ionic excipients, such as mannitol, without changing other desired features, such as non-opalescence. As such, it is within the scope of the invention to include formulations which are water-based and have high concentrations of protein, where, either during or following the transfer of the protein to water or during the course of the diafiltration, excipients are added which improve, for example, the osmolality or viscosity features of the formulation. Thus, it is also within the scope of the invention that such non-ionic excipients could be added during the process of the transfer of the protein into the final low ionic formulation. Examples of non-ionizable excipients which may be added to the aqueous formulation of the invention for altering desired characteristics of the formulation include, but are not limited to, mannitol, sorbitol, a non-ionic surfactant (e.g., polysorbate 20, polysorbate 40, polysorbate 60 or polysorbate 80), sucrose, trehalose, raffinose, and maltose.

The formulation herein may also contain more than one protein. With respect to pharmaceutical formulations, an additional, distinct protein may be added as necessary for the particular indication being treated, preferably those with complementary activities that do not adversely affect the other protein. For example, it may be desirable to provide two or more antibodies which bind to TNF or IL-12 in a single formulation. Furthermore, anti-TNF or anti-IL-12 antibodies may be combined in the one formulation. Such proteins are suitably present in combination in amounts that are effective for the purpose intended.

Examples of proteins that may be included in the aqueous formulation include antibodies, or antigen-binding fragments thereof. Examples of different types of antibodies, or antigen-binding fragments thereof, that may be used in the invention include, but are not limited to, a chimeric antibody, a human antibody, a humanized antibody, and a domain antibody (dAb). In one embodiment, the antibody used in the methods and compositions of the invention is an anti-TNFα antibody, or antigen-binding portion thereof, or an anti-IL-12 antibody, or antigen binding portion thereof. Additional examples of an antibody, or antigen-binding fragment thereof, that may be used in the invention includes, but is not limited to, 1D4.7 (anti-IL-12/anti-IL-23; Abbott Laboratories), 2.5(E)mg1 (anti-IL-18; Abbott Laboratories), 13C5.5 (anti-Il-13; Abbott Laboratories), J695 (anti-IL-12; Abbott Laboratories), Afelimomab (Fab 2 anti-TNF; Abbott Laboratories), HUMIRA® (adalimumab (D2E7); Abbott Laboratories), Campath® (Alemtuzumab), CEA-Scan Arcitumomab (fab fragment), Erbitux® (Cetuximab), Herceptin® (Trastuzumab), Myoscint (Imciromab Pentetate), ProstaScint® (Capromab Pendetide), REMICADE® (Infliximab), ReoPro® (Abciximab), Rituxan® (Rituximab), Simulect® (Basiliximab), Synagis® (Palivizumab), Verluma (Nofetumomab), Xolair® (Omalizumab), Zenapax® (Daclizumab), Zevalin® (Ibritumomab Tiuxetan), Orthoclone OKT3® (Muromonab-CD3), Panorex® (Edrecolomab), and Mylotarg® (Gemtuzumab ozogamicin) golimumab (Centocor), Cimzia® (Certolizumab pegol), Soliris® (Eculizumab), CNTO 1275 (ustekinumab), Vectibix® (panitumumab), Bexxar® (tositumomab and I[131] tositumomab) and Avastin® (bevacizumab).

In one alternative, the protein is a therapeutic protein, including, but not limited to, Pulmozyme® (Dornase alfa), REGRANEX® (Becaplermin), Activase® (Alteplase), Aldurazyme® (Laronidase), Amevive® (Alefacept), Aranesp® (Darbepoetin alfa), Becaplermin Concentrate, BETASERON® (Interferon beta-1b), BOTOX® (Botulinum Toxin Type A), Elitek® (Rasburicase), Elspar® (Asparaginase), EPOGEN® (Epoetin alfa), ENBREL® (Etanercept), Fabrazyme® (Agalsidase beta), INFERGEN® (Interferon alfacon-1), INTRON A® (Interferon alfa-2a), Kineret® (Anakinra), MYOBLOC® (Botulinum Toxin Type B), Neulasta® (Pegfilgrastim), NEUMEGA® (Oprelvekin), NEUPOGEN® (Filgrastim), Ontak® (Denileukin diftitox), PEGASYS® (Peginterferon alfa-2a), Proleukin® (Aldesleukin), Pulmozyme® (Dornase alfa), Rebif® (Interferon beta-1a), REGRANEX® (Becaplermin), Retavase® (Reteplase), Roferon-A® (Interferon alfa-2), TNKase® (Tenecteplase), and Xigris® (Drotrecogin alfa), ARCALYST® (Rilonacept), NPlate® (Romiplostim), MIRCERA® (methoxypolyethylene glycol-epoetin beta), Cinryze® (C1 esterase inhibitor), Elaprase® (idursulfase), Myozyme® (alglucosidase alfa), ORENCIA® (abatacept), Naglazyme® (galsulfase), Kepivance® (palifermin) and ACTIMMUNE® (interferon gamma-1b).

Other examples of proteins which may be included in the methods and compositions described herein, include mammalian proteins, including recombinant proteins thereof, such as, e.g., growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGFα and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β., and -γ.; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

IV. Uses of Invention

The formulations of the invention may be used both therapeutically, i.e., in vivo, or as reagents for in vitro or in situ purposes.
Therapeutic Uses The methods of the invention may also be used to make a water-based formulation having characteristics which are advantageous for therapeutic use. The aqueous formulation may be used as a pharmaceutical formulation to treat a disorder in a subject.

The formulation of the invention may be used to treat any disorder for which the therapeutic protein is appropriate for treating. A "disorder" is any condition that would benefit from treatment with the protein. This includes chronic and acute disorders or diseases including those pathological conditions which predispose the mammal to the disorder in question. In the case of an anti-TNFα antibody, a therapeutically effective amount of the antibody may be administered to treat an autoimmune disease, such as rheumatoid arthritis, an intestinal disorder, such as Crohn's disease, a spondyloarthropathy, such as ankylosing spondylitis, or a skin disorder, such as psoriasis. In the case of an anti-IL-12 antibody, a therapeutically effective amount of the antibody may be administered to treat a neurological disorder, such as multiple sclerosis, or a skin disorder, such as psoriasis. Other examples of disorders in which the formulation of the invention may be used to treat include cancer, including breast cancer, leukemia, lymphoma, and colon cancer.

The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

The term "treatment" refers to both therapeutic treatment and prophylactic or preventative measures. Those in need of treatment include those already with the disorder, as well as those in which the disorder is to be prevented.

The aqueous formulation may be administered to a mammal, including a human, in need of treatment in accordance with known methods of administration. Examples of methods of administration include intravenous administration, such as a bolus or by continuous infusion over a period of time, intramuscular, intraperitoneal, intracerobrospinal, subcutaneous, intra-articular, intrasynovial, intrathecal, intradermal, transdermal, oral, topical, or inhalation administration.

In one embodiment, the aqueous formulation is administered to the mammal by subcutaneous administration. For such purposes, the formulation may be injected using a syringe, as well as other devices including injection devices (e.g., the Inject-ease and Genject devices); injector pens (such as the GenPen); needleless devices (e.g., MediJector and Biojectorr 2000); and subcutaneous patch delivery systems. In one embodiment, the device, e.g., a syringe, autoinjector pen, contains a needle with a gauge ranging in size from 25 G or smaller in diameter. In one embodiment, the needle gauge ranges in size from 25 G to 33 G (including ranges intermediate thereto, e.g., 25 sG, 26, 26 sG, 27 G, 28 G, 29 G, 30 G, 31 G, 32 G, and 33 G). In a preferred embodiment, the smallest needle diameter and appropriate length is chosen in accordance with the viscosity characteristics of the formulation and the device used to deliver the formulation of the invention.

One advantage of the methods/compositions of the invention is that they provide large concentrations of a protein in a solution which may be ideal for administering the protein to a subject using a needleless device. Such a device allows for dispersion of the protein throughout the tissue of a subject without the need for an injection by a needle.

Examples of needleless devices include, but are not limited to, Biojectorr 2000 (Bioject Medical Technologies), Cool. Click (Bioject Medical Technologies), Iject (Bioject Medical Technologies), Vitajet 3, (Bioject Medical Technologies), Mhi500 (The Medical House PLC), Injex 30 (INJEX-Equidyne Systems), Injex 50 (INJEX-Equidyne Systems), Injex 100 (INJEX-Equidyne Systems), Jet Syringe (INJEX-Equidyne Systems), Jetinjector (Becton-Dickinson), J-Tip (National Medical Devices, Inc.), Medi-Jector VISION (Antares Pharma), MED-JET (MIT Canada, Inc.), DermoJet (Akra Dermojet), Sonoprep (Sontra Medical Corp.), PenJet (PenJet Corp.), MicroPor (Altea Therapeutics), Zeneo (Crossject Medical Technology), Mini-Ject (Valeritas Inc.), ImplaJect (Caretek Medical LTD), Intraject (Aradigm), and Serojet (Bioject Medical Technologies).

Also included in the invention are delivery devices that house the aqueous formulation. Examples of such devices include, but are not limited to, a syringe, a pen (such as an autoinjector pen), an implant, an inhalation device, a needleless device, and a patch. An example of an autoinjection pen is described in U.S. application Ser. No. 11/824,516, filed Jun. 29, 2007.

The invention also includes methods of delivering the formulations of the invention by inhalation and inhalation devices containing said formulation for such delivery. In one embodiment, the aqueous formulation is administered to a subject via inhalation using a nebulizer or liquid inhaler. Generally, nebulizers use compressed air to deliver medicine as wet aerosol or mist for inhalation, and, therefore, require that the drug be soluble in water. Types of nebulizers include jet nebulizers (air-jet nebulizers and liquid-jet nebulizers) and ultrasonic nebulizers.

Examples of nebulizers include Akita™ (Activaero GmbH) (see US2001037806, EP1258264). Akita™ is a table top nebulizer inhalation system (Wt: 7.5 kg, B×W×H: 260× 170×270) based on Pari's LC Star that provides full control over patient's breathing pattern. The device can deliver as much as 500 mg drug in solution in less than 10 min with a very high delivery rates to the lung and the lung periphery. 65% of the nebulized particles are below 5 microns and the mass median aerodynamic diameter (MMAD) is 3.8 microns at 1.8 bar. The minimum fill volume is 2 mL and the maximum volume is 8 mL. The inspiratory flow (200 mL/sec) and nebulizer pressure (0.3-1.8 bar) are set by the smart card. The device can be individually adjusted for each patient on the basis of a lung function test.

Another example of a nebulizer which may be used with compositions of the invention includes the Aeroneb® Go/Pro/Lab nebulizers (AeroGen). The Aeroneb® nebulizer is based on OnQ™ technology, i.e., an electronic micropump (⅜ inch in diameter and wafer-thin) comprised of a unique dome-shaped aperture plate that contains over 1,000 precision-formed tapered holes, surrounded by a vibrational element. Aeroneb® Go is a portable unit for home use, whereas Aeroneb® Pro is a reusable and autoclavable device for use in hospital and ambulatory clinic, and Aeroneb® Lab is a device for use in pre-clinical aerosol research and inhalation studies. The features of the systems include optimization and customization of aerosol droplet size; low-velocity aerosol delivery with a precisely controlled droplet size, aiding targeted drug delivery within the respiratory system; flexibility of dosing; accommodation of a custom single dose ampoule containing a fixed volume of drug in solution or suspension, or commercially available solutions for use in general purpose nebulizers; continuous, breath-activated or programmable; and adaptable to the needs of a broad range of patients, including children and the elderly; single or multi-patient use.

Aerocurrent™ (AerovertRx corp) may also be used with compositions of the invention (see WO2006006963). This nebulizer is a portable, vibrating mesh nebulizer that features a disposable, pre-filled or user filled drug cartridge.

Staccato™ (Alexza Pharma) may also be used with compositions of the invention (see WO03095012). The key to Staccato™ technology is vaporization of a drug without thermal degradation, which is achieved by rapidly heating a thin film of the drug. In less than half a second, the drug is heated to a temperature sufficient to convert the solid drug film into a vapor. The inhaler consists of three core components: a heating substrate, a thin film of drug coated on the substrate, and an airway through which the patient inhales. The inhaler is breath-actuated with maximum dose delivered to be 20-25 mg and MMAD in the 1-2 micron range.

AERx® (Aradigm) may also be used with compositions of the invention (see WO9848873, U.S. Pat. No. 5,469,750, U.S. Pat. No. 5,509,404, U.S. Pat. No. 5,522,385, U.S. Pat. No. 5,694,919, U.S. Pat. No. 5,735,263, U.S. Pat. No. 5,855,564). AERx® is a hand held battery operated device which utilizes a piston mechanism to expel formulation from the AERx® Strip. The device monitors patients inspiratory air flow and fires only when optimal breathing pattern is achieved. The device can deliver about 60% of the dose as emitted dose and 50-70% of the emitted dose into deep lung with <25% intersubject variability.

Another example of a nebulizer device which may also be used with compositions of the invention includes Respimat® (Boehringer). Respimat® is a multi-dose reservoir system that is primed by twisting the device base, which is compressed a spring and transfers a metered volume of formulation from the drug cartridge to the dosing chamber. When the device is actuated, the spring is released, which forces a micro-piston into the dosing chamber and pushes the solution through a uniblock; the uniblock consists of a filter structure with two fine outlet nozzle channels. The MMAD generated by the Respimat® is 2 um, and the device is suitable for low dose drugs traditionally employed to treat respiratory disorders.

Compositions of the invention may also be delivered using the Collegium Nebulizer™ (Collegium Pharma), which is a nebulizer system comprised of drug deposited on membrane. The dosage form is administered to a patient through oral or nasal inhalation using the Collegium Nebulizer after reconstitution with a reconstituting solvent.

Another example of a nebulizer device which may also be used with compositions of the invention includes the Inspiration® 626 (Respironics). The 626 is a compressor based nebulizer for home care. The 626 delivers a particle size between 0.5 to 5 microns.

Nebulizers which can be used with compositions of the invention may include Adaptive Aerosol Delivery® technology (Respironics), which delivers precise and reproducible inhaled drug doses to patients regardless of the age, size or variability in breathing patterns of such patients. AAD® systems incorporate electronics and sensors within the handpiece to monitor the patient's breathing pattern by detecting pressure changes during inspiration and expiration. The sensors determine when to pulse the aerosol delivery of medication during the first part of inspiration. Throughout the treatment, the sensors monitor the preceding three breaths and adapt to the patient's inspiratory and expiratory pattern. Because AAD® systems only deliver medication when the patient is breathing through the mouthpiece, these devices allow the patient to take breaks in therapy without medication waste. Examples of AAD® system nebulizers include the HaloLite® AAD®, ProDose® AAD®, and I-Neb® AAD®.

The HaloLite® Adaptive Aerosol Delivery (AAD)® (Respironics) is a pneumatic aerosolisation system powered by a portable compressor. The AAD® technology monitors the patient's breathing pattern (typically every ten milliseconds) and, depending upon the system being used, either releases pulses of aerosolized drug into specific parts of the inhalation, or calculates the dose drawn during inhalation from a "standing aerosol cloud" (see EP 0910421, incorporated by reference herein).

The ProDos AAD® (Respironics) is a nebulizing system controlled by "ProDose Disc™" system. (Respironics). ProDos AAD® is a pneumatic aerosol system powered by a portable compressor, in which the dose to be delivered is controlled by a microchip-containing disc inserted in the system that, among other things, instructs the system as to the dose to deliver. The ProDose Disc™ is a plastic disc containing a microchip, which is inserted into the ProDose AAD® System and instructs it as to what dose to deliver, the number of doses, which may be delivered together with various control data including drug batch code and expiry date (see EP1245244, incorporated by reference herein). Promixin® can be delivered via Prodose AAD® for management of

*pseudomonas aeruginosa* lung infections, particularly in cystic fibrosis. Promixin® is supplied as a powder for nebulization that is reconstituted prior to use.

The I-neb AAD® is a handheld AAD® system that delivers precise and reproducible drug doses into patients' breathing patterns without the need for a separate compressor ("I-Neb"). The I-neb AAD® is a miniaturized AAD® inhaler based upon a combination of electronic mesh-based aerosolisation technology (Omron) and AAD® technology to control dosing into patients' breathing patterns. The system is approximately the size of a mobile telephone and weighs less than 8 ounces. I-neb AAD® has been used for delivery of Ventavis® (iloprost) (CoTherix/Schering AG).

Another example of a nebulizer which may be used with compositions of the invention is Aria™ (Chrysalis). Aria is based on a capillary aerosol generation system. The aerosol is formed by pumping the drug formulation through a small, electrically heated capillary. Upon exiting the capillary, the formulation rapidly cooled by ambient air to produce an aerosol with MMAD ranging from 0.5-2.0 um.

In addition the TouchSpray™ nebulizer (Odem) may be used to deliver a composition of the invention. The TouchSpray™ nebulizer is a hand-held device which uses a perforate membrane, which vibrates at ultrasonic frequencies, in contact with the reservoir fluid, to generate the aerosol cloud. The vibration action draws jets of fluid though the holes in the membrane, breaking the jets into drug cloud. The size of the droplets is controlled by the shape/size of the holes as well as the surface chemistry and composition of the drug solution. This device has been reported to deliver 83% of the metered dose to the deep lung. Details of the TouchSpray™ nebulizer are described in U.S. Pat. No. 6,659,364, incorporated by reference herein.

Additional nebulizers which may be used with compositions of the invention include nebulizers which are portable units which maximize aerosol output when the patient inhales and minimize aerosol output when the patient exhales using two one-way valves (see PARI nebulizers (PARI GmbH). Baffles allow particles of optimum size to leave the nebulizer. The result is a high percentage of particles in the respirable range that leads to improved drug delivery to the lungs. Such nebulizers may be designed for specific patient populations, such a patients less than three years of age (PARI BABY™) and nebulizers for older patients (PARI LC PLUS® and PARI LC STAR®).

An additional nebulizer which may be used with compositions of the invention is the e-Flow® nebulizer (PARI GmbH) which uses vibrating membrane technology to aerosolize the drug solution, as well as the suspensions or colloidal dispersions (TouchSpray™; ODEM (United Kingdom)). An e-Flow® nebulizer is capable of handling fluid volumes from 0.5 ml to 5 ml, and can produce aerosols with a very high density of active drug, a precisely defined droplet size, and a high proportion of respirable droplets delivered in the shortest possible amount of time. Drugs which have been delivered using the e-Flow® nebulizer include aztreonam and lidocaine. Additional details regarding the e-Flow® nebulizer are described in U.S. Pat. No. 6,962,151, incorporated by reference herein.

Additional nebulizers which may be used with compositions of the invention include a Microair® electronic nebulizer (Omron) and a Mystic™ nebulizer (Ventaira). The Microair® nebulizer is extremely small and uses Vibrating Mesh Technology to efficiently deliver solution medications. The Microair® device has 7 mL capacity and produces drug particle MMAD size around 5 microns. For additional details regarding the Microair® nebulizer see US patent publication no. 2004045547, incorporated by reference herein. The Mystic™ nebulizer uses strong electric field to break liquid into a spray of nearly monodispersed, charged particles. The Mystic™ system includes a containment unit, a dose metering system, aerosol generation nozzles, and voltage converters which together offer multi-dose or unit-dose delivery options. The Mystic™ device is breath activated, and has been used with Corus 1030™ (lidocaine HCl), Resmycin® (doxorubicin hydrochloride), Acuair (fluticasone propionate), NCE with ViroPharm, and NCE with Pfizer. Additional details regarding the Mystic™ nebulizer may be found in U.S. Pat. No. 6,397,838, incorporated by reference herein.

Additional methods for pulmonary delivery of the formulation of the invention are provided in U.S. application Ser. No. 12/217,972, incorporated by reference herein.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

The formulations of the invention overcome the common problem of protein aggregation often associated with high concentrations of protein, and, therefore, provide a new means by which high levels of a therapeutic protein may be administered to a patient. The high concentration formulation of the invention provides an advantage in dosing where a higher dose may be administered to a subject using a volume which is equal to or less than the formulation for standard treatment. Standard treatment for a therapeutic protein is described on the label provided by the manufacturer of the protein. For example, in accordance with the label provided by the manufacturer, infliximab is administered for the treatment of rheumatoid arthritis by reconstituting lyophilized protein to a concentration of 10 mg/mL. The formulation of the invention may comprise a high concentration of infliximab, where a high concentration would include a concentration higher than the standard 10 mg/mL. In another example, in accordance with the label provided by the manufacturer, Xolair (omalizumab) is administered for the treatment of asthma by reconstituting lyophilized protein to a concentration of 125 mg/mL. In this instance, the high concentration formulation of the invention would include a concentration of the antibody omalizumab which is greater than the standard 125 mg/mL.

Thus, in one embodiment, the formulation of the invention comprises a high concentration which is at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 175%, at least about 200%, at least about 225%, at least about 250%, at least about 275%, at least about 300%, at least about 325%, at least about 350%, at least about 375%, at least about 400%, and so forth, greater than the concentration of a therapeutic protein in a known, standard formulation.

In another embodiment, the formulation of the invention comprises a high concentration which is at least about 2 times greater than, at least about 3 times greater than, at least about 4 times greater than, at least about 5 times greater than, at least about 6 times greater than, at least about 7 times greater than, at least about 8 times greater than, at least about 9 times greater than, at least about 10 times greater than and so forth, the concentration of a therapeutic protein in a known, standard formulation.

Characteristics of the aqueous formulation may be improved for therapeutic use. For example, the viscosity of an antibody formulation may be improved by subjecting an antibody protein solution to diafiltration using water without excipients as the diafiltration medium. As described above in Section II, excipients, such as those which improve viscosity, may be added back to the aqueous formulation such that the final concentration of excipient is known and the specific characteristic of the formulation is improved for the specified use. For example, one of skill in the art will recognize that the desired viscosity of a pharmaceutical formulation is dependent on the mode by which the formulation is being delivered, e.g., injected, inhaled, dermal absorption, and so forth. Often the desired viscosity balances the comfort of the subject in receiving the formulation and the dose of the protein in the formulation needed to have a therapeutic effect. For example, generally acceptable levels of viscosity for formulations being injected are viscosity levels of less than about 100 mPas, preferentially less than 75 mPas, even more preferentially less than 50 mPas. As such, viscosity of the aqueous formulation may be acceptable for therapeutic use, or may require addition of an excipient(s) to improve the desired characteristic.

In one embodiment, the invention provides an aqueous formulation comprising water and a human TNFα antibody, or antigen-binding portion thereof, wherein the formulation is excipient-free, wherein the formulation has viscosity which makes it advantageous for use as a therapeutic, e.g., low viscosity of less than 40 cP at 8° C., and less than 25 cP at 25° C. when the protein concentration is about 175 mg/mL. In one embodiment, the concentration of the antibody, or antigen-binding portion thereof, in a formulation having improved viscosity is at least about 50 mg/mL. In one embodiment, the formulation of the invention has a viscosity ranging between about 1 and about 2 mPas.

Non-Therapeutic Uses

The aqueous formulation of the invention may also be used for non-therapeutic uses, i.e., in vitro purposes.

Aqueous formulations described herein may be used for diagnostic or experimental methods in medicine and biotechnology, including, but not limited to, use in genomics, proteomics, bioinformatics, cell culture, plant biology, and cell biology. For example, aqueous formulations described herein may be used to provide a protein needed as a molecular probe in a labeling and detecting methods. An additional use for the formulations described herein is to provide supplements for cell culture reagents, including cell growth and protein production for manufacturing purposes.

Aqueous formulations described herein could be used in protocols with reduced concern regarding how an excipient in the formulation may react with the experimental environment, e.g., interfere with another reagent being used in the protocol. In another example, aqueous formulations containing high concentrations of proteins may be used as a reagent for laboratory use. Such highly concentrated forms of a protein would expand the current limits of laboratory experiments.

Another alternative use for the formulation of the invention is to provide additives to food products. Because the aqueous formulation of the invention consists essentially of water and protein, the formulation may be used to deliver high concentrations of a desired protein, such as a nutritional supplement, to a food item. The aqueous formulation of the invention provides a high concentration of the protein in water, without the concern for excipients needed for stability/solubility which may not be suitable for human consumption. For example, whey- and soy-derived proteins are lending versatility to foods as these proteins have an ability to mimic fat's mouthfeel and texture. As such, whey- and soy-derived proteins may be added to foods to decrease the overall fat content, without sacrificing satisfaction. Thus, an aqueous formulation comprising suitable amounts of whey- and soy-derived proteins may be formulated and used to supplement food products.

Articles of Manufacture

In another embodiment of the invention, an article of manufacture is provided which contains the aqueous formulation of the present invention and provides instructions for its use. The article of manufacture comprises a container. Suitable containers include, for example, bottles, vials (e.g., dual chamber vials), syringes (such as dual chamber syringes), autoinjector pen containing a syringe, and test tubes. The container may be formed from a variety of materials such as glass, plastic or polycarbonate. The container holds the aqueous formulation and the label on, or associated with, the container may indicate directions for use. For example, the label may indicate that the formulation is useful or intended for subcutaneous administration. The container holding the formulation may be a multi-use vial, which allows for repeat administrations (e.g., from 2-6 administrations) of the aqueous formulation. The article of manufacture may further comprise a second container. The article of manufacture may further include other materials desirable from a commercial and user standpoint, including other buffers, diluents, filters, needles, syringes, and package inserts with instructions for use.

The contents of all references, patents and published patent applications cited throughout this application are incorporated herein by reference This invention is further illustrated by the following examples which should not be construed as limiting.

EXAMPLES

The following examples describe experiments relating to an aqueous formulation comprising water as the solution medium. It should be noted that in some instances, decimal places are indicated using European decimal notation. For example, in Table 31 the number "0,296" is synonymous with "0.296".

Example 1

Diafiltration/Ultrafiltration with Adalimumab and J695

Materials and Methods

Adalimumab and J695 were diafiltered using pure water. After an at least 5-fold volume exchange with pure water, the protein solutions were ultrafiltered to a final target concentration of at least 150 mg/mL. Osmolality, visual inspection and protein concentration measurements (OD280) were performed to monitor the status of the proteins during DF/UF processing.

Size exclusion chromatography and ion exchange chromatography were used to characterize protein stability in each final DF/UF product as compared to the starting formulation, e.g., drug substance (DS) starting material and protein standard. Drug substance or "DS" represents the active pharmaceutical ingredient and generally refers to a therapeutic protein in a common bulk solution.

Adalimumab Drug Substance, (Adalimumab extinction coefficient 280 nm: 1.39 mL/mg cm). Drug Substance did not contain polysorbate 80. DS composition: 5.57 mM sodium phosphate monobasic, 8.69 mM sodium phosphate dibasic, 106.69 mM sodium chloride, 1.07 mM sodium citrate, 6.45 mM citric acid, 66.68 mM mannitol.

Adalimumab solution used for dynamic light scattering (DLS) measurements: Adalimumab solution that was diafiltered using pure water as exchange medium was adjusted to 1 mg/mL concentration by diluting the Adalimumab solution with Milli-Q water and excipient stock solutions (excipients dissolved in Milli-Q water), respectively.

J695 Drug Substance, (J695 extinction coefficient 280 nm: 1.42 mL/mg cm). DS composition: Histidine, Methionine, Mannitol, pH 5.8, and polysorbate 80.

Millipore Labscale™ Tangential Flow Filtration (TFF) system, equipped with a 500 mL reservoir. The Labscale TFF system was operated in discontinuous mode at ambient temperature according to Millipore Operating Instructions. Stirrer speed was set to approx. 1.5, and the pump speed was set to approximately 3. The target inlet and outlet pressures were 15 mm psig approximately 50 mm psig, respectively.

Minimate™ Tangential Flow Filtration capsule, equipped with an Omega™ PES membrane, 30 kDa cut-off. The capsule was rinsed for 30 min with 0.1 N NaOH and for another 30 min with Milli-Q water.

780 pH meter, Metrohm, equipped with pH probe Pt1000, No. 6.0258.010, calibrated with buffer calibration solutions VWR, pH 4.00 buffer solution red, Cat. No. 34170-127, and pH 7.00 buffer solution yellow, Cat. No. 34170-130.

Varian 50 Bio UV visible spectrophotometer, AI 9655, with a fixed Cary 50 cell was used for protein concentration measurements (280 nm wavelength). A 100 μL protein sample was diluted with water (Milli-Q water for HPLC) to a final volume of 50.00 mL for protein concentration measurements of all J695 samples and the Adalimumab solution after DF/UF. Concentration of all other Adalimumab samples was monitored by diluting 40 μL sample solution with 1960 μL Milli-Q water. Disposable UV cuvettes, 1.5 mL, semi-micro, Poly(methyl methacrylate) (PMMA), were used for concentration measurements, Milli-Q water was used as OD 280 blank.

Milli-Q water for HPLC grade was used as DF/UF medium.

A Malvern Zetasizer Nano ZS, Instrument No. A19494 was used for DLS measurements.

Hellma precision cells, suprasil, Type No. 105.251-QS, light path 3 mm, center 8.5, were used for DLS measurements (filled with 75 μL sample, Malvern Mastersizer Nano ZS, Item No. AI 9494).

Knauer Osmometer Automatic, Instr. No. 83963, Berlin, Germany, was used for osmolality measurement (calibrated with 400 mOsmol/kg NaCl calibration solution, Art. No. Y1241, Herbert Knauer GmbH, Berlin, Germany).

250 mL Corning cell culture flasks, 75 cm², polystyrene, sterile, Corning, N.Y., USA, were used for storage of the protein solutions after the DF/UF operation.

Sodium chloride: J. T. Baker was used for preparing a 2M NaCl stock solution. The stock solution was used to prepare 1 mg/mL Adalimumab solution in pure water with various concentrations of NaCl (10, 20, 30, and 50 mM)

D-sorbitol, Sigma Chemical Co., St. Louis, Mo. 63178 was used for preparing a 200 mg/mL sorbitol stock solution. The stock solution was used to prepare 1 mg/mL Adalimumab solution in pure water with various concentrations of sorbitol (10, 20, 30, and 40 mg/mL).

HPLC Methods

Adalimumab, SEC analysis: Sephadex 200 column (Pharmacia Cat. No. 175175-01, S/N 0504057). Mobile phase 20 mM sodium phosphate, 150 mM sodium chloride, pH 7.5, 0.5 mL/min flow rate, ambient temperature, detection UV 214 nm and 280 nm. Each sample was diluted to 1.0 mg/mL with Milli-Q water, sample injection load 50 μg (duplicate injection).

Adalimumab, IEC analysis: Dionex, Propac WCX-10 column (p/n 054993) along with a corresponding guard column (p/n 054994). Separation conditions: mobile phase A: 10 mM sodium phosphate, pH 7.5; mobile phase B 10 mM Sodium phosphate, 500 mM Sodium chloride, pH 5.5. 1.0 mL/min flow rate, ambient temperature. Each sample was diluted to 1.0 mg/mL with Milli-Q water, sample injection load 100 μg, duplicate injection.

J695, SEC analysis: Tosoh Bioscience G3000swx1, 7.8 mm×30 cm, 5 μm (Cat. No. 08541). Mobile phase 211 mM $Na_2SO_4$/92 mM $Na_2HPO_4$, pH 7.0. 0.3 mL/min flow rate, ambient temperature, detection UV 214 nm and 280 nm. Each sample was diluted to 2.5 mg/mL with Milli-Q water, sample injection load 50 μg (duplicate injection).

J695, IEC analysis: Dionex, Propac WCX-10 column (p/n 054993) along with a corresponding guard column (p/n 054994). Separation conditions: mobile phase A: 10 mM $Na_2HPO_4$, pH 6.0; mobile phase B 10 mM $Na_2HPO_4$, 500 mM NaCl, pH 6.0. 1.0 mL/min flow rate, 35° C. temperature. Each sample was diluted to 1.0 mg/mL with Milli-Q water, sample injection load 100 μg. J695 Reference standard 29001BF was run in triplicate as a comparison and was diluted to 1 mg/ml in Milli-Q water based on the concentration from the Certificate of Analysis.

Calculation of the Protein Concentration

Calculation Formula:

$$E = -lg\left(\frac{I}{I_0}\right) = \varepsilon \cdot c \cdot d \rightarrow c = \frac{E}{\varepsilon \times d}$$

$\varepsilon$ – absorption coefficient $c$ – concentration $d$ – length of cuvette that the light has to pass $E$ – absorbance $I_0$ – initial light intensity $I$ – light intensity after passing through sample $$\varepsilon_{Adalimumab} = 1.39 \frac{mL}{mg \times cm}$$

$$\varepsilon_{J695} = 1.42 \frac{mL}{mg \times cm}$$

$$\varepsilon_{HSA} = 1.042 \frac{mL}{mg \times cm}$$

1.1: DF/UF Processing of Adalimumab

DF/UF experiments are carried out following the standard operating procedures of the DF/UF equipment manufacturers. For example, the Millipore Labscale™ TFF system was equipped with a 500 mL reservoir and the system operated in discontinuous mode at ambient temperature, in accord with Millipore operating instructions. Stirrer speed was set to approximately 1.5, and the pump speed was set to approximately 3. The target inlet and outlet pressures were 15 mm psig and approximately 50 mm psig, respectively, and the target pressures were monitored to ensure that they were not exceeded.

A Minimate™ Tangential Flow Filtration capsule equipped with an Omega™ PES membrane (Pall Corp., Port Washington, N.Y.), 30 kDa MWCO, was used. The capsule was rinsed for 30 min with 0.1 N NaOH and for another 30 min with Milli-Q water before use.

Approximately 500 mL of Adalimumab solution were placed into the TFF reservoir and DF/UF processing was started in discontinuous mode. Table 1 provides details on the In-Process-Control (IPC) data characterizing the DF/UF process.

The DF/UF processing was stopped after an approximate 5-fold volume exchange (1 volume exchange accounting for approx. 250 mL diafiltration medium). Assuming an ideal 100% excipient membrane permeability, the theoretical final excipient concentration reached by the experiment parameters applied is $C_i(250/500)^5 = 0.03125 \cdot C_i$, with $C_i$ being the initial concentration. The maximum excipient reduction was therefore 96.875% (if constant volume diafiltration would have been used, the theoretical excipient reduction with 5 diafiltration volumes would have been $C_i e^{-5} = 0.00674$, i.e. an approximate 99.3% maximum excipient reduction). Adalimumab solution was drained from the TFF system to a 250 mL cell culture flask (low-volume rinse of the TFF system was performed using WFI yielding a 175.05 mg/mL concentration; without the rinse, the retentate concentration was 213.87 mg/mL). Samples were pulled for determination of pH, osmolality and Adalimumab concentration. Additionally, samples were pulled for characterization by SEC and IEC. Characteristic parameters of the Adalimumab solution before and after DF/UF processing, respectively, are listed in Table 2.

TABLE 2

Impact of DF/UF processing on Adalimumab solution

| parameter | solution before DF/UF | solution after DF/UF |
|---|---|---|
| pH | 5.19 | 5.22 |
| concentration (mg/mL) | 54.66 | 175.05 |
| osmolality (mOsmol/kg) | 305 | 24 |
| *SEC data (% aggregate, | 0.26 | 00.50 |

TABLE 1

Overview on Adalimumab DF/UF Processing

| Process Step | Volume of Milli-Q water added (mL) | Approx. volume of Adalimumab solution in retentate (mL) | Adalimumab concentration of retentate (mg/mL) | Osmolality (mOsmol/kg) | Adalimumab concentration of permeate (mg/mL) |
|---|---|---|---|---|---|
| 1 |  | 500 | 54.66 | 305 | — |
| 2 |  | 400 | 68.33 | 297 | 3.15 |
| 3 |  | 300 | — | — | — |
| 4 | 250 | 550 | 43.73 | 169 | 1.39 |
| 5 |  | 300 |  |  | 4.45 |
| 6 | 250 | 550 | 47.27 | 93 | 2.58 |
| 7 |  | 250 | — | — | — |
| 8 | 250 | 500 | — | — | — |
| 9 |  | 250 | — | — | — |
| 10 | 250 | 500 | — | — | — |
| 11 |  | 250 | — | — | — |
| 12 | 250 | 500 | 52.24 | 9 | 1.24 |
| 13 |  | 300 | 90.27 | 7.5 | — |
| 14 |  | 130 | 213.87 | — | 4.08 |

Fields filled with "—" indicate that no IPC samples were pulled at that step.

TABLE 2-continued

Impact of DF/UF processing on Adalimumab solution

| parameter | solution before DF/UF | solution after DF/UF |
|---|---|---|
| monomer, | 99.74 | 99.50 |
| fragment) | 0.00 | 0.00 |
| *IEC data (acidic regions, lys 0, | 13.89 | 14.07 |
| | 62.05 | 61.97 |
| lys 1, | 19.14 | 18.51 |
| lys 2, %) | 4.83 | 4.73 |

*samples were subjected to one freeze/thaw step (−80° C./25° C.) before analysis via SEC and IEC In the course of DF/UF processing, Adalimumab concentration exceeded 210 mg/mL. Throughout the experiment, the protein solution remained clear, and no solution haziness or protein precipitation, which would have indicated Adalimumab solubility limitations, was observed. Compared to the original Adalimumab DS solution (~55 mg/mL), Adalimumab solution diafiltered by using pure water as DF/UF exchange medium revealed lower opalescence, despite a more than 3-fold increase in protein concentration (~175 mg/mL).

1.2: Adalimumab Characterization Via Chromatography

FIG. 1 shows a SEC chromatogram of an Adalimumab reference standard (Adalimumab standard (bottom line)) compared to the Adalimumab drug standard solution before (middle line) and after (top line) the DF/UF processing procedure. Note that all samples were frozen at −80° C. prior to analysis.

Table 3 also contains the EEC chromatogram data (note all samples were frozen at −80° C. prior to analysis).

TABLE 3

IEC Data of Various Adalimumab Samples

| Sample Name | % Acidic Region 1 | % Acidic Region 2 | % 0 Lys | % 1 Lys | % 2 Lys |
|---|---|---|---|---|---|
| Reference standard | 2.69 | 11.66 | 60.77 | 19.42 | 5.40 |
| Adalimumab DS | 2.51 | 11.38 | 62.05 | 19.14 | 4.83 |
| Adalimumab, after DF/UF | 2.26 | 11.81 | 61.97 | 18.51 | 4.73 |

1.3: Impact of Excipients on Adalimumab Hydrodynamic Diameter ($D_h$)

It was previously determined that the hydrodynamic diameter of J695, as determined by dynamic light scattering (DLS) measurements, was notably decreased when formulating J695 into pure water. J695 in WFI had a $D_h$ of ~3 nm, far below the values that are expected for immunoglobulins. Upon addition of low amounts of ionizable NaCl, the Dh values increased to ~10 nm (independent of the NaCl concentration). Addition of non-ionizable mannitol increased J695 solution osmolality, but had no effect on J695 Dh.

Figure 2:
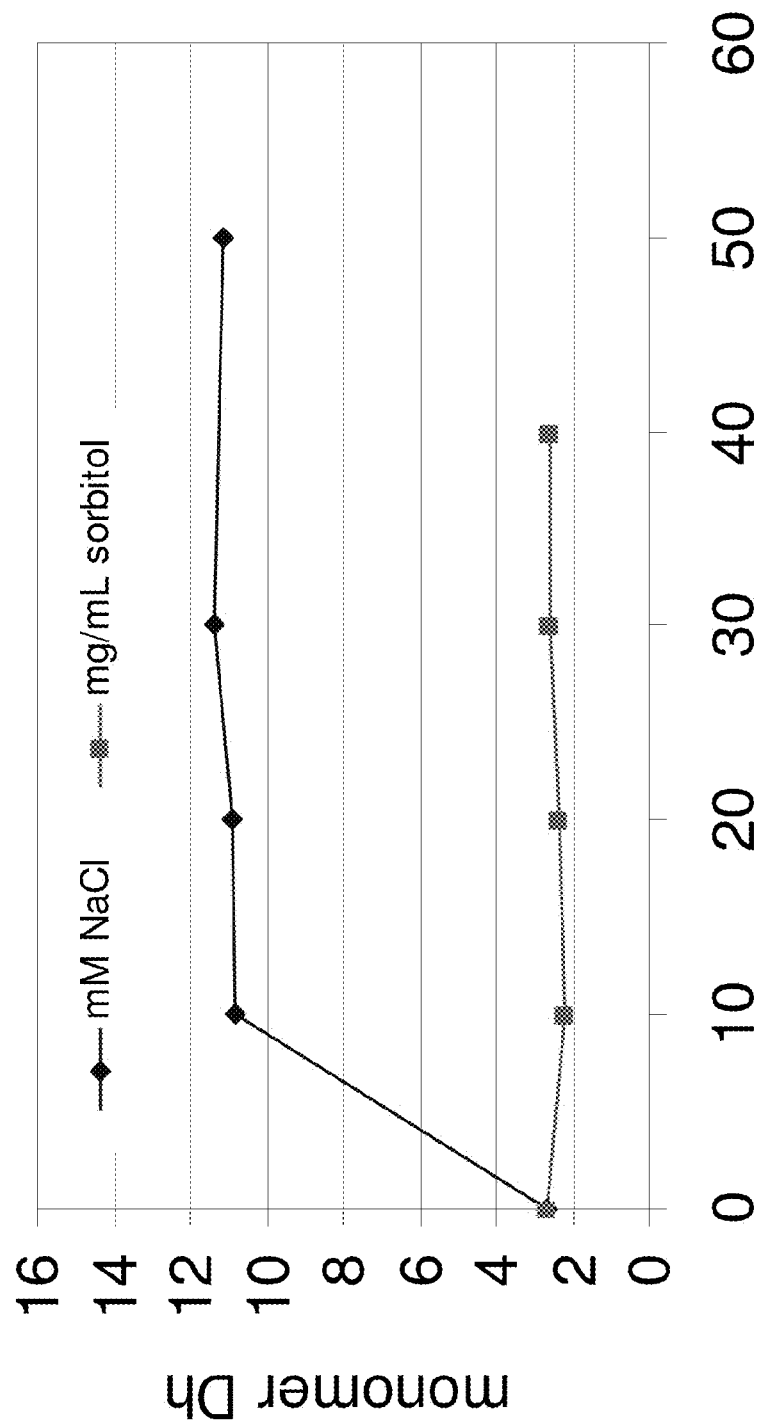
FIG. 2 shows the impact of sorbitol (a non-ionizable excipient) and NaCl (ionizable excipient) concentrations on the hydrodynamic diameter ($D_h$) of Adalimumab monomer upon addition of the excipient compound to DF/UF-processed Adalimumab monomer.

In order to assess the impact of excipients on the hydrodynamic diameter of Adalimumab that had been processed according to the above DF/UF procedure, the Adalimumab solution from the DF/UF experiment was used to formulate Adalimumab solutions in pure water, but with varying levels of NaCl (0-50 mM) and sorbitol (0-40 mg/mL), respectively. The impact of sorbitol (a non-ionizable excipient) and NaCl (ionizable excipient) concentrations on Dh of Adalimumab monomer is displayed in FIG. 2.

The hydrodynamic diameter of Adalimumab monomer in pure water was 2.65 nm. The Adalimumab Dh response to salt and non-ionic excipients was identical to the J695 response seen previously. Adalimumab Dh was virtually not impacted by the presence of sorbitol. Low concentrations of NaCl induced the monomer hydrodynamic diameter to increase to expected levels of ~11 nm. These findings demonstrate that protein hydrodynamic diameters as measured by dynamic light scattering are crucially impacted by the presence of ionizable excipients. Absence of ionizable excipients also is linked to solution viscosities.

These findings have implications for high-concentrated protein solutions: the lower the hydrodynamic diameter, the lower the spatial volume proteins occupy. In high-concentration scenarios, the viscosities of protein solutions that are prepared by using water as DF/UF exchange medium will be substantially lower than the viscosities of traditional protein formulations containing considerable amounts of ionizable buffer excipients. The Adalimumab data confirmed this, as viscosities of 200 mg/mL Adalimumab solutions in water for injection were found to be well below 50 mPas, independent of pH (e.g. pH 4, pH 5, and pH 6). More data on the effect of pH on $D_h$ can be found in Example 17 below.

Overall, these findings are useful in high-concentration protein formulation activities, where viscosity related manufacturing and dosing/delivery problems are well known. Furthermore, these findings show that the osmolality values of final Drug Product can be adjusted with non-ionizable excipients such as sugars or sugar alcohols as desired without inducing an increase in protein Dh and solution viscosity, respectively.

1.4: DF/UF Processing of J695 (Anti-IL12 Antibody)

Approximately 200 mL of J695 solution were adjusted to pH 4.4 with 1 M phosphoric acid and filled into the TFF reservoir (pH adjustment was made to ensure a positive zeta-potential of J695 monomers and thus avoid a potential impact of uncharged protein monomer on data). Then, 300 mL of Milli-Q water were added to the TFF reservoir, and DF/UF processing was started in discontinuous mode. 250 mL reservoir volume, 250 mL of Milli-Q water were added, and DF/UF processing was started again. The DF/UF processing was stopped after a total of 5 volume exchange steps were performed (1 volume exchange accounting for approx. 250 mL).

Assuming an ideal 100% excipient membrane permeability, the theoretical final excipient concentration reached by the experiment parameters applied is Ci(250/500) 5=0.03125*Ci, with Ci being the initial concentration. The maximum excipient reduction is therefore 96.875% (if constant volume diafiltration would have been used, the theoretical excipient reduction with 5 diafiltration volumes would have been Ci e−5=0.00674, i.e. an approx. 99.3% maximum excipient reduction). J695 solution was drained from the TFF system to a 250 mL cell culture flask (no rinse of the TFF system was performed). Samples were pulled for determination of pH, osmolality and J695 concentration. Additionally, samples were pulled for characterization by SEC and IEC. Characteristic parameters of the J695 solution before and after DF/UF processing, respectively, are listed in Table 4.

TABLE 4

Impact of DF/UF Processing on J695 Solution

| parameter | solution before DF/UF | solution after DF/UF |
|---|---|---|
| pH | 4.40 | 4.70 |
| concentration (mg/mL) | 122.9 | 192.8 |
| osmolality (mOsmol/kg) | 265 | 40 |
| SEC data (% aggregate, monomer, fragment) | 0.41<br>98.42<br>1.18 | 0.69<br>98.11<br>1.21 |
| IEC data (sum of isoforms, acidic species, basic species, %) | 92.00<br>5.17<br>2.83 | 92.11<br>5.30<br>2.59 |

As with Adalimumab, the DF/UF experiments on J695 substantiate the principal possibility of processing and formulating J695 by using pure water as exchange medium in DF/UF operations. Both SEC and IEC data suggest no substantial impact on J695 stability while DF/UF processing for an overall period of 1.5 days (process interruption overnight) at ambient temperature using Milli-Q water as diafiltration medium. Throughout the experiment, the protein solution remained clear, indicating no potential J695 solubility limitations.

1.5: J695 Characterization

Table 5 describes the percentages for aggregate, monomer and fragment content for the three solutions as determined by SEC chromatogram.

TABLE 5

Data from SEC chromatogram

| Sample Name | % Aggregate content | % Monomer content | % Fragment content |
|---|---|---|---|
| Reference standard | 0.45 | 98.00 | 1.56 |
| J695 before DF/UF | 0.41 | 98.42 | 1.18 |
| J695 after DF/UF | 0.69 | 98.11 | 1.21 |

Figure 3:
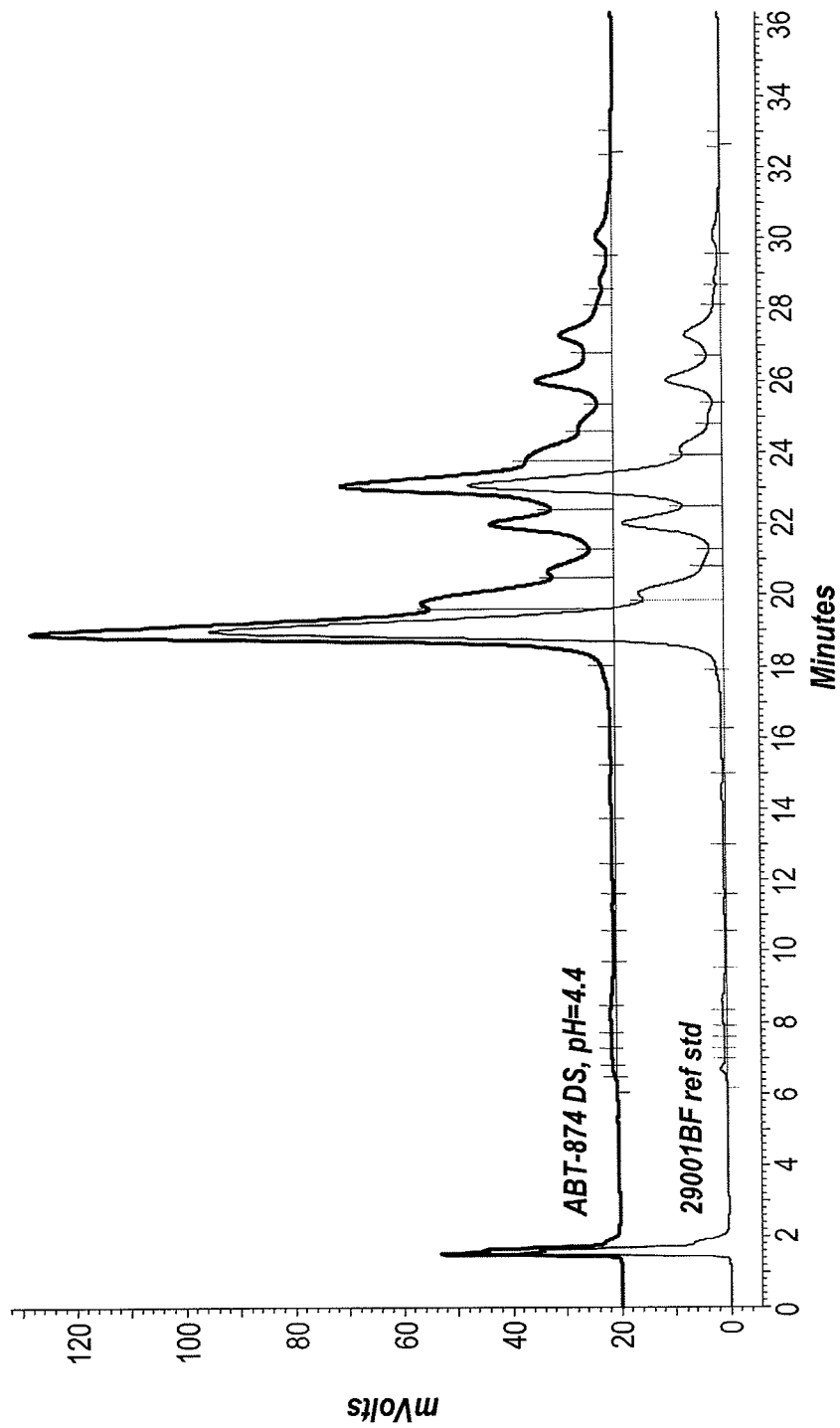
FIG. 3 shows the EEC profile of J695 reference standard (bottom graph) and J695 DS, pH adjusted to pH 4.4 (top graph).

FIG. 3 shows the IEC profile of J695 reference standard (bottom graph) and J695 DS, pH adjusted to pH 4.4 (top graph).

Only a small increase in aggregate content was observed in the J695 samples after DF/UF processing.

Figure 4:
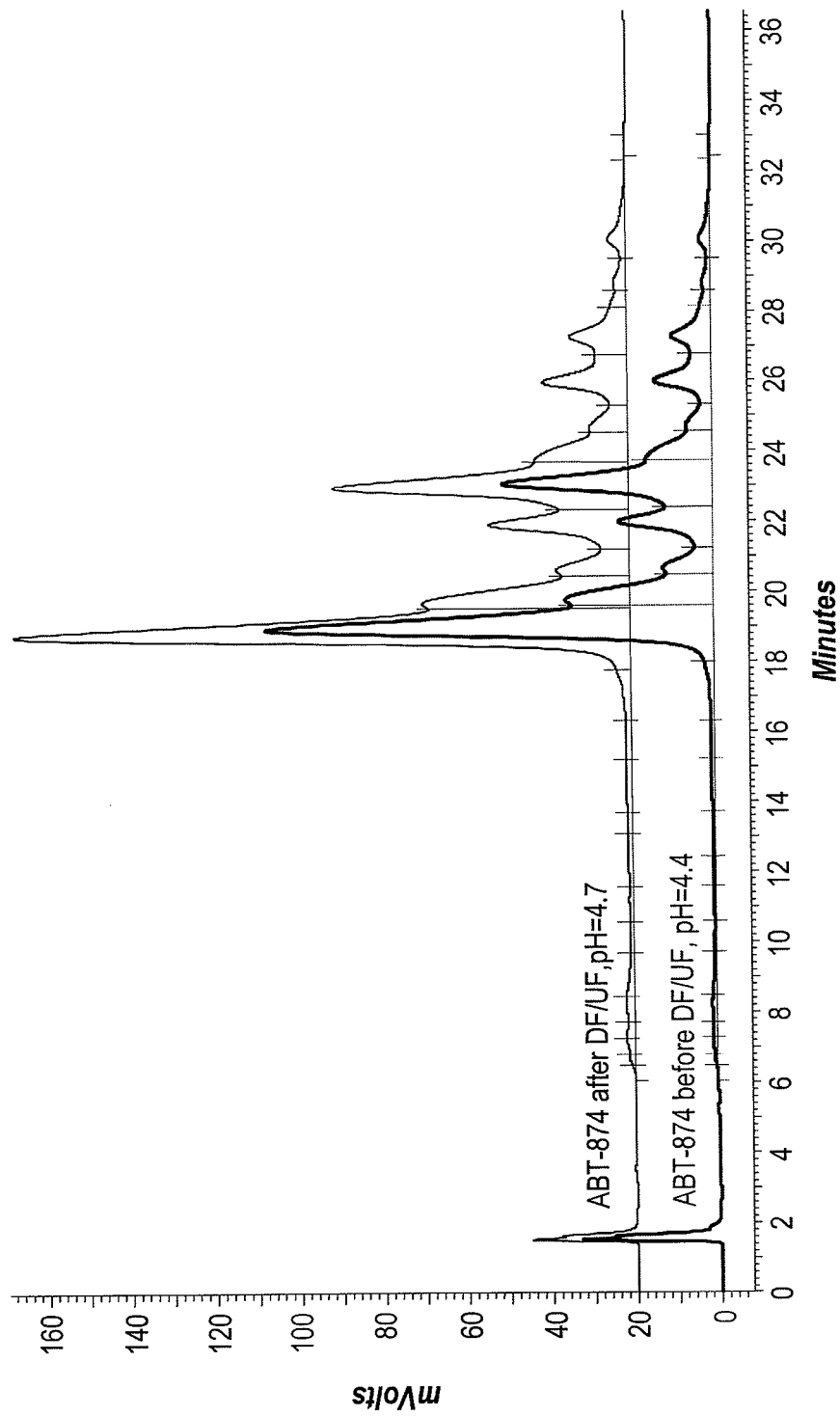
FIG. 4 shows the IEC profile of J695 after DF/UF with Milli-Q water, pH 4.7 (top graph), and J695 DS before DF/UF, pH adjusted to pH 4.4 (bottom curve).

FIG. 4 shows the IEC profile of J695 after DF/UF with Milli-Q water, pH 4.7 (top graph), and J695 DS before DF/UF, pH adjusted to pH 4.4 (bottom curve). As depicted in FIG. 4, the DF/UF step had no notable impact on J695 stability when monitored by IEC. The differences between the two J695 reference standards (refer to FIG. 3) can be attributed to differences in the manufacturing processes between the 3000 L and 6000 L DS campaigns. Table 6 highlights more details on IEC data.

TABLE 6

IEC Data of Various J695 Samples

| Sample Name | 0 glu (1) | other isoforms | acidic | basic |
|---|---|---|---|---|
| Reference standard | 43.57 | 50.06 | 4.47 | 1.90 |

TABLE 6-continued

IEC Data of Various J695 Samples

| Sample Name | 0 glu (1) | other isoforms | acidic | basic |
|---|---|---|---|---|
| J695 | 35.74 | 56.26 | 5.17 | 2.83 |
| J695 after DF/UF | 36.59 | 55.52 | 5.30 | 2.59 |

1.6: Conclusion

The above example provides a diafiltration/ultrafiltration (DF/UF) experiment where water (Milli-Q water for HPLC) was used as diafiltration medium for monoclonal antibodies Adalimumab and J695.

Adalimumab was subjected to DF/UF processing by using pure water as DF/UF exchange medium and was formulated at pH 5.2 at high concentrations (>200 mg/mL) without inducing solution haziness, severe opalescence or turbidity formation. Upon one subsequent freeze/thaw step, SEC and EEC data suggested no notable difference between Adalimumab solution formulated in water via DF/UF processing and the original Adalimumab DS.

J695 also was also subjected to DF/UF processing by using pure water as DF/UF exchange medium and was formulated at pH 4.7 without impacting J695 stability (visual inspection, SEC, IEC).

When formulated using such a DF/UF processing, the hydrodynamic diameter (Dh) of Adalimumab monomer was approx. 2.65 nm. The presence of non-ionic excipients such as sorbitol in concentrations up to 40 mg/mL was shown to have no impact on Dh data, whereas ionic excipients such as NaCl already in low concentrations were demonstrated to induce the Adalimumab monomer Dh to increase to approx. 11 nm (such Dh data are commonly monitored for IgG). Similar findings were made earlier for J695.

In conclusion, processing and formulating proteins using pure water as DF/UF exchange medium is feasible. Assuming an ideal 100% excipient membrane permeability, the theoretical final excipient concentration reached by the constant volume diafiltration with 5 diafiltration volumes would be $Ci\ e-5 = 0.00674$, i.e. an approx. 99.3% maximum excipient reduction. Using 6 diafiltration volume exchanges, an theoretical ~99.98% maximum excipient reduction would result.

Examples 2 to 5 describe experimental execution with respect to three different proteins which were concentrated into an aqueous formulation, and Examples 6 to 11 describe analysis of each of the aqueous formulations.

Materials and Methods for Examples 2-11

Adalimumab protein solution (10 mg/mL) in water for injection, Protein Drug Substance (DS) Material (49.68 mg/mL), DS contains Tween 80, Adalimumab, Adalimumab Drug Product (DP) (40 mg, solution for injection, filtered solution from commercial production). Protein absorption coefficient 280 nm: 1.39.

J695 protein solution (10 mg/mL) in water for injection, Protein Drug Substance (DS) (54 mg/mL), DS contains Tween 80. Absorption coefficient 280 nm: 1.42

HSA protein solution (10 mg/mL) in water for injection, DP without Tween 80, Grifols Human Serum Albumin Grifols®, 20%, 50 mL. Absorption coefficient 280 nm: 1.042

6 R vial and 10 R vial vial preparation: the vials were washed and autoclaved stoppers, 19 mm, West, 4110/40/grey sample repositories (e.g., Eppendorf sample repository, Safe-Lock or simple snap-fit, 1-2 mL)

single-use syringes, sterile, 20 mL; NormJect, 10 mL single use filter units (filter Millex®-GV, Syringe Driven Filter Unit, PVDF 0.22 μm; Millex®-GP, Syringe Driven Filter Unit, PES 0.22 μm, Sterivex® 0.22 μm Filter Unit)

Vivaspin concentrators (cut off 10 kDa, PES; cut off 3 kDa, PES)

Pipettes (e.g., Eppendorf, max.: 1000 μL)

Water for injection

Centrifuge (Eppendorf) and Centrifuge No. 1 (temperature-controlled)

Diafiltration equipment: Millipore Labscale™ TFF System, Millipore diafiltration membrane: Adalimumab: Polyethersulfone; J695: Polyethersulfone; HSA: regenerated cellulose pH probe (Metrohm pH-Meter, protein-suitable probe, biotrode 46)

Laminar-Air-Flow bench, Steag LF-Werkbank, Mp.-No. 12.5

NaCl; mannitol

Gemini 150 Peltier Plate Rheometer, Malvern

Rheometer MCR 301 [temperature-controlled P-PTD 200 (plate with Peltiertempering)] and cone/plate measurement system CP50/0.5° Ti as well as CP50/1° (stainless steel); Anton Paar Capillary viscometer, Schott, capillaries: type 537 20, type 537 10, type 537 13

1M hydrochloric acid (J. T. Baker)

Analytics

UV/VIS spectrophotometry (OD 280 nm); Photon Correlation Spectroscopy (PCS): for approximately 10 mg/mL and approximately 20 mg/mL: 1.1 mPas, 3 runs, 30 s, one measurement, 25° C., from approximately 30 mg/mL and above: 1.9 mPas, 30 s, 3 runs, one measurement, 25° C.

Size Exclusion Chromatography (SEC) and Ion Exchange Chromatography (IEC), as described below.

viscosity measurement: different viscometers with individual and different set-ups were used Calculation of the Protein Concentration Calculation Formula:

$$E = -lg\left(\frac{I}{I_0}\right) = \varepsilon \cdot c \cdot d \rightarrow c = \frac{E}{\varepsilon \times d}$$

$\varepsilon$ – absorption coefficient $c$ – concentration $d$ – length of cuvette that the light has to pass $E$ – absorbance $I_0$ – initial light intensity $I$ – light intensity after passing through sample $$\varepsilon_{Adalimumab} = 1.39 \frac{mL}{mg \times cm}$$

$$\varepsilon_{J695} = 1.42 \frac{mL}{mg \times cm}$$

$$\varepsilon_{HSA} = 1.042 \frac{mL}{mg \times cm}$$

Viscosity Data and Calculation for Adalimumab

Adalimumab Commercial Formulation (Approximately 194 mg/mL) Density:

$$\rho = 1,05475 \frac{g}{cm^3}$$

Adalimumab Commercial Formulation (Approximately 194 mg/mL) Kinematic Viscosity:

K—constant of the capillary t—the time the solution needs for passing the capillary[s]

ν—kinematic viscosity $$v = K \times t$$

$$= 0,03159 \frac{mm^2}{s^2} \times 279,36 \text{ s}$$

$$= 8,825 \frac{mm^2}{s}$$

Adalimumab Commercial Formulation (Approximately 194 mg/mL) Dynamic Viscosity:

η—dynamic viscosity

ρ—density $$\eta = v \times \rho$$

$$= 8,825 \frac{mm^2}{s} \times 1,05475 \frac{g}{cm^3}$$

$$= \underline{9,308 \text{ mPas}}$$

Viscosity Data and Calculation for Human Serum Albumin

HSA Commercial Formulation (Approximately 200 mg/mL) Density:

$$\rho = 1,05833 \frac{g}{cm^3}$$

HSA Commercial Formulation (App. 200 mg/mL) Kinematic Viscosity:

K—constant of the capillary t—the time the solution needs for passing the capillary[s]

ν—kinematic viscosity $$v = K \times t$$

$$= 0,01024 \frac{mm^2}{s^2} \times 337,69 \text{ s}$$

$$= \underline{3,46 \frac{mm^2}{s}}$$

HSA Commercial Formulation (Approximately 200 mg/mL) Dynamic Viscosity:
η—dynamic viscosity
ρ—density $$\eta = v \times \rho$$

$$= 3{,}46 \; \frac{mm^2}{s} \times 1{,}05833 \; \frac{g}{cm^3}$$

$$= 3{,}662 \; mpas$$

HSA in WFI (Approximately 180 mg/mL) Density:

$$\rho = 1{,}70905 \; \frac{g}{cm^3}$$

HSA in WFI (Approximately 180 mg/mL) Kinematic Viscosity:
K—constant of the capillary
t—the time the solution needs for passing the capillary[s]
v—kinematic viscosity $$v = K \times t$$

$$= 0{,}09573 \; \frac{mm^2}{s^2} \times 185{,}3 \; s$$

$$= 17{,}72 \; \frac{mm^2}{s}$$

HSA in WFI (Approximately 180 mg/mL) Dynamic Viscosity:
η—dynamic viscosity
ρ—density $$\eta = v \times \rho$$

$$= 17{,}72 \; \frac{mm^2}{s} \times 1{,}07905 \; \frac{g}{cm^3}$$

$$= \underline{19{,}121 \; mPas}$$

General Experimental Execution for Arriving at High Concentration Formulation

Generally, the process of the invention for arriving at a high concentration, salt-free, protein formulation includes diafiltration of the initial drug substance material, followed by a procedure to increase the concentration of the drug substance in the solution. This may be done in separate procedures or may be done in separate or coinciding steps within the same procedure.

Diafiltration

A sufficient amount of Drug Substance (DS) material (depending on protein concentration of DS) was subjected to diafiltration. Prior to diafiltration, the DS material was diluted with water for injection ~10 mg/ml. Note that in total approximately 540 mL of a 10 mg/mL solution was needed for the experiment.

Water for injection was used as diafiltration medium. The number of diafiltration steps performed was 5 to 7 (one diafiltration step equals one total volume exchange). In-Process-Control (IPC) samples were pulled prior to diafiltration and after diafiltration step (200 μL for osmolality, 120 μL for SEC).

Diafiltration with TFF equipment is performed by applying the following parameters:

stirrer: position 2
pump: position 2
pressure up-stream/inlet: max 20-30 psi
pressure down-stream/outlet: max 10 psi (Parameters used in this experiment were derived from manufacturer's recommendations. One with skill in the art would be able to alter the parameters of equipment operation to accommodate a particular protein or variances in equipment, formulation, viscosity, and other variables.)

After diafiltration, protein concentration was assessed by means of OD280. If protein concentration was >10 mg/mL, the protein concentration was adjusted to 10 mg/mL by appropriately diluting the solution with water for injection.

Concentration 20 mL of diafiltrated protein solution (e.g., Adalimumab, J695, HSA) were put into a Vivaspin 20 Concentrator. The concentrator was closed and put into the centrifuge. The protein solution was centrifuged at maximum speed (5000 rpm).

Sample Pulls

Samples of the concentrated solutions were pulled at: 10 mg/mL and then every 10 mg/mL (20, 30, 40 mg/ml etc.) or until the protein aggregates visibly, and samples were analyzed as follows:

The protein solution was homogenized in the Vivaspin concentrator and filled in an adequate vial.

Optical appearance was inspected directly in the vial.

300 μL was used for UV spectroscopy, 160 μL for PCS, 120 μL for SEC and 300 μL for IEX.

the samples for SEC and IEX were stored at −80° C.

Dynamic Light Scattering (DLS) Protocol

Dynamic light scattering was performed using the Zetasizer Nano ZS (Malvern Instruments, Southborough, Mass.) equipped with Hellma precision cells (Plainview, N.Y.), suprasil quartz, type 105.251-QS, light path 3 mm, center Z8.5 mm, with at least 60 μL sample fill, using protein samples as is and placed directly in measurement cell. Prior to measurement, the cell window was checked to verify that the solution was free of air bubbles or particles/dust/other contaminants that may impact DLS measurement. Measurements were taken under standard operating procedures ("general purpose" mode, 25° C., refractive index set to 1.45, measurement mode set to "manual", 1 run per measurement, each comprising 3 measurements of 30 s each, type of measurement set to "size"). Dispersion Technology Software, version 4.10b1, Malvern Instruments, was used to analyze data. About 70 μL of a sample solution were filled in precision cell for analysis of hydrodynamic diameters (Dh). Default sample viscosity was set 1.1 mPas for low concentrated protein solutions (e.g. <5 mg/mL). Underlying measurement principles concluded that minimal differences between real viscosity values of the sample solution to be measured and the use of default viscosities does not impact DLS data readout substantially. This was verified by performing DLS measurements of low protein concentration solutions (<5 mg/mL) where solution viscosities were determined and taken into account in subsequent DLS measurements. For all samples with higher protein concentration, viscosities were determined and taken into account during DLS measurements.

Example 2

Formulation Comprising High TNFα Antibody Concentration

2.1: Diafiltration

Prior to diafiltration, Adalimumab (49.68 mg/mL) was diluted with water for injection to a concentration of approximately 15 mg/mL. Therefore 140.8 mL Adalimumab solution (49.68 mg/mL) were filled in a 500 mL volumetric flask. The flask was filled up to the calibration mark with water for injection. The volumetric flask was closed and gently shaken for homogenization of the solution. The TFF labscale system was flushed with water. Then the membrane (PES) was adapted and was also flushed with 1 L distilled water. Next, the TFF labscale system and the membrane were flushed with approximately 300 mL of water for injection. The diluted Adalimumab solution was then filled in the reservoir of the TFF. A sample for an osmolality measurement (300 µL), UV spectrophotometry (500 µL) and a sample for SEC analysis (120 µL) were pulled. The system was closed and diafiltration was started. The DF/UF (diafiltration/ultrafiltration) was finished after 5 volume exchanges and after an osmolality value of 3 mosmol/kg was reached. The pH-value of the Adalimumab solution after diafiltration was pH 5.25.

Diafiltration with TFF equipment was performed by applying the following parameters:
stirrer: position 2
pump: position 2
pressure up-stream/inlet: max 20-30 psi
pressure down-stream/outlet: max 10 psi After diafiltration, protein concentration was assessed by means of OD280. The concentration was determined to be 13.29 mg/mL.

The Adalimumab solution was sterile filtered.

The TFF and the membrane were flushed with approximately 1 L distilled water and then with 500 mL 0.1M NaOH. The membrane was stored in 0.1M NaOH, the TFF was again flushed with approximately 500 mL distilled water.

2.2: Protein Concentration

Prior to concentrating the antibody, the protein concentration was again assessed by means of OD280. Adalimumab concentration was determined to be 13.3 mg/mL. The Adalimumab solution was then diluted to 10 mg/mL. 375.94 mL of Adalimumab solution (13.3 mg/mL) was filled in a 500 mL volumetric flask and the flask was filled up to the calibration mark with water for injection (WFI). 75.19 mL of Adalimumab solution (13.3 mg/mL) was also filled in a 100 mL volumetric flask, and filled up to the calibration mark with pure water, i.e., water for injection (WFI). Both flasks were gently shaken for homogenization. The solutions from both flasks were placed in a 1 L PETG bottle. The bottle was gently shaken for homogenization.

Four Vivaspin 20 concentrators (10 kDa) were used. In three Vivaspins, 20 mL of Adalimumab solution (10 mg/mL) were filled (in each). In the fourth Vivaspin device, water was filled as counterbalance weight while centrifuging. The concentrators were closed and put into the centrifuge. The Adalimumab solution was centrifuged applying 4500×g centrifugation force (in a swing out rotor).

2.3: Sample Pull

Samples of the concentrated Adalimumab solution were pulled when they reached a concentration of 10 mg/mL and at each subsequent 10 mg/mL concentration increment increase (at 20 mg/mL, 30 mg/mL, 40 mg/mL etc. until approximately 200 mg/mL). At 40 minute intervals, the concentrators were taken out of the centrifuge, the solution was homogenized, and the solution and the centrifuge adapters were cooled for approximately 10 min on ice. After each 10 mg/mL concentrating increment, the solutions in the concentrators were homogenized, the optical appearance was checked and samples were pulled for analysis via UV (300 µL), PCS (160 µL), SEC (120 µL) and IEC (300 µL). After sample pulls, the concentrators were filled up to approximately 20 mL with Adalimumab solution (10 mg/mL).

Visual Inspection and PCS analysis of protein precipitation were used to determine the solubility limit of Adalimumab protein (i.e. isoforms) in the solution.

At a concentration of approximately 80 mg/mL it became obvious that the Adalimumab solution was not opalescent anymore, opalescence being a known characteristic of Adalimumab solutions having a high amount of fragment. Therefore, it was suspected that fragmentation might have occurred during experiment execution. For further analysis, a sample of Adalimumab solution (approximately 80 mg/mL) was analyzed by SEC. The remainder of the solution in each Vivaspin, as well as the rest of Adalimumab solution (10 mg/mL), was removed to 50 mL falcon tubes and stored at −80° C. The SEC analysis showed a purity of 99.6% monomer.

The solution was thawed in water bath at 25° C. and sterile filtered. Afterwards the solutions from 3 falcon tubes were place into each Vivaspin. The concentrators were filled to approximately 20 mL and the concentration was continued. The experiment was finished as a concentration of approximately 200 mg/mL was reached.

All SEC and DEC samples were stored at −80° C. until further analysis. UV and PCS were measured directly after sample pull. The rest of the concentrated Adalimumab solution was placed in Eppendorf repositories and stored at −80° C.

Table 7 shown below describes calculation of volumes of protein solution to be refilled into the concentrators while concentrating Adalimumab solution. The scheme was calculated before experiment execution to define at which volume samples have to be pulled. The duration of centrifugation is shown in Table 8.

TABLE 7

Centrifugation Scheme

| | step | volume [ml] | concentration [mg/ml] | volume 10 mg/ml protein solution |
|---|---|---|---|---|
| | 0 | 20 | 10 | |
| conc. | 1 | 10 | 20 | |
| sampling | 2 | 9 | 20 | |
| filling | 3 | 20 | 14.5 | 11 |
| conc. | 4 | 9.66 | 30 | |
| sampling | 5 | 8.66 | 30 | |
| filling | 6 | 20 | 18.66 | 11.34 |
| conc. | 7 | 9.33 | 40 | |
| sampling | 8 | 8.33 | 40 | |
| filling | 9 | 20 | 22.49 | 11.67 |
| conc. | 10 | 8.99 | 50 | |
| sampling | 11 | 7.99 | 50 | |
| filling | 12 | 20 | 25.98 | 12.01 |
| conc. | 13 | 8.66 | 60 | |
| sampling | 14 | 7.66 | 60 | |
| filling | 15 | 20 | 29.15 | 12.34 |
| conc. | 16 | 8.32 | 70 | |
| sampling | 17 | 7.32 | 70 | |
| filling | 18 | 20 | 31.96 | 12.68 |
| conc. | 19 | 7.99 | 80 | |
| sampling | 20 | 6.99 | 80 | |
| filling | 21 | 20 | 34.46 | 13.01 |
| conc. | 22 | 7.65 | 90 | |
| sampling | 23 | 6.65 | 90 | |
| filling | 24 | 20 | 36.6 | 13.35 |

TABLE 7-continued

Centrifugation Scheme

| step | | volume [ml] | concentration [mg/ml] | volume 10 mg/ml protein solution |
|---|---|---|---|---|
| conc. | 25 | 7.32 | 100 | |
| sampling | 26 | 6.32 | 100 | |
| filling | 27 | 20 | 38.44 | 13.68 |
| conc. | 28 | 6.98 | 110 | |
| sampling | 29 | 5.98 | 110 | |
| filling | 30 | 20 | 39.9 | 14.02 |
| conc. | 31 | 6.65 | 120 | |
| sampling | 32 | 5.65 | 120 | |
| filling | 33 | 20 | 41.07 | 14.35 |
| conc. | 34 | 6.31 | 130 | |
| sampling | 35 | 5.31 | 130 | |
| filling | 36 | 20 | 41.86 | 14.69 |
| conc. | 37 | 5.98 | 140 | |
| sampling | 38 | 4.98 | 140 | |
| conc. | 39 | 4.64 | 150 | 154.14 |

TABLE 8

Centrifugation times required for concentrating the Adalimumab solution

| concentration [from –> to] [mg/mL] | time [min] |
|---|---|
| 10 to 20 | 15 |
| 20 to 30 | 20 |
| 30 to 40 | 27 |
| 40 to 50 | 30 |
| 50 to 60 | 40 |
| 60 to 70 | 50 |
| 70 to 80 | 60 |
| 80 to 90 | 67 |
| 90 to 100 | 80 |
| 100 to 110 | 100 |
| 110 to 200 | 206 |

Results from the concentration of Adalimumab are also shown below in Table 12.

2.4: Viscosity Measurement

Adalimumab solutions comprising either 50 mg/mL in WFI or 200 mg/mL in WFI were measured for viscosity. 50 mg/mL and 200 mg/mL in WFI were measured using a Gemini 150 Peltier Plate Rheometer, Malvern, and the 200 mg/mL in WFI solution was also measured via rheometer MCR 301 [temperature-controlled P-PTD 200 (plate with Peltier tempering)] and cone/plate measurement system CP50/1 (stainless steel); Anton Paar).

Adalimumab solutions (200 mg/mL) in repository tubes were thawed and homogenized in a 6 R vial. 1 mL Adalimumab (200 mg/mL) was diluted with 3 mL WFI to obtain the diluted solution (for a 50 mg/ml Adalimumab solution).

For the rheometer Gemini 150 approximately 2 mL were needed and for the MCR 301 less than 1 mL was needed for measurement.

Adalimumab (approximately 194 mg/mL) in the commercial formulation was obtained by using Vivaspin tubes. The tubes were filled with Adalimumab solution in commercial buffer and centrifugation was applied until a 194 mg/mL concentration was reached. Viscosity was measured with the capillary viscometer Schott.

2.5: Summary

In sum, Adalimumab was concentrated from 50 mg/mL to approximately 194 mg/mL in Vivaspin 20 tubes in four different tubes. At the beginning, 20 mL of Adalimumab solution (50 mg/mL) were in every tube (four tubes). At the end of the concentration, 5 mL of Adalimumab solution (approximately 194 mg/mL) were in every tube. The concentration step was performed at 5000 rpm (approximately 4500 g). After every hour, the oblong beakers and the protein solution in the Vivaspin tubes were cooled in crushed ice for approximately 10 to 15 min. The density was measured with density measurement device DMA 4500, Anton Paar. Further analysis of the high Adalimumab concentration formulation is provided in Examples 5 to 11.

Example 3

Formulation Comprising High Concentration 11-12 Antibody 3.1: Diafiltration

Prior to diafiltration, IL-12 antibody J695 (54 mg/mL) was diluted with water for injection to a concentration of approximately 15 mg/mL. This was done by placing 150 mL J695 solution (54 mg/mL) in a 500 mL volumetric flask and filling the flask to the calibration mark with water for injection. The volumetric flask was closed and gently shaken for homogenization of the solution. The TFF labscale system was flushed with water. Then the polyethersulfone membrane (PES) was adapted and was also flushed with 1 L of distilled water. Afterwards the TFF labscale system and the membrane were flushed with approximately 300 mL of water for injection. Next, the diluted J695 solution was placed in the reservoir of the TFF. A sample for osmolality measurement (300 μL), UV spectrophotometry (500 μL) and a sample for SEC analysis (120 μL) were pulled. The system was closed and diafiltration was started. After 200 mL of processing the DF volume, the diafiltration was stopped and another sample for UV measurement was pulled. The DF/UF was stopped after 1800 mL diafiltration volume (approximately factor 3.5 volume exchange), reaching an osmolality value of 4 mosmol/kg. The pH-value of the J695 solution after diafiltration was pH 6.48.

Diafiltration with TFF equipment was performed by applying the following parameters:
  stirrer: position 2
  pump: position 2
  pressure up-stream/inlet: max 20-30 psi
  pressure down-stream/outlet: max 10 psi After diafiltration, the protein concentration was assessed by means of OD280. The concentration was determined to be 16.63 mg/mL.

The J695 solution was sterile filtered.

The TFF instrument and the membrane were flushed with approximately 1 L of distilled water and then with 500 mL 0.1M NaOH. The membrane was stored in 0.1M NaOH and the TFF was again flushed with approximately 500 mL of distilled water.

3.2: Concentrating

Prior to concentrating, the J695 solution was diluted to 10 mg/mL: 316 mL of J695 solution (16.63 mg/mL) was placed in a 500 mL volumetric flask and the flask was filled to the calibration mark with water for injection (WFI). Additionally, 64 mL of J695 solution (16.63 mL) was placed in a 100 mL volumetric flask and filled to the calibration mark with WFI. Both flasks were gently shaken for homogenization. The solutions from both flasks were placed in a 1 L PETG bottle. The bottle was gently shaken for homogenization.

Four Vivaspin 20 concentrators (10 kDa cut-off) were used. 20 mL of J695 solution (10 mg/mL) were place in each of three Vivaspins. In the fourth Vivaspin concentrator device, water was filled as counterbalance weight while centrifuging.

The concentrators were closed and put into the centrifuge. The J695 solution was centrifuged applying 4500×g centrifugation force (in a swing out rotor).

3.3: Sample Pull

Samples of the concentrated J695 solution were pulled when they reached a concentration of 10 mg/mL and at each subsequent 10 mg/mL concentration increment increase (at 20 mg/mL, 30 mg/mL, 40 mg/mL etc. until 200 mg/mL). After every 40 minutes, the concentrators were taken out of the centrifuge, the solution was homogenized, and the solution and the centrifuge adapters were cooled for approximately 10 min on ice. After every 10 mg/mL concentration increase, the solutions in the concentrators were homogenized, the optical appearance was checked and samples were pulled for UV (300 µL), PCS (160 µL), SEC (120 µL) and IEC analysis (300 µL). After sample pulls, the concentrators were filled up to approximately 20 mL with J695 solution (10 mg/mL).

Visual Inspection and PCS analysis were used to determine the solubility (i.e., to check for potential precipitation) and stability of J695.

At the conclusion of the experiment, a concentration of approximately 200 mg/mL was reached.

All SEC and IEC samples were stored at −80° C. for further analysis (see below). UV spectrophotometry and PCS measurements were taken directly after each sample pull. The rest of the concentrated J695 solution was placed in Eppendorf repositories and stored at −80° C.

Details regarding the centrifugation scheme are provided above in Table 7. The duration of the J695 centrifugation are provided in Table 9.

TABLE 9

Centrifugation Times used to Concentrate the J695 Solution

| concentration [from −> to] [mg/mL] | time [min] |
|---|---|
| 10 to 20 | 13 |
| 20 to 30 | 22 |
| 30 to 40 | 27 |
| 40 to 50 | 38 |
| 50 to 60 | 45 |
| 60 to 70 | 80 |
| 70 to 80 | 90 |
| 80 to 90 | 105 |
| 90 to 100 | 165 |
| 100 to 200 | 270 |

3.4: Impact of Excipients on the Hydrodynamic Diameter of J695

In this experiment the impact of sodium chloride and mannitol, separately, on the hydrodynamic diameter of J695 was analyzed. For this purpose, stock solutions of sodium chloride (12 mg/mL) and of mannitol (120 mg/mL) were prepared. 1.2 g NaCl was weighed in a beaker, which was filled with approximately 70 mL of WFI, and 12.002 g of Mannitol was weighed in a beaker which was filled with approximately 70 mL of WFI. The two solutions were stirred for homogenization. Each solution was placed in a volumetric flask, which was filled to the calibration mark with WFI. The flasks were gently shaken for homogenization.

Approximately 8 mL of J695 solution (approximately 200 mg/mL) was thawed at 37° C. The solution was filled in a 10 R vial and homogenized. Seven 2 R vials were filled with 500 µL J695 solution (approximately 200 mg/mL) each. The filling scheme is described in Table 10 below.

TABLE 10

Filling Scheme for Preparation of J695 Solutions Containing Different Concentrations of NaCl or Mannitol

| excipient | concentration excipient | volume ABT-874 (200 mg/ml) [µL] | vol. NaCl stock solution (12 mg/mL) [µL] | vol. mannitol stock solution (12 mg/ml) [µL] | vol. WFI [µL] |
|---|---|---|---|---|---|
| — | — | 500 | — | — | 500 |
| NaCl | 2 mg/mL | 500 | 167 | — | 333 |
| NaCl | 4 mg/mL | 500 | 333 | — | 167 |
| NaCl | 6 mg/mL | 500 | 500 | — | — |
| mannitol | 20 mg/mL | 500 | — | 167 | 333 |
| mannitol | 40 mg/mL | 500 | — | 333 | 167 |
| mannitol | 60 mg/mL | 500 | — | 500 | — |

The 2 R vials were gently homogenized via shaking. Thereafter, PCS and osmolality measurements were taken of the different J695 solutions (100 mg/mL).

To prepare samples for PCS analysis, the cuvettes were first flushed with 50 µL of the sample. Then measurements were taken using 100 µL of the sample.

Further analysis of the high J695 concentration formulation is provided in Examples 5 to 11.

Example 4

High Concentration Human Serum Albumin (HSA) Formulation 4.1: Diafiltration

Prior to diafiltration, HSA solution (200 mg/mL, commercial formulation) was diluted with water for injection to a concentration of 15.29 mg/mL. To achieve this, 38 mL HSA (200 mg/mL) were filled in a 500 mL volumetric flask. The flask was filled to the calibration mark with water for injection. The volumetric flask was closed and gently shaken for homogenization of the solution. The TFF labscale system was flushed with water. Then the membrane (regenerated cellulose) was adapted and was also flushed with 1 L of distilled water. Afterwards the TFF labscale system and the membrane were flushed with approximately 300 mL water for injection. Next, the diluted HSA solution was filled in the reservoir of the TFF. Samples for osmolality measurement (300 µL), UV spectrophotometry (500 µL) and a sample for SEC analysis (120 µL) were pulled. The system was closed and diafiltration was started. After diafiltration of approximately 300 mL of volume, a UV measurement of the permeate was taken. The permeate revealed a concentration of 2.74 mg/mL, indicating that protein was passing through the membrane. The diafiltration was stopped after approximately 500 mL of DF, and another sample for UV measurement was pulled (HSA concentration 11.03 mg/mL). The DF/UF was finished after 950 mL of diafiltration volume (approximately 2 volume exchanges) and after reaching an osmolality value of 4 mosmol/kg. The pH-value of the HSA solution after diafiltration was pH 7.13.

UV spectrophotometric measurement of the permeate was performed three times (n=3).

Diafiltration with TFF equipment was performed by applying the following parameters:
stirrer: position 2
pump: position 2
pressure up-stream/inlet: max 20-30 psi
pressure down-stream/outlet: max 10 psi After diafiltration, protein concentration was assessed by means of OD280. The concentration was determined 9.41 mg/mL.

The HSA solution was sterile filtered. The TFF and the membrane were flushed with approximately 1 L of distilled water. Afterwards an integrity test was done (see Operating Instructions Labscale™ TFF System, page 5-3 to 5-5, 1997). The volume flow was 1.2 mL/min, thus, the integrity test was passed (acceptable maximal limit 3 mL/min). The membrane was once more flushed with 500 mL of distilled water and then with 500 mL of 0.05 M NaOH. The membrane was stored in 0.05 M NaOH, the TFF was again flushed with approximately 500 mL of distilled water.

4.2: Concentration Process

Prior to concentrating the HSA protein solution, the concentration was assessed by means of OD280 and was determined to be 9.52 mg/mL. Four Vivaspin 20 concentrators (10 kDa) were used. 20 mL of HSA solution (9.52 mg/mL) were placed in each of 3 Vivaspin concentrators. In the fourth Vivaspin, water was filled as counterweight balance while centrifuging. The concentrators were closed and put into the centrifuge. The HSA solution was centrifuged applying 4500×g centrifugation force (in a swing out rotor).

4.3: Sample Pull

Samples of the concentrated HSA solution were pulled when the concentration reached 10 mg/mL and subsequently after every 10 mg/mL concentration increment increase (at 20 mg/mL, 30 mg/mL, 40 mg/mL etc. until approximately 180 mg/mL). Every 40 minutes the concentrators were taken out of the centrifuge, the solution was homogenized, and the solution and the centrifuge adapters were cooled for approximately 10 min on ice. After every 10 mg/mL concentration increment increase, the solutions in the concentrators were homogenized, the optical appearance was checked and samples were pulled for analysis via UV (300 µL), PCS (160 µL), SEC (120 µL) and IEC (300 µL). After the sample pull, HSA solution (9.52 mg/mL) was added to the concentrators, up to approximately 20 mL.

When the projected concentration for the HSA solution in the concentrator reached approximately 20 mg/mL, permeate was measured via OD280, revealing a concentration of 0.5964 mg/mL. The concentration of the HSA solution was only 15.99 mg/mL, which was less than expected. A sample of concentrated HSA in WFI (10 mg/mL) was analyzed via SEC to scrutinize for potential fragmentation. The HSA solution (15.99 mg/mL) in the Vivaspins was placed in falcon tubes and stored at −80° C. The remainder of the original HSA solution (9.52 mg/mL) used to fill the concentrators was also stored at −80° C.

SEC analysis was performed to determine whether the HSA protein underwent degradation, producing small fragments that could pass through the membrane. The SEC analysis, however, revealed a monomer amount of 92.45% for 10 mg/mL HSA in WFI with virtually no fragments.

The solutions that were stored at −80° C. were thawed at 25° C. and sterile filtered. The solutions in the falcon tubes were transferred in one Vivaspin 20 concentrator each (3 kDa cut-off). The Vivaspins were filled up with HSA solution (9.52 mg/mL) and centrifuged (refer to 3.2 concentration process described above).

Visual Inspection and PCS analysis were used to determine the solubility limit of HSA.

At the completion of the experiment, a concentration of approximately 180 mg/mL HSA was reached.

All SEC and IEC samples were stored at −80° C. until further analysis. UV and PCS measurements were performed directly after sample pull. The rest of the concentrated HSA solution was placed in Eppendorf repositories and stored at −80° C.

An overview of the centrifugation scheme is described above in Table 7. The duration of the centrifugation used to concentrate HSA is described in Table 11.

TABLE 11

Centrifugation Times Necessary to Concentrate HSA Solution

| concentration [from -> to] [mg/mL] | time [min] |
| --- | --- |
| 10 to 20 | 9 |
| 20 to 30 | 30 |
| 30 to 40 | 40 |
| 40 to 50 | 50 |
| 50 to 60 | 80 |
| 60 to 70 | 90 |
| 70 to 80 | 110 |
| 80 to 90 | 130 |
| 90 to 100 | 170 |
| 100 to 180 | 360 |

4.4: Impact of the pH Value on the Hydrodynamic Diameter of HSA

The following part of the experiment was performed to evaluate a potential impact of pH on the hydrodynamic diameter of HSA when the protein is dissolved in WFI. Four 6 R vials were filled with 5.09 mL HSA solution (9.83 mg/mL), and pH values from 3 to 6 were set up with 1M HCl (actual pH: 3.04, 3.99, 5.05, 6.01). These solutions were each transferred to a separate 10 mL volumetric flask. The flasks were then filled to the calibration mark and gently shaken for homogenization.

The HCl solutions were placed in 10 R vials and analyzed via PCS. The solutions were sterile filtered and measured again via PCS. Also, 5.09 mL HSA solution (9.83 mg/mL) were transferred in a 10 mL volumetric flask and this was filled with WFI to the calibration mark. The flask was gently shaken for homogenization and then the solution was sterile filtered and measured via PCS.

Sample Preparation for PCS Measurement:

The cuvettes were flushed with 50 µL of sample. Measurement was performed with 100 µL of sample volume.

4.5: Viscosity Measurement

For HSA in commercial formulation (200 mg/mL) and for HSA in WFI (approximately 180 mg/mL) the viscosity was measured with a capillary viscometer (Schott, M P.-No. 33.2).

A 15 mL aliquot was pulled from a 50 mL bottle of commercial formulation HSA. HSA in WFI was thawed at approximately 20° C. and approximately 9 mL were aliquotted in a Falcon tube. The density was measured with density measurement device DMA 4500, Anton Paar.

Further analysis of the high HSA concentration formulation is provided in Examples 5 to II.

Example 5

Analysis of High Protein Formulations—Optical Appearance

In contrast to Adalimumab in the commercial formulation, Adalimumab in WFI did not reveal opalescence. J695 also did not reveal any opalescence phenomena when dissolved in WFI. Despite the fact that the protein concentration of Adalimumab was 80 mg/mL and 200 mg/mL in WFI, there was virtually no opalescence observed. In contrast, the commercial formulation comprising 50 mg/mL Adalimumab revealed notable opalescence in the commercial formulation. Thus, the use of pure water, i.e., WFI, as a dissolution medium had a positive effect on protein solution opalescence.

It was a surprising observation that (in addition to being soluble at all at such a high protein concentration) Adalimumab in WFI appeared to have a low viscosity, even at higher concentrations such as 200 mg/mL.

Depending on the concentration, the optical characteristics/color of HSA solutions changed from clear and slightly yellow (10 mg/mL in WFI) to clear and yellow (approximately 180 mg/mL in WFI).

During the concentration process, no precipitation was observed for the Adalimumab solution and HSA solution. Precipitation would have been an indication for solubility limitations. The solutions stayed clear until the experiment was finalized. It is to be highlighted that the experiments were not finished because potential solubility limits were approached and precipitation occurred, but were finished because the solution volumes remaining in the concentrators were not sufficient to proceed with concentrating (i.e. lack of material). It appears very likely that the solubility limits of Adalimumab, J695, and HSA are well beyond 220 mg/mL.

In the J695 solution a crystal like precipitate was observed when the high-concentrated solution was stored over night at 2-8° C. in the concentrators (approximately 120 mg/mL). The crystal like precipitate redissolved after approximately 3-5 min when the solution was stored at ambient temperature. Thus the environment created by dissolving J695 at high concentration in pure water provides conditions where protein crystallization might be performed by mere temperature cycling (e.g., from ambient temperature to 2-8° C.).

Example 6

Analysis of High Protein Formulations—Protein Concentration

The calculation of the protein concentrations is provided above in the Materials and Methods section.

An overview of the concentration of Adalimumab, J695, and HSA into pure water, high protein formulation is provided below in Tables 12-14:

TABLE 12

Concentrations of Adalimumab as Assessed Via OD280 during the Concentration Process

| sample name | | absorbance | average value | dilution | concentration |
|---|---|---|---|---|---|
| Adalimumab in WFI | 10 mg/mL | 0.680 | 0.650 | 20 | 9.35 |
| | | 0.695 | | | |
| | | 0.575 | | | |
| Adalimumab in WFI | 20 mg/mL 1 | 1.064 | 0.813 | 40 | 23.40 |
| | | 0.688 | | | |
| | | 0.687 | | | |
| Adalimumab in WFI | 20 mg/mL 2 | 0.781 | 0.788 | 40 | 22.68 |
| | | 0.793 | | | |
| | | 0.791 | | | |
| Adalimumab in WFI | 20 mg/mL 3 | 0.870 | 0.824 | 40 | 23.71 |
| | | 0.883 | | | |
| | | 0.719 | | | |
| Adalimumab in WFI | 30 mg/mL 1 | 0.817 | 0.807 | 60 | 34.84 |
| | | 0.812 | | | |
| | | 0.793 | | | |
| Adalimumab in WFI | 30 mg/mL 2 | 0.839 | 0.827 | 60 | 35.69 |
| | | 0.813 | | | |
| | | 0.829 | | | |
| Adalimumab in WFI | 30 mg/mL 3 | 0.770 | 0.744 | 60 | 32.10 |
| | | 0.729 | | | |
| | | 0.732 | | | |
| Adalimumab in WFI | 40 mg/mL 1 | 0.494 | 0.491 | 100 | 35.35 |
| | | 0.493 | | | |
| | | 0.488 | | | |
| Adalimumab in WFI | 40 mg/mL 2 | 0.499 | 0.501 | 100 | 36.06 |
| | | 0.516 | | | |
| | | 0.489 | | | |
| Adalimumab in WFI | 40 mg/mL 3 | 0.495 | 0.512 | 100 | 36.81 |
| | | 0.523 | | | |
| | | 0.517 | | | |
| Adalimumab in WFI | 50 mg/mL 1 | 0.574 | 0.585 | 100 | 42.11 |
| | | 0.579 | | | |
| | | 0.603 | | | |
| Adalimumab in WFI | 50 mg/mL 2 | 0.671 | 0.634 | 100 | 45.63 |
| | | 0.630 | | | |
| | | 0.601 | | | |
| Adalimumab in WFI | 50 mg/mL 3 | 0.579 | 0.574 | 100 | 41.27 |
| | | 0.574 | | | |
| | | 0.568 | | | |
| Adalimumab in WFI | 60 mg/mL 1 | 0.838 | 0.837 | 100 | 60.21 |
| | | 0.833 | | | |
| | | 0.840 | | | |
| Adalimumab in WFI | 60 mg/mL 2 | 0.793 | 0.777 | 100 | 55.89 |
| | | 0.767 | | | |
| | | 0.770 | | | |
| Adalimumab in WFI | 60 mg/mL 3 | 0.802 | 0.780 | 100 | 56.10 |
| | | 0.759 | | | |

TABLE 12-continued

Concentrations of Adalimumab as Assessed Via OD280 during the Concentration Process

| sample name | | absorbance | average value | dilution | concentration |
|---|---|---|---|---|---|
| Adalimumab in WFI | 70 mg/mL 1 | 0.779<br>0.911<br>0.866 | 0.878 | 100 | 63.15 |
| Adalimumab in WFI | 70 mg/mL 2 | 0.857<br>1.012<br>0.976 | 0.996 | 100 | 71.68 |
| Adalimumab in WFI | 70 mg/mL 3 | 1.001<br>0.879<br>0.874 | 0.871 | 100 | 62.66 |
| Adalimumab in WFI | 80 mg/mL 1 | 0.861<br>0.512<br>0.489 | 0.510 | 200 | 73.45 |
| Adalimumab in WFI | 80 mg/mL 2 | 0.531<br>0.542<br>0.519 | 0.526 | 200 | 75.64 |
| Adalimumab in WFI | 80 mg/mL 3 | 0.517<br>0.551<br>0.511 | 0.531 | 200 | 76.42 |
| Adalimumab in WFI | 90 mg/mL 1 | 0.531<br>0.550<br>0.550 | 0.547 | 200 | 78.64 |
| Adalimumab in WFI | 90 mg/mL 2 | 0.539<br>0.549<br>0.551 | 0.548 | 200 | 78.80 |
| Adalimumab in WFI | 90 mg/mL 3 | 0.543<br>0.532<br>0.533 | 0.534 | 200 | 76.81 |
| Adalimumab in WFI | 100 mg/mL 1 | 0.537<br>0.640<br>0.621 | 0.628 | 200 | 90.36 |
| Adalimumab in WFI | 100 mg/mL 2 | 0.623<br>0.748<br>0.735 | 0.747 | 200 | 107.41 |
| Adalimumab in WFI | 100 mg/mL 3 | 0.757<br>0.625<br>0.616 | 0.621 | 200 | 89.39 |
| Adalimumab in WFI | 110 mg/mL 1 | 0.623<br>0.674<br>0.671 | 0.669 | 200 | 96.19 |
| Adalimumab in WFI | 110 mg/mL 2 | 0.660<br>0.693<br>0.690 | 0.668 | 200 | 96.05 |
| Adalimumab in WFI | 110 mg/mL 3 | 0.620<br>0.604<br>0.664 | 0.640 | 200 | 92.05 |
| Adalimumab in WFI | 200 mg/mL 1 | 0.652<br>0.863<br>0.612 | 0.698 | 400 | 201.00 |
| Adalimumab in WFI | 200 mg/mL 2 | 0.621<br>1.055<br>0.658 | 0.791 | 400 | 227.53 |
| Adalimumab in WFI | 200 mg/mL 3 | 0.659<br>0.732<br>0.648<br>0.615 | 0.665 | 400 | 191.44 |

TABLE 13

Concentrations of J695 as Assessed Via OD280 during the Concentration Process

| sample name | | absorbance | average value | dilution | concentration |
|---|---|---|---|---|---|
| ABT-874 in WFI | 10 mg/mL | 0.715<br>0.708<br>0.705 | 0.703 | 20 | 9.90 |
| ABT-874 in WFI | 20 mg/mL 1 | 0.686 | — | 40 | 19.31 |
| ABT-874 in WFI | 20 mg/mL 2 | 0.684 | — | 40 | 19.26 |
| ABT-874 in WFI | 20 mg/mL 3 | 0.685 | — | 40 | 19.29 |
| ABT-874 in WFI | 30 mg/mL 1 | 0.700 | — | 60 | 29.59 |
| ABT-874 in WFI | 30 mg/mL 2 | 0.703 | — | 60 | 29.70 |
| ABT-874 in WFI | 30 mg/mL 3 | 0.684 | — | 60 | 28.91 |

TABLE 13-continued

Concentrations of J695 as Assessed Via OD280 during the Concentration Process

| sample name | | absorbance | average value | dilution | concentration |
|---|---|---|---|---|---|
| ABT-874 in WFI | 40 mg/mL 1 | 0.539 | — | 100 | 37.97 |
| ABT-874 in WFI | 40 mg/mL 2 | 0.540 | — | 100 | 38.02 |
| ABT-874 in WFI | 40 mg/mL 3 | 0.520 | — | 100 | 36.65 |
| ABT-874 in WFI | 50 mg/mL 1 | 0.698 | — | 100 | 49.15 |
| ABT-874 in WFI | 50 mg/mL 2 | 0.653 | — | 100 | 45.95 |
| ABT-874 in WFI | 50 mg/mL 3 | 0.623 | — | 100 | 43.87 |
| ABT-874 in WFI | 60 mg/mL 1 | 0.834 | — | 100 | 58.75 |
| ABT-874 in WFI | 60 mg/mL 2 | 0.781 | — | 100 | 55.02 |
| ABT-874 in WFI | 60 mg/mL 3 | 0.778 | — | 100 | 54.76 |
| ABT-874 in WFI | 70 mg/mL 1 | 1.103 | — | 100 | 77.69 |
| ABT-874 in WFI | 70 mg/mL 2 | 1.102 | — | 100 | 77.62 |
| ABT-874 in WFI | 70 mg/mL 3 | 1.110 | — | 100 | 78.13 |
| ABT-874 in WFI | 80 mg/mL 1 | 0.671 | — | 200 | 94.45 |
| ABT-874 in WFI | 80 mg/mL 2 | 0.746 | — | 200 | 105.06 |
| ABT-874 in WFI | 80 mg/mL 3 | 0.664 | — | 200 | 93.45 |
| ABT-874 in WFI | 90 mg/mL 1 | 0.826 | — | 200 | 116.37 |
| ABT-874 in WFI | 90 mg/mL 2 | 0.809 | — | 200 | 113.92 |
| ABT-874 in WFI | 90 mg/mL 3 | 0.804 | — | 200 | 113.27 |
| ABT-874 in WFI | 100 mg/mL 1 | 0.861 | — | 200 | 121.21 |
| ABT-874 in WFI | 100 mg/mL 2 | 0.993 | — | 200 | 139.80 |
| ABT-874 in WFI | 100 mg/mL 3 | 0.985 | — | 200 | 138.73 |
| ABT-874 in WFI | 200 mg/mL 1 | 0.681 | 0.805 | 400 | 226.67 |
| | | 0.864 | | | |
| | | 0.869 | | | |
| ABT-874 in WFI | 200 mg/mL 2 | 0.690 | 0.767 | 400 | 216.10 |
| | | 0.828 | | | |
| | | 0.784 | | | |
| ABT-874 in WFI | 200 mg/mL 3 | 0.708 | 0.745 | 400 | 209.83 |
| | | 0.789 | | | |
| | | 0.738 | | | |

Tables 14a and 14b: Concentrations of HSA as Assessed Via OD280 during the Concentration Process

TABLE 14a

| sample name | | absorbance | dilution | concentration |
|---|---|---|---|---|
| HSA in WFI | 10 mg/mL | 0.515 | 20 | 9.88 |
| HSA in WFI | 30 mg/mL 1 | 0.398 | 60 | 22.94 |
| HSA in WFI | 30 mg/mL 2 | 0.395 | 60 | 22.73 |
| HSA in WFI | 30 mg/mL 3 | 0.400 | 60 | 23.00 |
| HSA in WFI | 40 mg/mL 1 | 0.383 | 100 | 36.78 |
| HSA in WFI | 40 mg/mL 2 | 0.389 | 100 | 37.33 |
| HSA in WFI | 40 mg/mL 3 | 0.368 | 100 | 35.29 |
| HSA in WFI | 50 mg/mL 1 | 0.479 | 100 | 45.97 |
| HSA in WFI | 50 mg/mL 2 | 0.496 | 100 | 47.61 |
| HSA in WFI | 50 mg/mL 3 | 0.465 | 100 | 44.61 |
| HSA in WFI | 60 mg/mL 1 | 0.609 | 100 | 58.47 |
| HSA in WFI | 60 mg/mL 2 | 0.653 | 100 | 62.69 |

TABLE 14a-continued

| sample name | | absorbance | dilution | concentration |
|---|---|---|---|---|
| HSA in WFI | 60 mg/mL 3 | 0.568 | 100 | 54.52 |
| HSA in WFI | 70 mg/mL 1 | 0.645 | 100 | 61.89 |
| HSA in WFI | 70 mg/mL 2 | 0.623 | 100 | 59.76 |
| HSA in WFI | 70 mg/mL 3 | 0.618 | 100 | 59.28 |
| HSA in WFI | 80 mg/mL 1 | 0.393 | 200 | 75.37 |
| HSA in WFI | 80 mg/mL 2 | 0.436 | 200 | 83.69 |
| HSA in WFI | 80 mg/mL 3 | 0.363 | 200 | 69.67 |
| HSA in WFI | 90 mg/mL 1 | 0.484 | 200 | 92.90 |
| HSA in WFI | 90 mg/mL 2 | 0.439 | 200 | 84.22 |
| HSA in WFI | 90 mg/mL 3 | 0.419 | 200 | 80.50 |
| HSA in WFI | 100 mg/mL 1 | 0.604 | 200 | 115.93 |
| HSA in WFI | 100 mg/mL 2 | 0.573 | 200 | 110.00 |
| HSA in WFI | 100 mg/mL 3 | 0.585 | 200 | 112.30 |

TABLE 14b

| sample name | | absorbance | average value | dilution | concentration |
|---|---|---|---|---|---|
| HSA in WFI | 180 mg/mL 1 | 0.946 | 0.952 | 200 | 182.79 |
| | | 0.950 | | | |
| | | 0.961 | | | |
| HSA in WFI | 180 mg/mL 2 | 0.994 | 0.929 | 200 | 178.24 |
| | | 0.906 | | | |
| | | 0.886 | | | |
| HSA in WFI | 180 mg/mL 3 | 0.843 | 0.896 | 200 | 172.05 |
| | | 0.963 | | | |
| | | 0.884 | | | |

All three proteins evaluated remained soluble in the concentration ranges evaluated (i.e. >200 mg/mL for Adalimumab and J695, >175 mg/mL for HSA). No indications of insolubility, e.g., the clouding phenomena or precipitation occurring in the solution, were observed. For Adalimumab, the results indicate that, over the concentration range evaluated, all Adalimumab isoforms (i.e. lysine variants) remained soluble, as no precipitation occurred at all. This observation is also consistent with ion exchange chromatography data described in Example 11, which describes that the sum of lysine variants stayed virtually consistent regardless of Adalimumab concentration.

Example 7

Analysis of High Protein Formulations—Viscosity 7.1: Adalimumab Viscosity

The viscosity of Adalimumab (approximately 50 mg/mL) in water for injection was determined to be around 1.5-2 mPas. For Adalimumab (approximately 200 mg/mL) in WFI, two values were determined. The one value determined with cone/plate rheometer from Malvern (Gemini 150) was approximately 6-6.5 mPas, while the other value (measured with cone/plate rheometer from Anton Paar, MCR 301) was approximately 12 mPas.

Adalimumab commercial formulation (approximately 194 mg/mL) viscosity:
K—constant of the capillary
t—the time the solution needs for passing the capillary[s]
v—kinematic viscosity
η—dynamic viscosity
ρ—density

| time [s] | K [mm2/s2] | v [mm2/s] | ρ [g/cm3] | η [mPas] |
|---|---|---|---|---|
| 279.36 | 0.03159 | 8.825 | 1.05475 | 9.31 |

The viscosity of Adalimumab in WFI (approximately 200 mg/mL) was determined to be approximately 12 mPas with the viscosimeter from Anton Paar and approximately 6 mPas determined with the viscometer from Malvern. In contrast, the viscosity of Adalimumab in the commercial formulation (approximately 194 mg/mL) is higher, at 9.308 mPas (measured with the capillary viscometer from Schott).

7.2: Human Serum Albumin Viscosity

HSA Commercial Formulation (Approximately 200 mg/mL) Viscosity:
K—constant of the capillary
t—the time the solution needs for running through the capillary[s]
v—kinematic viscosity
η—dynamic viscosity
ρ—density

| time [s] | K [mm2/s2] | v [mm2/s] | ρ [g/cm3] | η [mPas] |
|---|---|---|---|---|
| 337.69 | 0.01024 | 3.46 | 1.05475 | 3.66 |

HSA in WFI (Approximately 180 mg/mL) Viscosity:
K—constant of the capillary
t—the time the solution needs for running through the capillary[s]
v—kinematic viscosity
η—dynamic viscosity
ρ—density

| time [s] | K [mm2/s2] | v [mm2/s] | ρ [g/cm3] | η [mPas] |
|---|---|---|---|---|
| 185.3 | 0.09573 | 17.72 | 1.07905 | 19.12 |

The viscosity of HSA in WFI (approximately 180 mg/mL) was determined to be approximately 19.121 mPas. The viscosity of HSA in the commercial formulation (approximately 194 mg/mL) was determined to be 9.308 mPas (measured with the capillary viscometer from Schott).

7.3: Analysis of the Viscosities of Adalimumab and HSA

The dynamic viscosity of Adalimumab 50 mg/mL in WFI was lower than the viscosity of Adalimumab 200 mg/mL in WFI and in commercial buffer, respectively. For HSA the dynamic viscosity for a concentration of 180 mg/mL in WFI was about six-fold higher than for a concentration of 200 mg/mL in commercial buffer. Thus, it seems that the intensity of viscosity change (i.e. increase and decrease, respectively) due to effects conveyed by pure water as dissolution medium may depend on the individual protein.

Example 8

Analysis of the Hydrodynamic Diameters of High Protein Formulations—Photon Correlation Spectroscopy (PCS)

The following example provides an analysis of the hydrodynamic diameter (Dh) (the z-average of the mean hydrodynamic molecule diameter) of various proteins in aqueous formulations obtained using the DF/UF methods of the invention.

8.1: Adalimumab Hydrodynamic Diameter

Figure 5:
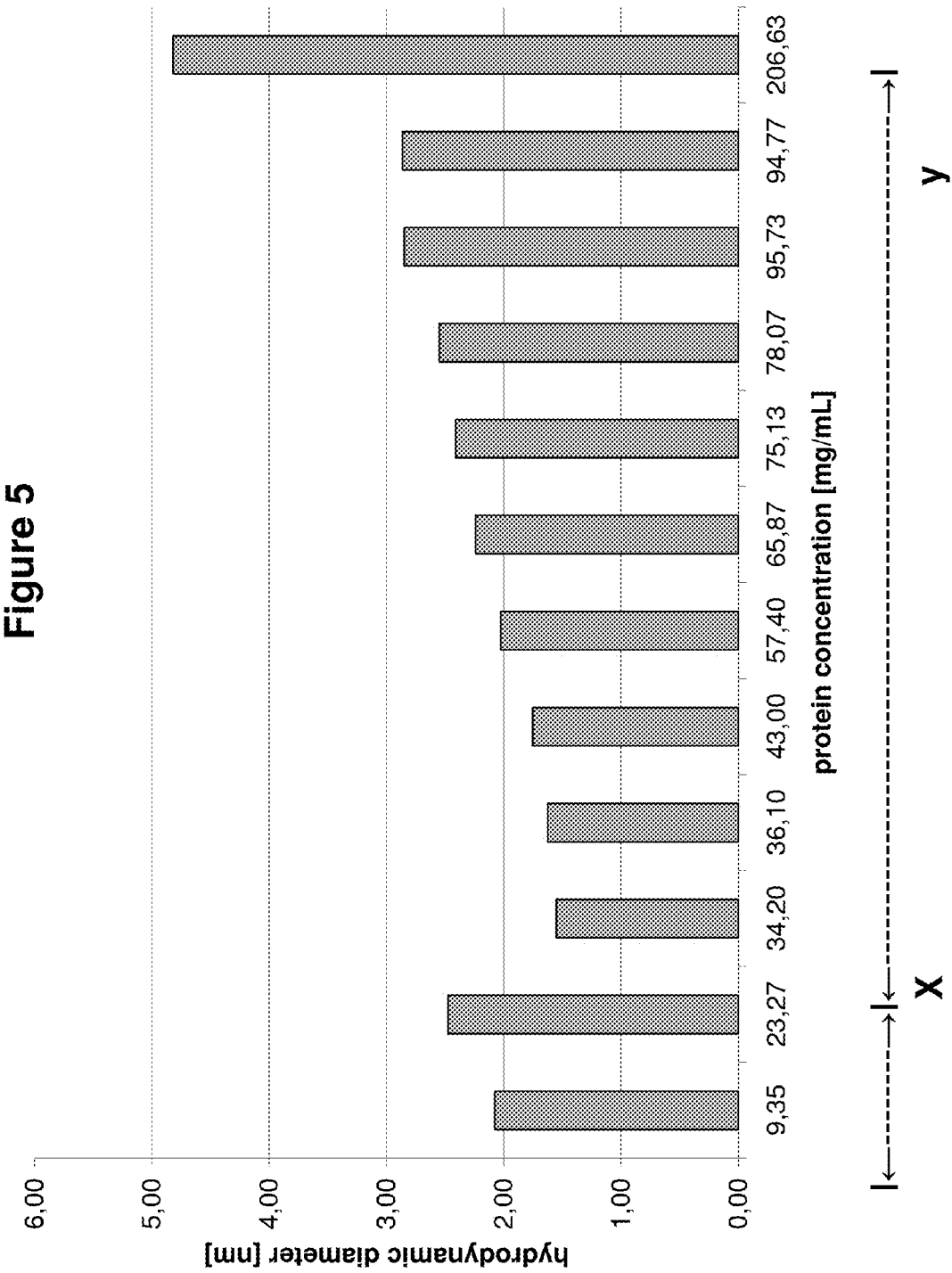
FIG. 5 graphically depicts the correlation of hydrodynamic diameter (z-average) and concentration of Adalimumab (dissolved in WFI). X: determined with an SOP using 1.1 mPas as assumed sample viscosity. y: determined with an SOP using 1.9 mPas as assumed sample viscosity.
Figure 6:
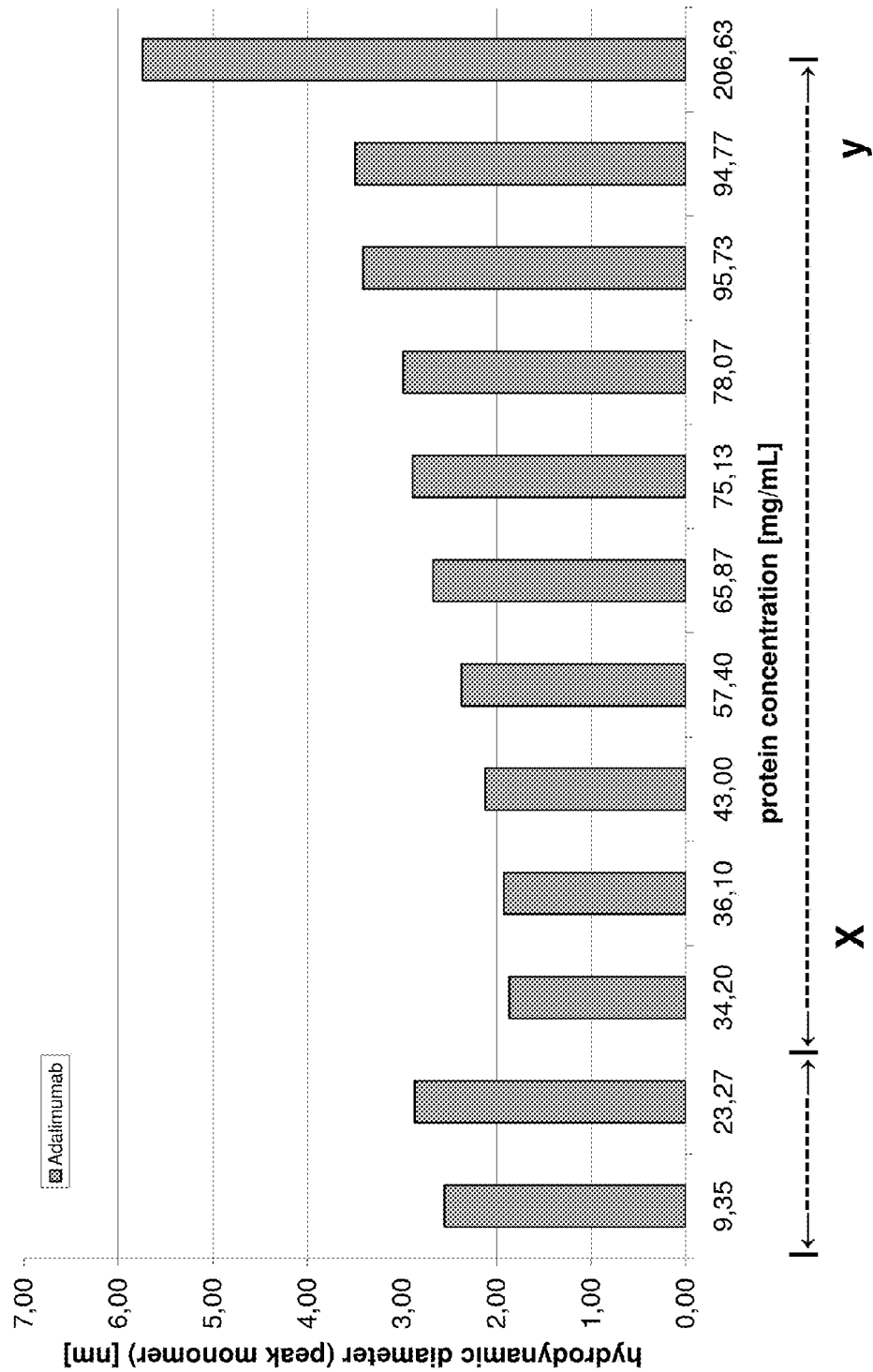
FIG. 6 graphically depicts the correlation of hydrodynamic diameter (peak monomer) and concentration of Adalimumab (dissolved in WFI). X: determined with an SOP using 1.1 mPas as assumed sample viscosity. y: determined with an SOP using 1.9 mPas as assumed sample viscosity FIG. 7 graphically depicts the correlation of hydrodynamic diameter (z-average) and concentration of J695 (dissolved in WFI). X: determined with an SOP using 1.1 mPas as assumed sample viscosity: determined with an SOP using 1.9 mPas as assumed sample viscosity FIG. 8 graphically depicts the correlation of hydrodynamic diameter (peak monomer) and concentration of J695 (dissolved in WFI). X: determined with an SOP using 1.1 mPas as assumed sample viscosity. y: determined with an SOP using 1.9 mPas as assumed sample viscosity.

As shown in FIGS. 5 and 6, a trend can be observed where the hydrodynamic diameter ($D_h$) increases with increasing Adalimumab concentration. FIG. 5 shows the correlation between hydrodynamic diameter (z-average) and the concentration of Adalimumab in WFI. FIG. 6 shows the correlation between hydrodynamic diameter (peak monomer) and the concentration of Adalimumab in WFI.

The difference between the $D_h$ determined from the 23.27 mg/mL sample compared to the 34.20 mg/mL sample exists because of assumptions made in the Standard Operating Procedure (SOP) for hydrodynamic diameter measurement. For Adalimumab samples having ≦23.27 mg/mL concentration, PCS measurements were performed with a SOP that assumes a 1.1 mPas value for the viscosity of the samples. For Adalimumab samples having ≧34.20 mPas, a SOP assuming a 1.9 mPas sample viscosity was used. It is known that PCS data are strongly influenced by the given viscosity of the sample solution, as PCS data is based on random Brownian motion of the sample specimen, which is impacted by sample viscosity. Thus, the increase in the hydrodynamic diameter with increasing protein concentration can be explained, as increasing protein concentration raises the viscosity of the solution (higher viscosity leads to lower Brownian motion and higher calculated $D_h$ data). The protein molecules experience a lower random Brownian motion and thus, for a given viscosity, the hydrodynamic diameters of the sample specimen are calculated higher. Overall, the z-average based $D_h$ values and the $D_h$ values of the monomer match well. Additionally, no increase in $D_h$ indicative for protein insolubility is observed with increasing concentration (i.e. high molecular weight aggregates and precipitate (if present) would induce a substantial increase in $D_h$).

8.2: J695 Hydrodynamic Diameter

Figure 7:
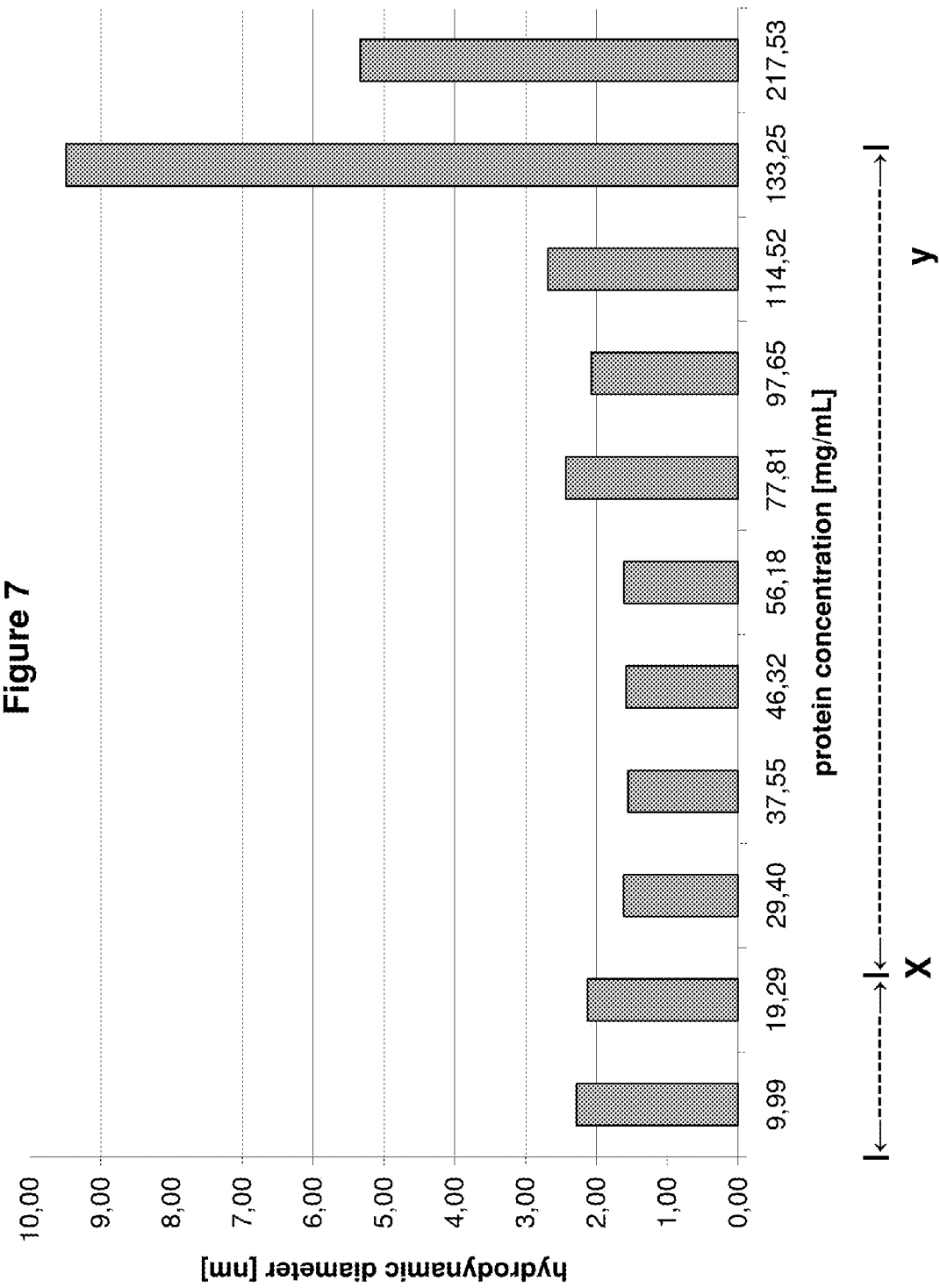
Figure 8:
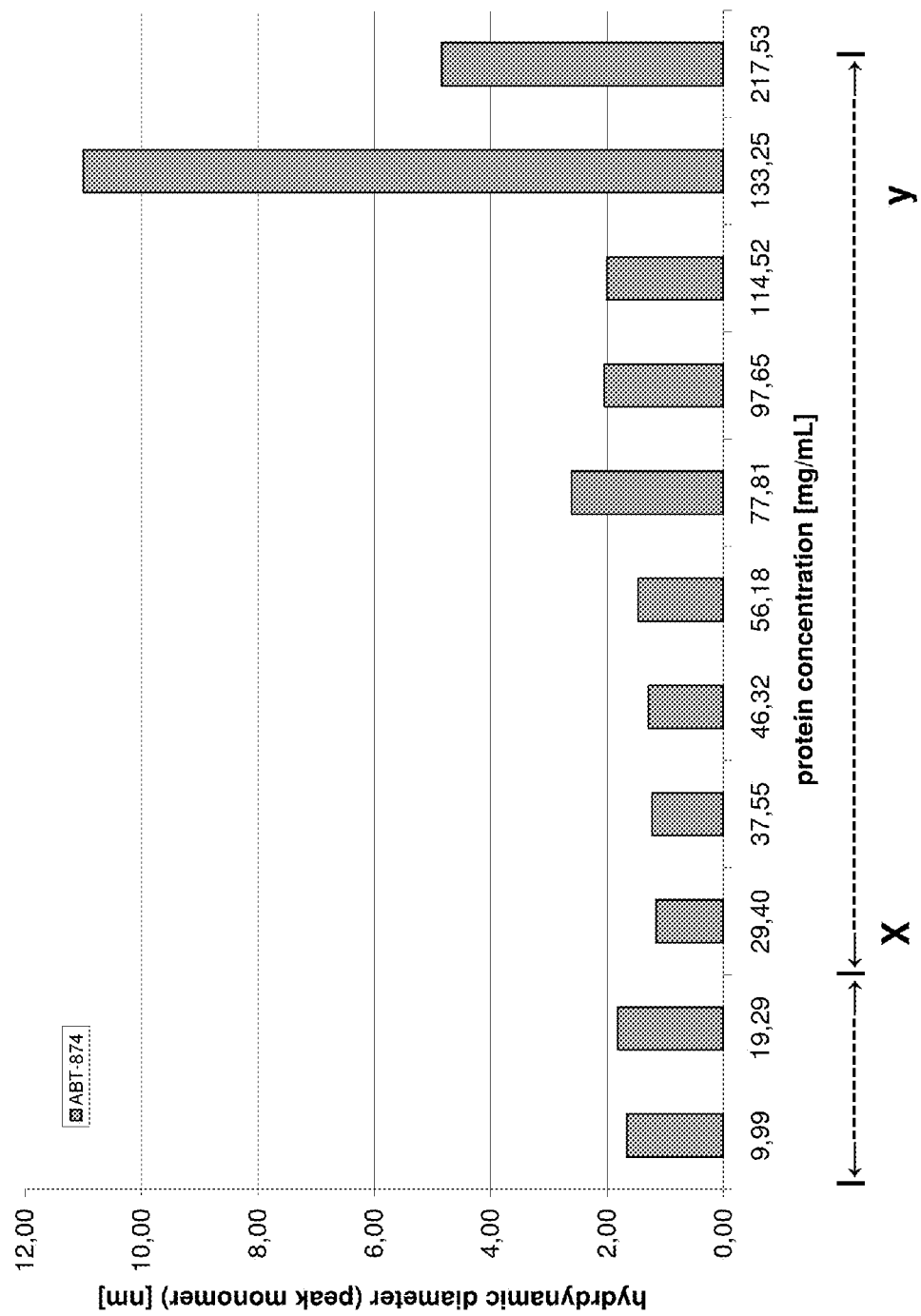

FIGS. 7 and 8 show that the hydrodynamic diameter of J695 was relatively independent from the protein concentration until a 114.52 mg/mL concentration was reached. Increasing the J695 concentration from 114.52 mg/mL to 133.25 mg/mL induced a rapid increase in $D_h$. The hydrodynamic diameter at the 217.53 mg/mL concentration was higher than at 114.52 mg/mL. This finding was not surprising as both protein solutions were measured using the same SOP (assuming same viscosity of 1.9 mPas), when in reality the viscosity increases as the protein concentration increases. The strong increase from 114.52 mg/mL to 133.25 mg/mL thus can be explained as an artifact.

8.3: Human Serum Albumin Hydrodynamic Diameter

The hydrodynamic diameter of HSA in WFI was found to decrease as concentrations rose from 9.88 mg/mL to 112.74 mg/mL. From 112.74 mg/mL to 177.69 mg/mL, however, the hydrodynamic diameter was found to increase.

HSA showed a general tendency of increasing hydrodynamic diameters (peak monomer) with increasing protein concentration which is in-line with underlying theoretical principles. The $D_h$ decrease from 9.88 mg/mL to 22.89 mg/mL is caused by a change in the measurement SOP (switching from assumed viscosity of 1.1 mPas to an assumed viscosity of 1.9 mPas).

Numerical data describing the above is provided in Appendix A.

Example 9

J695: Impact of Excipients of the Hydrodynamic Diameter

Having found the surprising result that proteins can be dissolved in high concentrations in pure water, the impact of ionizable and non-ionizable excipients typically used in parenteral formulations on the hydrodynamic diameter was evaluated. J695 was used as a model protein.

Table 15 shows that the solution osmolality is directly proportional to the concentration of sodium chloride. The osmolality in the protein solution rises along with the NaCl concentration (an almost linear correlation). Interestingly, the hydrodynamic diameter of J695 protein increased with increasing salt concentration. NaCl is an ionic excipient and dissociated into positively charged sodium ions and negatively charged chloride ions which might adsorb at the surface of the protein. Without salt being present, the hydrodynamic diameter of J695 was dramatically lower than what normally is expected for J695 (usually values around 10 nm are determined).

As illustrated in Table 15, the osmolality increased linearly with an increase in concentration of mannitol in the protein solution. In contrast, the hydrodynamic diameter did not show a dependence on mannitol concentration. Mannitol is a non-ionic sugar alcohol/polyol. Mannitol or polyols are used as stabilizers during parenteral formulation development and in final formulations. Mannitol stabilizes the protein by preferential exclusion. As other osmolytes, mannitol is preferentially excluded from the surface of the protein and it is outside of the hydrate shell of the protein. Thus the folded state of the protein is stabilized because the unfolded state, which has a larger surface, becomes thermodynamically less favorable (Foster, T. M., *Thermal instability of low molecular weight urokinase during heat treatment. III. Effect of salts, sugars and Tween* 80, 134 International Journal of Pharmaceutics 193 (1996); Singh, S, and Singh, J., *Effect of polyols on the conformational stability and biological activity of a model protein lysozyme*, 4 AAPS PharmSciTech, Article 42 (2003)). However, it is interesting that the osmolality can be adjusted basically as desired—which would be an important feature of the protein findings described herein—without impacting the $D_h$ of the protein. These findings may be useful in high-concentration protein formulation, where viscosity related manufacturing and dosing issues may be present, as the osmolality adjustment with mannitol is not mirrored by an increase in protein $D_h$ (meaning viscosity is expected to remain constant).

TABLE 15

Impact of Excipients on J695 Osmolality and Z-Average

| | osmolality [mosmol/kg] | z-average [nm] |
|---|---|---|
| NaCl concentration [mg/mL] | | |
| 0 | 16 | 4.19 |
| 2 | 92 | 12.2 |
| 4 | 158 | 16.2 |
| 6 | 230 | 17 |
| mannitol concentration [mg/mL] | | |
| 0 | 16 | 4.19 |
| 20 | 148 | 5.49 |
| 40 | 276 | 3.22 |
| 60 | 432 | 3.54 |

Example 10

Analysis of High Protein Formulations with Size Exclusion Chromatography (SEC)

For the SEC analysis, samples of Adalimumab, J695 and HSA were diluted to 2 mg/mL before injection. The injection volume for Adalimumab was 20 μL. For J695 and HSA, a 10 μL injection volume was used.

10.1: SEC Analysis of Adalimumab

The amount of monomer of Adalimumab tended to slightly decrease from 99.4% to 98.8% while concentrating from 9.35 mg/mL to 206.63 mg/mL. That decrease of monomer is associated with an increase in the amount of aggregate in Adalimumab solution from 0.4% to 1.1% while concentrating from 23.27 mg/mL to 206.62 mg/mL, respectively. The amount of fragment remained constant at 0.1%, independent of protein concentration (see table in Appendix B). Thus, Adalimumab was stable in WFI.

Overall, the increase in protein aggregation with increasing protein concentration is deemed only minor. A similar trend in monomer decrease would be expected when either the protein was formulated in a buffer system and when additionally surfactants are added. Adalimumab protein appears to be surprisingly stable when formulated in pure water.

10.2: SEC Analysis of J695

The amount of J695 monomer slightly decreased from 99.4% to 98.6% with increasing protein concentration from 9.99 mg/mL to 217.53 mg/mL. The decrease of monomer was associated with an increase in aggregate from about 0.4% to about 1.2% with increasing protein concentration from 9.99 mg/mL to 217.53 mg/mL. Independent from protein concentration, the amount of fragment was almost constant with 0.17% to 0.23% with increasing protein concentration from 9.99 mg/mL to 217.53 mg/mL.

Overall, the increase in protein aggregation with increasing protein concentration was deemed only minor. A similar trend in monomer decrease would be expected when the protein is formulated in buffer systems and when additional surfactants are added. Thus, J695 protein appears to be surprisingly stable when formulated in pure water.

10.3: SEC Analysis of HSA

The amount of monomer HSA decreased from 95.9% to 92.75% while concentrating from 9.88 mg/ml to 112.74 mg/mL. For the sample with 177.69 mg/mL, an increase in monomer up to 94.5% was determined. The decrease of the amount of monomer goes along with an increase in protein aggregate from 4.1% to 7.25% while concentrating from 9.88 mg/mL to 112.74 mg/mL. Thus, HSA protein also appears to be stable when formulated in pure water.

Numerical data describing the above-mentioned SEC experiments is provided in Appendix B.

Example 11

Analysis of High Protein Formulations—Ion-Exchange-Chromatography (IEC)

For the IEC analysis the samples of Adalimumab, J695 and HSA were diluted to 1 mg/mL before injection. The injection volume for all proteins was 100 μL.

11.1: IEC Analysis of Adalimumab

Figure 9:
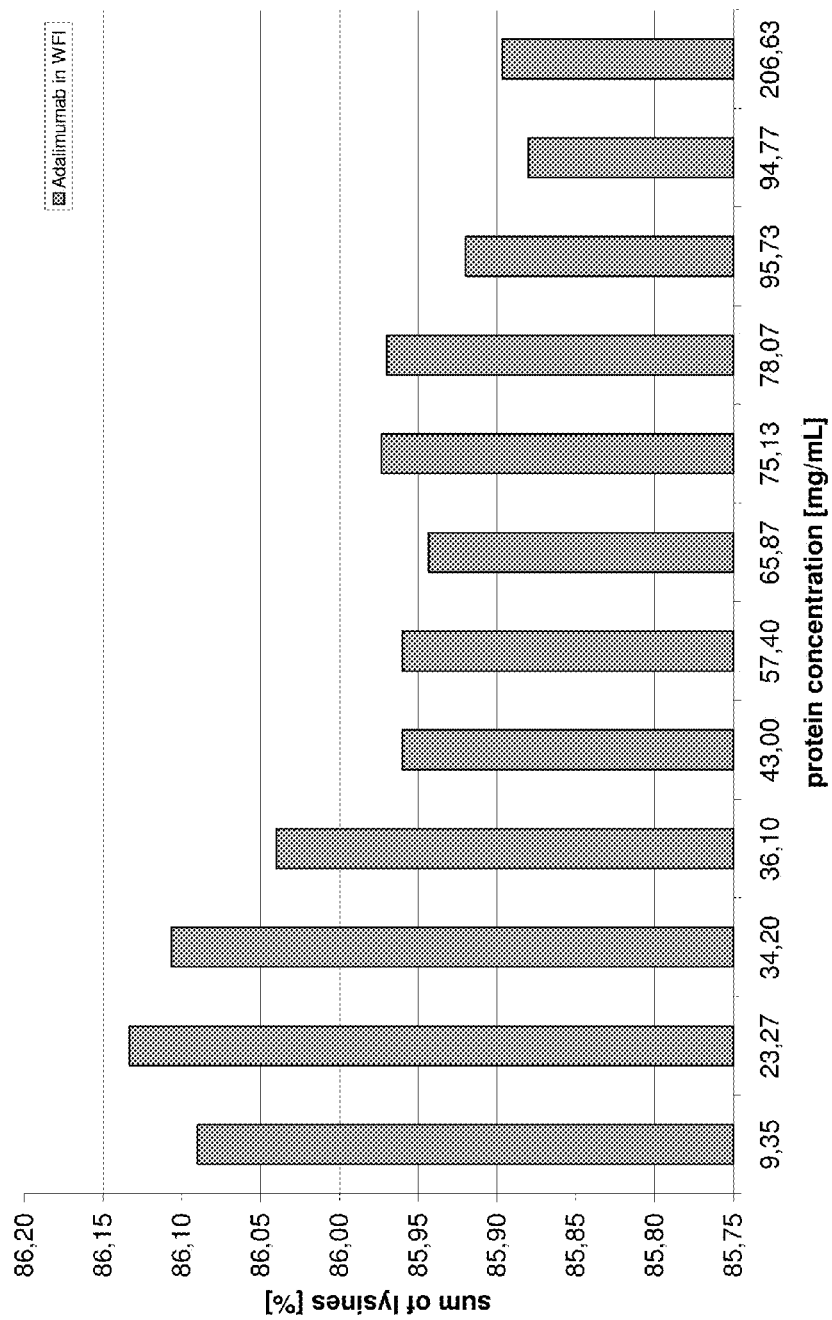
FIG. 9 shows the sum of lysine 0, 1 and 2 of Adalimumab [%] in dependence on Adalimumab concentration in water for injection.

As shown in FIG. 9, Adalimumab was stable in WFI. FIG. 9 shows a slight trending which may be interpreted as indicating that the sum of lysine variants (lysine 0, 1 and 2) decreases with an increase concentration of Adalimumab in WFI. Overall, however, the percentage of lysine variants varied less than 0.25%.

11.2: IEC Analysis of J695

Figure 10:
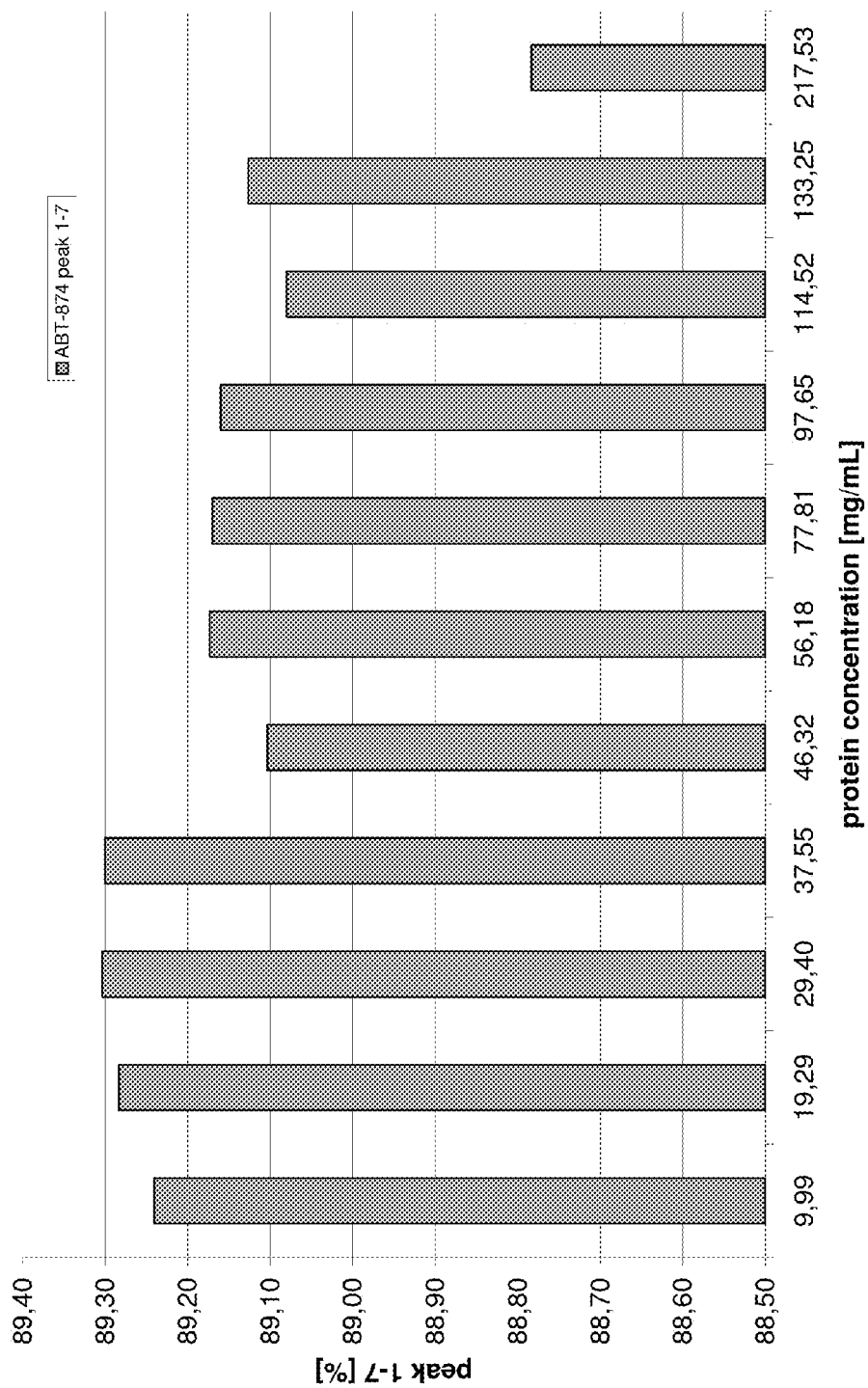
FIG. 10 shows the sum of peak 1 to 7 of J695 [%] in dependence on J695 concentration in water for injection.
Figure 11:
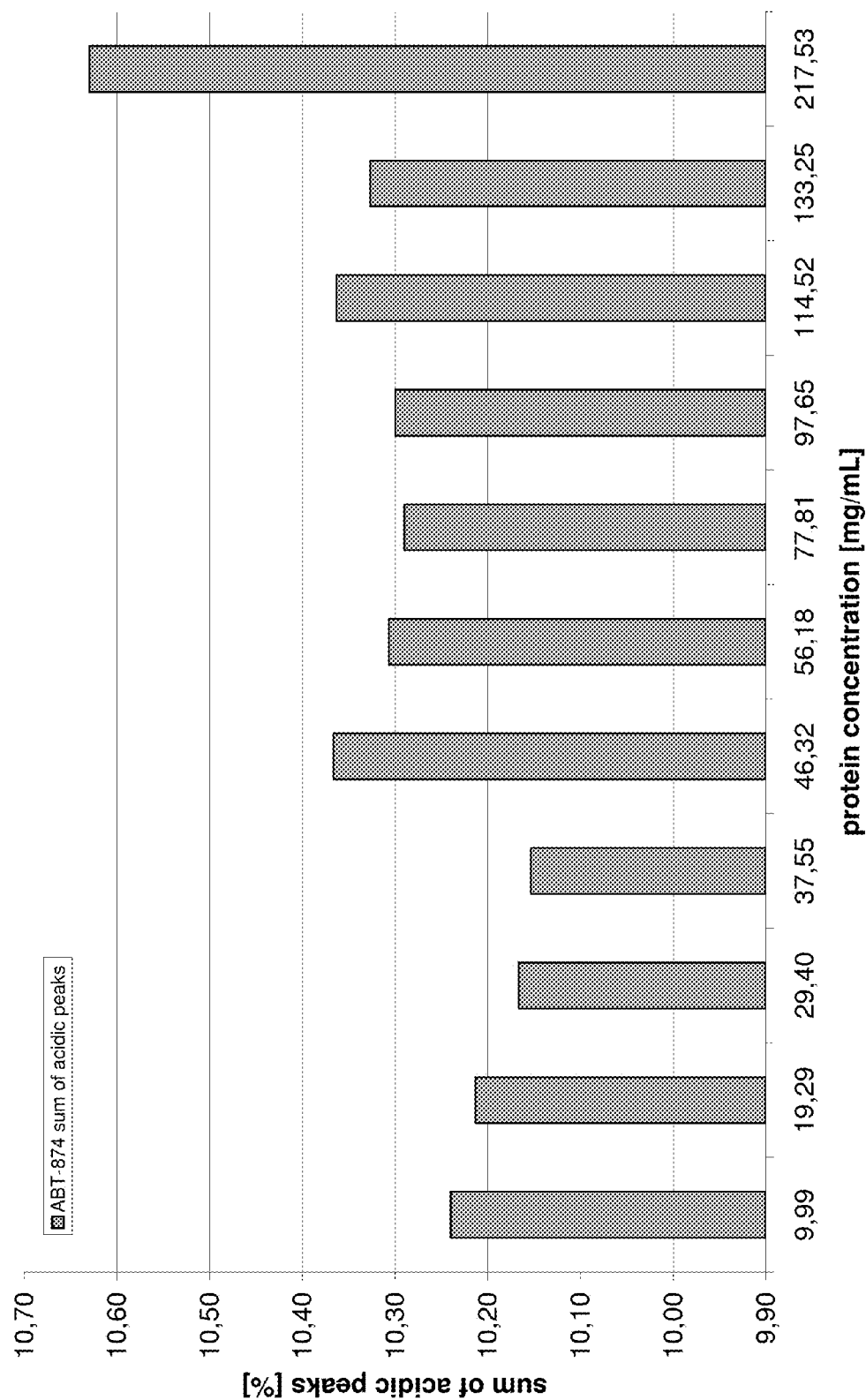
FIG. 11 shows the sum of acidic peaks of J695 [%] in dependence on J695 concentration in water for injection.
Figure 12:
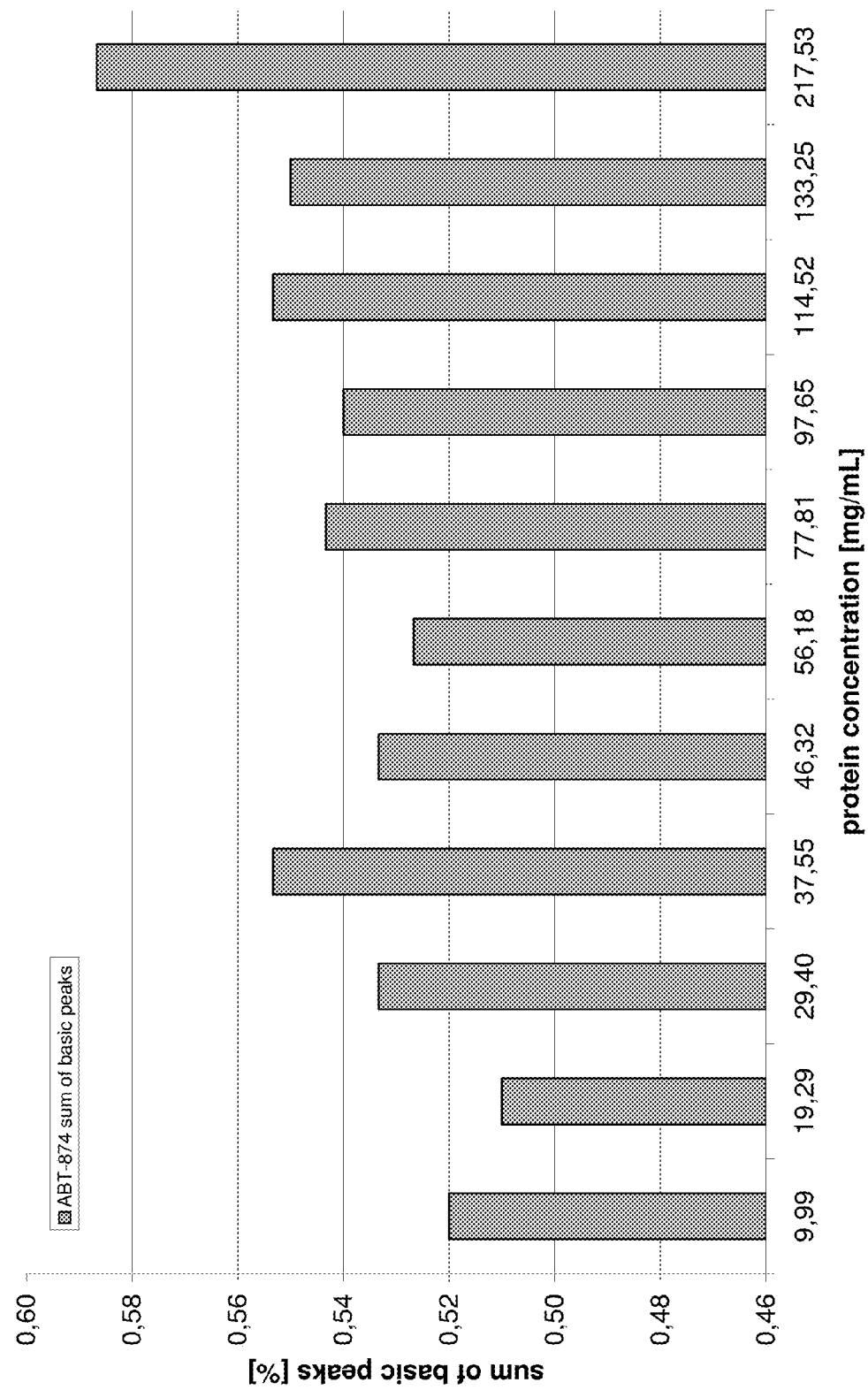
FIG. 12 shows the sum of basic peaks of J695 [%] in dependence on J695 concentration in water for injection (WFI).

FIG. 10 shows that the sum of the J695 peaks 1 to 7 is slightly decreasing with increasing J695 concentration. With the decrease in peak 1-7 the sum of acidic and basic peaks is slightly increasing, with the increase in the acidic peaks being a little more pronounced (see FIGS. 11 and 12). The sum of acidic peaks slightly increases from approximately 10.2% to 10.6% and the sum of basic peaks from 0.52% to 0.59%, respectively.

Overall, it can be stated that no major instability effects or insolubility effects of J695 formulations in pure water were observed via IEC.

Numerical data describing the above IEC experiments is provided in Appendix C.

Summary of Findings in Examples 2-11

It was initially thought that transferring proteins, such as antibodies, into WFI would likely induce protein precipitation by concentrating the protein beyond its solubility limit in pure water. The above studies demonstrate that proteins, including antibodies, not only can be transferred into pure WFI at lower concentrations without encountering any precipitation phenomena and solubility limitations, but that, surprisingly, Adalimumab (as well as the other two test proteins) can be concentrated in pure water to ultra-high concentrations beyond 200 mg/mL using UF/DF and centrifugation techniques (e.g., TFF equipment, Vivaspin devices). In addition, Adalimumab opalescence was unexpectedly found to be substantially reduced when the protein was formulated in WFI. Osmolality was monitored to ensure that the Adalimumab buffer medium was completely exchanged by pure, salt free water (i.e. WFI). Moreover, freeze-thaw processing was performed during sample preparation for analysis, and virtually no instability phenomena were observed with SEC and IEC analysis.

The approach of formulating proteins, e.g., Adalimumab, at high concentrations in WFI revealed the potential to reduce viscosity phenomena, which often impedes straightforward Drug Product development at high protein concentrations.

Finally, the hydrodynamic diameter (determined via photon correlation spectroscopy, PCS) of Adalimumab was found to be notably lower in WFI than in commercial buffer (indicative of lower viscosity proneness).

Overall, it was concluded that the findings of antibodies and the globular model protein HSA being soluble in pure water in ultra-high concentrations have potential to provide new insight into fundamental protein regimes and to potentially offer new approaches in protein drug formulation and manufacturing, for instance by:

reducing opalescence of high-concentrated protein formulations reducing viscosity of high-concentrated protein formulations enabling to adjust osmolality as desired in protein-WFI solutions by adding non-ionic excipients such as mannitol without changing features such as viscosity and non-opalescence (it was demonstrated for J695 that hydrodynamic diameter and opalescence did not change when mannitol was added, but increased dramatically when NaCl was added)

providing a new paradigm in Drug Substance formulation and processing, as it was demonstrated that proteins can be subjected to operations such as DF/UF for concentrating the protein in WFI to ultra-high concentrations and to freeze and thaw without substantial stability implications. Given the background that it is well-known that during DF/UF the composition of protein formulations, especially during processing to high concentrations, necessarily changes (Stoner, M. et al., *Protein-solute interactions affect the outcome of ultrafiltration/diafiltration operations*, 93 J. Pharm. Sci. 2332 (2004)), these new findings could beneficially be applied by either adjusting the Drug Substance concentration by DF/UF of the protein in pure water, and add excipients at high DS concentrations subsequently (by this avoiding the risk of DS formulation changes during process unit operations). Alternatively, the excipients could be added to Drug Substance during final Drug Product fill-finishing.

Example 12

Preparation of Adalimumab in Water Formulation

The following example illustrates the scaling up the DF/UF procedures resulting in large scale production of adalimumab in water.

12.1: Evaluation of Process Parameters

Figure 13:
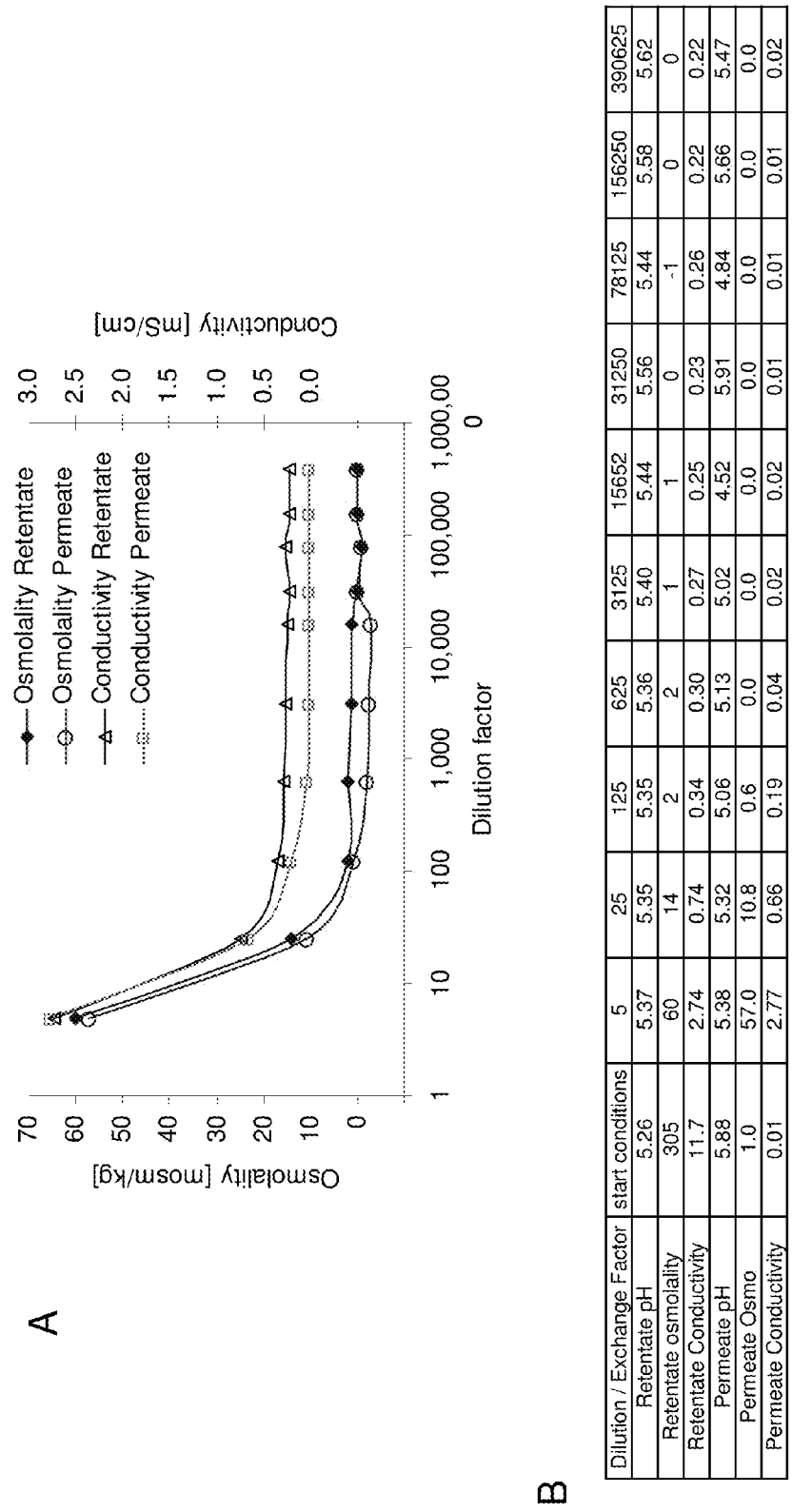
FIG. 13 shows the efficiency of the dialysis performed in Example 12, in terms of the reduction of components responsible for osmolality and conductivity of the formulation (BDS, 74 mg/ml, 10 ml sample volume, SpectraPor7 MWCO10k).
Figure 14:
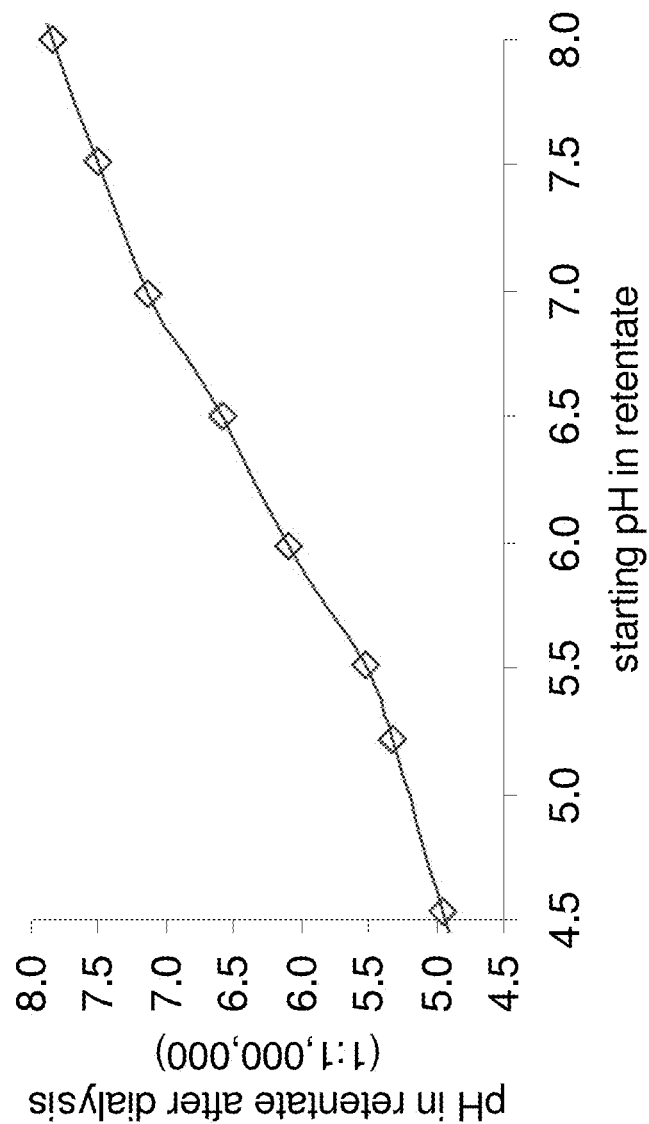
FIG. 14 shows the stability of pH levels in dialyzed Adalimumab Bulk Solutions. pH levels before and after dialysis against deionized water (1:1,000,000) are shown. (BDS, 74 mg/ml, 10 ml sample volume, SpectraPor7 MWCO10k)
Figure 16:
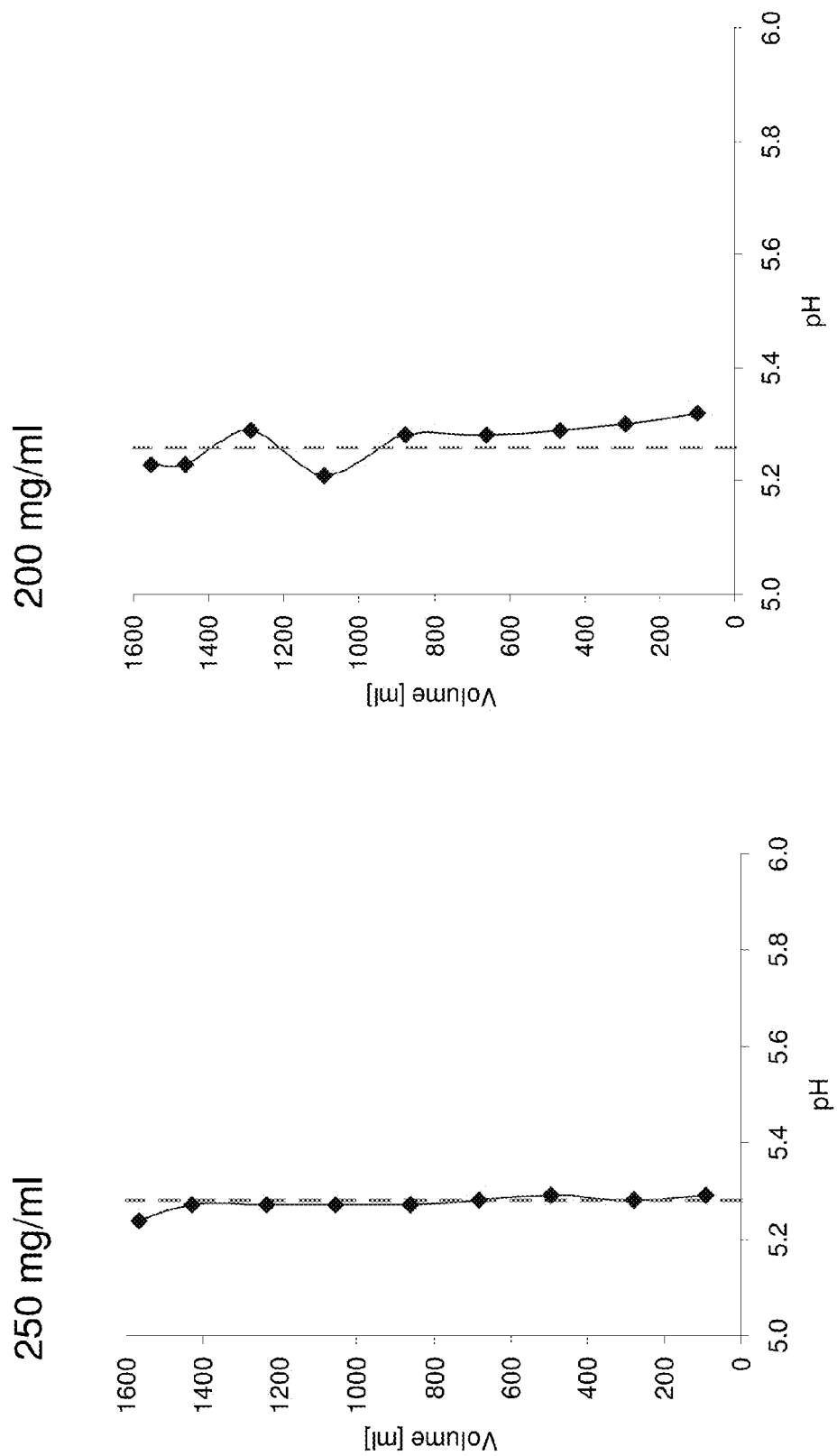
FIG. 16 shows bottle mapping pH data for 250 mg/ml and 200 mg/ml low-ionic Adalimumab solutions after freeze thaw.
Figure 17:
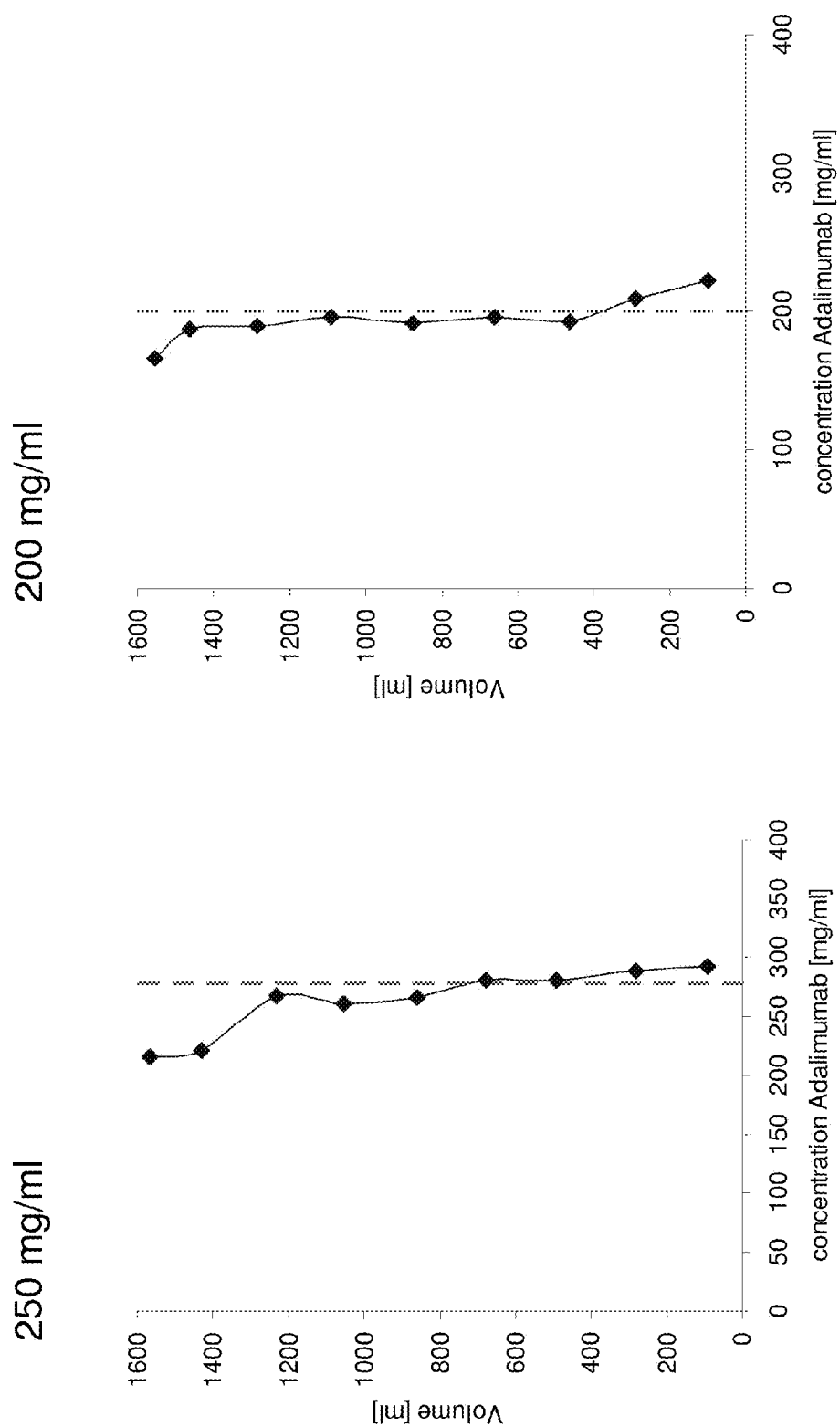
FIG. 17 shows bottle mapping concentration data for 250 mg/ml and 200 mg/ml low-ionic Adalimumab solutions after freeze thaw.
Figure 18:
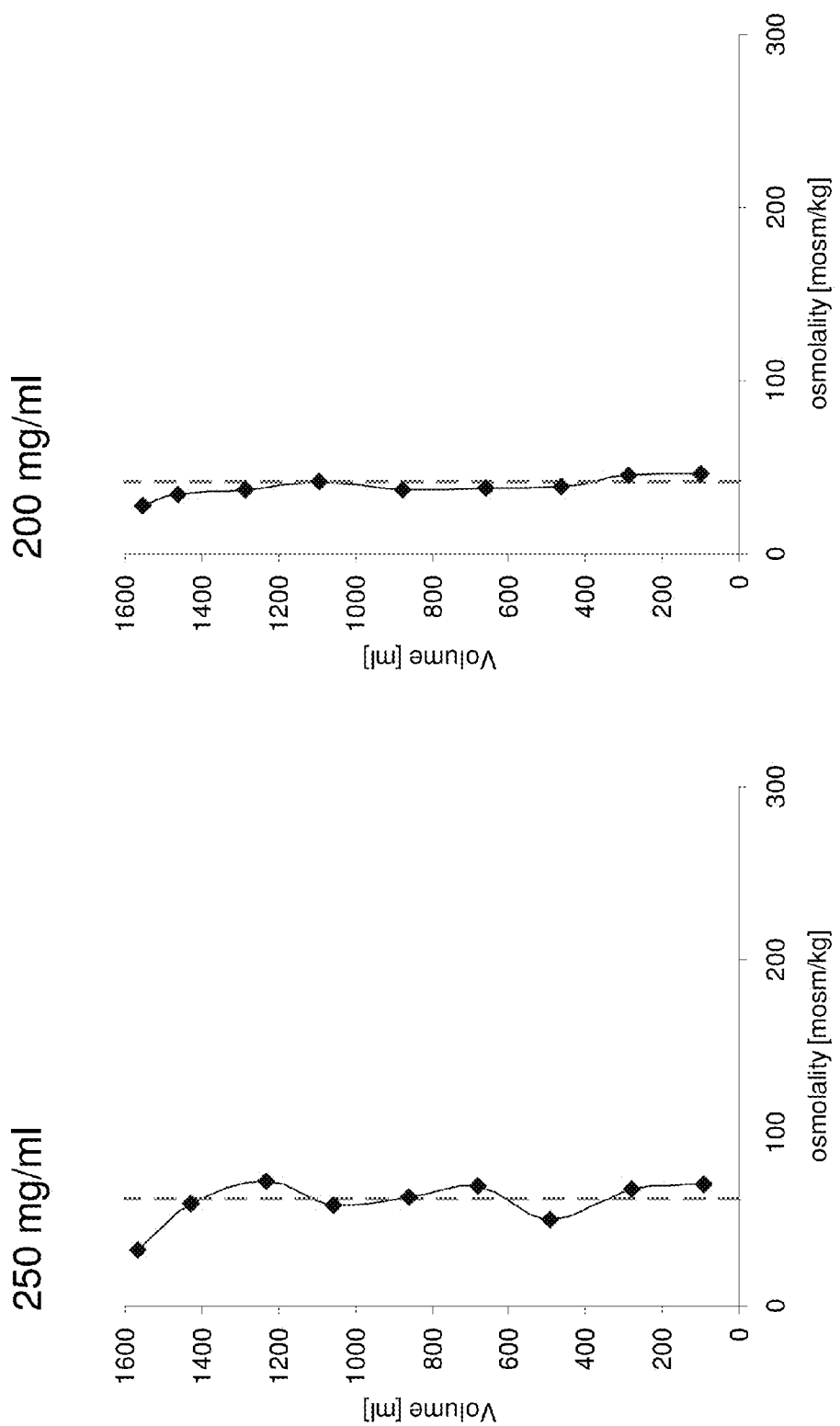
FIG. 18 shows bottle mapping osmolality data for 250 mg/ml and 200 mg/ml low-ionic Adalimumab solutions after freeze thaw.
Figure 19:
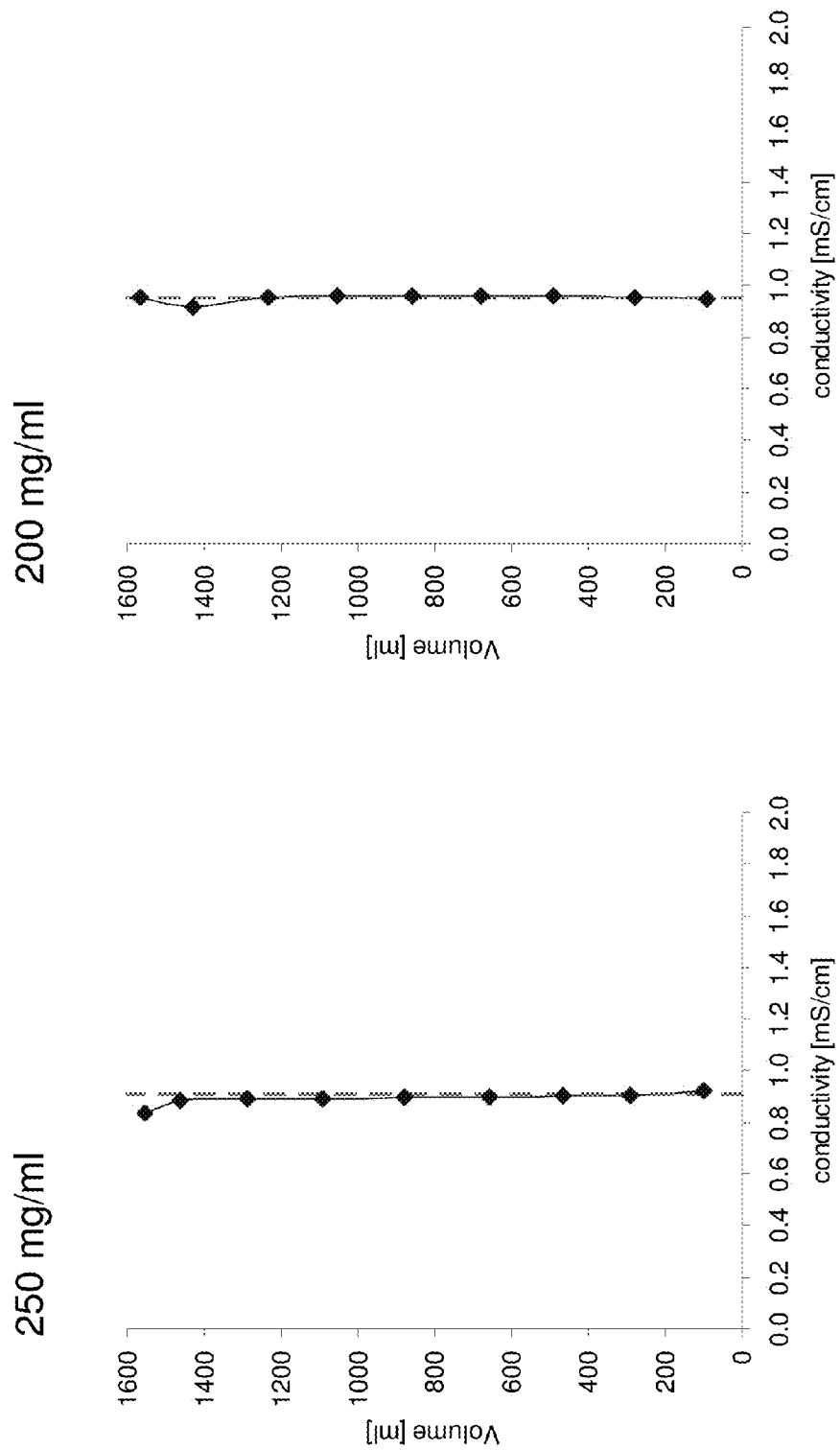
FIG. 19 shows bottle mapping conductivity data for 250 mg/ml and 200 mg/ml low-ionic Adalimumab solutions after freeze thaw.

Dialysis process evaluation studies were performed on a laboratory scale to define suitable parameters for the dialysis of Bulk Adalimumab Drug Solution formulated in a phosphate/citrate buffer system containing other excipients, e.g., mannitol and sodium chloride (FIGS. 13 and 14).

Conductivity measurements may be taken with any commercially available conductivity meter suitable for conductivity analysis in protein solutions, e.g. conductivity meter Model SevenMulti, with expansion capacity for broad pH range (Mettler Toledo, Schwerzenbach, Switzerland). The instrument is operated according to the manufacturers instructions (e.g., if the conductivity sensor is changed in the Mettler Toledo instrument, calibration must be performed again, as each sensor has a different cell constant; refer to Operating Instructions of Model SevenMulti conductivity meter). If the instructions are followed, conductivity measurements can be taken by directly immersing the measuring probe into the sample solution.

FIG. 13 shows the efficiency of the dialysis procedure, in terms of the reduction of components responsible for the osmolality and the conductivity of the formulation containing adalimumab at 74 mg/ml. After a reduction of the solutes in the antibody solution by a factor of 100, osmolality and conductivity measurements largely stabilized at levels far below the original measurements of these parameters from the commercial formulation.

FIG. 14 shows the stability of pH in dialyzed Adalimumab bulk solutions. pH levels before and after dialysis against deionized water (1:1,000,000) are shown for Adalimumab solutions with a range of different initial pH readings. pH levels remained nearly the same in the retentate before and after dialysis.

12.2: Production of High-Concentrated Adalimumab in Water Bulk Drug Solution

In a first step, the formulated bulk drug solution (Phosphate/Citrate Buffer system containing other excipients, e.g., Mannitol and Sodium Chloride) was up-concentrated by Ultrafiltration/Diafiltration to a concentration of approximately 100 mg/ml (12 L scale, Millipore Pellicon 2 Mini Bio-A MWCO 10k columns). In a second step, the up-concentrated solution was dialyzed against deionized water (SpectraPor7 MWCO10k, dilution factor 1:100,000). As a third step the dialyzed solution was up-concentrated by Ultrafiltration/Diafiltration to a concentration of approximately 250 mg/ml using Millipore Pellicon 2 Mini Bio-A MWCO 10k columns.

Table 16a shows the results of analysis of highly concentrated Adalimumab in water (DF/UF processed) bulk drug solutions after Step 3 of the procedure.

TABLE 16a

Osmolality and Conductivity Data for DF/UF Bulk-Processed Adalimumab

| osmolality mosm/kg | conductivity mS/cm | pH | density g/cm3 | Adalimumab conc mg/ml |
|---|---|---|---|---|
| 62 | 0.95 | 5.28 | 1.0764 | 277.8 |

12.3: Freeze/Thaw (F/T) Procedure Simulating Manufacturing Conditions

Freezing was conducted using an ultra-low temperature freezer (Revco Ultima II, 20 cu.ft.) with a manufacturing scale load of 47 kg of liquid to be frozen at a temperature below −50° C., typically −70° C. to −80° C. The liquid was packaged in individual bottles of 1.6 kg fill weight (e.g., Nalgene 2 L PETG square media). Freezing was completed after 48 hours. Thawing was conducted in a circulating water bath (e.g., Lindergh/Blue) with a manufacturing scale load of 24 kg at a temperature between 20° C. and 40° C., typically 30° C., until the material was completely thawed.

12.4: Bottle Mapping During Freeze and Thaw

Individual horizontal solution layers in the bottle volume were isolated and analyzed. At protein concentrations of 250 mg/ml and 200 mg/ml, only minimal gradient formation was detected in the Adalimumab water solution, as seen in FIGS. 15 through 19. Freezing and thawing of formulated Adalimumab solutions (solutions with a Phosphate/Citrate Buffer system containing other excipients, e.g., Mannitol and Sodium Chloride) at 250 mg/ml and 200 mg/ml, however, led to the formation of precipitate on the bottom of the bottle.

12.5: Gradient Formation in Commercial and Low-Ionic Formulations of Adalimumab

The formation of gradients by freeze thaw procedures in commercial and low-ionic (water) formulations of Adalimumab was compared. Table 16b shows the results of visual inspection of commercial Adalimumab solutions of various concentrations after a f/t step. The formation of precipitates indicates that instability was created in the solution by the f/t procedure. Above 100 mg/ml, significant precipitate formation was observed. Table 17 shows the analytical data of two 50 mg/ml solutions and one 100 mg/ml low-ionic formulation before the freeze-thaw experiment.

TABLE 16b

Observed Precipitation in Commercial Adalimumab Solutions after F/T

| | 250 mg/ml | 220 mg/ml | 200 mg/ml | 150 mg/ml | 120 mg/ml | 100 mg/ml | 60 mg/ml |
|---|---|---|---|---|---|---|---|
| Commericial freezing process in ultra low temp freezer: −70° C./ 23° C. | Precipitate | Precipitate | Precipitate | Precipitate | Partial Precipitate | Clear | Clear |

TABLE 17

Solution Analytical Data before Freeze-Thaw

| formulation | | pH | Density (g/cm³) | Osmolality (mOsmol/kg) | Protein conc (mg/mL) |
|---|---|---|---|---|---|
| E167 130 01 CL 50 mg/mL in water | low-ionic | 5.18 | 1.0121 | 5 | 49.3 |
| E167 140 01 CL 50 mg/mL in buffer | Commercial formulation | 5.20 | 1.0224 | 280 | 48.7 |
| 100 mg/mL in water | low-ionic | 5.32 | 1.0262 | 12 | 99.8 |

About 1600 mL (50 mg/ml solutions) or 800 ml (100 mg/ml solution) of each formulation were placed into PETG bottles and subjected to a conventional freeze (−80° C.) thaw (23° C., water bath) procedures. Samples were then pulled from top, center and bottom of the PETG bottles and analyzed for pH, density, osmolality, and protein concentration. Analysis results are shown in Table 18.

TABLE 18

Analysis of Bottle-Mapped Layers from Frozen/Thawed Solutions

| sample | pH | density g/cm3 | osmolality mOsmol/kg | protein content (volumetric) mg/mL |
|---|---|---|---|---|
| 50 mg/mL in water | | | | |
| top | 5.20 | 1.0119 | 6 | 48.72 |
| middle | 5.19 | 1.0120 | 8 | 49.35 |
| bottom | 5.17 | 1.0120 | 6 | 49.76 |
| commercial formulation | | | | |
| top | 5.16 | 1.0165 | 236 | 37.9 |
| middle | 5.13 | 1.0221 | 306 | 45.58 |
| bottom | 5.12 | 1.0257 | 368 | 55.48 |
| 100 mg/mL in water | | | | |
| top | 5.29 | 1.0259 | 13 | 98.7 |
| middle | 5.3 | 1.0262 | 16 | 99.9 |
| bottom | 5.28 | 1.0262 | 14 | 101.2 |

The commercial formulation of Adalimumab revealed significant gradients upon freeze/thaw with regard to density (indicating heterogeneities/gradients of protein and excipients), osmolality (indicating excipient gradients), and protein content. In contrast, no gradients were found in the 50 mg/ml low-ionic Adalimumab formulation upon freeze/thaw.

At higher protein concentrations, gradient formation may sometimes be expected to become worse. However, no gradients were found in the 100 mg/ml low-ionic Adalimumab formulation upon freeze/thaw with regard to pH, density, osmolality and protein concentration.

Example 13

Stability of J695 after DF/UF

The following example provides data on the stability of J695 after DF/UF processing in accordance with the methods of the invention.

Protein samples from J695 in normal DS buffer were analyzed, either after pH adjustment or after diafiltration. pH was adjusted to pH 4.4 with 0.1M phosphoric acid, protein concentration 112 mg/mL. For concentrated samples in WFI, protein samples were diafiltered (DF/UF) against water for approximately 1.5 days at ambient temperature, using a TFF equipped with a 30 kDa RC membrane. The protein concentration after DF/UF was determined approx. 192 mg/mL. pH 4.7.

13.1: Size Exclusion Analysis (SEC) Experimental Procedures

A size exclusion method was developed for the purity assessment of J695. Size exclusion chromatography (SEC) separates macromolecules according to molecular weight. The resin acts as a sieving agent, retaining smaller molecules in the pores of the resin and allowing larger molecules to pass through the column. Retention time and resolution are functions of the pore size of the resin selected.

Each sample was diluted to 2.5 mg/mL with purified water (Milli-Q) based on the stated concentration. 50 μg of each sample was injected onto the column in duplicate. A Tosoh Bioscience G3000swx1, 7.8 mm×30 cm, 5 μm (Cat #08541) SEC column is used for separation. For Buffer A, 211 mM $Na_2SO_4$/92 mM $Na_2HPO_4$, pH 7.0 was used. Detection was performed at 280 nm and 214 nm. The column was kept at room temperature with a flow rate of 0.3 mL/min.

This chromatography utilized an isocratic gradient with a 100% mobile phase A solvent for 50 minutes duration.

13.2: SEC Data

Table 19 describes data from size exclusion chromatography experiments.

TABLE 19

SEC Analysis Data for J695 Reference Standard, DS and Post-DF/UF (in water)

| ABT-874 | load | HM | Monom | Frag | |
|---|---|---|---|---|---|
| BF Ref Std | 50 u | 0.49 | 97.9 | 1.28 | 0.26 |
| BF Ref Std dup | 50 u | 0.41 | 98.0 | 1.29 | 0.27 |
| BF Ref std avg | | 0.45 | 98.0 | 1.29 | 0.27 |
| std | | 0.06 | 0.05 | 0.01 | 0.01 |
| % RS | | 12.5 | 0.05 | 0.55 | 2.67 |
| DS in Buffer pH 4.4 | 50 u | 0.42 | 98.3 | 1.04 | 0.16 |
| DS in Buffer pH 4.4 dup | 50 u | 0.40 | 98.4 | 1.01 | 0.13 |
| Ds in Buffer pH 4.4 avg | | 0.41 | 98.4 | 1.03 | 0.15 |
| std | | 0.01 | 0.06 | 0.02 | 0.02 |
| % RS | | 3.45 | 0.06 | 2.07 | 14.6 |
| DS UF/DF in Water pH 4.7 | 50 u | 0.69 | 98.1 | 1.04 | 0.14 |
| UF/DF in Water pH 4.7 dup | 50 u | 0.69 | 98.0 | 1.07 | 0.16 |
| DS UF/DF in Water pH 4.7 avg | | 0.69 | 98.1 | 1.06 | 0.15 |
| std | | 0.00 | 0.04 | 0.02 | 0.01 |
| % RS | | 0.00 | 0.04 | 2.01 | 9.43 |

13.3: SEC Analysis Conclusions

The data in Table 19 shows that the commercial formulation of J695 (DS PFS, pH=4.4) has comparable levels of fragments and aggregate as the J695 reference standard. There was a difference noted in the aggregate amount between the commercial formulation J695 control and the J695 that had undergone DF/UF, in water (DS in H2O, pH=4.7, 192 mg/ml): an increase from 0.4% to 0.7% in aggregation was seen. This was not a significant increase and may be due to time spent at room temperature during the UF/DF. There is no change to the fragments.

13.4: IEC (WCX-10) Experimental Procedure

A cation exchange method was developed for the assessment of the heterogeneity of J695 using the Dionex WCX-10 column. Generally, cation exchange chromatography separates protein isoforms according to the apparent pI and the surface charge interaction with the resin. The protein of interest is bound to the column under specific low salt starting conditions and is eluted from the column by increasing the salt concentration through a gradient. Proteins with lower apparent pI bind less tightly to a cation exchange column and are the first to elute and proteins with a higher apparent pI bind tighter and are the last to elute.

Cation exchange chromatography using WCX-10 was used in quality control as a lot release assay. The assay conditions were modified to improve separation of known J695 isoforms.

The sample was diluted to 1.0 mg/mL with purified water (Milli-Q). Reference standard was run in triplicate as a comparison and was diluted to 1 mg/ml in purified water (Milli-Q).

Dionex Propac WCX-10 columns (p/n 054993), along with corresponding guard columns (p/n 054994), were used for separation. Buffers used in the procedure included Buffer A (10 mM $Na_2HPO_4$, pH=6.0) and Buffer B (10 mM $Na_2HPO_4$, 500 mM NaCl, pH=6.0). Column temperature was maintained at 35° C. and column flow rate was 1 mL/min. Injection volumes were 100 µl for a 100 µg load and detection was performed at 280 nm. Buffer gradients over the course of the chromatographic separation are provided in Table 20.

TABLE 20

Buffer Gradients used in IEC Analysis of J695

| Time (min) | % MPA | % MPB |
| --- | --- | --- |
| 0 | 75 | 25 |
| 3 | 60 | 40 |
| 33 | 40 | 60 |
| 36 | 0 | 100 |
| 41 | 0 | 100 |
| 43 | 75 | 25 |
| 48 | 75 | 25 |

13.5: IEC Data

Table 21 provides results from experiments comparing the J695 Reference Standard to J695 in commercial buffer (DS pH=4.4), as well as a comparison of the commercial buffer formulation to J695 after DF/UF (DF/UF H2O, pH=4.7).

engineering run sample and are attributed to differences in the manufacturing processes between the 3000 L and 6000 L campaigns. There were no notable differences between the DS, pH 4.4 control and the J695 in $H_2O$ pH=4.7, 192 mg/ml sample.

Example 14

Stability of Adalimumab after DF/UF and Long-Term Storage at 2-8° C.

The following example provides data showing the stability of Adalimumab in an aqueous formulation in accordance with the methods of the invention, after 22.5 months storage at 2-8° C.

Adalimumab samples for SEC and WCX-10 analysis were diafiltered against water and concentrated to about 177 mg/mL. Samples were stored and analyzed at various time points for stability.

Standard Adalimumab solution (DS, pH approx. 5.2) in commercial Humira buffer was used as a starting material for generating a concentrated solution in water. Protein solution samples were diafiltered (DF/UF) against water for approximately 1.5 days at ambient temperature, using a TFF equipped with a 30 kDa RC membrane. Protein concentration after DF/UF was determined approximately 177 mg/mL, pH 5.2. The sample was stored at 2-8° C. for 22.5 months before analysis.

14.1: SEC Experimental Procedure

A size exclusion method was previously developed to check for the presence of antibody fragments and aggregates. Size exclusion chromatography (SEC) separates macromolecules according to molecular weight. The resin acts as a sieving agent, retaining smaller molecules in the pores of the resin and allowing larger molecules to pass through the column. Retention time and resolution are functions of the pore size of the resin selected.

Each sample was diluted to 1.0 mg/mL with milli Q water and 50 µg of each sample was injected onto the column. For

TABLE 21

IEC Data for J695 Reference Standard, Commercial Formulation (DS) and after DF/UF (in water)

| | 0 glu (1) | 0 glu (2 + 2a) | 1 glu (3) | 1 glu (4) | 1 glu (5) + (5a) | 2 glu (6) | 2 glu (7) | acidic | basic |
| --- | --- | --- | --- | --- | --- | --- | --- | --- | --- |
| ref std | 43.77 | 7.55 | 8.00 | 21.87 | 4.28 | 4.82 | 3.75 | 4.05 | 1.92 |
| ref std dup | 43.49 | 7.49 | 7.98 | 21.70 | 4.26 | 4.81 | 3.75 | 4.61 | 1.90 |
| ref std dup | 43.44 | 7.49 | 8.00 | 21.65 | 4.24 | 4.81 | 3.74 | 4.75 | 1.89 |
| ref std avg | 43.57 | 7.51 | 7.99 | 21.74 | 4.26 | 4.81 | 3.75 | 4.47 | 1.90 |
| SD | 0.20 | 0.04 | 0.01 | 0.12 | 0.01 | 0.01 | 0.00 | 0.40 | 0.01 |
| % RSD | 0.45 | 0.56 | 0.18 | 0.55 | 0.33 | 0.15 | 0.09 | 8.86 | 0.74 |
| ABT-874 DS pH = 4.4 | 35.65 | 14.74 | 7.26 | 18.06 | 6.76 | 5.32 | 3.98 | 5.55 | 2.70 |
| ABT-874 DS pH = 4.4 Dup | 35.82 | 14.73 | 7.29 | 18.14 | 6.82 | 5.39 | 4.06 | 4.79 | 2.95 |
| ABT-874 DS pH = 4.4 avg | 35.74 | 14.74 | 7.28 | 18.10 | 6.79 | 5.36 | 4.02 | 5.17 | 2.83 |
| SD | 0.12 | 0.01 | 0.02 | 0.06 | 0.04 | 0.05 | 0.06 | 0.54 | 0.18 |
| % RSD | 0.34 | 0.05 | 0.29 | 0.31 | 0.62 | 0.92 | 1.41 | 10.39 | 6.26 |
| ABT-874 DF/UF H2O pH = 4.7 | 36.57 | 14.51 | 7.26 | 18.09 | 6.57 | 5.22 | 3.91 | 5.28 | 2.61 |
| ABT-874 DF/UF H2O pH = 4.7 Dup | 36.60 | 14.43 | 7.25 | 18.02 | 6.66 | 5.18 | 4.00 | 5.31 | 2.56 |
| ABT-874 DF/UF H2O pH = 4.7 | 36.59 | 14.47 | 7.26 | 18.06 | 6.62 | 5.20 | 3.96 | 5.30 | 2.59 |
| SD | 0.02 | 0.06 | 0.01 | 0.05 | 0.06 | 0.03 | 0.06 | 0.02 | 0.04 |
| % RSD | 0.06 | 0.39 | 0.10 | 0.27 | 0.96 | 0.54 | 1.61 | 0.40 | 1.37 |

13.6: IEC Analysis Conclusions

There were some differences noted between the J695 Reference Standard and the commercial formulation (DS, pH 4.4). These differences were noted in the initial run of the DS SE-HPLC, a Sephadex 200 column (Pharmacia cat#175175-01, S/N 0504057) or a TSK gel G3000SW (cat#08541; for analysis of 22.5 month samples) were used. The mobile phase of the column comprised 20 mM Sodium phosphate and 150 mM Sodium chloride, pH 7.5. Detection was performed at 280 nm and 214 nm. Columns were kept at ambient temperature and the flow rate was 0.5 mL/min (Sephadex column), or 0.3 mL/min (TSK column).

14.2: SEC Data

Figure 20:
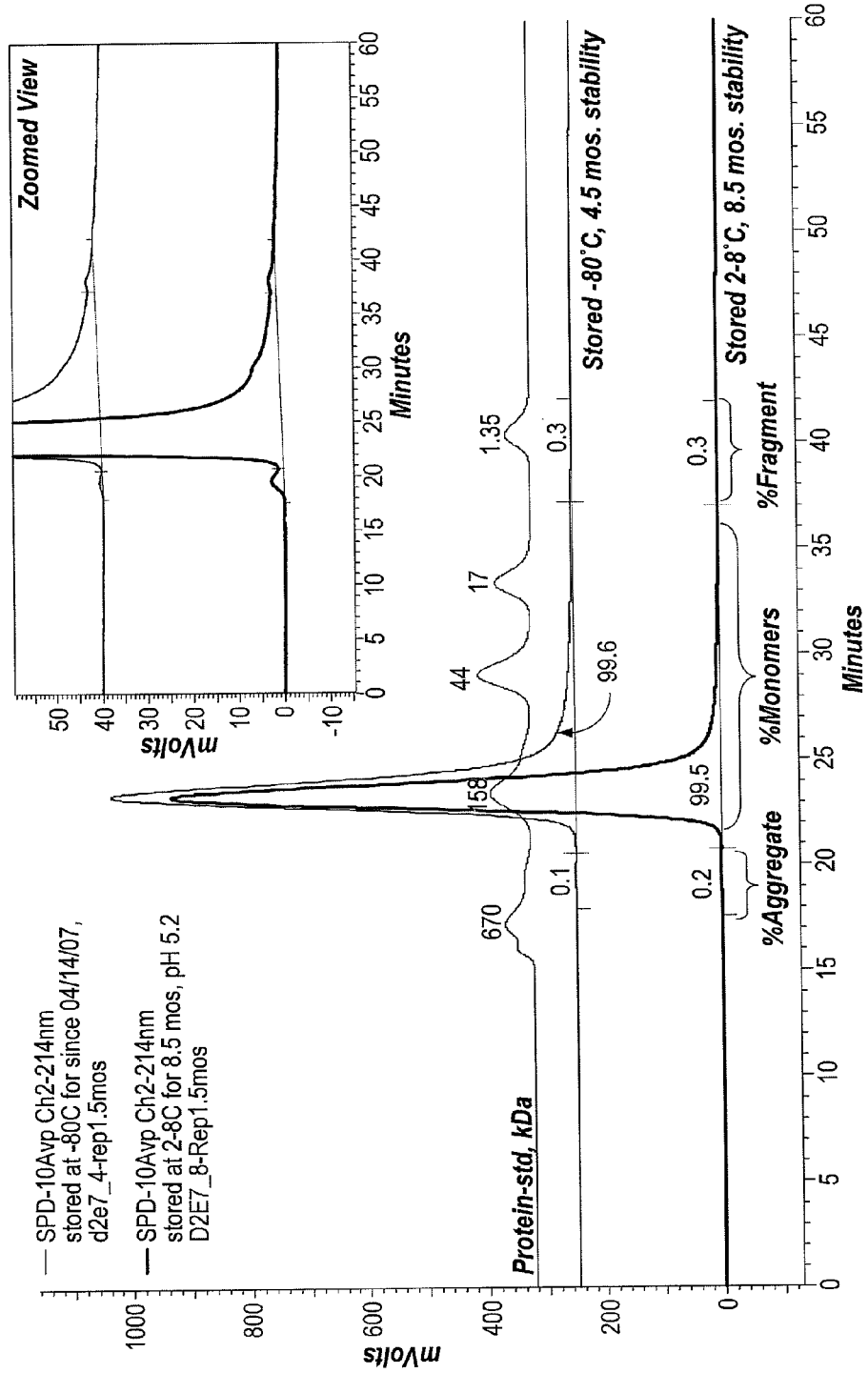
FIG. 20 shows SEC analysis of low-ionic Adalimumab (referred to as D2E7 in FIG. 20) solutions that were either stored at 2-8° C. for 8.5 months after DF/UF (bottom curve) or stored at −80° C. for 4.5 months after DF/UF (top curve).

FIG. 20 and Table 22 contain results of the analysis of a low-ionic Adalimumab solution stored as a liquid at 2-8° C. for 8.5 months compared to the same solution stored at −80° C. Table 23 contains analysis data for a low-ionic Adalimumab solution stored at 2-8° C. for 22.5 months compared to a reference standard sample of Adalimumab.

TABLE 22

SEC Analysis Data Comparing Adalimumab from Frozen Storage versus Adalimumab from Long-Term Refrigerated Storage

| Sample | Load | % HMW | % Monomer | % LMW |
|---|---|---|---|---|
| DF/UF against water, 177 mg/mL, 4.5 months at −80° C. | 50 μg | 0.1 | 99.6 | 0.3 |
| DF/UF against water, 177 mg/mL, 9 months at 2-8° C. | 50 μg | 0.2 | 99.5 | 0.3 |

TABLE 23

SEC Analysis Data Comparing Adalimumab Reference Standard against Adalimumab from Long-Term Refrigerated Storage

| Sample | Load | % HMW | % Monomer | % LMW |
|---|---|---|---|---|
| Reference Std. Adalimumab | 50 μg | 0.31 | 98.85 | 0.84 |
| DF/UF against water, 177 mg/mL, 22.5 months at 2-8° C. | 50 μg | 1.42 | 97.59 | 0.98 |

As can be seen in Table 22, SEC analysis revealed that adalimumab in water was stable even after 9 months at 2-8° C. or for 4.5 months at −80° C., as the percent aggregate (% HMW) and percent fragment (% LMW) were minimal over time.

14.3: SEC Analysis Conclusions

After 8.5 months storage at 2-8° C., the Adalimumab solution (DF/UF against water) revealed a small fraction of high molecular weight (HMW) species (0.2%) and a small fraction of fragment (0.3%). Storage for 4.5 months at −80° C. and subsequent thaw (water bath, 23° C.) did not impact Adalimumab stability (0.1% aggregate, 0.3% fragment).

Analysis of a sample stored for 22.5 months at 2-8° C. also shows comparable fragment content to Adalimumab reference standard (Table 23). However, the aggregate levels detected in the 22.5 month stability sample (1.66%) are somewhat higher than aggregate levels detected in the reference standard.

It is known that self-association of antibodies is highly dependent on the antibody concentration, i.e. the formation of non-covalent aggregate and associate complexes is most pronounced at high protein concentration. This self-association is reversible, and dilution with buffer solution results in reduced self-association tendencies (Liu, J. et al., 94 Journal of Pharmaceutical Sciences 1928 (2004)).

Thus, it is likely that differences in sample preparations and different lag-times between Adalimumab solution dilution (from 177 mg/mL to 1 mg/mL) and subsequent sample analysis by SEC are the reason for the differences in aggregate content of the 8.5 month and the 9 month stability samples.

14.4: IEC Experimental Procedure

A cation exchange method was developed for the assessment of antibody charge heterogeneity using the Dionex WCX-10 column. Cation exchange chromatography separates protein isoforms according to the apparent pI and the surface charge interaction with the resin. The protein of interest is bound to the column under specific low salt starting conditions and is eluted from the column by increasing the salt concentration through a gradient. Proteins with lower apparent pI bind less tightly to a cation exchange column and are the first to elute and proteins with a higher apparent pI bind tighter and are the last to elute.

Before the procedure, samples were diluted to 1.0 mg/mL with milli Q water. Dionex Propac WCX-10 columns (p/n 054993), along with a corresponding guard columns (p/n 05499), were used for separation. Two mobile phase buffers were prepared, 10 mM Sodium phosphate, pH 7.5 (Buffer A) and 10 mM Sodium phosphate, 500 mM Sodium chloride, pH 5.5 (Buffer B). Columns were kept at ambient temperature and the flow rate was 1.0 mL/min. Injection volumes were 100 μl for a 100 μg load and detection was performed at 280 nm. Buffer gradients over the course of the chromatographic separation are provided in Table 24.

TABLE 24

Buffer Gradients used in IEC Analysis of Adalimumab

| Time (min) | % MPA | % MPB |
|---|---|---|
| 0.05 | 94 | 6 |
| 20 | 84 | 16 |
| 22 | 0 | 100 |
| 26 | 0 | 100 |
| 28 | 94 | 6 |
| 34 | 94 | 6 |
| 35 | 94 | 6 |

14.5: Ion Exchange Data

Table 25 shows the ion exchange chromatographic data for the Adalimumab reference standard, commercial formulation (150 mg/ml) and post-DF/UF low-ionic solution before storage. Table 26 shows data for the reference standard compared to the low-ionic solution after 22.5 months of storage at 2-8° C.

TABLE 25

IEC Analysis Data of Adalimumab Reference Standard, DS/Commercial Formulation and After DF/UF (in water)

| Sample Name | % Acidic Region 1 | % Acidic Region 2 | % 0 Lys | % 1 Lys | % 2 Lys |
|---|---|---|---|---|---|
| Adalimumab Ref. Std. | 2.69 | 11.66 | 60.77 | 19.42 | 5.40 |
| Adalimumab DS 150 mg/ml | 2.51 | 11.38 | 62.05 | 19.14 | 4.83 |
| Adalimumab diafiltered against water, 177 mg/ml | 2.26 | 11.81 | 61.97 | 18.51 | 4.73 |

TABLE 26

IEC Analysis Data Comparing Reference Standard to DF/UF Sample from Long-Term Refrigerated Storage

| Sample Name | % Acidic Region 1 | % Acidic Region 2 | % 0 Lys | % 1 Lys | % 2 Lys |
|---|---|---|---|---|---|
| Adalimumab Ref. Std. | 2.1 | 10.9 | 63.8 | 18.4 | 4.6 |

TABLE 26-continued

IEC Analysis Data Comparing Reference Standard
to DF/UF Sample from Long-Term Refrigerated Storage

| Sample Name | % Acidic Region 1 | % Acidic Region 2 | % 0 Lys | % 1 Lys | % 2 Lys |
|---|---|---|---|---|---|
| Adalimumab DF/UF against water, 177 mg/mL, 22.5 months at 2-8° C. | 2.7 | 13.4 | 62 | 16.7 | 4.1 |

14.6: Ion Exchange Analysis Conclusions

For the T0 samples, data show no significant difference in the percentage of acidic region 1, 2, 0 Lys, 1 Lys, or 2 Lys (i.e., charge heterogeneity) between reference standard Adalimumab, commercial formulation Adalimumab (used as DS to formulate Adalimumab into water by DF/UF), and Adalimumab diafiltered against water and concentrated to 177 mg/ml (Table 25).

Also, after 22.5 months storage of the 177 mg/mL Adalimumab sample in water, only slight differences in 0 Lys, 1 Lys and 2 Lys fractions can be seen when compared to the Adalimumab reference standard. In summary, no significant chemical instability tendencies are observed when Adalimumab is formulated into water by DF/UF processing and stored for 22.5 months at 2-8° C. at a concentration of 177 mg/mL.

Example 15

Freeze/Thaw Stability of Low-Ionic 1D4.7 Solution

1D4.7 protein (an immunoglobulin G1) anti-IL 12/anti-IL 23 was formulated in water by dialysis (using slide-a-lyzer cassettes, used according to operating instructions of the manufacturer, Pierce; Rockford, Ill.) was demonstrated to be stable during repeated freeze/thaw (f/t) processing (−80° C./25° C. water bath) at 2 mg/mL concentration, pH 6. Data were compared with routine formulations (2 mg/mL, pH 6), and it was found that the stability of 1D4.7 formulated in water exceeded the stability of 1D4.7 formulated in routinely screened buffer systems (e.g. 20 mM histidine, 20 mM glycine, 10 mM phosphate, 10 mM citrate) and even exceeded the stability of 1D4.7 formulations based on universal buffer (10 mM phosphate, 10 mM citrate) with a variety of excipients that are commonly used in protein formulation, e.g. 10 mg/mL mannitol, 10 mg/mL sorbitol, 10 mg/mL sucrose, 0.01% polysorbate 80, 20 mM NaCl.

Figure 21:
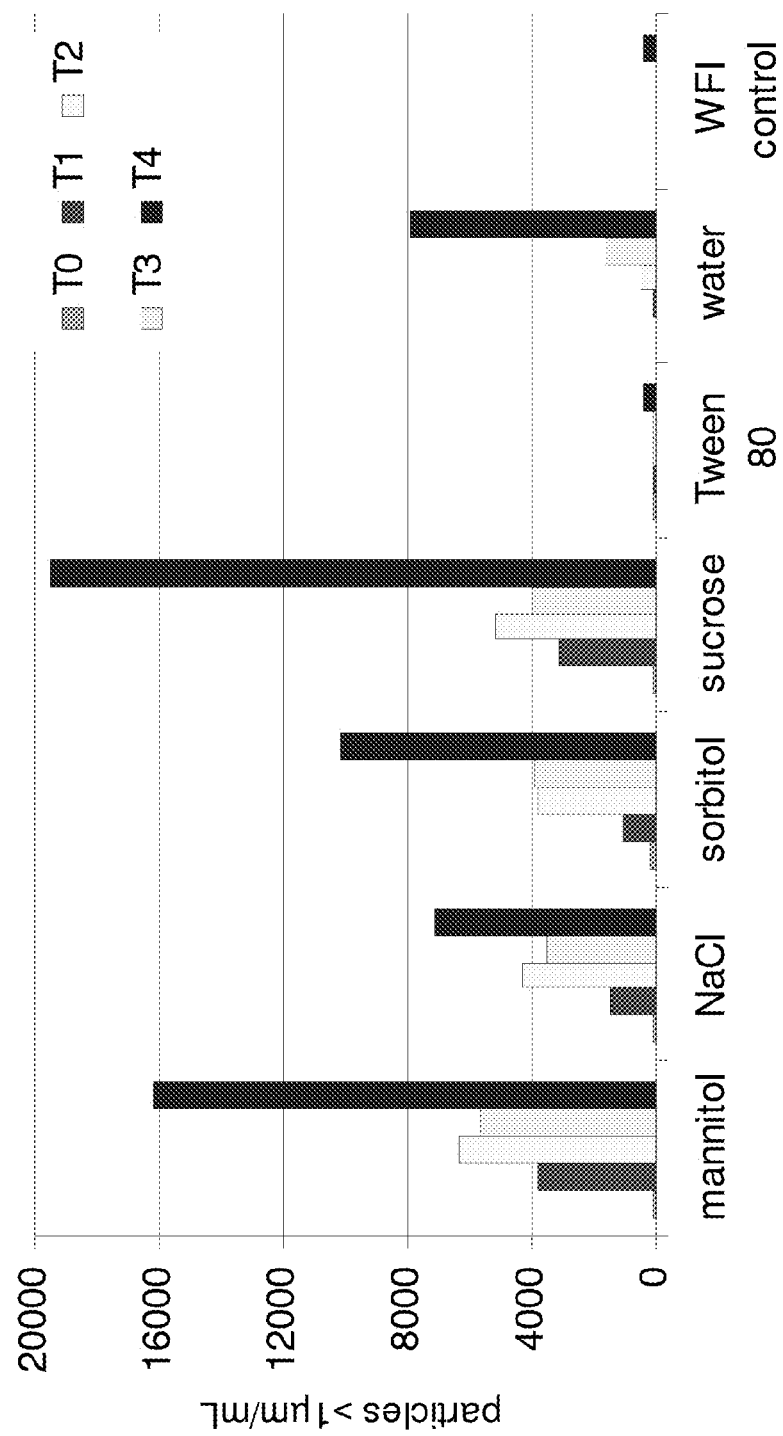
FIG. 21 shows the stability of the monoclonal antibody 1D4.7 formulated in various solutions and in water before freeze-thaw procedures (T0) and after each of four freeze-thaws (T1, T2, T3 and T4).

SEC, DLS and particle counting was performed to monitor protein stability, and particle counting was performed by using a particle counting system with a 1-200 μm measurement range (e.g. particle counter Model Syringe, Markus Klotz GmbH, Bad Liebenzell, Germany). Experiment details are as follows:

1D4.7 formulated in water compared with formulations listed above
4 freeze/thaw cycles applied
30 mL PETG repository, about 25 mL fill, 2 mg/mL, pH 6
sampling at T0, T1 (i.e. after one f/t step), T2, T3, and T4
analytics: visual inspection, SEC, DLS, subvisible particle measurement FIG. 21 shows 1D4.7 stability during repeated f/t cycling (−80° C./25° C.), mirrored by formation of subvisible particles >1 μm. 1D4.7 was formulated in universal buffer (10 mM citrate, 10 mM phosphate) and then the following excipient variations were tested: sorbitol (10 mg/mL), mannitol (10 mg/mL), sucrose (10 mg/mL), NaCl (100 mM), and polysorbate 80(0.01%). 1D4.7 was also formulated in water (by dialysis) with no excipients added at all. Water for injection was also subjected to f/t cycling and subvisible particle testing to evaluate a potential impact of material handling, f/t, and sample pull on particle load.

The stability of 1D4.7 formulated in water upon f/t exceeded the stability of 1D4.7 solutions formulated with excipients typically used in protein formulations. Mannitol, sucrose, and sorbitol are known to act as lyoprotectant and/or cryoprotectant, and polysorbate 80 is a non-ionic excipient prevalently known to increase physical stability of proteins upon exposure to hydrophobic-hydrophilic interfaces such as air-water and ice-water, respectively. Thus, 1D4.7 solutions formulated in water appeared to be stable when analyzed with other methodologies applied (e.g. SEC, visual inspection, etc.).

Example 16

Freeze/Thaw Stability of Low-Ionic 13C5.5 Antibody Solution

13C5.5 anti IL-13 protein formulated in water was demonstrated to be stable during repeated freeze/thaw processing (−80° C./25° C. water bath) at 2 mg/mL concentration, pH 6. Data were compared with routine formulations (2 mg/mL, pH 6), and it was found that the stability of 13C5.5 formulated in water exceeded the stability of 13C5.5 formulated in routinely screened buffer systems (e.g. 20 mM histidine, 20 mM glycine, 10 mM phosphate, 10 mM citrate) and even exceeded the stability of 13C5.5 formulations based on universal buffer (10 mM phosphate, 10 mM citrate) with a variety of excipients that are commonly used in protein formulation (e.g. 10 mg/mL mannitol, 10 mg/mL sorbitol, 10 mg/mL sucrose, 0.01% polysorbate 80, 20 mM NaCl, 200 mM NaCl).

Sample preparation, experiment processing, sample pull and sample analysis was performed in the same way as outlined in Example 15 for 1D4.7.

Figure 22:
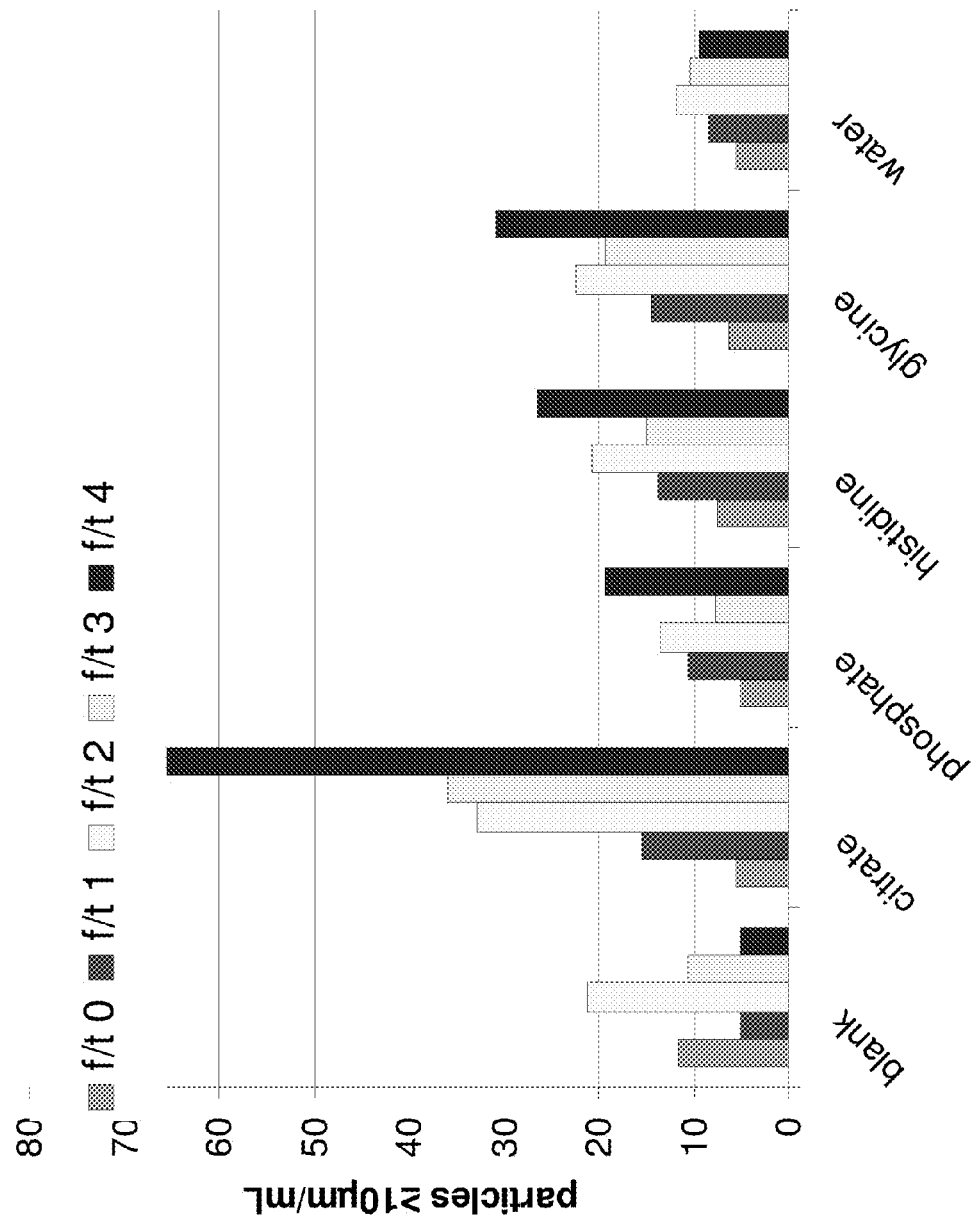
FIG. 22 shows the stability of the monoclonal antibody 13C5.5 formulated in water and with various buffers before freeze-thaw procedures (T0) and after each of four freeze-thaws (T1, T2, T3 and T4). Blank=WFI control sample.

13C5.5 formulated in water compared with formulations listed above
4 freeze/thaw cycles applied
30 mL PETG repository
2 mg/mL, pH 6
sampling at T0, T1, T2, T3, and T4
analytics: visual inspection, SEC, DLS, subvisible particle measurement FIG. 22 shows 13C5.5 stability during repeated f/t cycling (−80° C./25° C.), mirrored by formation of subvisible particles >10 μm. 13C5.5 was formulated in either 10 mM phosphate buffer, 10 mM citrate buffer, 20 mM glycine buffer, and 20 mM histidine buffer. 13C5.5 was also formulated in water (by dialysis) with no excipients added at all. Water for injection was also subjected to f/t cycling and subvisible particle testing to evaluate a potential impact of material handling, f/t, and sample pull on particle load (blank).

The stability of 13C5.5 formulated in water upon f/t exceeded the stability of 13C5.5 solutions formulated in buffers typically used in protein formulations. No instabilities of 13C5.5 solutions formulated in water have been observed with other analytical methodologies applied (e.g. SEC, visual inspection, etc.)

Figure 23:
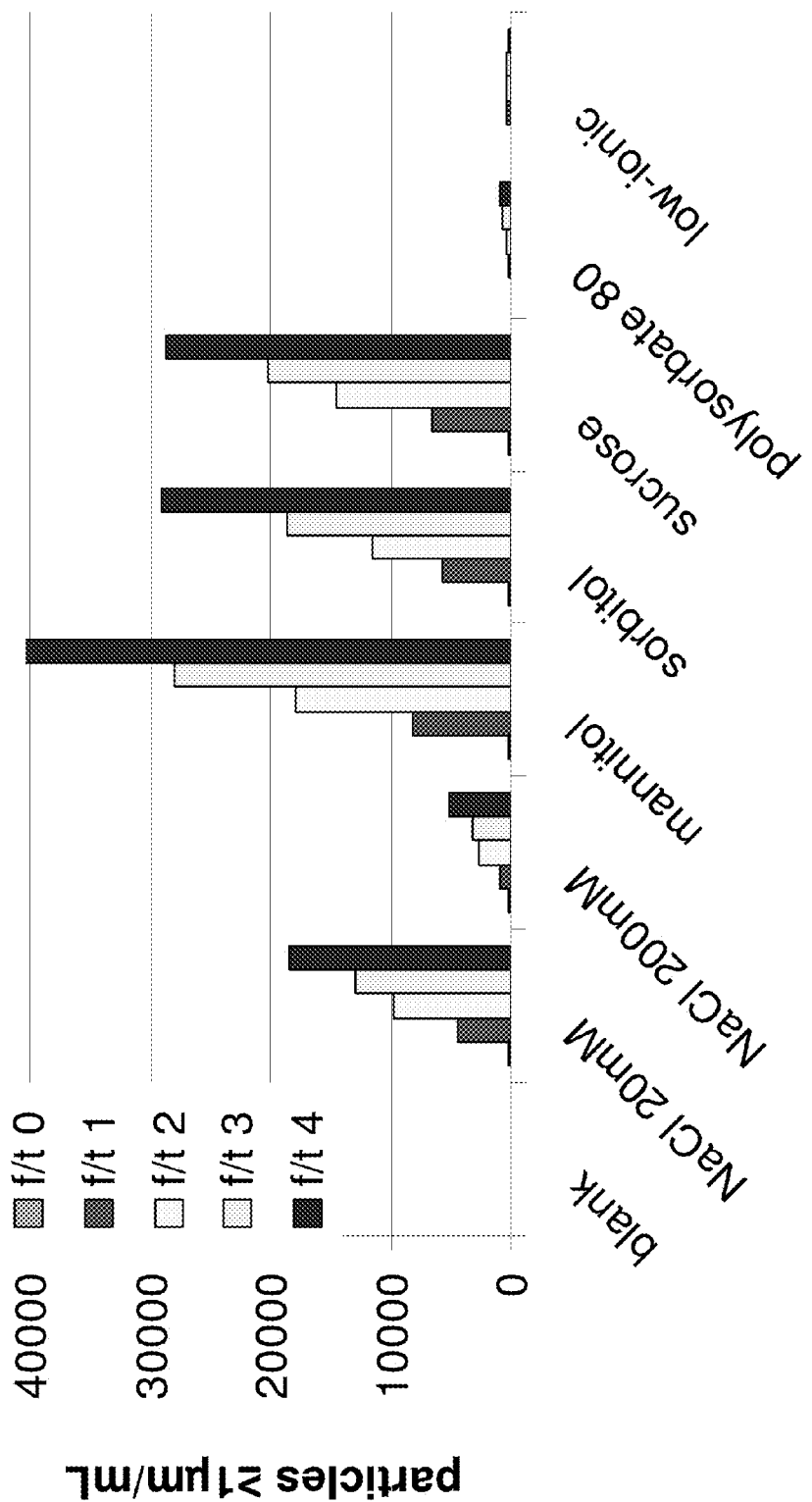
FIG. 23 shows the stability of the monoclonal antibody 13C5.5 formulated in water and with various excipients added, before freeze-thaw procedures (T0) and after each of four freeze-thaws (T1, T2, T3 and T4). Blank=WFI control sample.

FIG. 23 shows 13C5.5 stability during repeated f/t cycling (−80° C./25° C.), mirrored by formation of subvisible particles >1 μm. 13C5.5 was formulated in universal buffer (10 mM citrate, 10 mM phosphate) and then the following excipient variations were tested: sorbitol (10 mg/mL), mannitol (10 mg/mL), sucrose (10 mg/mL), NaCl (200 mM), NaCl (20 mM) and polysorbate 80 (0.01%). 13C5.5 was also formulated in water (by dialysis) with no excipients added at all for comparison (pure water). Water for injection was also subjected to f/t cycling and subvisible particle testing to evaluate a potential impact of material handling, f/t, and sample pull on particle load.

The stability of 13C5.5 formulated in water upon f/t exceeded the stability of 13C5.5 solutions formulated with excipients typically used in protein formulations. Mannitol, sucrose, and sorbitol are known to act as lyoprotectant and/or cryoprotectant, and polysorbate 80 is a non-ionic excipient prevalently known to increase physical stability of proteins upon exposure to hydrophobic-hydrophilic interfaces such as air-water and ice-water, respectively.

No instabilities of 13C5.5 solutions formulated in water have been observed with other analytical methodologies applied, (e.g. SEC, visual inspection, etc.).

DLS analysis of 13C5.5 solutions after f/t procedures was performed as described above. An 13C5.5 solution with 0.01% Tween-80 contained significant high molecular weight (HMW) aggregate forms after only 1 f/t step, whereas 13C5.5 in water contained no HMW aggregate forms, even after 3 f/t steps.

Example 17

Impact of Solution pH on Adalimumab In WFI

The following experiments were performed to determine the impact of solution pH on physico-chemical characteristics of highly concentrated Adalimumab formulated in WFI. The following concentrations were tested: 2 mg/mL, 50 mg/mL, 100 mg/mL, 150 mg/mL, 200 mg/mL, and 250 mg/mL.

Materials
  Adalimumab Drug Substance (DS), commercial material
  25° C. water bath (circulating) used for thawing
  Diafiltration equipment: Sartorius Sartocon Slice, membrane: PES 50 kD, 1000 cm$^2$
  Diafiltration equipment: Millipore Labscale™ TFF System, membrane: PLCTK 30 kD, regenerated Cellulose, size: 50 cm$^2$
  Eppendorf Centrifuge 5810 R
  Amicon Ultra-15 repositories for centrifugation, Ultracel-30k, Regenerated Cellulose 30,000 MWCO
  Millex GV 0.22 µm, Millipore for sterile filtration of samples
  Sample repositories (Eppendorf sample repository 1.5 mL, Roth cryovials 5 mL, PETG bottle 125 mL)
  Analytics:
  pH measurement using Biothrode
  Density measurement
  Osmolality measurement
  UV/VIS spectrophotometer for protein concentration measurement
  Photon Correlation Spectroscopy (PCS)
  Viscosity measurement
  Turbidity measurement
  Size Exclusion Chromatography (SEC)
  Fourier transform mid infrared spectroscopy (FT-M-IR)

17.1 Overview of Preparation for DF/UF of Adalimumab Commercial Formulation

The Adalimumab DS solution (120 mg/mL) was divided into 7 volume portions which were adjusted to pH3, pH4, pH5, pH6, pH7, pH8, pH9 with 0.25N NaOH and 0.25N HCl, respectively. Then the samples were diluted with Adalimumab buffer of the respective pH to 100 mg/mL. The solutions revealed a slight cloudyness that disappeared after sterile filtration (0.22 µm, PVDF sterile filter). After dilution, the pH value were monitored again (see Table 27 below).

The following samples of the 100 mg/mL solutions were pulled from each solution:
  4 mL for turbidity and subsequent zetapotential measurement
  1 mL for viscosity measurement (using dropping-ball viscometer)
  0.15 mL for osmolality measurement
  2 mL for density measurement
  0.15 mL for PCS (sample viscosity taken into account for measurements)
  1 mL for FT-M-IR
  2 mL for viscosity and static light scattering measurements The samples for zetapotential, viscosity and static light scattering measurements were frozen (−80° C.). The remaining volumes of pH 4, pH 5, pH 6, pH 7, and pH 8 solutions were subjected to continuous mode diafiltration using water for injection as exchange medium. The samples were first frozen at −80° C. Before DF/UF, the samples were thawed at 25° C. in a Julabo water bath.

17.2 DF/UF and Concentration Procedures

Adalimumab solutions in commercial formulation, with concentrations of 100 mg/ml, with pH levels of 4, 5, 6, 7 and 8, were subject to DF/UF processing and further subject to concentration process with UF in a centrifuge. This section describes the processing of the pH 6 Adalimumab solution as an example. Processing for the other solutions was done in a similar manner.

The Adalimumab solution (100 mg/mL, pH 6) was thawed in a water bath at 25° C. and then homogenized. Then, the solution was subjected to diafiltration using water for injection as exchange medium with TFF equipment M.P. 33.4 by applying the following parameters:
  stirrer: speed 2
  pump: speed 1
  pressure up-stream/inlet: 2-2.4 bar
  pressure down-stream/outlet: 0.6-0.8 bar
  membrane: regenerated Cellulose, cut off 30 kD
  continuous mode DF/UF
  about 6-fold volume exchange applied during DF/UF operation After applying 6-volume exchange steps, the concentration of Adalimumab was determined by means of OD280, photometer M.P. 9.7. The osmolality of permeate and retentate was checked.
  concentration: 125.1 mg/mL
  osmolality permeate: 57 mOsmol/kg
  osmolality retentate: 12 mOsmol/kg The Adalimumab solution in water after DF was diluted with water for injection to 100 mg/mL and sterile filtered. The following samples were pulled from 100 mg/mL solution after the DF/UF process:
  4 mL for turbidity and subsequent zetapotential measurement
  1 mL for viscosity measurement
  0.15 mL for osmolality measurement
  2 mL for density measurement
  0.15 mL for PCS (viscosity taken into account during measurement)
  0.15 mL for SEC
  pH—measurement
  1 mL for FT-M-IR
  2 mL for viscosity and static light scattering measurements A portion of the 100 mg/mL Adalimumab solution was diluted with water for injection to create 50 mg/mL and 2 mg/mL solutions. The following samples were pulled from both solutions:
- 4 mL for turbidity and subsequent zetapotential measurement
- 2 mL for viscosity measurement
- 0.15 mL for osmolality measurement
- 2 mL for density measurement
- 0.15 mL for PCS (viscosity taken into account)
- pH— measurement Adalimumab solutions (pH 6, 100 mg/mL) in water were subjected to concentration experiments using centrifugation. Centrifugation was performed with Eppendorf Centrifuge (5810R M.P. 33.57). Each centrifugation step was applied for 15 min. at 4000 rpm. After that, homogenization of sample solution in the centrifuge concentration device was performed by gentle upside-down rotation in order to homogenized the solution and thereby to avoid gel formation in areas immediately adjacent to the membrane. Temperature during concentration was 15° C. The centrifugation was performed to about 250 mg/mL. The concentration was determined by means of measuring OD280, photometer M.P. 9.7. The Adalimumab solutions were then diluted to concentrations of 250 mg/mL, 200 mg/mL and 150 mg/mL.

The following samples were pulled after the concentration procedure and after each individual step of dilution. Sample volumes pulled from 250 mg/mL and 150 mg/mL solutions were:
- 2 mL for viscosity-measurement
- 0.15 mL for PCS (viscosity taken into account)
- 0.15 mL for osmolality measurement
- 0.15 mL for SEC
- pH—measurement Sample volumes pulled from the 200 mg/mL solution were:
- 4 mL for turbidity and subsequent zetapotential measurement
- 1 mL for viscosity measurement
- 0.15 mL for osmolality measurement
- 2 mL for density measurement
- 0.15 mL for PCS (viscosity taken into account)
- 0.15 mL for SEC
- pH—measurement
- 2 mL for analytical work to be performed at ABC (viscosity and static light scattering measurements)

The concentration processing of Adalimumab solution in water was halted at approximately 250 mg/mL at each pH value because the viscosity of Adalimumab solution in water at higher concentrations, and especially at pH values close to the pI (about pH 8.5 for Adalimumab), increased dramatically (viscosities approaching gel formation).

17.3 Visual Inspection of Adalimumab Solutions

After DF/UF and concentration to 250 mg/mL, the Adalimumab solutions in water at various pH appeared less opalescent than the Adalimumab solution in buffer (commercial formulation). All of the Adalimumab solutions in water appeared as clear solutions at each pH value. None of the Adalimumab solutions revealed opalescence after dilution. Overall, during concentration and dilution procedures, no precipitation was observed in Adalimumab solutions in water.

17.4 Viscosity

The viscosity measurements were performed taking into account the density of pH 5 Adalimumab solutions at each of the respective concentrations. A dropping-ball viscometer was used. Viscosities higher than 200 mPa*s were measured using capillary viscometer.

Figure 24:
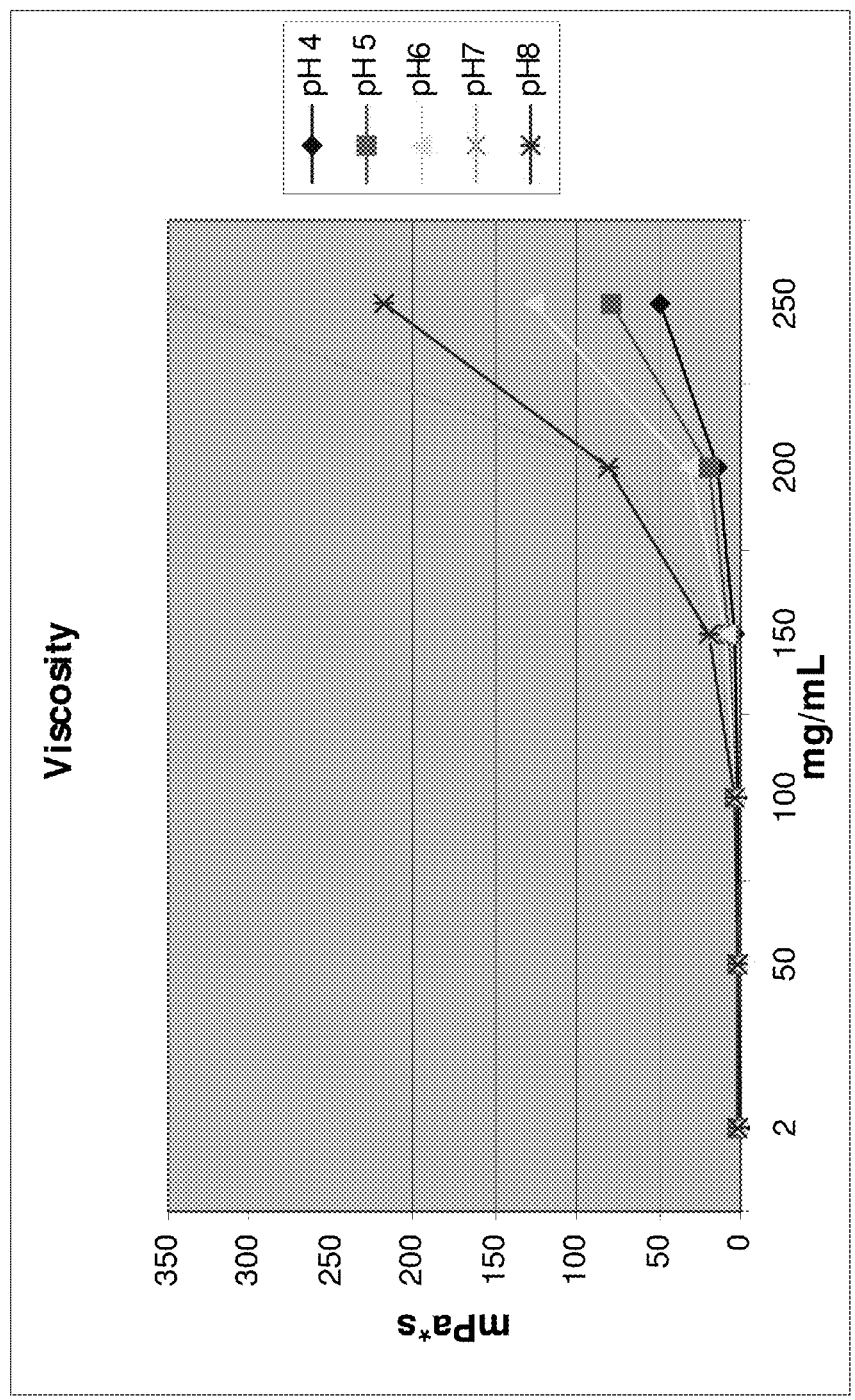
FIG. 24 shows the impact of the concentration of Adalimumab (WFI formulation) and solution pH on solution viscosity.

FIG. 24 provides an overview of viscosity data of Adalimumab solutions in water with pH ranging from 4 to 8, at various concentrations (2 mg/mL to 250 mg/mL, in 50 mg/mL concentration steps). There is a clear correlation between solution pH, concentration and viscosity. The viscosity increases with increases of protein concentration, independent of the solution pH. At solution pH values close to the pI of Adalimumab (i.e. pH 7 and pH 8), increases in solution viscosity were most pronounced, especially at higher protein concentrations (i.e. 200 mg/mL, 250 mg/mL).

17.5 Turbidity

Figure 25:
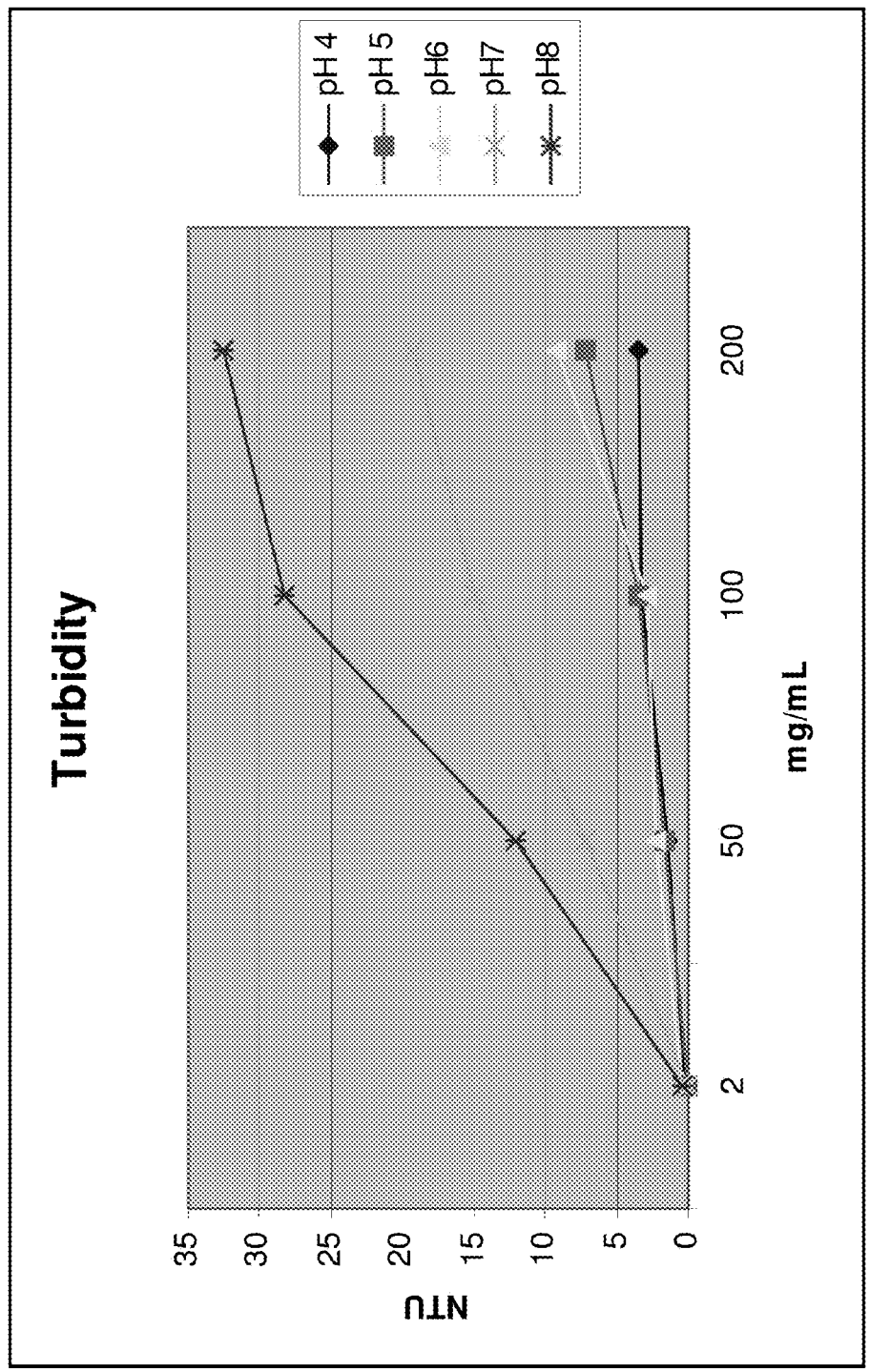
FIG. 25 shows turbidity data for Adalimumab solutions (WFI formulations) of various concentrations and pH values.

As seen in FIG. 25, the same trend was found for turbidity data, (i.e., the turbidity increased with increasing concentration and with increasing pH). All samples were sterile filtered (0.22 µm) before turbidity measurement.

17.6 Hydrodynamic Diameter (PCS)

The PCS measurements were performed taking into account the viscosity for each sample, at each concentration and at each pH value. Solutions at 200 mg/mL and 250 mg/mL were measured but were outside the testing parameters of the Zetasizer nano series (Malvern Instruments) equipment, and consequently the data from these measurements was not analyzed.

Figure 26:
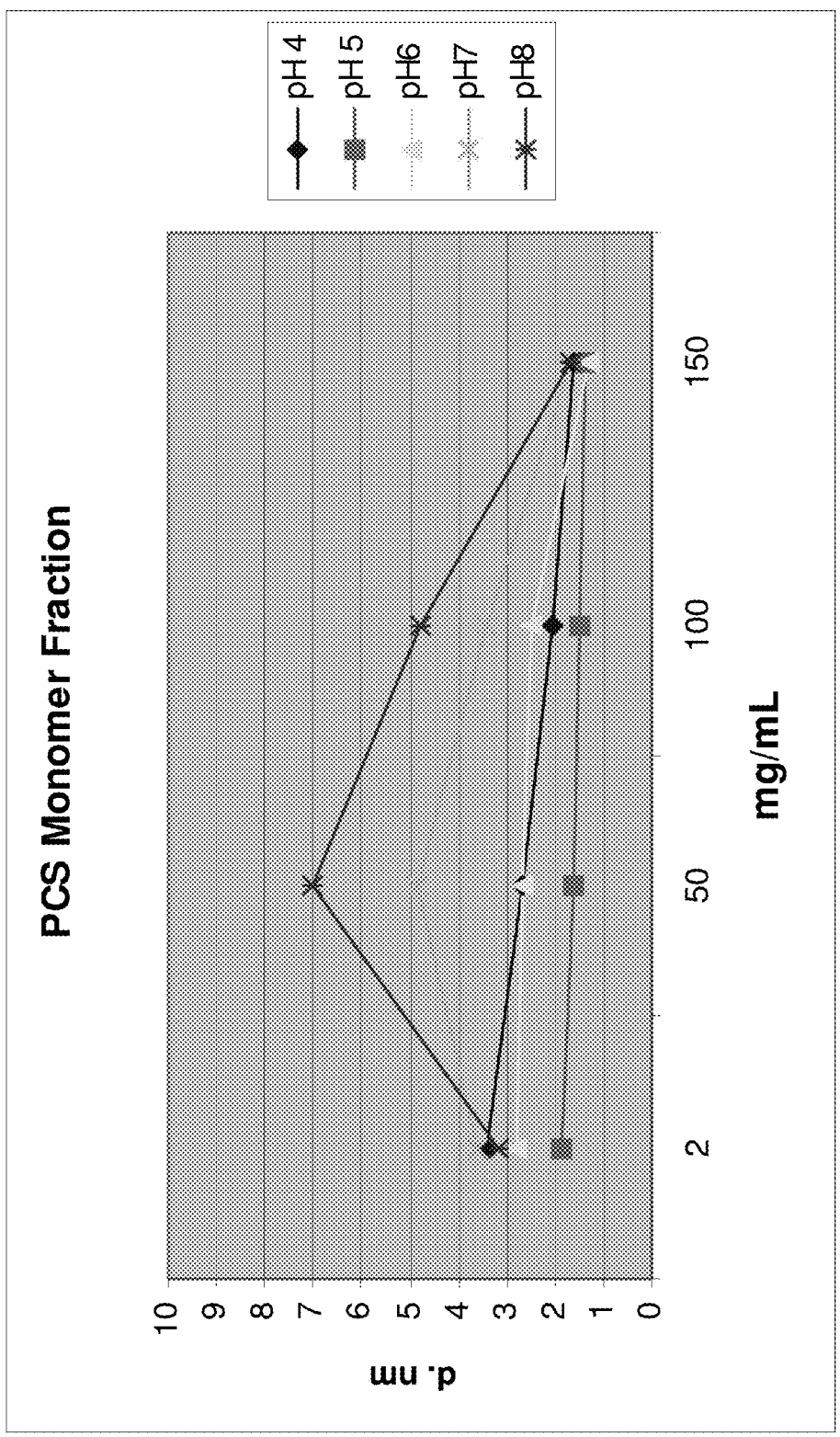
FIG. 26 shows hydrodynamic diameter ($D_h$) data for Adalimumab solutions (WFI formulations) at various pH values and concentrations.

The hydrodynamic diameter (Dh) was found to be notably decreased when Adalimumab was formulated in water ($D_h$ about 2 nm at 50 mg/mL, pH 5) in comparison to Adalimumab formulated into commercial formulation ($D_h$ about 7 nm). FIG. 26 illustrates the PCS data (also found in Table 39). Corresponding data tables are shown below in part 17.11.

Figure 27:
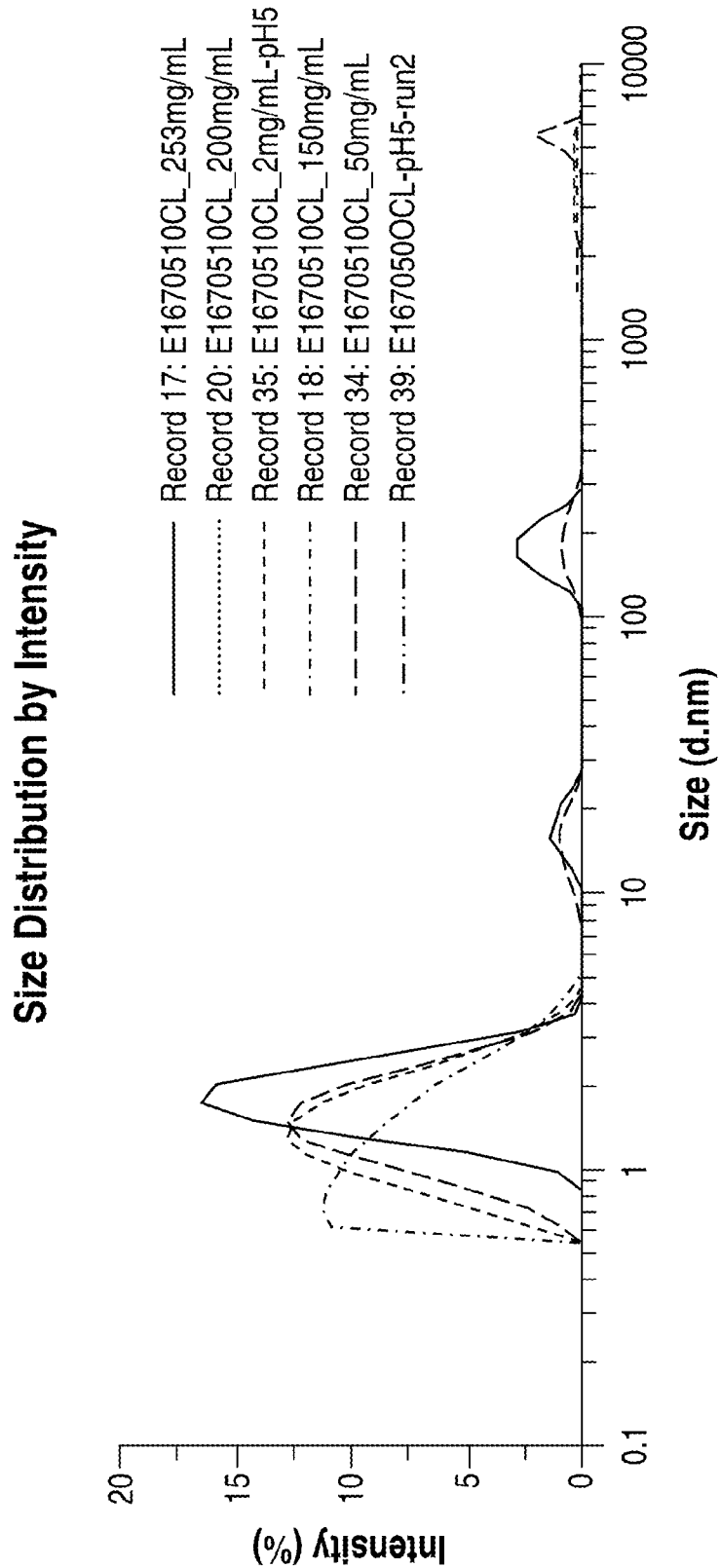
FIG. 27 shows a size distribution by intensity graph ($D_h$ measurements) for Adalimumab in water solutions, pH 5, at various concentrations.
Figure 28:
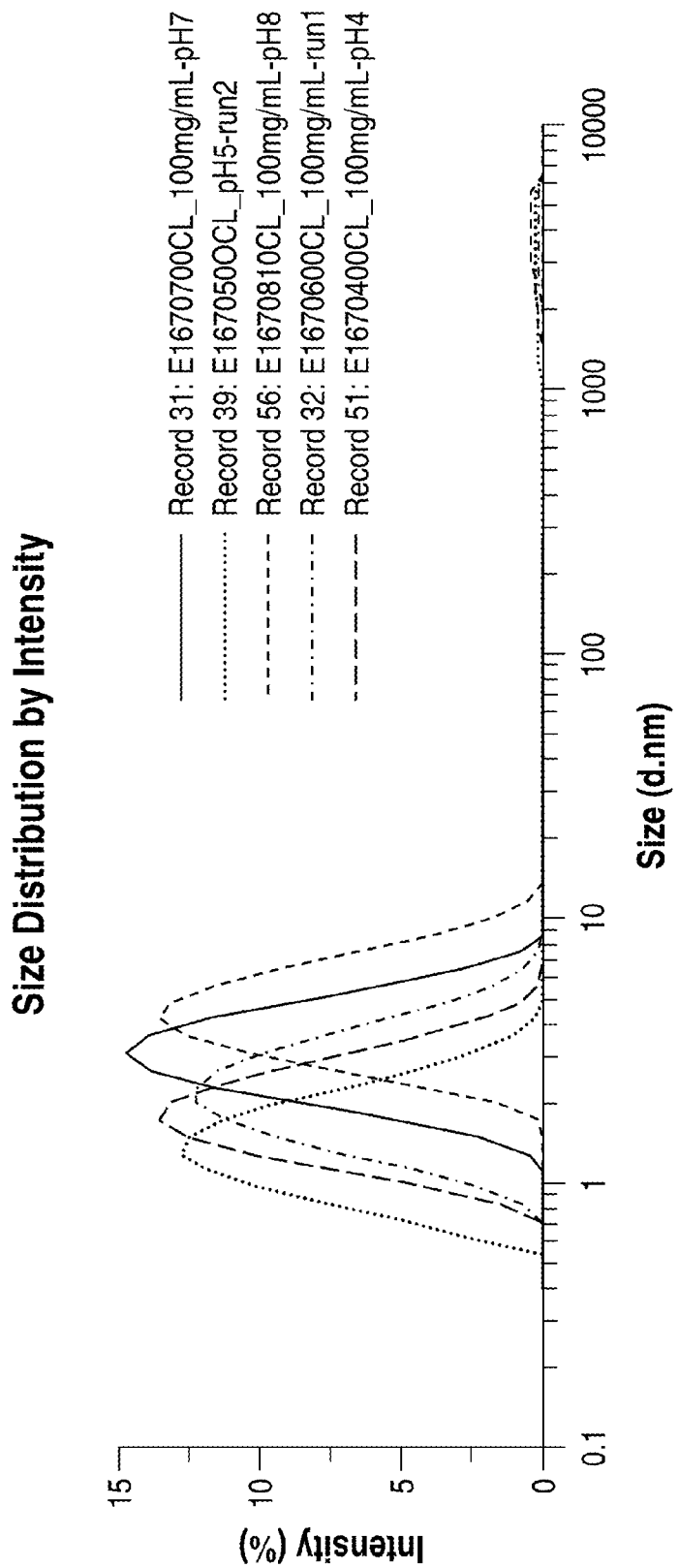
FIG. 28 shows size distribution by intensity for 100 mg/mL Adalimumab in water at various pH levels.
Figure 29:
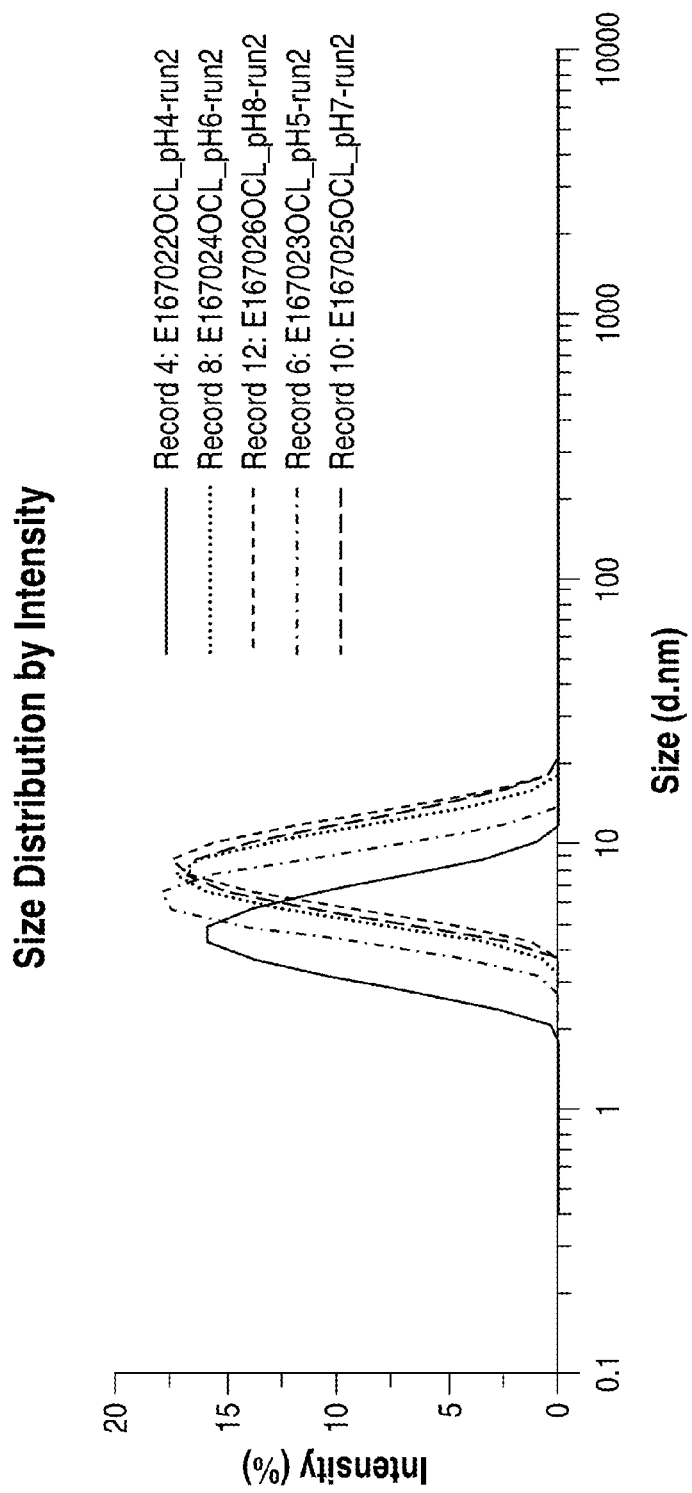
FIG. 29 also shows size distribution by intensity for 100 mg/mL Adalimumab in water at various pH levels.

As shown in FIG. 26, for solutions at pH values of 4, 5 and 6, the Dh of Adalimumab monomer decreased constantly with increased protein concentration. In contrast, solutions with pH values closer to the pI of Adalimumab (i.e., at pH 7 and pH8) showed considerable increases in Dh as concentration increased from 2 mg/mL to 50 mg/mL. As concentrations rose beyond 50 mg/mL in pH 7 and 8 solutions, however, Dh decreased. At a concentration of 150 mg/mL, all of the solutions had lower Dh values than the corresponding pH solution at 2 mg/mL. FIG. 27 shows Dh size distributions for pH 5 solutions of various concentrations. FIG. 28 shows Dh size distributions for five Adalimumab solutions formulated in water, each having a 100 mg/mL protein concentration and a different pH value. FIG. 29 shows data similar to data in FIG. 28, except that the five Adalimumab solutions were formulated in buffer.

17.7 pH—Measurement

Measurements of solution pH were performed at 100 mg/mL before and after DF/UF using water (i.e., performed on Adalimumab formulated in buffer and in water, respectively). Table 27 shows the results. The pH values stay constant at pH 5, pH 6 and pH 7 before and after DF/UF. The solution pH does not change because of a medium change. The pH value at pH 4 slightly increases and at pH 8 slightly decreases after DF/UF using water.

TABLE 27 pH values before and after DF/UF with water

| | pH 4 | pH 5 | pH 6 | pH 7 | pH 8 |
|---|---|---|---|---|---|
| Adalimumab 100 mg/mL in buffer | 4.00 | 4.99 | 6.00 | 7.03 | 8.00 |
| Adalimumab 100 mg/mL in water | 4.29 | 4.98 | 5.98 | 7.02 | 7.67 |

17.8 Osmolality measurements

During DF/UF of the pH 5 solution samples, solution osmolality was measured after each volume exchange step (i.e., after 100 mL permeate, 200 mL permeate, etc.) to check whether a 5-fold volume exchange is sufficient to reduce osmolality to values below 15 mOsmol/kg. Table 28 shows the results.

TABLE 28

Osmolality change during DF/UF using water, pH 5 solution

| Volume exchange step in mL | Retentate mOsmol/kg | Permeate mOsmol/kg |
|---|---|---|
| 100 | 96 | 166 |
| 200 | 28 | 115 |
| 300 | 29 | 89 |
| 400 | 12 | 67 |
| 500 | 15 | 49 |

At pH 4, pH 6, pH 7 and pH 8, the osmolality was measured at the end of the DF/UF process only. Table. 29 shows the osmolality results (in mOsmol/kg units) for each pH.

TABLE 29

Osmolality at various pH values, before and after DF/UF with water

| | pH 4 | pH 5 | pH 6 | pH 7 | pH 8 |
|---|---|---|---|---|---|
| Adalimumab 100 mg/mL in buffer | 287 | 298 | 297 | 286 | 279 |
| Adalimumab 100 mg/mL in water | 40 | 13 | 11 | 5 | 5 |

The osmolality measurements were performed with a freezing point viscometer.

17.9 Fragmentation (SEC)

Figure 30:
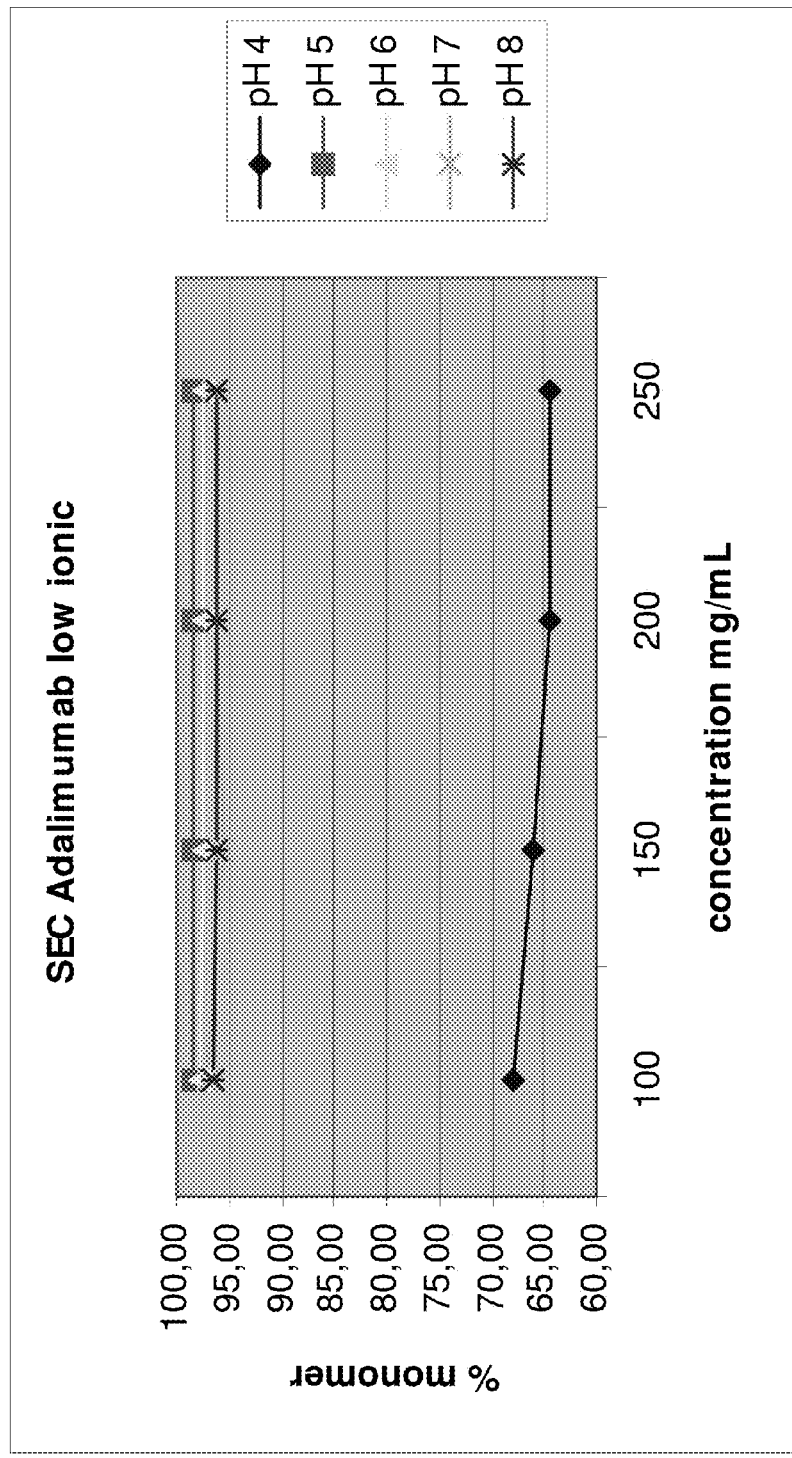
FIG. 30 shows monomer content (SEC) for Adalimumab in water.
Figure 31:
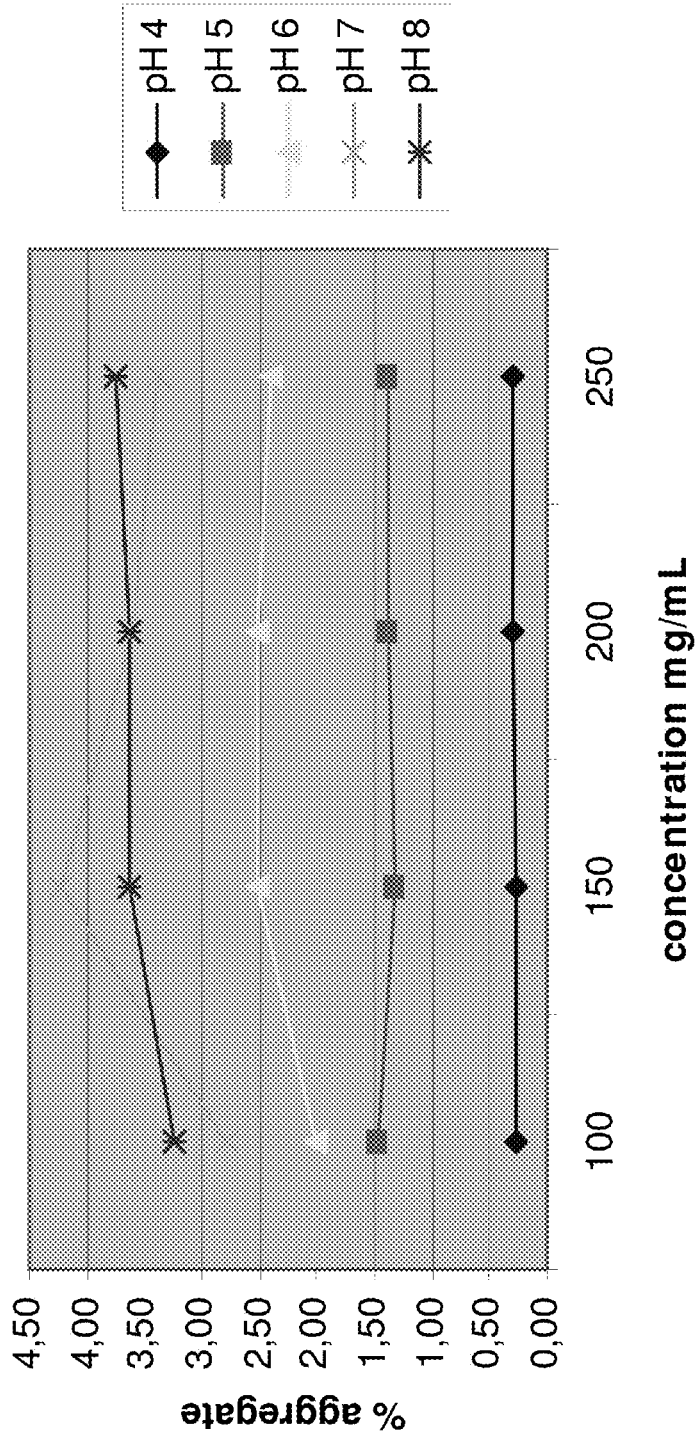
FIG. 31 shows aggregate content (SEC) for Adalimumab in water.

The SEC data show a relative pronounced fragmentation of the protein in ph 4 solutions over the whole concentration range (100-250 mg/mL), while there almost no fragmentation detected at pH ranging from 5 to 8 over the same concentration range. Consequently, the monomer content of pH 4 solutions decreased accordingly (FIG. 30). Aggregate values were found to increase with increasing pH values (from pH 4 to pH 8), independent of the concentration (FIG. 31).

17.10 Conclusions

This experiment was designed to examine the impact of solution pH and protein concentration on viscosity and Dh (hydrodynamic diameter) of Adalimumab solutions formulated in water by DF/UF processing. Such solutions are referred to as low-ionic solutions. A pH range of 4-8 was evaluated, and protein concentrations tested were in a range between 2 and 250 mg/mL.

With regard to viscosity (Section 17.4), it was found that low-ionic Adalimumab solutions have the same characteristics as Adalimumab solutions formulated in the presence of ions (i.e. ionic excipients such as organic buffer components or salts):

The higher the protein concentration, the higher solution viscosity. This concentration-viscosity correlation was more pronounced for solutions with pH values close to the Adalimumab pI (i.e., pH 7 and pH 8). Conversely, for solutions at a constant concentration, viscosity correlated with the closeness of the solution's pH value to the pI of Adalimumab.

With regard to DLS data (Section 17.6), the following conclusions can be drawn:

Adalimumab Dh values determined by DLS of low ionic Adalimumab solutions were found to be lower than Dh values measured in Adalimumab commercial formulations, especially at very low solution pH.

The lower the solution pH, the lower Dh values determined by DLS.

The higher the protein concentration, the lower the Dh values in low-ionic Adalimumab solutions of a given pH.

The explanation for this behavior is that the ionic strength (i.e. the presence of ions and ionizable excipients) in protein solutions is crucial for the extent of protein-protein interactions. Especially at lower solution pH, charge-charge repulsions are more pronounced in low ionic Adalimumab solutions. When a protein is formulated in water by using water as exchange medium in DF/UF processing, the amount of ionizable counter ions present that can compose both the Helmholtz layer and the Gouy-Chapman layer is notably reduced. Consequently, intermolecular charge-charge interactions (due to the charges of amino acid residues present at the protein's surface) may be more pronounced than in an environment where ionizable counter ions (e.g. ionizable excipients) are abundant, and charge-charge repulsion between protein monomers (leading to molecule motion in case of charge-charge repulsion) and random Brownian motion contribute to the mobility/motion of the protein molecule measured by DLS. In DLS experiments, greater molecule mobilities are translated into greater molecular diffusion coefficients, which usually are assigned to molecules with smaller hydrodynamic sizes via using the Stokes-Einstein equation. This can explain why the hydrodynamic diameter of proteins is reduced in low-ionic formulations.

Charge-charge interactions between antibody molecules can be repulsive (at lower solution pH) and attractive (at higher solution pH close to the protein's pI).

17.11 Data Tables

TABLE 30

| Adalimumab 100 mg/mL in buffer before DF versus water | | | | | | | |
|---|---|---|---|---|---|---|---|
| | pH 3 | pH 4 | pH 5 | pH 6 | pH 7 | pH 8 | pH 9 |
| turbity (NTU) | 9.9 | 15.4 | 28.5 | 36.3 | 45.0 | 48.4 | 46.5 |
| viscosity (mPa * s) | 2.5197 | 2.7935 | 3.2062 | 3.1512 | 3.5116 | 3.5494 | 3.5844 |
| viscosity (mm2/s) | 2.4366 | 2.6991 | 3.0969 | 3.0444 | 3.3893 | 3.4261 | 3.4589 |
| density (g/cm3) | 1.0341 | 1.0350 | 1.0353 | 1.0351 | 1.0361 | 1.0360 | 1.0363 |
| osmolality (mOsmol/kg) | 293 | 287 | 298 | 297 | 286 | 279 | 285 |
| Z-Ave d (nm) PCS | 4.3 | 4.3 | 6.0 | 7.3 | 7.7 | 8.0 | 7.8 |
| pH | | 4.00 | 4.99 | 6.00 | 7.03 | 8.00 | 9.03 |

TABLE 31

Adalimumab after DF versus water, before concentration, diluted with water to

|  | pH 4 2 mg/mL | pH 4 50 mg/mL | pH 4 100.5 mg/mL |
|---|---|---|---|
| turbity (NTU) | 0.296 | 1.46 | 3.30 |
| viscosity (mPa*s) | 0.9653 | 1.4471 | 2.2411 |
| viscosity (mm2/s) | 0.9665 | 1.4298 | 2.1834 |
| density (g/cm3) | | | |
| osmolality (mOsmol/kg) | | | 40 |
| Z-Ave d (nm) PCS | 3.37 | 2.24 | 1.81 |
| pH | | | 4.29 |

Adalimumab after concentration and dilution with water to

|  | pH 4 150.5 mg/mL | pH 4 219.0 mg/mL | pH 4 251.8 mg/mL |
|---|---|---|---|
| turbity (NTU) | | 3.56 | |
| viscosity (mPa*s) | 4.0283 | 13..304 | 48.642 |
| viscosity (mm2/s) | 3.8712 | 12.614 | 45.567 |
| density (g/cm3) | | | |
| osmolality (mOsmol/kg) | 64 | 96 | 141 |
| Z-Ave d (nm) PCS | 1.32 | 0.458 | 0.162 |
| pH | 4.32 | | 4.54 |

Adalimumab after DF versus water, before concentration, diluted with water to

|  | pH 5 2 mg/mL | pH 5 50 mg/mL | pH 5 97.5 mg/mL |
|---|---|---|---|
| turbity (NTU) | 0.02 | 1.66 | 3.54 |
| viscosity (mPa*s) | 1.0563 | 1.6664 | 2.8661 |
| viscosity (mm2/s) | 1.0576 | 1.6465 | 2.7924 |
| density (g/cm3) | 0.9988 | 1.0121 | 1.0264 |
| osmolality (mOsmol/kg) | | | 13 |
| Z-Ave d (nm) PCS | 157 | 32.4 | 1.3 |
| pH | 4.55 | 4.83 | 4.98 |

Adalimumab after concentration and dilution with water to

|  | pH 5 150.7 mg/mL | pH 5 200.2 mg/mL | pH 5 253.0 mg/mL |
|---|---|---|---|
| turbity (NTU) | | 7.24 | |
| viscosity (mPa*s) | 7.0866 | 19.539 | 79.272 |
| viscosity (mm2/s) | 6.8102 | 18.525 | 74.26 |
| density (g/cm3) | 1.0406 | 1.0547 | 1.0675 |
| osmolality (mOsmol/kg) | 78 | 80 | 96 |
| Z-Ave d (nm) PCS | 0.727 | 0.335 | 0.255 |
| pH | 5.03 | 5.05 | 5.08 |

TABLE 32

Adalimumab after DF versus water, before concentration, diluted with water to

|  | pH 6 2 mg/mL | pH 6 50 mg/mL | pH 6 100 mg/mL |
|---|---|---|---|
| turbity (NTU) | 0.458 | 2.24 | 2.95 |
| viscosity (mPa*s) | 1.0696 | 1.8003 | 3.1147 |
| viscosity (mm2/s) | 1.0708 | 1.7789 | 3.0385 |
| density (g/cm3) | 0.9989 | 1.012 | 1.0251 |
| osmolality (mOsmol/kg) | 3 + 11 = 14:2 = 7 | 27 | 11 |
| Z-Ave d (nm) PCS | 30.8 | 2.78 | 2.48 |
| pH | 5.72 | 5.95 | 5.98 |

TABLE 33

Adalimumab after concentration and diluted with water to

|  | pH 6 146.6 mg/mL | pH 6 201.8 mg/mL | pH 6 248.5 mg/mL |
|---|---|---|---|
| turbity (NTU) | | 9.29 | |
| viscosity (mPa*s) | 9.0193 | 32.352 | 126.06 |
| viscosity (mm2/s) | 8.6775 | 30.709 | 118.07 |
| density (g/cm3) | 1.0394 | 1.0535 | 1.0677 |
| osmolality (mOsmol/kg) | 37 | 58 | 95 |
| Z-Ave d (nm) PCS | 0.989 | 0.355 | 0.108 |
| pH | 5.92 | 6.05 | 6.03 |

TABLE 34

Adalimumab after DF versus water, before concentration, diluted with water to

|  | pH 7 2 mg/mL | pH 7 50 mg/mL | pH 7 103.2 mg/mL |
|---|---|---|---|
| turbity (NTU) | 0.1 | 7.13 | 14.9 |
| viscosity (mPa*s) | 1.1252 | 1.6898 | 4.2257 |
| viscosity (mm2/s) | 1.1268 | 1.6688 | 4.1146 |
| density (g/cm3) | 0.9986 | 1.0126 | 1.027 |
| osmolality (mOsmol/kg) | 0 | 2 | 5 |
| Z-Ave d (nm) PCS | 3.31 | 4.16 | 2.89 |
| pH | 6.63 | 6.93 | 7.02 |

TABLE 35

Adalimumab after concentration and diluted with water to

|  | pH 7 143.0 mg/mL | pH 7 203.4 mg/mL | pH 7 251.7 mg/mL |
|---|---|---|---|
| turbity (NTU) | | 19.3 | |
| viscosity (mPa*s) | 14.024 | 74.987 | 343.881 |
| viscosity (mm2/s) | 13.492 | 70.928 | 321.144 |
| density (g/cm3) | | 1.0571 | 1.0708 |
| osmolality (mOsmol/kg) | 65 | 106 | 160 |
| Z-Ave d (nm) PCS | 1.27 | 0.346 | 0.0876 |
| pH | 6.9 | 7.01 | 7.2 |

TABLE 36

Adalimumab after DF versus water, before concentration, diluted with water to

|  | pH 8 2 mg/mL | pH 8 50 mg/mL | pH 8 96.1 mg/mL |
|---|---|---|---|
| turbity (NTU) | 0.41 | 12.10 | 28.300 |
| viscosity (mPa*s) | 1.261 | 1.8444 | 4.3486 |
| viscosity (mm2/s) | 1.2625 | 1.8224 | 4.2368 |
| density (g/cm3) | | | |
| osmolality (mOsmol/kg) | | | 5 |
| Z-Ave d (nm) PCS | 5.59 | 5.62 | 4.28 |
| pH | | | 7.67 |

TABLE 37

| Adalimumab after concentration and dilution with water to | | | |
|---|---|---|---|
| | pH 8<br>148.5 mg/mL | pH 8<br>200.6 mg/mL | pH 8<br>230.7 mg/mL |
| turbity (NTU) | | 32.5 | |
| viscosity (mPa*s) | 20.102 | 85.5 | 233.14 |
| viscosity (mm2/s) | 19.318 | 81.066 | 218.04 |
| density (g/cm3) | | | |
| osmolality (mOsmol/kg) | | | |
| Z-Ave d (nm) PCS | 1.42 | 0.398 | 0.168 |
| pH | | 7.6 | |

TABLE 38

PCS data: Adalmumab in buffer

| | | Z-Ave d · nm | PDI | Pk1 d · nm | Pk1 Area % | Pk2 d · nm | Pk2 Area % | Pk3 d · nm | Pk3 Area % |
|---|---|---|---|---|---|---|---|---|---|
| pH 3 | 100 mg/mL | 4.23 | 0.283 | 4.43 | 86.4 | 54.1 | 13.6 | 0 | 0 |
| pH 4 | 100 mg/mL | 4.3 | 0.101 | 4.81 | 100 | 0 | 0 | 0 | 0 |
| pH 5 | 100 mg/mL | 6.01 | 0.065 | 6.5 | 100 | 0 | 0 | 0 | 0 |
| pH 6 | 100 mg/mL | 7.25 | 0.063 | 7.82 | 100 | 0 | 0 | 0 | 0 |
| pH 7 | 100 mg/mL | 7.64 | 0.094 | 8.53 | 100 | 0 | 0 | 0 | 0 |
| pH 8 | 100 mg/mL | 7.95 | 0.099 | 8.88 | 100 | 0 | 0 | 0 | 0 |
| pH 9 | 100 mg/mL | 7.7 | 0.133 | 8.98 | 100 | 0 | 0 | 0 | 0 |

TABLE 39

PCS data: Adalmumab in water

| | | Z-Ave d · nm | PDI | Pk1 d · nm | Pk1 Area % | Pk2 d · nm | Pk2 Area % | Pk3 d · nm | Pk3 Area % |
|---|---|---|---|---|---|---|---|---|---|
| pH 4 | 2 mg/ml | 3.37 | 0.219 | 3.39 | 88.8 | 73.3 | 11.2 | 0 | 0 |
| pH 4 | 50 mg/ml | 2.24 | 0.194 | 2.65 | 97.7 | 3300 | 2.3 | 0 | 0 |
| pH 4 | 100.5 mg/ml | 1.81 | 0.172 | 2.02 | 97.4 | 3390 | 2.6 | 0 | 0 |
| pH 4 | 150.5 mg/ml | 1.32 | 0.181 | 1.64 | 100 | 0 | 0 | 0 | 0 |
| pH 4 | 219.0 mg/ml | 0.458 | 0.217 | 4070 | 62 | 0.621 | 38 | 0 | 0 |
| pH 4 | 251.8 mg/ml | 0.162 | 0.263 | 0 | 0 | 0 | 0 | 0 | 0 |
| pH 5 | 2 mg/ml | 157 | 0.468 | 1.88 | 84.3 | 181 | 10.7 | 17 | 5 |
| pH 5 | 50 mg/ml | 32.4 | 0.17 | 1.6 | 87.7 | 15.5 | 4.8 | 186 | 4.7 |
| pH 5 | 97.4 mg/ml | 1.32 | 0.183 | 1.52 | 97.4 | 3290 | 2.6 | 0 | 0 |
| pH 5 | 150.7 mg/ml | 0.931 | 0.209 | 1.36 | 98.7 | 3710 | 1.3 | 0 | 0 |
| pH 5 | 200.2 mg/ml | 0.335 | 0.203 | 0 | 0 | 0 | 0 | 0 | 0 |
| pH 5 | 253.0 mg/ml | 0.107 | 0.255 | 0 | 0 | 0 | 0 | 0 | 0 |
| pH 6 | 2 mg/ml | 30.8 | 0.382 | 2.78 | 60.9 | 273 | 30.2 | 5070 | 5 |
| pH 6 | 50 mg/ml | 2.78 | 0.247 | 2.68 | 86.4 | 1600 | 7.8 | 114 | 5.8 |
| pH 6 | 100 mg/ml | 2.01 | 0.171 | 2.48 | 100 | 0 | 0 | 0 | 0 |
| pH 6 | 146.6 mg/ml | 0.989 | 0.219 | 1.32 | 96.9 | 3770 | 301 | 0 | 0 |
| pH 6 | 201.8 mg/ml | 0.355 | 0.231 | 0 | 0 | 0 | 0 | 0 | 0 |
| pH 6 | 248.5 mg/ml | 0.108 | 0.301 | 0 | 0 | 0 | 0 | 0 | 0 |
| pH 7 | 2 mg/ml | 3.31 | 0.211 | 3.58 | 93.9 | 1250 | 6.1 | 0 | 0 |
| pH 7 | 50 mg/ml | 4.16 | 0.132 | 4.84 | 100 | 0 | 0 | 0 | 0 |
| pH 7 | 103.2 mg/ml | 2.89 | 0.141 | 3.39 | 100 | 0 | 0 | 0 | 0 |
| pH 7 | 143.3 mg/ml | 1.27 | 0.212 | 1.68 | 100 | 0 | 0 | 0 | 0 |
| pH 7 | 203.4 mg/ml | 0.346 | 0.306 | 0 | 0 | 0 | 0 | 0 | 0 |
| pH 7 | 251.7 mg/ml | 0.0876 | 0.497 | 0 | 0 | 0 | 0 | 0 | 0 |
| pH 8 | 2 mg/ml | 5.59 | 0.365 | 3.15 | 67.4 | 244 | 30.2 | 26.5 | 2.4 |
| pH 8 | 50 mg/ml | 5.62 | 0.174 | 7 | 100 | 0 | 0 | 0 | 0 |
| pH 8 | 96.1 mg/ml | 4.28 | 0.192 | 4.81 | 96.9 | 3640 | 3.1 | 0 | 0 |
| pH 8 | 148.5 mg/ml | 1.43 | 0.253 | 1.68 | 93.9 | 2910 | 6.1 | 0 | 0 |
| pH 8 | 200.6 mg/ml | 0.398 | 0.246 | 4920 | 100 | 0 | 0 | 0 | 0 |
| pH 8 | 230.7 mg/ml | 0.168 | 0.3 | 0 | 0 | 0 | 0 | 0 | 0 |

TABLE 40

| | | SEC data | | | |
|---|---|---|---|---|---|
| pH | conc. mg/mL | % aggregate | % monomer | % fragmente | Area (mVs) |
| 4 | 100 | 0.28 | 67.95 | 31.76 | 45195.348 |
| 4 | 150 | 0.26 | 66.07 | 33.68 | 44492.803 |
| 4 | 200 | 0.30 | 64.59 | 35.11 | 52558.050 |
| 4 | 250 | 0.29 | 64.40 | 35.31 | 48491.299 |
| 5 | 100 | 1.46 | 98.44 | 0.11 | 48127.249 |
| 5 | 150 | 1.33 | 98.56 | 0.11 | 43226.397 |
| 5 | 200 | 1.39 | 98.50 | 0.11 | 43634.282 |
| 5 | 250 | 1.38 | 98.52 | 0.11 | 41643.062 |
| 6 | 100 | 2.00 | 97.90 | 0.10 | 44338.373 |
| 6 | 150 | 2.52 | 97.37 | 0.11 | 41899.182 |
| 6 | 200 | 2.52 | 97.37 | 0.11 | 43869.183 |
| 6 | 250 | 2.39 | 97.50 | 0.11 | 34969.456 |
| 7 | 100 | 2.78 | 97.12 | 0.10 | 46194.824 |
| 7 | 150 | 4.24 | 95.65 | 0.11 | 47443.014 |
| 7 | 200 | 3.61 | 96.29 | 0.10 | 41916.220 |
| 7 | 250 | 3.39 | 96.50 | 0.11 | 38185.208 |
| 8 | 100 | 3.24 | 96.65 | 0.12 | 42334.491 |
| 8 | 150 | 3.64 | 96.18 | 0.18 | 40305.890 |
| 8 | 200 | 3.63 | 96.25 | 0.13 | 40280.342 |
| 8 | 250 | 3.76 | 96.05 | 0.19 | 32067.297 |

Example 18

Impact of pH on J695 Viscosity

Viscosity data were generated for J695 after DF/UF processing using water as exchange medium. J695 DS (see Example 1) was diafiltered against water, applying at least 5 DF/UF steps. Viscosity was then determined at various temperatures using a plate-plate viscometer, 100 rpm shear rate, 150 μm gap, 60 mm plate diameter (equipment: Bohlin Geminim viscometer (Malvern Instruments, Southborough, Mass.), temperature range evaluated 8-25° C.).

Figure 32:
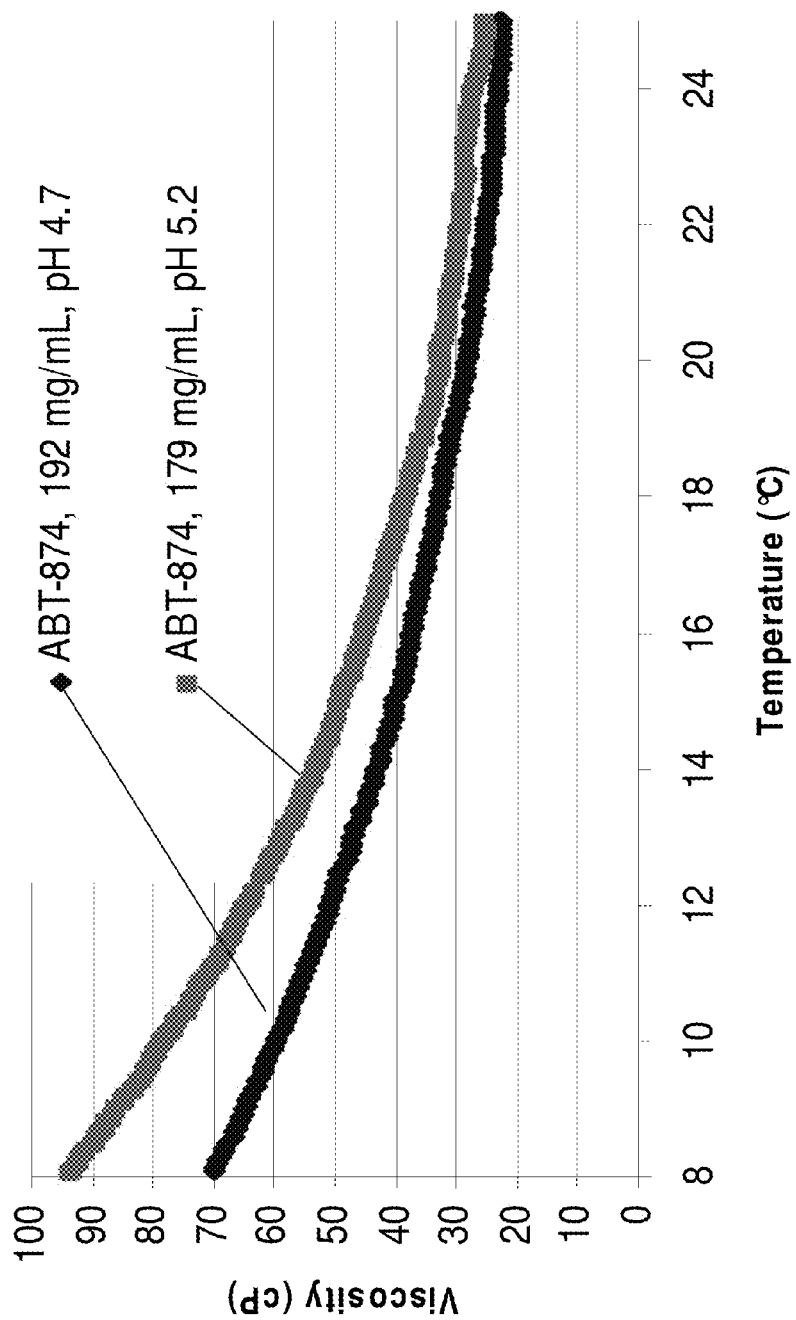
FIG. 32 shows the viscosity of two J695 solutions (WFI formulations) as a function of solution temperature.

As seen in FIG. 32, at concentrations of 179 mg/mL and 192 mg/mL, respectively, J695 solution viscosities were below 70 cP at 12° C., below 40 cP at 20° C., and below 30 cP at 25° C.

Example 19

Pharmacokinetics (PK) of an Antibody in Pure Water

The goal of this study was to evaluate potential impact of formulation parameters (i.e. low ionic protein formulation containing water vs conventional protein formulations using ionic excipients such as buffers and salts) on local tolerability and PK after sub-cutaneous (s.c.) dosing with Afelimomab. In addition, systemic toxicity and toxicokinetic data of the formulations was investigated. Protein concentrations used ranged from 50 mg/mL to 200 mg/mL and ionic strengths ranged from 3 mOsm/kg to 300 mOsm/kg.

A single (s.c.) dose feasibility study was carried out with Afelimomab (MAK195F—mouse anti human TNF F(ab')2 (Abbott Laboratories)) in male Sprague-Dawley rats to assess the local tolerance and toxicity of Afelimomab in rats following s.c. administration of liquid formulations at 50 and 200 mg/kg. Single s.c. doses were followed by an observation/recovery period. Limited blood sampling was carried out to measure circulating Afelimomab levels and assess absorption and half-life. The administered dose volume was 1 mL/kg body weight. The experimental groups included the following:

| | Experimental Groups | | |
|---|---|---|---|
| 01 | Control (vehicle) | | |
| 02 | 50 mg/ml Afelimomab, liquid, standard formulation | | |
| 07 | 200 mg/ml Afelimomab, liquid, water formulation | | |
| Group A | Observation period 2 days | | |
| Group B | Observation period 7 days | | |
| Group C | Observation period 14 days | | |
| Grouping and rat identification (N = 1 per group) | | | |
| | | Animal number | |
| Group | Group A | Group B | Group C |
| 01 | 1 | 2 | 3 |
| 02 | 4 | 5 | 6 |
| 07 | 19 | 20 | 21 |

The animals were repeatedly observed for clinical signs and mortality on day 1 at 15 min, 1, 3, 5, and 24 hours past administration and at least once daily afterwards. Body weights were measured on the days of dosing (day 1) and necropsy (day 3, 15 or 21, respectively) and twice weekly, if applicable. Blood samples for drug analysis were collected on Day 1 (4 hours past administration), and on Days 2, 3, 5, 8, and 15 as applicable. Prior to necropsy blood was collected and hematological and clinical chemistry parameters were evaluated. Blood smears were prepared of each animal prior to necropsy. At necropsy, macroscopy of body cavities was performed. Organ weight measurement was performed on liver, kidneys, thymus, spleen, and lymph nodes. Preliminary histopathology was performed on the injection site and on liver, kidneys, thymus, spleen, and lymph nodes.

All animals survived the study until scheduled necropsy. The rat administered the water formulation showed crusts in the cervical region from Day 14 to 15. No test item-related effect on body weight was observed. Hematology and clinical chemistry values were variable. No clearly test item-related changes were identified in haematology or clinical chemistry. No test item-related changes were noted in urinalysis. Measurement of organ weights resulted in high variability and no clearly test item-related changes in organ weights.

At gross observation reddening of the subcutis at the area of injection was noted in the rat receiving the water formulation at Day 3. All other changes belonged to the spectrum of spontaneous findings commonly seen in Sprague-Dawley rats of this strain and age.

Microscopic Findings were as follows:
No findings in Groups 01, 02
Minimal diffuse subcutaneous inflammation in Group 07
Focal subcutaneous hemorrhage correlating with reddening on gross pathology in Group 07 (Day 3), thought to be administration related
Preliminary immunohistochemistry results of pan-T, suppressor/cytotoxic T cells/natural killer cells, pan-B cells and pan-macrophage markers on the local reactions indicate mainly macrophages and natural killer cells involved in the subcutaneous inflammations/infiltrations. Thus, so far there are no hints for a local immunogenic response to the formulations used.

All other changes belonged to the spectrum of spontaneous findings commonly seen in Sprague-Dawley rats of this strain and age.

Following subcutaneous administration Afelimomab absorption appeared to be fast with maximum serum levels reached 0.2-3 days after injection. The absolute levels of Afelimomab in all samples tested were low. Large variability was observed between the samples, likely because of the limited sampling frequency and the low number of animals used. In most samples, no Afelimomab could be detected in serum after 5-8 days. This drop in serum levels is probably due to the high clearance of the F(ab')$_2$. The observed T½ for most samples were in the range of 1-2 days in agreement with previous observations. The longer half-life of the low-ionic formulation (7.8 d) may represent a protracted absorption of the sample. Data are presented in Tables 41 and 42.

TABLE 41

Plasma exposure levels of MAK195F

| | Time | Concentration (µg/ml) | | | Average | |
|---|---|---|---|---|---|---|
| | (day) | Rat 4 | Rat 5 | Rat 6 | (µg/ml) | STD |
| 50 mg/kg liquid standard formulation | 0.167 | 1.40 | 1.17 | 1.38 | 1.32 | 0.13 |
| | 2 | 0.76 | 0.97 | 0.66 | 0.80 | 0.16 |
| | 3 | 0.45 | 0.67 | 0.47 | 0.53 | 0.12 |
| | 5 | | LLOQ | LLOQ | LLOQ | |
| | 8 | | LLOQ | LLOQ | LLOQ | |
| | 15 | | | LLOQ | LLOQ | |

| | Time | Concentration (µg/ml) | | | Average | |
|---|---|---|---|---|---|---|
| | (day) | Rat 19 | Rat 20 | Rat 21 | (µg/ml) | STD |
| 200 mg/kg water formulation | 0.167 | 1.27 | 3.01 | 3.17 | 2.48 | 1.05 |
| | 2 | 0.17 | 1.57 | 1.53 | 1.09 | 0.80 |
| | 3 | LLOQ | 1.54 | 1.56 | 1.55 | 0.02 |
| | 5 | | 0.64 | 0.66 | 0.65 | 0.02 |
| | 8 | | 0.40 | 0.37 | 0.38 | 0.02 |
| | 15 | | | 0.25 | 0.25 | 0.00 |

LLOQ = below quantitation limit

There were no aggregation state findings for liquids, neither Afelimomab or control substance.

For the low-ionic strength formulation, minimal diffuse s.c. injection site inflammation was seen Inflammation, either minimal to slight, or slight to moderate, was seen with increased protein concentration (50 mg/mL and 200 mg/mL, respectively). Some local s.c. hemorrhage was seen, correlating with reddening on gross pathology; this was considered to be the consequence of blood vessel puncture during injection. Some subcutaneous reddening at the injection site was observed at Day 3 for the water formulation, but was not considered detrimental. Overall, the formulation was tolerated locally.

In Table 42 below, PK data of conventional liquid formulation vs. the water formulation is presented.

detectable serum levels and 'half-life' than in conventional MAK195F liquid formulation.

Afelimomab half-lives were in the range of 1-2 days in standard formulation in agreement with previous observations for F(ab')$_2$ molecules. However, a seemingly longer half-life was observed for the low-ionic formulation (7.8 d). Accordingly, the mean residence time of MAK 195F in this formulation appeared to be longer compared to the standard formulation tested.

Example 20

DF/UF of 2.5(E)mg1 (Anti IL-18 Antibody)

Diafiltration/ultrafiltration (continuous mode) of 2.5(E)mg1 bulk solution (59.6 mg/mL) was performed, applying an about 4-fold volume exchange using water for injection (in the following referred to as "water"). The DF/UF operation was controlled by monitoring turbidity, protein concentration (OD280), pH and osmolarity of retentate, and DLS measurements. During DF/UF, permeate osmolarities were also monitored to control the excipient reduction of the 2.5(E)mg1 bulk solutions.

Materials and Methods 2.5(E)mg1 Bulk Drug Substance (methionine, histidine, free of polysorbate 80) (Abbott Bioresearch Center, Worcester, Mass.): 2 PETG bottles with a total of 589.12 g solution, solution concentration 59.6 mg/mL.

Ampuwa (water for injection) (Fresenius Medical Care, Waltham, Mass.).

Millipore Labscale TFF DF/UF unit including 2× Pellicon XL filter cassettes, Millipore, PLCTK 30 kDa membrane, regenerated cellulose UV/VIS spectrophotometer, Specord 50 using 280 nm wavelength Metrohm pH-meter, type 744 with Biotrode probe No. 57

Osmometer: Knauer, K-7400 density measurements using equipment of Paar, DMA 4100

Laminar air flow box Hereaus turbidity measurements: Hach, 2100AN viscometer: Paar, AMVn scales: Mettler Toledo, AT261 and 33.45 filters: Millex AP 20 (fiberglass) and Minisart High Flow Filter (celluloseacetate), 0.20 µm pore size.

TABLE 42

Pharmacokinetic parameters of MAK 195F after subcutaneous dosing in different formulations.

| Dose (mg/kg) | Formulation | Half-life (day) | Tmax (day) | Cmax (µg/ml) | AUC (day * µg/ml) | Mean Residence Time (day) | Time of Last Detectable Conc. (day) | Last Detectable Conc. (µg/ml) |
|---|---|---|---|---|---|---|---|---|
| 50 | liquid | 0.5 | 0.2 | 1.32 | 3.3 | 1.5 | 3 | 0.53 |
| 200 | water formulation | 5.9 | 0.2 | 2.48 | 11.8 | 7.5 | 15 | 0.25 |

An increase in duration of detectable serum levels was seen with low ionic formulation (i.e. Afelimomab formulated in water), as seen in Table 42.

In this study, the observed absolute levels of MAK195F in low ionic solution (water) provided a better exposure, longer 20.1 Experimental Procedures Thawing of 2.5(E)mg1 DS samples: 2 L PETG bottles containing frozen DS were thawed within 2 hrs using a circulating water bath at 23° C. The thawed DS was clear, slightly opalescent, and free from visible particles.

Concentration of DS by DF/UF: due to the DF/UF unit reservoir volume limit of 530 mL, the 2.5(E)mg1 DS was concentrated to a final volume of 525 mL.

DF/UF using water (buffer exchange): the DS (methionine, histidine, 2.5(E)mg1) was subjected to DF/UF, applying a 4-fold volume exchange. Table 43 gives the amounts of water that were used throughout the experiment and Table 44 provides the experimental parameters.

TABLE 43

| | |
|---|---|
| DF/UF water volume exchanges | |
| Volume exchange | Volume of water used (cumulative) |
| 1-fold | 576 mL |
| 2-fold | 1152 mL |
| 3-fold | 1728 mL |
| 4-fold (end of experiment) | 2304 mL |

TABLE 44

| | |
|---|---|
| DF/UF procedure parameters | |
| Labscale TFF DF | settings |
| Pump speed | 1.5-2 |
| Pressure of pump | 20-30 psi |

TABLE 44-continued

| | |
|---|---|
| DF/UF procedure parameters | |
| Labscale TFF DF | settings |
| Stirring speed | ~3 |
| Experiment duration | 8 hrs |

Osmolarity measurement of permeate was performed at about every 200 mL of permeate processed.

After DF/UF against water, the volume of the 2.5(E)mg1 solution was 450 mL and the protein concentration 76.6 mg/mL. This solution, containing 2.5(E)mg1 dissolved essentially in water, was then concentrated.

TABLE 45

| | |
|---|---|
| DF/UF process parameters for solution concentration | |
| Labscale TFF UF | settings |
| Pump speed | 1.5-2 |
| Pressure of pump | max. 30 psi |
| Stirring speed | ~3 |
| Experiment duration | 51 min. |
| Final weight of solution: | 257.83 g |

The concentrated solution (~130 mg/mL) was subjected to 0.2 µm filtration. The solution was cooled to 2-8° C. and then stored at −80° C.

20.2 Data Collected During DF/UF of 2.5(E)mg1

TABLE 46

| | | | | | | |
|---|---|---|---|---|---|---|
| In Process control data | | | | | | |
| DF steps | Volume [mL] | time | Temperature solution/Room temperature [° C.] | turbidity [NTU] | pH | Osmolality [mOsmol/kg] | conc [mg/ml] |
| | 2.5(E)mg1 | | | 14.5 | 5.91 | 150 | 59.6 |
| 0[1] | 0 | 08:00 | 19.0/24.1 | N/A | 5.91 | 125 | 65.2 |
| 1 | 575 | 10:02 | 24.4/24.4 | 10.1 | 5.92 | 50 | 70.1 |
| 2 | 1150 | 11:50 | 24.3/24.7 | 6.67 | 5.94 | 16 | 72.8 |
| 3 | 1730 | 13:50 | 25.0/24.8 | 6.55 | 5.97 | 6 | 74.6 |
| ca. 4 | 2200 | 15:35 | 25.8/25.5 | 10.1 | 5.97 | 5 | 76.7 |

TABLE 47

| | | | | | | |
|---|---|---|---|---|---|---|
| Osmolalty of permeate (fractionated and measured during process) | | | | | | |
| Sample no. | time | Temperature solution/Room temperature [° C.] | Permeate [ml] | Permeate cumulative [ml] | No. Of DF/UF steps | osmolality [mOsmol/kg] |
| 0[3] | 07:35 | N/A | 90 | N/A | N/A | 125 |
| 1 | 08:00 | 19.0/24.1 | 200 | 200 | 0.3 | 124 |
| 2 | 08:50 | 23.0/24.1 | 200 | 400 | 0.7 | 82 |
| 3 | 09:27 | 24.0/24.2 | 200 | 600 | 1.0 | 53 |
| 4 | 10:12 | 24.4/24.4 | 200 | 800 | 1.4 | 37 |
| 5 | 10:50 | 24.5/24.3 | 200 | 1000 | 1.7 | 25 |
| 6 | 11:25 | 24.6/24.3 | 200 | 1200 | 2.1 | 16 |
| 7 | 12:10 | 24.7/24.3 | 230 | 1430 | 2.5 | 7 |
| 8 | 12:55 | 24.7/24.4 | 170 | 1600 | 2.8 | 4 |

TABLE 47-continued

Osmolalty of permeate (fractionated and measured during process)

| Sample no. | time | Temperature solution/Room temperature [° C.] | Permeate [ml] | Permeate cumulative [ml] | No. Of DF/UF steps | osmolality [mOsmol/kg] |
|---|---|---|---|---|---|---|
| 9 | 13:25 | 24.8/24.4 | 200 | 1800 | 3.1 | 2 |
| 10 | 14:15 | 25.1/24.8 | 200 | 2000 | 3.5 | 0 |
| 11 | 14:55 | 25.8/25.5 | 200 | 2200 | 3.8 | 1 |

TABLE 48

Concentration of 2.5(E)mg1 solution after buffer exchange

| time | Solution temperature [° C.] | Volume in reservoir (i.e. retentate) [ml] | pH |
|---|---|---|---|
| 15:54 | 25.9 | 450 | 5.94 |
| 16:02 | 26.1 | 400 | 5.96 |
| 16:07 | 26.1 | 375 | 5.96 |
| 16:20 | 26.2 | 350 | 5.96 |
| 16:28 | 26.3 | 300 | 5.98 |
| 16:35 | 26.5 | 275 | 5.98 |
| 16:45 | 26.5 | 250 | 5.99 |

TABLE 49

Analytical characterization of concentrated 2.5(E)mg1 solution (before and after 0.2 μm filtration):

| | lot | |
|---|---|---|
| parameter | before filtration | after filtration |
| turbidity [NTU] | 15.4 | 9.58 |
| osmolality [mOsmol/kg] | 6 | N/A |
| density [g/ml] | 1.0346 | N/A |
| pH | 5.99 | N/A |
| Dyn. Viscosity (25° C.) [mPas] | N/A | 7.9998 |

TABLE 50

Dynamic light scattering data (determination of Dh of monomer and z-average value of Dh = Dh of all specimen present in solution) during DF/UF

| | Sample pull | | | | | |
|---|---|---|---|---|---|---|
| DLS data | DV 1-fold | DV 2-fold | DV 3-fold | DV 4-fold | After concentration | After filtration |
| Peak 1 | | | | | | |
| diameter monomer | 4.32 | 3.68 | 3.54 | 3.48 | 2.03 | 2.13 |
| intensity [%] | 100.0 | 100.0 | 100.0 | 89.6 | 87.0 | 100.0 |
| Z-Average [nm] | 3.95 | 3.28 | 3.20 | 3.53 | 2.12 | 1.89 |
| Pdl | 0.077 | 0.106 | 0.094 | 0.245 | 0.287 | 0.113 |
| Peak 2 | | | | | | |
| diameter [nm] | N/A | N/A | N/A | 984 | 411 | N/A |
| intensity [%] | | | | 10.4 | 11.8 | |
| Peak 3 | | | | | | |
| diameter [nm] | N/A | N/A | N/A | N/A | 4260 | N/A |
| intensity [%] | | | | | 1.2 | |

20.3 Discussion

The experiment demonstrated that 2.5(E)mg1 (buffered in methionine, histidine) can be formulated in essentially water at higher concentration (no solubility limitations observed at 130 mg/mL). After 3 volume exchanges using water osmolality of permeate and retentate were below 10 mOsmol/kg, demonstrating that buffer excipients have been effectively reduced. The opalescence of the 2.5(E)mg1 solution was reduced during DF/UF using water (optimal appearance), mirrored also by reduces turbidity values (nephelometric turbidity units (NTU) of DS starting solution 14.5, after 3-fold volume exchange 6.55, after 4-fold volume exchange 10.5.

As seen with other antibodies, the hydrodynamic diameter as determined by DLS decreased due to excipient reduction (intermolecular charge-charge repulsion adding to random Brownian motion, resulting in higher molecule mobility, translates to lower Dh values calculated). The pH of the 2.5(E)mg1 solution was basically the same before (pH 5.94) and after (pH 5.99) the DF/UF operation.

As shown by DLS monitoring, the 2.5(E)mg1 remained stable during the DF/UF operation. No substantial increase in high molecular weight specimen was detected.

Example 21

Preparation of Adalimumab Formulated in Water and Stability Studies Thereof

The following example describes the stability of a formulation comprising adalimumab originating from processes described in the above examples, i.e., adalimumab was successfully dialyzed into water.

Materials and Methods 3323.6 g Adalimumab solution (71.3 mg/mL) were diafiltered using pure water. After a 7-fold volume exchange with pure water (theoretical excipients reduction, 99.9%), the protein solution was diluted/ultrafiltered to final target concentrations of 220 and 63 mg/mL, respectively. PH, osmolality, viscosity, conductivity, PCS, visual inspection and protein concentration measurements (OD280) were performed to monitor the status of the protein after DF/UF processing.

After DF/UF processing, the protein solutions were sterile filtered (0.22 μm Millipak-60 and Millipak-200 membrane filters) and subsequently filled into BD HyPak SCF™ 1 mL long syringes, equipped with 27.5 G RNS needles and sterile BD HyPak BSCF 4432/50 stoppers. The filling volume was around 0.825 mL per syringe.

After filling the syringes were stored at 2-8° C., 25° C. and 40° C., respectively, and analyzed as indicated in the sample pull scheme depicted below.

Adalimumab Drug Substance (Adalimumab extinction coefficient 280 nm: 1.39 mL/mg cm): Drug Substance did not contain polysorbate 80. DS buffer, pH 5.38.

Sortorius Sartocon Slice diafiltration system, equipped with Ultrasert PES membrane cassettes (50 kDa and 30 kDa cutoff). The Sartocon Slice system was operated in continuous mode at ambient temperature according to Sartorius Operating Instructions.

pH electrodes

PerkinElmer UV visible spectrophotometer, Lambda 35, was used for protein concentration measurements (280 nm wavelength). Disposable UV cuvettes, 1.5 mL, semi-micro, Poly(methyl methacrylate) (PMMA), were used for the concentration measurements.

Sterilized water for injection Ph.Eur./USP was used as DF/UF medium.

A Vogel Osmometer OM815, was used for osmolality measurements (calibrated with 400 mOsmol/kg NaCl calibration solution, Art. No. Y1241, Herbert Knauer GmbH, Berlin, Germany).

Anton Paar Microviscosimeter, type AWVn, was used for viscosity assessment of the protein solutions according to Anton Paar Operating Instructions. Viscosity was assessed at 20° C.

An InoLab Cond Level2 WTW device was used for conductivity measurements normalized to 25° C.

A Malvern Instruments Zetasizer nano ZS, was used for determination of Z-average values, applying a standard method. Measurements were performed at 25° C., using viscosity data obtained by falling ball viscosimetry (Anton Paar Microviscosimeter, type AWVn, at 25° C.).

HPLC Methods

Adalimumab, SEC analysis: Sephadex 200 column (Pharmacia Cat. No. 175175-01). Mobile phase 20 mM sodium phosphate, 150 mM sodium chloride, pH 7.5, 0.5 mL/min flow rate, ambient temperature, detection UV 214 nm and 280 nm. Each sample was diluted to 1.0 mg/mL with Milli-Q water, sample injection load 50 μg (duplicate injection).

Adalimumab, IEC analysis: Dionex, Propac WCX-10 column (p/n 054993) along with a corresponding guard column (p/n 054994). Separation conditions: mobile phase A: 10 mM sodium phosphate, pH 7.5; mobile phase B 10 mM Sodium phosphate, 500 mM Sodium chloride, pH 5.5. 1.0 mL/min flow rate, ambient temperature. Each sample was diluted to 1.0 mg/mL with Milli-Q water, sample injection load 100 μg, duplicate injection.

Calculation of the Protein Concentration

Calculation Formula:

$$E = -lg\left(\frac{I}{I_0}\right) = \varepsilon \cdot c \cdot d \rightarrow c = \frac{E}{\varepsilon \times d}$$

$\varepsilon$ – absorption coefficient $c$ – concentration $d$ – length of cuvette that the light has to pass $E$ – absorbance $I_0$ – initial light intensity $I$ – light intensity after passing through sample $$\varepsilon_{Adalimumab} = 1.39 \frac{mL}{mg \times cm}$$

Sample Pull Scheme

Samples of the prepared solutions are stored at the temperatures listed below and pulled (x) at the indicated time points after study start.

| Temp. | T0 | 1 m | 3 m |
|---|---|---|---|
| 5° C. | — | x | x |
| 25° C. | x | x | x |
| 40° C. | — | x | x |

| Test parameter | Test method |
|---|---|
| Visible particles | analogous DAC (EA 4.43) |
| Subvisible particles | analogous Ph. Eur./USP EA 4.44 |
| Turbidity | analogous Ph. Eur. (EA 4.42) |
| Color (visual) | Ph. Eur. (EA 4.50) |
| pH | Ph. Eur. (EA 4.24) |
| Size exclusion HPLC | Desribed in the text above |
| Cation exchange HPLC | Desribed in the text above |

DF/UF Processing of Adalimumab

Table 51 describes the adalimumab characteristics after diafiltration.

TABLE 51

| Sample | Protein Concentration [mg/mL] | pH | Osmolality [mosmol/kg] | Viscosity [cP] | Visual Inspection | Conductivity [µS/cm] | PCS [Z-average/ d · nm] |
|---|---|---|---|---|---|---|---|
| High concentration | 220 | 5.57 | 26 | 27.9 | Slightly opalescent, essentially free from visible particles | 1167 | 0.34 |
| Low concentration | 63 | 5.44 | 5 | 1.8 | Slightly opalescent, essentially free from visible particles | 522 | 1.85 |

Adalimumab characterization upon storage, including clarity and opalescence, degree of coloration of liquids, SEC, at different temperature degrees is described in Appendix D.

Conclusion

The above example provides a diafiltration/ultrafiltration (DF/UF) experiment where water (sterilized water for injection Ph.Eur./USP) was used as diafiltration medium for the monoclonal antibody Adalimumab.

Adalimumab was subjected to DF/UF processing by using pure water as DF/UF exchange medium and was formulated at pH 5.57 at high concentration (220 mg/mL) and at pH 5.44 at lower concentration (63 mg/mL) without inducing solution haziness, severe opalescence or turbidity formation.

Adalimumab from the DF/UF experiments was stored in SCF syringes at 2-8° C., 25° C. and 40° C. for 3 months. Data obtained points at favorable overall stability of the protein.

In conclusion, processing and formulating proteins using pure water as DF/UF exchange medium is feasible. Assuming an ideal 100% excipient membrane permeability, an approx. 99.9% maximum excipient reduction can be estimated.

Example 22

Stability Studies of Adalimumab Formulated in Water Using Non-Ionic Excipients

The following example describes stability studies of a formulation containing an antibody, i.e., adalimumab, in water with additional non-ionic excipients.

Materials and Methods

Adalimumab material was the same as in example 21 (DF/UF processing). After DF/UF processing, the protein solutions were formulated as denoted in Table 52. Mannitol was chosen as example from the group of sugar alcohols, like mannitol, sorbitol, etc. Sucrose was chosen as example from the group of sugars, like sucrose, trehalose, raffinose, maltose, etc. Polysorbate 80 was chosen as example from the group of non-ionic surfactants, like polysorbate 80, polysorbate 20, pluronic F68, etc. ~10.7 mL were prepared for any formulation. Osmolality, viscosity and PCS measurements were performed for any formulation after preparation.

TABLE 52

| Final protein concentration | Mannitol (mg/mL) | Sucrose (mg/mL) | Polysorbate 80 (% w/w) | Sample Name |
|---|---|---|---|---|
| 50 mg/mL | 50 | — | — | LI50/01 |
| 50 mg/mL | — | 80 | — | LI50/02 |
| 50 mg/mL | 50 | — | 0.01 | LI50/03 |
| 50 mg/mL | — | 80 | 0.01 | LI50/04 |
| 50 mg/mL | 50 | — | 0.1 | LI50/05 |
| 50 mg/mL | — | 80 | 0.1 | LI50/06 |
| 50 mg/mL | — | — | 0.01 | LI50/07 |
| 50 mg/mL | — | — | 0.1 | LI50/08 |
| 200 mg/mL | 50 | — | — | LI200/01 |
| 200 mg/mL | — | 80 | — | LI200/02 |
| 200 mg/mL | 50 | — | 0.01 | LI200/03 |
| 200 mg/mL | — | 80 | 0.01 | LI200/04 |
| 200 mg/mL | 50 | — | 0.1 | LI200/05 |
| 200 mg/mL | — | 80 | 0.1 | LI200/06 |
| 200 mg/mL | — | — | 0.01 | LI200/07 |
| 200 mg/mL | — | — | 0.1 | LI200/08 |

Polysorbate 80 stock solution 0.5% and 5% in sterile water for injection: Addition in 1:50 ratio (210 µL to 10.5 mL Adalimumab solution, addition of 210 µL water for injection to samples formulated without surfactant to assure equal protein concentration in all samples) Addition of mannitol/sucrose in solid form (525 mg/840 mg, respectively).

The preparations were sterile filtered (Millex GV, Millipore, 0.22 µm, Ø33 mm, Art. SLGV033RS) and subsequently filled into BD HyPak SCF™ 1 mL long syringes, equipped with 27.5 G RNS needles and sterile BD HyPak BSCF 4432/50 stoppers. The filling volume was around 0.6 mL per syringe.

After filling the syringes were stored at 2-8° C., 25° C. and 40° C., respectively, and analyzed as indicated in the sample pull scheme depicted below.

Adalimumab Drug Substance (Adalimumab extinction coefficient 280 nm: 1.39 mL/mg cm): Drug Substance did not contain polysorbate 80. DS buffer, pH 5.38.

PH electrodes

Sterilized water for injection Ph.Eur./USP was used as DF/UF medium.

Mannitol, polysorbate 80, and sucrose, all matching Ph.Eur. quality

A Vogel Osmometer OM815, was used for osmolality measurements (calibrated with 400 mOsmol/kg NaCl calibration solution, Art. No. Y1241, Herbert Knauer GmbH, Berlin, Germany).

Anton Paar Microviscosimeter, type AWVn, was used for viscosity assessment of the protein solutions according to Anton Paar Operating Instructions. Viscosity was assessed at 20° C.

Fluostar Optima, BMG Labtech (absorption measurement at 344 nm in well plates, assessment of turbidity)

A Malvern Instruments Zetasizer nano ZS, was used for determination of Z-average values, applying a standard method. Measurements were performed at 25° C., using viscosity data obtained by falling ball viscosimetry (Anton Paar Microviscosimeter, type AWVn, at 25° C.).

HPLC Methods

Adalimumab, SEC analysis: Sephadex 200 column (Pharmacia Cat. No. 175175-01). Mobile phase 20 mM sodium phosphate, 150 mM sodium chloride, pH 7.5, 0.5 mL/min flow rate, ambient temperature, detection UV 214 nm and 280 nm. Each sample was diluted to 1.0 mg/mL with Milli-Q water, sample injection load 50 μg (duplicate injection).

Adalimumab, IEC analysis: Dionex, Propac WCX-10 column along with a corresponding guard column. Separation conditions: mobile phase A: 10 mM sodium phosphate, pH 7.5; mobile phase B 10 mM Sodium phosphate, 500 mM Sodium chloride, pH 5.5. 1.0 mL/min flow rate, ambient temperature. Each sample was diluted to 1.0 mg/mL with Milli-Q water, sample injection load 100 μg, duplicate injection.

Sample Pull Scheme

Samples of the prepared solutions were stored at 5° C., 25° C., and 40° C. and pulled at either 1 minute (5° C. and 40° C.) or at T0 and 1 minute (25° C.) after study start. Test parameters were measured according to appropriate methods, e.g., color was determined visually, turbidity was determined at an absorption at 344 nm.

Initial Formulation Characterization

Table 53 described the initial formulation osmolalities and viscosities.

TABLE 53

| Lot. | comp. | osmolarity [mosmol] | viscosity [mPas] |
|---|---|---|---|
| LI 50/01 | 50 mg/mL mannitol | 309 | 1,9796 |
| LI 50/02 | 80 mg/mL sucrose | 272 | 2,1284 |
| LI 50/03 | 50 mg/mL mannitol; 0.01% Tween 80 | 307 | 1,9843 |
| LI 50/04 | 80 mg/mL sucrose; 0.01% Tween 80 | 269 | 2,1194 |
| LI 50/05 | 50 mg/mL mannitol; 0.1% Tween 80 | 307 | 1,9980 |
| LI 50/06 | 80 mg/mL sucrose; 0.1% Tween 80 | 272 | 2,1235 |
| LI 50/07 | 0.01% Tween 80 | 8 | 1,7335 |
| LI 50/08 | 0.1% Tween 80 | 8 | 1,8162 |
| LI 200/01 | 50 mg/mL mannitol | 396 | 21,395 |
| LI 200/02 | 80 mg/mL sucrose | 351 | 21,744 |
| LI 200/03 | 50 mg/mL mannitol; 0.01% Tween 80 | 387 | 21,233 |
| LI 200/04 | 80 mg/mL sucrose; 0.01% Tween 80 | 350 | 21,701 |
| LI 200/05 | 50 mg/mL mannitol; 0.1% Tween 80 | 387 | 21,592 |
| LI 200/06 | 80 mg/mL sucrose; 0.1% Tween 80 | 355 | 21,943 |
| LI 200/07 | 0.01% Tween 80 | 27 | 21,296 |
| LI 200/08 | 0.1% Tween 80 | 28 | 21,889 |

All formulations of one concentration demonstrated equal viscosities. Those of sucrose containing formulations were slightly higher. The reduced viscosities of the highly concentrated formulations in comparison to the highly concentrated formulation in water (example A, viscosity 27.9 cP) is explained by sample dilution with polysorbate 80 stock solutions or plain water, leading to a final concentration of ~215 mg/mL vs. 220 mg/mL in example 21.

Table 54 describes the PCS data determined for each sample.

TABLE 54

| Sample | PCS [Z-average/d · nm] |
|---|---|
| LI50/01 | 2.58 |
| LI50/02 | 2.22 |
| LI50/03 | 2.13 |
| LI50/04 | 2.22 |
| LI50/05 | 2.25 |
| LI50/06 | 2.55 |
| LI50/07 | 2.87 |
| LI50/08 | 1.94 |
| LI200/01 | 0.50 |
| LI200/02 | 0.43 |
| LI200/03 | 0.36 |
| LI200/04 | 0.38 |
| LI200/05 | 0.37 |
| LI200/06 | 0.41 |
| LI200/07 | 0.35 |
| LI200/08 | 0.36 |

The data provided in Table 54 shows that z-average values do not significantly differ from the values obtained from Adalimumab solutions in non-ionic excipient free systems (63 mg/mL, 1.85 d·nm, 220 mg/mL, 0.34 d·nm, example 21).

Adalimumab Characterization Upon Storage

Appendix E provides data on Adalimumab stability upon storage.

Conductivity of Placebo Solutions

Table 55 describes the influence of non-ionic excipients on the conductivity of the various adalimumab formulations. All placebo solutions were prepared using sterilized water for injection Ph.Eur./USP.

TABLE 55

| Mannitol (mg/mL) | Sucrose (mg/mL) | Polysorbate 80 (% w/w) | Conductivity (μS/cm) |
|---|---|---|---|
| — | — | — | 1.1 |
| 50 | — | — | 1.2 |
| — | 80 | — | 2.2 |
| 50 | — | 0.01 | 2.3 |
| — | 80 | 0.01 | 1.4 |
| 50 | — | 0.1 | 2.6 |
| — | 80 | 0.1 | 3.6 |
| — | — | 0.01 | 1.2 |
| — | — | 0.1 | 2.6 |

Conclusion

The preparations were stored in SCF syringes at 2-8° C., 25° C. and 40° C. for 1 month. Data obtained from the storage study showed that there was overall stability of the protein in all formulations tested. The stability data was comparable to the stability of samples from example 21. Measurement of the conductivity of non-ionic excipient containing placebo solutions demonstrates a marginal increase of conductivity for some excipients in the range of some μS/cm. PCS measurements demonstrate no significant increase in hydrodynamic diameters in comparison to non-ionic excipient free systems.

In conclusion, processing proteins using pure water as DF/UF exchange medium and formulation with non-ionic excipients is feasible. Adalimumab was also assessed by PCS in a buffer of following composition: 10 mM phosphate buffer, 100 mM sodium chloride, 10 mM citrate buffer, 12 mg/mL mannitol, 0.1% polysorbate 80, pH 5.2. The Adalimumab concentration was 50 mg/mL and 200 mg/mL, respectively. The z-average values were 11.9 d·nm for the 50 mg/mL formulation and 1.01 d·nm for the 200 mg/mL formulation, respectively. Thus, it was clearly demonstrated that hydrodynamic diameters at a given protein concentration are dependent on the ionic strength (clearly higher diameters in salt containing buffers).

Example 23

Preparation of J695 Formulated in Water With Non-Ionic Excipients

The following example describes the preparation of a formulation containing an antibody, i.e., adalimumab, in water with additional non-ionic excipients. The example also describes the stability (as measured for example by SE-HPLC and IEC) of J695 formulated in water with additional non-ionic excipients.

Materials and Methods

2×30 mL J695 solution (~125 mg/mL) at different pH were dialyzed using pure water applying Slide-A-Lyzer dialysis cassettes. Dialysis of the samples was performed for 3 times against 3 L pure water, respectively (theoretical excipients reduction, 1:1,000,000). The protein solutions were ultrafiltered to final target concentrations of 200 mg/mL, by using Vivaspin 20 concentrators. PH, osmolality, viscosity, conductivity, PCS, visual inspection, HPLC and protein concentration measurements (OD280) were performed to monitor the status of the protein during and after processing.

After processing, the protein solutions were formulated as denoted in the following. Mannitol was chosen as an example to use from the group of sugar alcohols, like mannitol, sorbitol, etc. Sucrose was chosen as an example to use from the group of sugars, like sucrose, trehalose, raffinose, maltose, etc. Polysorbate 80 was chosen as an example to use from the group of non-ionic surfactants, like polysorbate 80, polysorbate 20, pluronic F68, etc. A volume of 0.5 mL was prepared for each of these formulations. PH, osmolality, visual inspection, and HPLC analysis were performed to monitor the status of the protein after sample preparation.

TABLE 56

Description of various J695 formulations

| Final protein concentration | Mannitol (mg/mL) | Sucrose (mg/mL) | Polysorbate 80 (% w/w) | Sample Name* |
|---|---|---|---|---|
| 200 mg/mL | 50 | — | — | LI200/01/5 |
| 200 mg/mL | — | 80 | — | LI200/02/5 |
| 200 mg/mL | 50 | — | 0.01 | LI200/03/5 |
| 200 mg/mL | — | 80 | 0.01 | LI200/04/5 |
| 200 mg/mL | 50 | — | 0.1 | LI200/05/5 |
| 200 mg/mL | — | 80 | 0.1 | LI200/06/5 |
| 200 mg/mL | — | — | 0.01 | LI200/07/5 |
| 200 mg/mL | — | — | 0.1 | LI200/08/5 |
| 200 mg/mL | 50 | — | — | LI200/01/6 |
| 200 mg/mL | — | 80 | — | LI200/02/6 |
| 200 mg/mL | 50 | — | 0.01 | LI200/03/6 |
| 200 mg/mL | — | 80 | 0.01 | LI200/04/6 |
| 200 mg/mL | 50 | — | 0.1 | LI200/05/6 |
| 200 mg/mL | — | 80 | 0.1 | LI200/06/6 |
| 200 mg/mL | — | — | 0.01 | LI200/07/6 |
| 200 mg/mL | — | — | 0.1 | LI200/08/6 |

*The term "/5" or "/6" is added to any sample name to differentiate between samples at pH 5 and 6.
Polysorbate 80 stock solution 0.5% and 5% in sterile water for injection: Addition in 1:50 ratio (10 μL to 0.5 mL J695 solution, addition of 10 μL water for injection to samples formulated without surfactant to assure equal protein concentration in all samples)
Addition of mannitol/sucrose in solid form (25 mg/40 mg, respectively).

J695 Drug Substance (J695 extinction coefficient 280 nm: 1.42 mL/mg cm): Drug Substance did not contain polysorbate 80. DS buffer, pH 6.29.

pH electrodes

Demineralized and sterile filtered water was used as dialysis medium.

Mannitol, polysorbate 80, and sucrose, all matching Ph.Eur. quality

A Vogel Osmometer OM815, was used for osmolality measurements (calibrated with 400 mOsmol/kg NaCl calibration solution, Art. No. Y1241, Herbert Knauer GmbH, Berlin, Germany).

Anton Paar Microviscosimeter, type AWVn, was used for viscosity assessment of the protein solutions according to Anton Paar Operating Instructions. Viscosity was assessed at 20° C.

Fluostar Optima, BMG Labtech (absorption measurement at 344 nm in well plates, assessment of turbidity)

Eppendorf Centrifuge 5810 R

Slide-A-Lyzer dialysis cassettes, Pierce Biotechnology (Cat No 66830)

Vivaspin 20 concentrators, 10 $K_D$a PES membranes (Vivascience, Product number VS2001), used according to standard Operating Instructions PerkinElmer UV visible spectrophotometer, Lambda 35, was used for protein concentration measurements (280 nm wavelength). Disposable UV cuvettes, 1.5 mL, semi-micro, Poly(methyl methacrylate) (PMMA), were used for the concentration measurements.

An InoLab Cond Level2 WTW device was used for conductivity measurements normalized to 25° C.

A Malvern Instruments Zetasizer nano ZS, was used for determination of Z-average values, applying a standard method. Measurements were performed at 25° C., using viscosity data obtained by falling ball viscosimetry (Anton Paar Microviscosimeter, type AWVn, at 25° C.).

HPLC Methods

J695, SEC analysis: Tosoh Bioscience G3000swxl, 7.8 mm×30 cm, 5 μm (Cat. No. 08541). Mobile phase 211 mM $Na_2SO_4$/92 mM $Na_2HPO_4$, pH 7.0.0.25 mL/min flow rate, ambient temperature, detection UV 214 nm and 280 nm. Each sample was diluted to 2.0 mg/mL with Milli-Q water, sample injection load 20 μg (duplicate injection).

J695, IEC analysis: Dionex, Propac WCX-10 column (p/n 054993) along with a corresponding guard column (p/n 054994). Separation conditions: mobile phase A: 10 mM $Na_2HPO_4$, pH 6.0; mobile phase B 10 mM Na$_2$HPO$_4$, 500 mM NaCl, pH 6.0. 1.0 mL/min flow rate, 35° C. temperature. Each sample was diluted to 1.0 mg/mL with Milli-Q water, sample injection load 100 μg.

Calculation of the Protein Concentration

Calculation Formula:

$$E = -lg\left(\frac{I}{I_0}\right) = \varepsilon \cdot c \cdot d \rightarrow c = \frac{E}{\varepsilon \times d}$$

$\varepsilon$ – absorption coefficient $c$ – concentration $d$ – length of cuvette that the light has to pass $E$ – absorbance $I_0$ – initial light intensity $I$ – light intensity after passing through sample $$\varepsilon_{Adalimumab} = 1.42 \frac{mL}{mg \times cm}$$

Processing of J695

J695 in water was characterized prior to the addition of any non-ionic excipients. Table 57 provides details of the J695 characterization during dialysis/ultrafiltration.

TABLE 57

| Sample | Protein Concentration [mg/mL] | pH | Osmolality [mosmol/kg] | Viscosity [cP] | Visual Inspection | Conductivity [μS/cm] | PCS [Z-average/ d · nm] |
|---|---|---|---|---|---|---|---|
| Starting material | ~125 mg/mL | 6.29 (for low pH samples, adjusted to 4.77 with 0.01M hydrochloric acid) | N/A | N/A | Slightly opalescent, essentially free from visible particles | N/A | N/A |
| After dialysis, low pH | 42.5 mg/mL | 5.21 | 7 | 1.60 | Slightly opalescent, essentially free from visible particles | 602 | 1.5 |
| After dialysis, high pH | 56.9 mg/mL | 6.30 | 6 | 2.11 | Slightly opalescent, essentially free from visible particles | 500 | 2.7 |
| After concentration, low pH | 206 mg/mL | 5.40 | 50 | 39.35 | Slightly opalescent, essentially free from visible particles | 1676 | 0.21 |
| After concentration, high pH | 182 mg/mL | 6.46 | 39 | 47.76 | Slightly opalescent, essentially free from visible particles | 1088 | 0.21 |

Characterization of Formulations with Non-Ionic Excipients

Following the addition of the various non-ionic excipients to the J695 formulation (see description in Table 56), each formulation was analysed. Results from osmolality and visual inspection, and pH are described below in Table 58.

TABLE 58

| Sample | pH | Osmolality [mosmol/kg] | Visual Inspection |
|---|---|---|---|
| LI200/01/5 | 5.39 | 473 | Slightly opalescent, essentially free from visible particles |
| LI200/02/5 | 5.38 | 402 | Slightly opalescent, essentially free from visible particles |
| LI200/03/5 | 5.37 | 466 | Slightly opalescent, essentially free from visible particles |
| LI200/04/5 | 5.37 | 397 | Slightly opalescent, essentially free from visible particles |
| LI200/05/5 | 5.37 | 458 | Slightly opalescent, essentially free from visible particles |
| LI200/06/5 | 5.37 | 396 | Slightly opalescent, essentially free from visible particles |
| LI200/07/5 | 5.36 | 50 | Slightly opalescent, essentially free from visible particles |
| LI200/08/5 | 5.36 | 48 | Slightly opalescent, essentially free from visible particles |
| LI200/01/6 | 6.43 | 428 | Slightly opalescent, essentially free from visible particles |
| LI200/02/6 | 6.42 | 405 | Slightly opalescent, essentially free from visible particles |
| LI200/03/6 | 6.43 | 348 | Slightly opalescent, essentially free from visible particles |
| LI200/04/6 | 6.43 | 383 | Slightly opalescent, essentially free from visible particles |
| LI200/05/6 | 6.42 | 432 | Slightly opalescent, essentially free from visible particles |
| LI200/06/6 | 6.42 | 402 | Slightly opalescent, essentially free from visible particles |
| LI200/07/6 | 6.43 | 38 | Slightly opalescent, essentially free from visible particles |
| LI200/08/6 | 6.43 | 39 | Slightly opalescent, essentially free from visible particles |

HPLC Data

Each of the non-ionic excipient containing J695 formulations were also examined using SE-HPLC and IEX. The data from these analyses are provided in Tables 59 and 60 and provide an overview of J695 stability during processing and formulation.

TABLE 59

SE-HPLC results of various J695 formulations

| sample name | Sum Aggregates [%] | Monomer [%] | Sum Fragments [%] |
|---|---|---|---|
| pH 5 | 0.608 | 98.619 | 0.773 |
| 125 mg/mL | 0.619 | 98.598 | 0.783 |
| starting mat. | 0.614 | 98.608 | 0.778 |
| pH 6 | 0.427 | 98.809 | 0.764 |
| 125 mg/mL | 0.392 | 99.005 | 0.603 |
| starting mat. | 0.409 | 98.907 | 0.683 |
| pH 5 | 0.654 | 98.604 | 0.742 |
| 42.5 mg/mL | 0.677 | 98.560 | 0.763 |
| after dialysis | 0.666 | 98.582 | 0.753 |
| pH 6 | 0.748 | 98.541 | 0.711 |
| 56.9 mg/mL | 0.739 | 98.597 | 0.665 |
| after dialysis | 0.743 | 98.569 | 0.688 |
| pH 5 | 0.913 | 98.416 | 0.671 |
| 206 mg/mL | 0.923 | 98.356 | 0.721 |
| In Water | 0.918 | 98.386 | 0.696 |
| pH 5 | 0.928 | 98.312 | 0.760 |
| 50 mg/mL mannitol | 0.926 | 98.339 | 0.736 |
| LI 200/01/5 | 0.927 | 98.325 | 0.748 |
| pH 5 | 0.925 | 98.319 | 0.755 |
| 80 mg/mL sucrose | 0.929 | 98.332 | 0.738 |
| LI 200/02/5 | 0.927 | 98.326 | 0.747 |
| pH 5, 50 mg mannitol | 0.942 | 98.326 | 0.732 |
| 0.01% Tween 80 | 0.942 | 98.300 | 0.758 |
| LI 200/03/5 | 0.942 | 98.313 | 0.745 |
| pH 5, 80 mg sucrose | 0.944 | 98.315 | 0.741 |
| 0.01% Tween 80 | 0.944 | 98.339 | 0.717 |
| LI 200/04/5 | 0.944 | 98.327 | 0.729 |
| pH 5, 50 mg mannitol | 0.941 | 98.348 | 0.711 |
| 0.1% Tween 80 | 0.967 | 98.299 | 0.734 |
| LI 200/05/5 | 0.954 | 98.323 | 0.722 |
| pH 5, 50 mg mannitol | 0.944 | 98.346 | 0.710 |
| 0.1% Tween 80 | 0.948 | 98.340 | 0.712 |
| LI 200/06/5 | 0.946 | 98.343 | 0.711 |
| pH 5, 50 mg mannitol | 0.946 | 98.348 | 0.706 |
| 0.1% Tween 80 | 0.953 | 98.328 | 0.719 |
| LI 200/07/5 | 0.949 | 98.338 | 0.713 |
| pH 5, 50 mg mannitol | 0.987 | 98.313 | 0.701 |
| 0.1% Tween 80 | 0.994 | 98.283 | 0.723 |
| LI 200/08/5 | 0.991 | 98.298 | 0.712 |
| pH 6 | 1.091 | 98.169 | 0.739 |
| 182 mg/mL | 1.075 | 98.221 | 0.703 |
| In Water | 1.083 | 98.195 | 0.721 |
| pH 6 | 0.998 | 98.350 | 0.652 |
| 50 mg/mL mannitol | 1.002 | 98.364 | 0.634 |
| LI 200/01/6 | 1.000 | 98.357 | 0.643 |
| pH 6 | 1.028 | 98.243 | 0.729 |
| 80 mg/mL sucrose | 0.983 | 98.355 | 0.662 |
| LI 200/02/6 | 1.006 | 98.299 | 0.695 |
| pH 6, 50 mg mannitol | 1.005 | 98.322 | 0.673 |
| 0.01% Tween 80 | 1.008 | 98.317 | 0.676 |
| LI 200/03/6 | 1.006 | 98.319 | 0.674 |
| pH 6, 80 mg sucrose | 0.987 | 98.363 | 0.649 |
| 0.01% Tween 80 | 0.987 | 98.321 | 0.692 |
| LI 200/04/6 | 0.987 | 98.342 | 0.671 |
| pH 6, 50 mg mannitol | 0.996 | 98.326 | 0.678 |
| 0.1% Tween 80 | 0.996 | 98.338 | 0.666 |
| LI 200/05/6 | 0.996 | 98.332 | 0.672 |
| pH 6, 80 mg sucrose | 0.998 | 98.305 | 0.697 |
| 0.1% Tween 80 | 0.984 | 98.345 | 0.671 |
| LI 200/06/6 | 0.991 | 98.325 | 0.684 |
| pH 6 | 1.000 | 98.325 | 0.675 |
| 0.01% Tween 80 | 0.994 | 98.347 | 0.659 |
| LI 200/07/6 | 0.997 | 98.336 | 0.667 |
| pH 6 | 1.003 | 98.314 | 0.682 |
| 0.01% Tween 80 | 0.998 | 98.338 | 0.664 |
| LI 200/08/6 | 1.001 | 98.326 | 0.673 |

TABLE 60

IEX results of various J695 formulations

| Sample name | Sum Acicid Peaks [%] | Sum Glutamine [%] | Sum Basic Peaks [%] |
|---|---|---|---|
| pH 5 | 4.598 | | 3.303 |
| 125 mg/mL | 4.599 | | 3.177 |
| starting mat. | 4.599 | 92.162 | 3.240 |
| pH 6 | 4.597 | | 3.159 |
| 125 mg/mL | 4.629 | | 3.156 |
| starting mat. | 4.613 | 92.229 | 3.158 |
| pH 5 | 4.706 | | 3.177 |
| 42.5 mg/mL | 4.725 | | 3.205 |
| after dialysis | 4.715 | 92.094 | 3.191 |
| pH 6 | 4.739 | | 3.182 |
| 56.9 mg/mL | 4.752 | | 3.167 |
| after dialysis | 4.746 | 92.080 | 3.174 |
| pH 5 | 4.655 | | 3.167 |
| 206 mg/mL | 4.676 | | 3.210 |
| In Water | 4.666 | 92.146 | 3.189 |
| pH 5 | 4.721 | | 3.321 |
| 50 mg/mL mannitol | 4.733 | | 3.356 |
| LI 200/01/5 | 4.727 | 91.935 | 3.338 |
| pH 5 | 4.715 | | 3.299 |
| 80 mg/mL sucrose | 4.687 | | 3.338 |
| LI 200/02/5 | 4.701 | 91.981 | 3.318 |
| pH 5, 50 mg mannitol | 4.767 | | 3.246 |
| 0.01% Tween 80 | 4.736 | | 3.253 |
| LI 200/03/5 | 4.752 | 91.999 | 3.250 |
| pH 5, 80 mg sucrose | 4.751 | | 3.257 |
| 0.01% Tween 80 | 4.742 | | 3.229 |
| LI 200/04/5 | 4.746 | 92.011 | 3.243 |
| pH 5, 50 mg mannitol | 4.780 | | 3.420 |
| 0.1% Tween 80 | 4.720 | | 3.394 |
| LI 200/05/5 | 4.750 | 91.843 | 3.407 |
| pH 5, 80 mg sucrose | 4.756 | | 3.421 |
| 0.1% Tween 80 | 4.894 | | 3.375 |
| LI 200/06/5 | 4.825 | 91.777 | 3.398 |
| pH 5 | 4.813 | | 3.425 |
| 0.01% Tween 80 | 4.757 | | 3.413 |
| LI 200/07/5 | 4.785 | 91.796 | 3.419 |
| pH 5 | 4.769 | | 3.361 |
| 0.1% Tween 80 | 4.842 | | 3.335 |
| LI 200/08/5 | 4.806 | 91.846 | 3.348 |
| pH 6 | 4.882 | | 3.452 |
| 182 mg/mL | 4.886 | | 3.451 |
| In Water | 4.884 | 91.664 | 3.451 |
| pH 6 | 4.843 | | 3.456 |
| 50 mg/mL mannitol | 4.833 | | 3.393 |
| LI 200/01/6 | 4.838 | 91.737 | 3.425 |
| pH 6 | 4.923 | | 3.407 |
| 80 mg/mL sucrose | 4.896 | | 3.491 |
| LI 200/02/6 | 4.909 | 91.642 | 3.449 |
| pH 6, 50 mg mannitol | 4.864 | | 3.423 |
| 0.01% Tween 80 | 4.899 | | 3.392 |
| LI 200/03/6 | 4.882 | 91.711 | 3.408 |
| pH 6, 80 mg sucrose | 4.870 | | 3.320 |
| 0.01% Tween 80 | 4.928 | | 3.369 |
| LI 200/04/6 | 4.899 | 91.756 | 3.345 |
| pH 6, 50 mg mannitol | 4.905 | | 3.385 |
| 0.1% Tween 80 | 4.922 | | 3.489 |
| LI 200/05/6 | 4.914 | 91.649 | 3.437 |
| pH 6, 80 mg sucrose | 4.973 | | 3.443 |
| 0.1% Tween 80 | 4.962 | | 3.335 |
| LI 200/06/6 | 4.968 | 91.644 | 3.389 |
| pH 6 | 4.934 | | 3.413 |
| 0.01% Tween 80 | 4.899 | | 3.392 |
| LI 200/07/6 | 4.916 | 91.681 | 3.402 |
| pH 6 | 4.884 | | 3.410 |
| 0.1% Tween 80 | 4.934 | | 3.366 |
| LI 200/08/6 | 4.909 | 91.703 | 3.388 |

Conclusion

The above example provides an experiment where water (demineralised and sterile filtered water) was used as dialysis medium for the monoclonal antibody J695.

J695 was subjected to dialysis and concentration processing by using pure water as exchange medium and was formulated at pH 5.40 as well as 6.46 at high concentration (206 and 182 mg/mL, respectively) without inducing solution haziness, severe opalescence or turbidity formation.

J695 from the processing experiment was characterized, and formulated with various non-ionic excipients. Data obtained points at favorable overall stability of the protein in the formulations tested.

In conclusion, processing proteins using pure water as exchange medium and formulation with non-ionic excipients is feasible. Assuming an ideal 100% excipient membrane permeability, an approx. 99.9% maximum excipient reduction can be estimated.

Example 24

Syringeability of Adalimumab Formulated in Water

The formulations from example 21 (63 and 220 mg/mL Adalimumab) were subjected to force measurements upon syringe depletion. 220 mg/mL samples of Adalimumab were diluted to 200 mg/mL, 150 mg/mL and 100 mg/mL, respectively, and were also assessed. A Zwick Z2.5/TN1S was used at a constant feed of 80 mm/min. Finally, viscosity data of the formulations was assessed using an Anton Paar Microviscosimeter, type AWVn, at 20° C. The following data collection suggests that both needle and syringe diameters have a significant effect on the gliding forces upon syringe depletion. Surprisingly, the highly concentrated solution at 220 mg/mL (viscosity 27.9 cP at 20° C.) can be delivered by applying equivalent depletion forces as with the lower concentrated formulation at 63 mg/mL (viscosity 1.8 cP at 20° C.).

state and the liquid state. Freezing was performed by means of a temperature controlled −80° C. freezer, and thawing was performed by means of a 25° C. temperature controlled water bath. About 25 mL of antibody solution each were filled in 30 mL PETG repositories for these experiment series.

Formation of subvisible particles presents a major safety concern in pharmaceutical protein formulations. Subvisible protein particles are thought to have the potential to negatively impact clinical performance to a similar or greater degree than other degradation products, such as soluble aggregates and chemically modified species that are evaluated and quantified as part of product characterization and quality assurance programs (Carpenter, J F et al. Commentary: Overlooking subvisible particles in therapeutic protein products: baps that may compromise product quality. *J. Pharm. Sci.*, 2008). As demonstrated in the examples listed below, a number of antibodies were surprisingly stable—especially with regard to subvisible particle formation—when formulated in the formulation of invention.

Example 25

Freeze/Thaw Stability of Adalimumab Formulated in Water and with Non-Ionic Excipients The following example describes the stability of an antibody, e.g., adalimumab, in a water formulation and in water formulations in which non-ionic excipients have been added. Aliquots of samples from examples 21 and 22 were subjected to freeze/thaw experiments and analyzed by SE-HPLC. Data

TABLE 61

Gliding Force Values obtained for Adalimumab solutions in different packaging systems.

| | | D HyPak SCF ™ 1 mL long syringes, equipped with | | | |
|---|---|---|---|---|---|
| Adaliumab Concentration (Viscosity) | BD HyPak SCF ™ 1 mL long syringes, equipped with 27.5G RNS needles BD HyPak BSCF 4432/50 stoppers | 25G × ⅝" needles (Sterican) BD HyPak BSCF 4432/50 stoppers | 26G × ½" needles (Sterican) BD HyPak BSCF 4432/50 stoppers | 27G × ½" needles (Sterican) BD HyPak BSCF 4432/50 stoppers | 1 mL Soft-Ject ® Tuberkulin syringes (smaller diameter than BD HyPak syringes), equipped with 27G × ½" needles (Sterican) |
| 63 mg/mL (1.8 cP) | 3.9 N | — | — | — | — |
| 100 mg/mL (2.9 cP) | 3.30 N | 1.02 N | 1.33 N | 1.69 N | 1.00 N |
| 150 mg/mL (7.4 cP) | 4.63 N | 1.16 N | 1.58 N | 2.93 N | 1.33 N |
| 200 mg/mL (15.7 cP) | 7.25 N | 2.16 N | 3.24 N | 6.25 N | 2.55 N |
| 220 mg/mL (27.9 cP) | 14.5 N | 2.99 N | 3.97 N | 9.96 N | 3.16 N |

The above suggests that even with high concentrations of protein, such formulations are conducive to administration using a syringe, e.g., subcutaneous.

Examples 25-28

Examples 25-28 describe freeze/thaw stability experiments of various antibody formulations containing the antibody formulated in water (referred to in examples 26-28 as low-ionic strength protein formulations). The freeze thaw behavior of a number of antibodies was evaluated by cycling various protein formulations up to 4 times between the frozen was compared to SE-HPLC results derived from freeze/thaw experiments using Adalimumab in a buffer of the following composition: 10 mM phosphate buffer, 100 mM sodium chloride, 10 mM citrate buffer, 12 mg/mL mannitol, 0.1% polysorbate 80, pH 5.2. Adalimumab in this latter buffer was used at 50 mg/mL and 200 mg/mL, respectively. Freeze/thaw cycles were performed in Eppendorf caps, by freezing to −80° C. and storage in the freezer for 8 hours, followed by thawing at room temperature for 1 hour and subsequent sample pull. Each formulation was subjected to 5 cycles, i.e., cycles 0, 1, 2, 3, 4, and 5 described in the tables below.

HPLC Method

Adalimumab, SEC analysis: Sephadex 200 column (Pharmacia Cat. No. 175175-01). Mobile phase 20 mM sodium phosphate, 150 mM sodium chloride, pH 7.5, 0.5 mL/min flow rate, ambient temperature, detection UV 214 nm and 280 nm. Each sample was diluted to 1.0 mg/mL with Milli-Q water, sample injection load 50 µg (duplicate injection).

Adalimumab Characterization Upon Freeze/Thaw Cycling

Table 62 describes Adalimumab purity during the freeze/thaw experiments. For sample composition, refer to examples 21 and 22.

TABLE 62

| | | | | Freeze/thaw - Low ionic Adalimumab - 50 mg/mL | | | | |
|---|---|---|---|---|---|---|---|---|
| cycle | LI 50/01 | LI 50/02 | LI 50/03 | LI 50/04 | LI 50/05 | LI 50/06 | LI 50/07 | LI 50/08 |
| | | | | Fraction monomere [%] | | | | |
| 0 | 99.605 | 99.629 | 99.632 | 99.626 | 99.619 | 99.626 | 99.653 | 99.655 |
| 1 | 99.743 | 99.768 | 99.739 | 99.759 | 99.731 | 99.725 | 99.686 | 99.669 |
| 2 | 99.715 | 99.726 | 99.571 | 99.661 | 99.721 | 99.721 | 99.601 | 99.619 |
| 4 | 99.668 | 99.689 | 99.632 | 99.678 | 99.523 | 99.724 | 99.491 | 99.542 |
| 5 | 99.627 | 99.771 | 99.539 | 99.772 | 99.525 | 99.773 | 99.357 | 99.445 |
| | | | | Fraction aggregate [%] | | | | |
| 0 | 0.106 | 0.104 | 0.119 | 0.136 | 0.139 | 0.145 | 0.158 | 0.159 |
| 1 | 0.149 | 0.134 | 0.153 | 0.150 | 0.149 | 0.166 | 0.206 | 0.201 |
| 2 | 0.192 | 0.178 | 0.320 | 0.242 | 0.178 | 0.184 | 0.319 | 0.261 |
| 4 | 0.213 | 0.185 | 0.239 | 0.187 | 0.357 | 0.170 | 0.393 | 0.353 |
| 5 | 0.301 | 0.151 | 0.384 | 0.150 | 0.398 | 0.150 | 0.568 | 0.484 |
| | | | | Fraction fragmente [%] | | | | |
| 0 | 0.289 | 0.267 | 0.249 | 0.238 | 0.242 | 0.229 | 0.189 | 0.186 |
| 1 | 0.108 | 0.098 | 0.108 | 0.091 | 0.120 | 0.108 | 0.107 | 0.130 |
| 2 | 0.093 | 0.097 | 0.108 | 0.097 | 0.100 | 0.094 | 0.080 | 0.119 |
| 4 | 0.119 | 0.126 | 0.130 | 0.135 | 0.120 | 0.106 | 0.116 | 0.105 |
| 5 | 0.072 | 0.078 | 0.078 | 0.078 | 0.077 | 0.077 | 0.075 | 0.071 |
| | | | | Freeze/thaw - Low ionic Adalimumab - 200 mg/mL | | | | |
| cycle | LI 200/01 | LI 200/02 | LI 200/03 | LI 200/04 | LI 200/05 | LI 200/06 | LI 200/07 | LI 200/08 |
| | | | | Fraction monomere [%] | | | | |
| 0 | 99.294 | 99.296 | 99.348 | 99.333 | 99.313 | 99.349 | 99.320 | 99.290 |
| 1 | 99.286 | 99.267 | 99.259 | 99.256 | 99.120 | 99.254 | 98.999 | 99.126 |
| 2 | 99.305 | 99.311 | 99.249 | 99.214 | 99.296 | 99.288 | 99.149 | 99.128 |
| 4 | 99.303 | 99.272 | 99.261 | 99.301 | 99.296 | 99.283 | 99.004 | 99.061 |
| 5 | 99.320 | 99.322 | 99.330 | 99.331 | 99.327 | 99.333 | 98.939 | 98.949 |
| | | | | Fraction aggregate [%] | | | | |
| 0 | 0.489 | 0.509 | 0.491 | 0.484 | 0.492 | 0.488 | 0.515 | 0.575 |
| 1 | 0.590 | 0.574 | 0.584 | 0.586 | 0.680 | 0.582 | 0.785 | 0.718 |
| 2 | 0.604 | 0.604 | 0.616 | 0.630 | 0.607 | 0.607 | 0.731 | 0.736 |
| 4 | 0.591 | 0.592 | 0.612 | 0.581 | 0.604 | 0.596 | 0.868 | 0.836 |
| 5 | 0.593 | 0.586 | 0.583 | 0.596 | 0.597 | 0.589 | 0.985 | 0.981 |
| | | | | Fraction fragmente [%] | | | | |
| 0 | 0.218 | 0.196 | 0.161 | 0.183 | 0.195 | 0.163 | 0.165 | 0.135 |
| 1 | 0.124 | 0.159 | 0.157 | 0.159 | 0.200 | 0.164 | 0.216 | 0.157 |
| 2 | 0.091 | 0.085 | 0.135 | 0.156 | 0.097 | 0.105 | 0.120 | 0.136 |
| 4 | 0.106 | 0.136 | 0.127 | 0.118 | 0.100 | 0.121 | 0.128 | 0.103 |
| 5 | 0.087 | 0.092 | 0.087 | 0.073 | 0.075 | 0.078 | 0.076 | 0.070 |
| | | Freeze/thaw - Adalimumab Commercial and in water | | | |
| cycle | from example A, low conc. | from example A, high conc. | Standard, 50 mg/mL | Standard, 200 mg/mL |
| | | Fraction monomer [%] | | | |
| 0 | 99.733 | 99.286 | 99.374 | 99.227 |
| 1 | 99.689 | 99.212 | 99.375 | 99.215 |
| 2 | 99.614 | 99.130 | 99.370 | 99.218 |
| 4 | 99.489 | 99.029 | 99.361 | 99.196 |
| 5 | 99.430 | 98.945 | 99.362 | 99.177 |
| | | Fraction aggregates [%] | | | |
| 0 | 0.186 | 0.635 | 0.358 | 0.502 |
| 1 | 0.226 | 0.706 | 0.359 | 0.516 |

TABLE 62-continued

| | | | | |
|---|---|---|---|---|
| 2 | 0.304 | 0.780 | 0.364 | 0.513 |
| 4 | 0.428 | 0.888 | 0.372 | 0.535 |
| 5 | 0.485 | 0.971 | 0.373 | 0.553 |
| Fraction fragments [%] | | | | |
| 0 | 0.080 | 0.079 | 0.268 | 0.272 |
| 1 | 0.085 | 0.083 | 0.266 | 0.269 |
| 2 | 0.082 | 0.090 | 0.266 | 0.269 |
| 4 | 0.083 | 0.083 | 0.267 | 0.270 |
| 5 | 0.085 | 0.085 | 0.265 | 0.269 |

Conclusion

The above example provides an experiment where Adalimumab DF/UF processed into water (Sterilized water for injection Ph.Eur./USP) and formulated with various non-ionic excipients was subjected to freeze/thaw cycling. Data obtained (described in Table 62) indicates favorable overall stability of the protein in all formulations tested. All formulations contained above 98.5% monomeric species after 5 freeze/thaw cycles, with minimal amounts of aggregate or fragments as cycles continued.

Example 26

Freeze/Thaw Stability of Low-Ionic 1D4.7 Solutions

1D4.7 protein (an anti-IL 12/anti-IL 23 IgG1) was formulated in water by dialysis (using slide-a-lyzer cassettes, used according to operating instructions of the manufacturer, Pierce, Rockford, Ill.) and was demonstrated to be stable during repeated freeze/thaw (f/t) processing (−80° C./25° C. water bath) at 2 mg/mL concentration, pH 6. Data were compared with data of various formulations (2 mg/mL protein, pH 6) using buffers and excipients commonly used in parenteral protein formulation development. It was found that the stability of 1D4.7 formulated in water exceeded the stability of 1D4.7 formulated in established buffer systems (e.g. 20 mM histidine, 20 mM glycine, 10 mM phosphate, or 10 mM citrate) and even exceeded the stability of 1D4.7 formulations based on universal buffer (10 mM phosphate, 10 mM citrate) combined with a variety of excipients that are commonly used to stabilize protein formulations, e.g. 10 mg/mL mannitol, 10 mg/mL sorbitol, 10 mg/mL sucrose, 0.01% polysorbate 80, or 20 mM NaCl.

Figure 33:
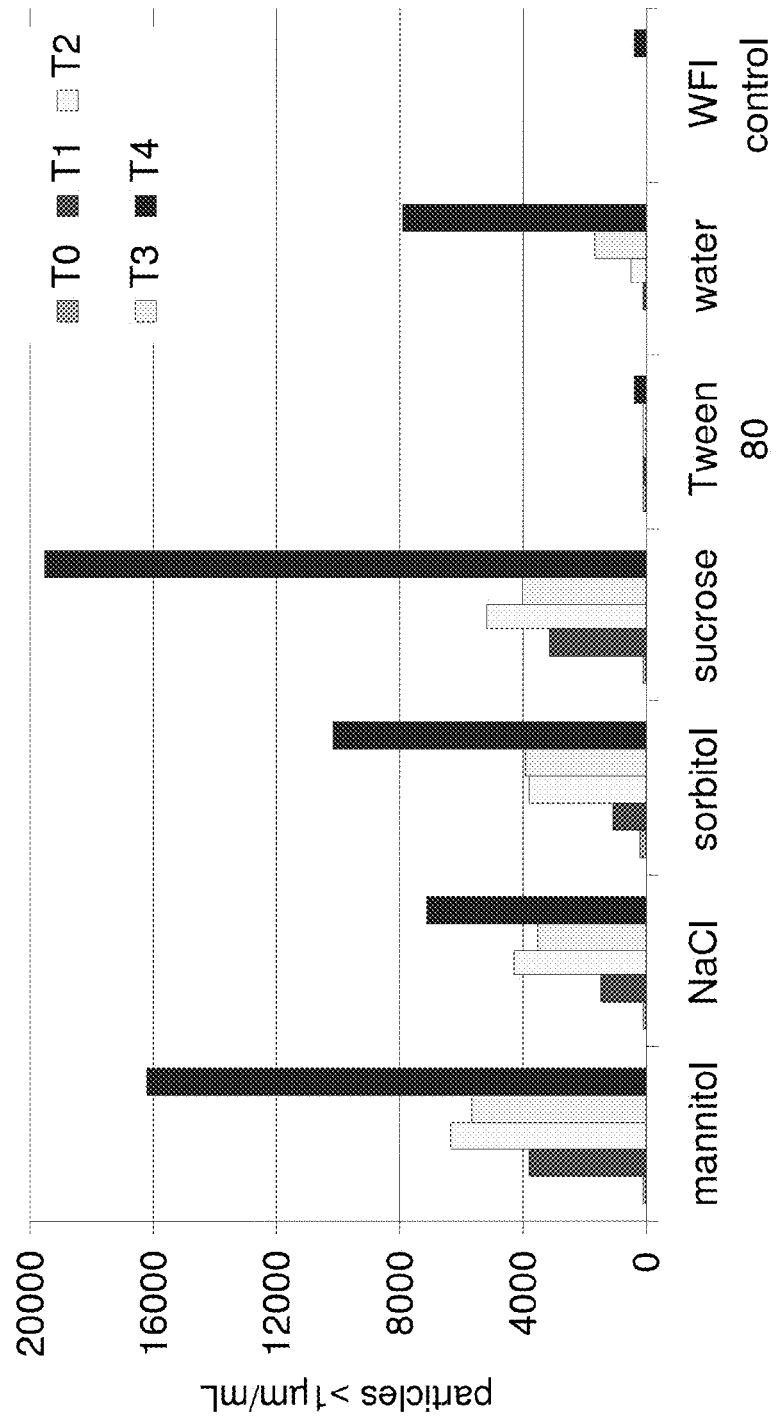
FIG. 33 graphically depicts 1D4.7 antibody stability as measured by subvisible particle (>1 μm) during repeated freeze/thaw (f/t) cycles for a number of different formulations.

SEC, DLS and particle counting analysis were applied to monitor protein stability, and particle counting was performed using a particle counting system with a 1-200 μm measurement range (particle counter Model Syringe, Markus Klotz GmbH, Bad Liebenzell, Germany). Experiment details are as follows:

1D4.7 formulated in water compared with formulations listed above
4 freeze/thaw cycles applied
30 mL PETG repository, about 20 mL fill, 2 mg/mL protein, pH 6
sampling at T0, T1 (i.e. after one f/t step), T2, T3, and T4
analytics: visual inspection, SEC, DLS, subvisible particle measurement FIG. 33 shows 1D4.7 stability during repeated f/t cycling (−80° C./25° C.), mirrored by formation of subvisible particles >1 μm. 1D4.7 was formulated in universal buffer (10 mM citrate, 10 mM phosphate) and then the following excipient variations were tested: sorbitol (10 mg/mL), mannitol (10 mg/mL), sucrose (10 mg/mL), NaCl (100 mM), and polysorbate 80 (0.01%). 1D4.7 was also formulated in water (by dialysis) with no excipients added at all ("water" in FIG. 33). Water for injection was also subjected to f/t cycling and subvisible particle testing to evaluate a potential impact of material handling, f/t, and sample pull on particle load.

The stability of 1D4.7 formulated in water upon f/t exceeded the stability of 1D4.7 solutions formulated with excipients typically used in protein formulations. Mannitol, sucrose, and sorbitol are known to act as lyoprotectant and/or cryoprotectant, and polysorbate 80 is a non-ionic excipient prevalently known to increase physical stability of proteins upon exposure to hydrophobic-hydrophilic interfaces such as air-water and ice-water, respectively.

In summary, 1D4.7 solutions formulated in water appeared to be surprisingly stable when analyzed with various analytical methodologies typically applied to monitor stability of pharmaceutical proteins upon freeze-thaw processing (e.g. SEC, visual inspection, dynamic light scattering, and especially light obscuration).

Example 27

Freeze/Thaw Stability of Low-Ionic 13C5.5 Solutions

13C5.5 (an anti IL-13 IgG1) formulated in water was demonstrated to be stable during repeated freeze/thaw processing (−80° C./25° C. water bath) at 2 mg/mL concentration, pH 6. Data were compared with other formulations (2 mg/mL protein, pH 6), and it was found that the stability of 13C5.5 formulated in water exceeded the stability of 13C5.5 formulated in buffer systems often used in parenteral protein formulations (e.g. 20 mM histidine, 20 mM glycine, 10 mM phosphate, or 10 mM citrate) and even exceeded the stability of 13C5.5 formulations based on universal buffer (10 mM phosphate, 10 mM citrate) that has been combined with a variety of excipients that are commonly used in protein formulation (e.g. 10 mg/mL mannitol, 10 mg/mL sorbitol, 10 mg/mL sucrose, 0.01% polysorbate 80, 20 mM NaCl, 200 mM NaCl).

Sample preparation, experiment processing, sample pull and sample analysis was performed in the same way as outlined in the above examples.

Figure 34:
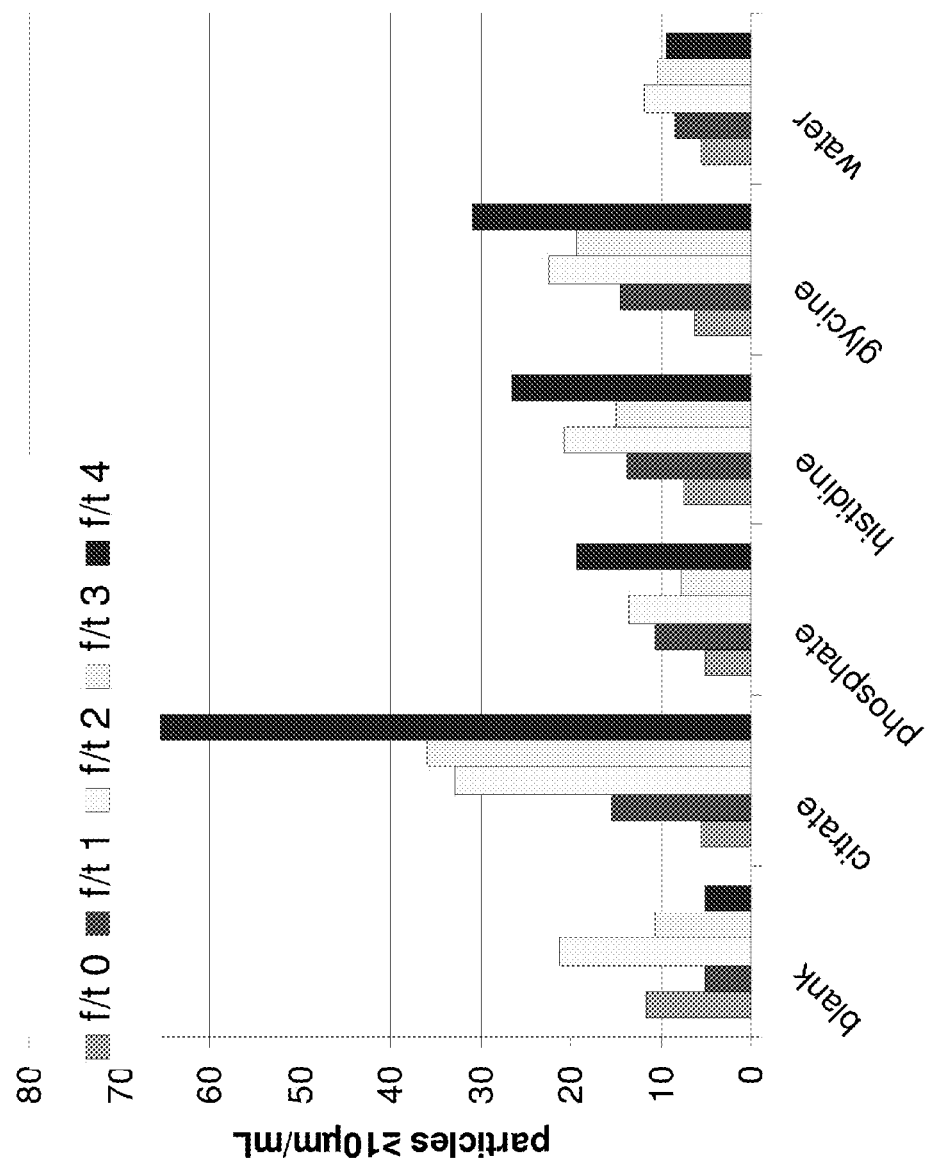
FIG. 34 graphically depicts 13C5.5 antibody stability as measured by subvisible particle (>10 μm) during repeated freeze/thaw (f/t) cycles for a number of different formulations.

13C5.5 formulated in water compared with formulations listed above
4 freeze/thaw cycles applied
30 mL PETG repository
2 mg/mL, pH 6
sampling at T0, T1, T2, T3, and T4
analytics: visual inspection, SEC, DLS, subvisible particle measurement FIG. 34 shows 13C5.5 stability during repeated f/t cycling (−80° C./25° C.), mirrored by formation of subvisible particles >10 μm. 13C5.5 was formulated in either 10 mM phosphate buffer, 10 mM citrate buffer, 20 mM glycine buffer, and 20 mM histidine buffer. 13C5.5 was also formulated in the formulation of invention (by dialysis) with no excipients added at all. Water for injection was also subjected to f/t cycling and subvisible particle testing to evaluate a potential impact of material handling, f/t, and sample pull on particle load (referred to as blank).

The stability of 13C5.5 formulated in water upon f/t exceeded the stability of 13C5.5 solutions formulated in buffers typically used in protein formulations. No instabilities of 13C5.5 solutions formulated in water have been observed with other analytical methodologies applied (e.g. SEC, visual inspection, etc.)

Figure 35:
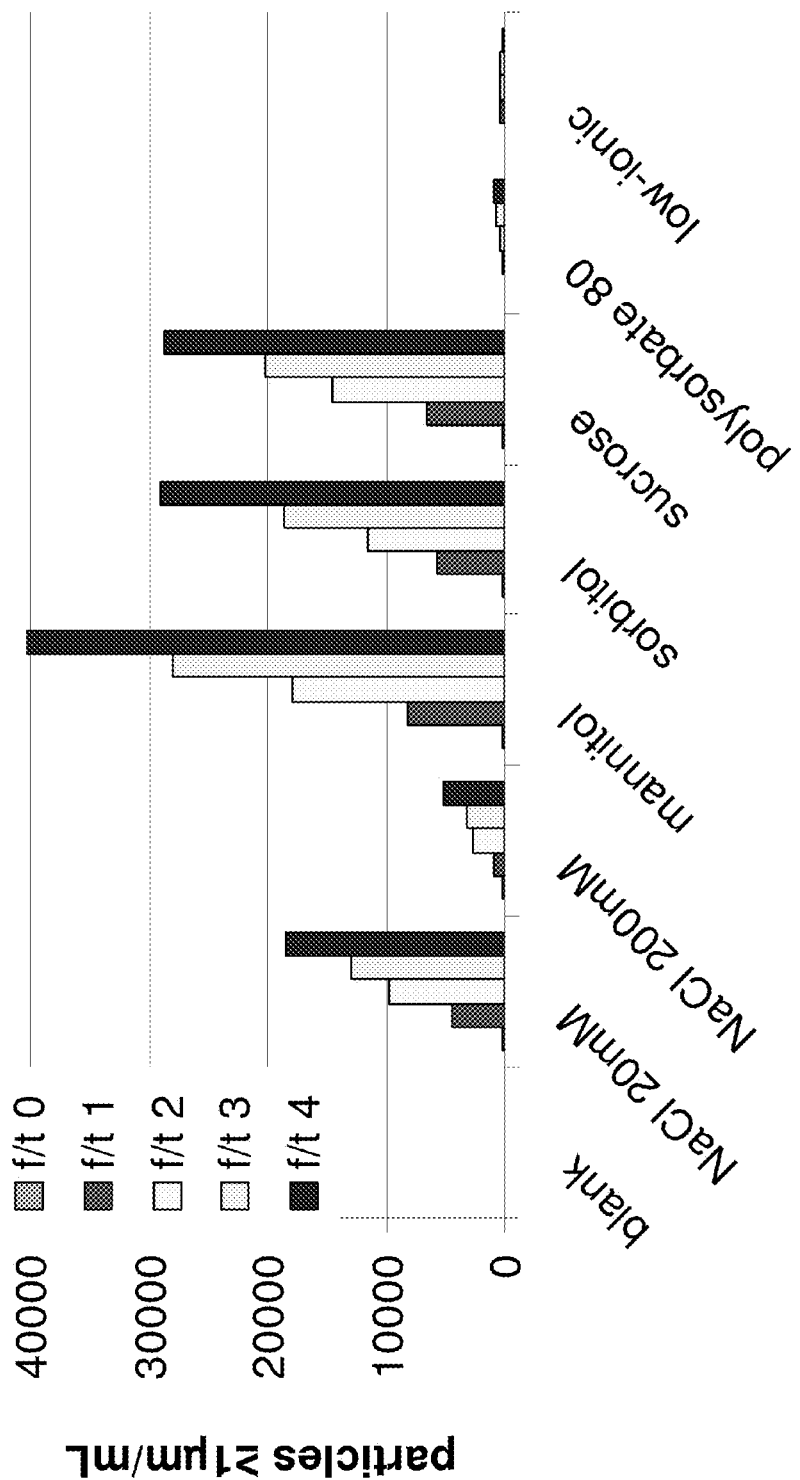
FIG. 35 graphically depicts 13C5.5 antibody stability as measured by subvisible particle (>1 μm) during repeated freeze/thaw (f/t) cycles for a number of different formulations.

FIG. 35 shows 13C5.5 stability during repeated f/t cycling (−80° C./25° C.), mirrored by formation of subvisible particles >1 µm. 13C5.5 was formulated in universal buffer (10 mM citrate, 10 mM phosphate) and in universal buffer combined with the following excipient variations were tested: sorbitol (10 mg/mL), mannitol (10 mg/mL), sucrose (10 mg/mL), NaCl (200 mM), NaCl (20 mM) and polysorbate 80 (0.01%). 13C5.5 was also formulated in water (by dialysis) with no excipients added at all for comparison (pure water). Water for injection was also subjected to f/t cycling and subvisible particle testing to evaluate a potential impact of material handling, f/t, and sample pull on particle load.

The stability of 13C5.5 formulated in water upon f/t exceeded the stability of 13C5.5 solutions formulated with excipients typically used in protein formulations. Mannitol, sucrose, and sorbitol are known to act as lyoprotectant and/or cryoprotectant, and polysorbate 80 is a non-ionic excipient prevalently known to increase physical stability of proteins upon exposure to hydrophobic-hydrophilic interfaces such as air-water and ice-water, respectively. The low number of subvisible particles in 13C5.5 samples formulated into the formulation of invention was found to be at surprisingly low levels, demonstrating the high safety and stability potential of such formulations.

No instabilities of 13C5.5 solutions formulated in water have been observed with other analytical methodologies applied, (e.g. SEC, visual inspection, etc.).

DLS analysis of 13C5.5 solutions after f/t procedures was performed as described above. Results from the DLS analysis showed that an 13C5.5 solution with 0.01% Tween-80 contained significant high molecular weight (HMW) aggregate forms after only 1 f/t step, whereas 13C5.5 in water contained no HMW aggregate forms, even after 3 f/t steps applied.

In summary, 13C5.5 solutions formulated in water appeared to be surprisingly stable when analyzed with various analytical methodologies typically applied to monitor stability of pharmaceutical proteins upon freeze-thaw processing (e.g. SEC, visual inspection, dynamic light scattering, and especially light obscuration).

Example 28

Freeze/Thaw Stability of Low-Ionic 7C6 Solutions

7C6 (an anti amyloid beta IgG1) formulated in water was demonstrated to be stable during repeated freeze/thaw processing (−80° C./30° C. water bath) at 2 mg/mL concentration, pH 6. Data were compared with other formulations (2 mg/mL protein, pH 6), and it was found that the stability of 7C6 formulated in water exceeded the stability of 7C6 formulated in buffer systems often used in parenteral protein formulations and even exceeded the stability of 7C6 formulations based on universal buffer (10 mM phosphate, 10 mM citrate) that has been combined with a variety of excipients that are commonly used in protein formulation.

The following solution compositions were evaluated for their potential to maintain 7C6 physical stability during freeze/thaw experiments:
  Phosphate buffer, 15 mM
  Citrate buffer, 15 mM
  Succinate buffer, 15 mM
  Histidine buffer, 15 mM
  Arginine buffer, 15 mM
  Low ionic protein formulation, no excipients added
  Universal buffer, sorbitol (10 mg/mL)
  Universal buffer, mannitol (10 mg/mL)
  Universal buffer, sucrose (10 mg/mL)
  Universal buffer, trehalose (10 mg/mL)
  Universal buffer, 0.01% (w/w) polysorbate 80

Sample preparation, experiment processing, sample pull and sample analysis was performed in very similar way as outlined in Examples 26 and 27.
  7C6 formulated in water compared with formulations listed above
  4 freeze/thaw cycles applied
  30 mL PETG repository, approx. 20 mL fill
  2 mg/mL, pH 6
  sampling at T0, T1, T2, T3, and T4
  Analytics: Aβ-antibody stability was assessed by the following methods:
  Visual inspection of the protein solution was performed in polypropylene round-bottom tubes wherein the samples were filled for light obscuration measurements. It was carefully inspected against both a black and a white background for signs indicating protein physical instability such as haziness, turbidity and particle formation.

Dynamic light scattering (eZetasizer Nano ZS, Malvern Instruments, AI9494; equipped with Hellma precision cells, suprasil quartz, type 105.251-QS, light path 3 mm, center Z8.5 mm, at least 60 µL sample fill, protein sample remaining from light obscuration measurements in PP round-bottom tubes were used for DLS measurements). Automated measurements (1 measurement per sample) were performed.

Light obscuration analysis. 3.5 mL of sample were filled in 5 mL round bottom tube under laminar air flow conditions, measurement was performed in n=3 mode (0.8 mL per single measurement) after an initial 0.8 mL rinse.

Figure 36:
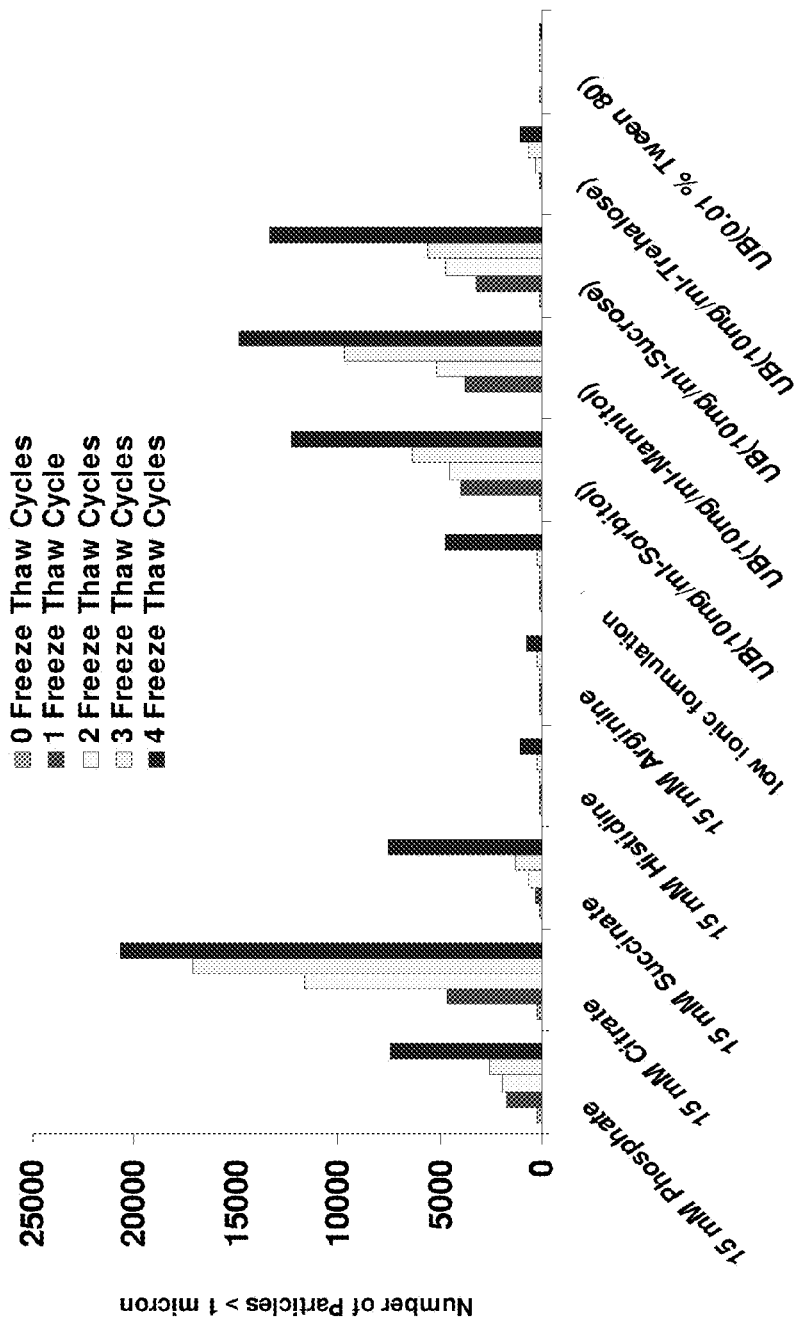
FIG. 36 graphically depicts 7C6 antibody stability as measured by subvisible particle (>1 μm) during repeated freeze/thaw (f/t) cycles for a number of different formulations.

Size-exclusion chromatography, combined with $UV_{214}/UV_{280}$ and multi-angle light scattering. Mobile phase: 100 mM Na2HPO4/200 mM Na2SO4, pH 7.0 (49.68 g anhydrous disodium hydrogen phosphate and 99.44 g anhydrous sodium sulfate were dissolved in approx. 3300 mL Milli-Q water, the pH was adjusted to 7.0 using 1 M phosphoric acid, filled to a volume of 3500 mL with Milli-Q water, and the solution was filtered through a membrane filter). SEC column, TSK gel G3000SW (cat. no. 08541) 7.8 mm×30 cm, 5 µm combined with a TSK gel guard (cat. no. 08543) 6.0 mm×4.0 cm, 7 µm. Flow 0.3 mL/min, injection volume 20 µL (equivalent to 20 µg sample), column temperature room temperature, autosampler temp. 2 to 8° C., run time 50 minutes, gradient isocratic, piston rinsing with 10% isopropyl alcohol, detection via UV absorbance, diode array detector: wavelength 214 nm, peak width >0.1 min, band width: 8 nm, reference wavelength 360 nm, band width 100 nm FIG. 36 shows 7C6 stability during repeated f/t cycling (−80° C./25° C.), mirrored by formation of subvisible particles >1 µm. The stability of 7C6 formulated in water upon f/t for many formulations exceeded the stability of 7C6 solutions formulated in buffers typically used in protein formulations. No instabilities of 7C6 solutions formulated in water have been observed with other analytical methodologies applied (e.g. SEC, visual inspection, dynamic light scattering)

Surprisingly, the stability of 7C6 formulated in water upon f/t exceeded the stability of 7C6 solutions formulated with excipients typically used in protein formulations. Mannitol, sucrose, and sorbitol are known to act as lyoprotectant and/or cryoprotectant, and polysorbate 80 is a non-ionic excipient prevalently known to increase physical stability of proteins upon exposure to hydrophobic-hydrophilic interfaces such as air-water and ice-water, respectively. The low number of sub-visible particles in 7C6 samples formulated into the formulation of invention was found to be at surprisingly low levels, demonstrating the high safety and stability potential of such formulations.

In summary, 7C6 solutions formulated in water appeared to be surprisingly stable when analyzed with various analytical methodologies typically applied to monitor stability of pharmaceutical proteins upon freeze-thaw processing (e.g. SEC, visual inspection, dynamic light scattering, and especially light obscuration).

Example 29

Preparation of J695 Formulated in Water and Stability Studies Thereof

Materials and Methods 427.1 g (80 mg/mL) of J695 were diluted to 40 mg/mL and diafiltered using purified water. After a 5-fold volume exchange with purified water (theoretical excipients reduction, 99.3%), the protein solution was ultrafiltered to target concentration of 100 mg/mL. pH, osmolality, density, visual inspection and protein concentration measurements (OD280) were performed to monitor the status of the protein after DF/UF processing.

After DF/UF processing, the protein solution was sterile filtered (0.22 μm Sterivex GV membrane filter) into a 60 mL PETG bottle (Nalgene) and subsequently stored at −80° C. for 3 months.

After thawing at 37° C., the solution was sterile filtered (0.22 μm Sterivex GV membrane filter) and filled into sterile BD Hypak Physiolis SCF™ 1 mL long syringes 29 G, ½ inch, 5-bevel, RNS TPE and closed with sterile BD Hypak SCF™ 1 ml W4023/50 Flur Daikyo stoppers. The filling volume was 1.000 mL per syringe.

After filling, the syringes were stored at 2-8° C. and 40° C., respectively, and analyzed as indicated in the sample pull scheme depicted below.

- J695 Drug Substance (extinction coefficient at 280 nm: 1.42 mL/mg cm): Drug Substance, pH 6.0, did not contain polysorbate 80.
- Sartorius Sartocon Slice diafiltration system, equipped with Ultrasert PES membrane cassettes (50 kDa cutoff). The Sartocon Slice system was operated in continuous mode at ambient temperature according to Sartorius Operating Instructions.
- pH electrodes
- Perkin Elmer UV/Vis spectrophotometer, Lambda 25, was used for protein concentration measurements (280 nm wavelength). Disposable UV cuvettes, 1.5 mL, semi-micro, were used for the concentration measurements.
- 0.22 μm filtered purified water was used as DF/UF medium.
- Anton Paar Density Meter DMA 4100 was used for density measurements
- A Knauer Osmometer Type ML, was used for osmolality measurements (calibrated with 400 mOsmol/kg NaCl calibration solution, Art. No. Y1241, Herbert Knauer GmbH, Berlin, Germany).

Analytical Methods

J695, SEC analysis: Superdex 200 column (Pharmacia). Mobile phase 92 mM di-sodium hydrogen phosphate, 211 mM sodium sulfate, pH 7.0, 0.75 mL/min flow rate, ambient temperature, detection UV 214 nm. Each sample was diluted to 2.0 mg/mL with mobile phase, sample injection load 20 μg (duplicate injection).

J695, IEC analysis: Dionex, Propac WCX-10 column along with a corresponding guard column. Separation conditions: mobile phase A: 20 mM di-sodium hydrogen phosphate and 20 mM sodium acetate, pH 7.0; mobile phase B 20 mM di-sodium hydrogen phosphate, 400 mM Sodium chloride, pH 5.0. 1.0 mL/min flow rate, ambient temperature. Each sample was diluted to 1.0 mg/mL with Milli-Q water, sample injection load 100 μg (duplicate injection).

J695, SDS-PAGE analysis: Novex acryl amide slab gels (8-16% for non-reducing conditions, 12% for reducing conditions, Invitrogen), Coomassie staining (Invitrogen). Separation under reducing (β-mercaptoethanol) and non-reducing conditions using Tris-Glycine buffer made of 10× stock solution (Invitrogen).

J695, quantitation of buffer components:
- Mannitol: separation per ReproGel Ca column (Dr. Maisch, Germany) and RI detection, mobile phase: deionized water, 0.6 mL/min flow rate, 20 μL sample injection. Quantitation was performed using external calibration standard curve.
- Histidine and Methionine: fluorescence labelling of the amino acids with OPA (ortho-phthalic aldehyde) and HPLC separation per ReproSil ODS-3 column (Dr. Maisch, Germany) and fluorescence detection at 420 nm (extinction at 330 nm), mobile phase A: 70% citric acid (10.51 g/L) buffer, pH 6.5, 30% methanol, mobile phase B: methanol, 1.0 mL/min flow rate, 20 μL sample injection. Quantitation was performed using external calibration standard curve.

J695, PCS analysis: was performed undiluted at 100 mg/mL in single-use plastic cuvettes at 25° C. using a A Malvern Instruments Zetasizer nano ZS at 173° angle assuming solution viscosity of 4.3875 mPas, refractive index of the protein of 1.450 and refractive index of the buffer solution of 1.335. The averaged results of 20 scans, 20 seconds each, are reported.

Calculation of the Protein Concentration

Calculation Formula:

$$E = -lg\left(\frac{I}{I_0}\right) = \varepsilon \cdot c \cdot d \rightarrow c = \frac{E}{\varepsilon \times d}$$

$\varepsilon$ – absorption coefficient $c$ – concentration $d$ – length of cuvette that the light has to pass $E$ – absorbance $I_0$ – initial light intensity $I$ – light intensity after passing through sample $$\varepsilon_{J695} = 1.42 \frac{mL}{mg \times cm}$$

Sample Pull Scheme

Samples of the prepared solutions were stored at the temperatures listed below and pulled (x) at the indicated time points after study start (Table 63). Test parameters and methods are described in Table 64.

TABLE 63

| Temp. | T0 | 1 m | 3 m | 6 m |
|---|---|---|---|---|
| 5° C. | x | x | x | x |
| 40° C. |   | x | x | x |

TABLE 64

| Test parameter | Test method |
|---|---|
| Appearance | Visual inspection |
| Visible particles | analogous DAC (EA 4.43) |
| Sub-visible particles | analogous Ph. Eur./USP EA 4.44 |
| Clarity | Ph. Eur. (EA 4.42) |
| Color (visual) | Ph. Eur. (EA 4.50) |
| pH | Ph. Eur. (EA 4.24) |
| Size exclusion HPLC | See above |
| Cation exchange HPLC | See above |
| SDS-PAGE | See above |
| PCS | See above |

DF/UF Processing of J695

Table 65 provides the J695 status after diafiltration.

TABLE 65

| Sample | Protein Concentration [mg/mL] | pH | Osmolality [mosmol/kg] | Visual Inspection |
|---|---|---|---|---|
| after DF/UF | 107 | 6.4 | 10 | Slightly opalescent, slightly yellow essentially free from visible particles |

After DF/UF the concentrations of the originating buffer components were quantitatively monitored to assess the DF effectiveness. All results were found to be below the practical detection limits (see Table 66) of the corresponding analytical methods (HPLC with RI for Mannitol and fluorescence detection for the methionine and histidine after OPA labeling, respectively).

TABLE 66

| Sample | Methionine [mg/mL] | Histidine [mg/mL] | Mannitol [mg/mL] |
|---|---|---|---|
| before DF/UF | 0.669 | 0.586 | 18.36 |
| after DF/UF | <0.13 | <0.14 | <3.20 |

J695 Characterization upon storage Table 67 below supports the stability of J695 DF/UF at 100 mg/mL upon storage.

| Test criteria | Specification | Duration of testing [months] | Storage conditions [° C./% RH] +5 | +40/75 |
|---|---|---|---|---|
| Appearance | solution | Initial | complies | |
|  |  | 1 | complies | complies |
|  |  | 3 | complies | complies |
|  |  | 6 | complies | complies |
| Clarity | Report Results, Compare to reference suspensions acc. to Ph. Eur. | Initial | — | — |
|  |  | 1 | — | — |
|  |  | 3 | ≦RSII | ≦RSII |
|  |  | 6 | ≦RSII | ≦RSIII |
| Particulate contamination Visible particles | Report Result Visual Score (number of samples tested) | Initial | 2.0 (1) | |
|  |  | 1 | 2.0 (1) | 3.0 (1) |
|  |  | 3 | 1.6 (5) | 1.0 (5) |
|  |  | 6 | 1.1 (9) | 1.6 (9) |
| Particulate contamination Subvisible particles | ≧10 μm: ≦6000 particles per container ≧25 μm: ≦600 particles per container | initial ≧10 μm >25 μm | 290 16 | |
|  |  | 1 ≧10 μm ≧25 μm |  |  |
|  |  | 3 ≧10 μm ≧25 μm |  |  |
|  |  | 6 ≧10 μm ≧25 μm | 124 1 | 54 3 |
| Size Exclusion HPLC | Report Results (%) for Aggregates (A) Monomer (M) Fragments (F) | initial A M F | 0.9 98.9 0.2 | |
|  |  | 1 A M F | 0.8 99.0 0.1 | 2.3 97.1 0.6 |

| Test criteria | Specification | Duration of testing [months] | Storage conditions [° C./% RH] +5 | +40/75 |
|---|---|---|---|---|
| | | 3 | | |
| | | A | 1.0 | 3.4 |
| | | M | 98.8 | 95.1 |
| | | F | 0.1 | 1.4 |
| | | 6 | | |
| | | A | 1.4 | 5.5 |
| | | M | 98.4 | 85.6 |
| | | F | 0.1 | 8.9 |
| SDS-PAGE (Non-reducing conditions) | The predominant banding pattern is comparable to that of the reference standard. | Initial | complies | |
| | | 1 | complies | complies |
| | | 3 | complies | complies |
| | | 6 | complies | complies |
| SDS-PAGE (reducing conditions) | The predominant banding pattern is comparable to that of the reference standard. | Initial | complies | |
| | | 1 | complies | complies |
| | | 3 | complies | complies |
| | | 6 | complies | complies |
| PCS | Report Results for Z-Average [nm] and PDI | initial | 0.9 | |
| | | | 0.23 | |
| | | 1 | 0.9 | 1.0 |
| | | | 0.23 | 0.23 |
| | | 3 | 0.9 | 1.1 |
| | | | 0.23 | 0.24 |
| | | 6 | 0.9 | 1.3 |
| | | | 0.23 | 0.29 |
| Cation Exchange HPLC | Report Results (%) for Acidic Species (A) Main Isoforms (M) Basic Species (B) | initial | | |
| | | A | 5.9 | |
| | | M | 91.5 | |
| | | B | 2.5 | |
| | | 1 | | |
| | | A | 5.6 | 10.6 |
| | | M | 92.0 | 98.9 |
| | | B | 2.4 | 0.5 |
| | | 3 | | |
| | | A | 5.7 | 14.4 |
| | | M | 92.1 | 85.0 |
| | | B | 2.1 | 0.6 |
| | | 6 | | |
| | | A | 6.0 | 29.6 |
| | | M | 91.6 | 69.4 |
| | | B | 2.3 | 1.0 |

Conclusion

The above example provides a diafiltration/ultrafiltration (DF/UF) experiment where water (0.22 µm filtered purified water) was used as diafiltration medium for the monoclonal antibody J695.

J695 was subjected to DF/UF processing using pure water as DF/UF exchange medium and was formulated at about pH 6.4 at high concentration (100 mg/mL) without inducing solution haziness, severe opalescence or turbidity formation.

J695 from the DF/UF experiments was stored in SCF syringes at 2-8° C. and 40° C. for up to 6 months. Data obtained points to a favourable overall stability of the protein.

In conclusion, processing and formulating proteins using pure water as DF/UF exchange medium is feasible. Assuming an ideal 100% excipient membrane permeability, an approx. 99.3% maximum excipient reduction can be estimated. Evidence is given by specific methods that after DF/UF the excipient concentration is below the practical detection limits.

Example 30

Freeze/Thaw Characteristics and Stability Testing of High Concentration Adalimumab Water Solution-Homogeneity and Physical Stability Preparation of Low-Ionic Adalimumab Solutions 1.6 L of Drug Substance (DS) material in 2 L PETG bottle was thawed at 25° C. in a water bath, homogenized and subjected to DF/UF using water for injection as a diafiltration exchange medium. Diafiltration was performed in continuous mode with Sartorius Sartocon Slice equipment by applying the following parameter:

Pump output: 8%

Pressure inlet: max 1 bar (0.8 bar)

Membrane: 2×PES, cut off 50 kD

During the diafiltration 5-fold volume exchange was sufficient to reduce osmolality to 8 mOsmol/kg.

In-Process-Control (IPC) samples were pulled prior to diafiltration (SEC, protein concentration by means of OD280, pH, osmolality and density) and after diafiltration (protein concentration by means of OD280, pH, osmolality and density). The IPC-samples were not sterile.

After diafiltration the ~70 mg/mL Adalimumab formulated in water was diluted to 50 mg/mL with water for injection and the pH value was adjusted to 5.2.

1.6 L of the Adalimumab 50 mg/mL formulated in water pH 5.2 was refilled in 2 L PETG bottle. The remaining volume of Adalimumab solution was subjected to DF/UF to increase the concentration to 100 mg/mL.

The Adalimumab 100 mg/mL formulated in water pH 5.3 was sterile filtered and 0.8 L of them was filled in 1 L PETG bottle.

Analytics
- Size exclusion chromatography (SEC)
- pH—measurement
- Osmolality measurement
- Density measurement
- Protein concentration by means of OD280
- Optical appearance
- Ion exchange chromatography (IEC)

Freeze/thaw Experiment of Adalimumab 1 L Containers

Adalimumab 100° mg/mL formulated in water in 1 L PETG containers was precooled to 2-8° C. and than froze at −80° C., freezing cycle >12 hrs. The frozen samples in 1 L PETG bottles were successively thawed at 25° C. in a water bath. During thawing the bottles of the frozen solutions dipped in the water bath up to liquid level. The following samples were pulled just after thawing without homogenization and after homogenization by 15 and 30 turn top over end.

TABLE 68

Sample pull scheme:

| Turns of each bottle | Sample | Analytical tests |
|---|---|---|
| 1 | 0 | 5 mL top | protein content, osmolality, |
| 2 | 0 | 5 mL middle | pH, density, SEC |
| 3 | 0 | 5 mL bottom | |
| 4 | 15 | 5 mL top | protein content, osmolality, |
| 5 | 15 | 5 mL middle | pH, density, SEC |

TABLE 68-continued

Sample pull scheme:

| Turns of each bottle | Sample | Analytical tests |
|---|---|---|
| 6 | 15 | 5 mL bottom | |
| 7 | 30 | 5 mL top | protein content, osmolality, |
| 8 | 30 | 5 mL middle | pH, density, SEC and |
| 9 | 30 | 5 mL bottom | subvisible particles |

Characterization of Adalimumab Solutions

Adalimumab 50 mg/mL and 100 mg/mL formulated in water appeared every time clearly, light yellow, not opalescent and without wave pattern after gentle movement.

Also after freezing and thawing the Adalimumab formulated in water did not change the appearance ((just after thawing and also after 15 and 30 times turn top over end).

A slight wave patterns were seen after gentle movement of the bottle just after thawing and dipping the needle into the solution during sample pull just after thawing.

In contrast to similar experiments with Adalimumab in commercial buffer the Adalimumab solution 50 mg/mL in water did not show any gradient of protein concentration, density and osmolality.

The Adalimumab solution 100 mg/mL did also not show any gradient of protein concentration, density, osmolality.

Stability was assessed after 6 months storage at −30° C. and −80° C., respectively.

In the following the respective analytical data are outlined:

TABLE 69

Adalimumab 50 and 100 mg/mL, before freeze/thaw processing

| | pH | density g/cm3 | osmolality mOsmol/kg | protein content (gravimertic) mg/mL | subvisible particles 1 mL >= 1 µm | 1 mL >= 10 µm | 1 mL >= 25 µm |
|---|---|---|---|---|---|---|---|
| 50 mg/mL in water | 5.18 | 1.0121 | 5 | 49.3 | 7953 | 5 | 0 |
| 100 mg/mL in water | 5.32 | 1.0262 | 12 | 99.8 | 154 | 4 | 2 |

TABLE 70

Adalimumab 50 mg/mL, pH 5.2 formulated in water, after freeze/thaw processing

| turn | sample | pH | density g/cm3 | osmolality mOsmol/kg | protein content mg/mL | purity (SEC) % | subvisible particles 1 mL >= 1 µm | 1 mL >= 10 µm | 1 mL >= 25 µm |
|---|---|---|---|---|---|---|---|---|---|
| 0 | top | 5.20 | 1.0119 | 6 | 48.7 | 99.597 | — | — | — |
| 0 | middle | 5.19 | 1.0120 | 8 | 49.4 | 99.576 | — | — | — |
| 0 | bottom | 5.17 | 1.0120 | 6 | 49.8 | 99.649 | — | — | — |
| 15 | top | 5.20 | 1.0120 | 4 | 49.7 | 99.649 | — | — | — |
| 15 | middle | 5.18 | 1.0120 | 5 | 49.2 | 99.678 | — | — | — |
| 15 | bottom | 5.17 | 1.0120 | 4 | 49.1 | 99.637 | — | — | — |
| 30 | top | 5.19 | 1.0120 | 5 | 49.7 | 99.647 | 1280 | 4 | 0 |
| 30 | middle | 5.17 | 1.0120 | 3 | 50.4 | 99.637 | 2055 | 13 | 0 |
| 30 | bottom | 5.18 | 1.0120 | 6 | 48.9 | 99.611 | 3889 | 37 | 11 |

TABLE 71

Adalimumab 100 mg/mL, pH 5.2 formulated in water, after freeze/thaw processing

| turn | sample | pH | density g/cm3 | osmolality mOsmol/kg | protein content mg/mL | purity (SEC) % | subvisible particles 1 mL >= 1 μm | 1 mL >= 10 μm | 1 mL >= 25 μm |
|---|---|---|---|---|---|---|---|---|---|
| 0 | top | 5.29 | 1.0259 | 13 | 98.7 | 99.424 | — | — | — |
| 0 | middle | 5.3 | 1.0262 | 16 | 99.9 | 99.468 | — | — | — |
| 0 | bottom | 5.28 | 1.0262 | 14 | 101.2 | 99.48 | — | — | — |
| 15 | top | 5.27 | 1.0261 | 13 | 98.9 | 99.511 | — | — | — |
| 15 | middle | 5.27 | 1.0261 | 16 | 97.7 | 99.466 | — | — | — |
| — | bottom | 5.28 | 1.0261 | 15 | 97.0 | 99.483 | — | — | — |
| 30 | top | 5.29 | 1.0261 | 16 | 96.6 | 99.439 | 231 | 58 | 49 |
| 30 | middle | 5.28 | 1.0261 | 16 | 97.0 | 99.467 | 169 | 21 | 9 |
| 30 | bottom | 5.28 | 1.0261 | 16 | 99.3 | 99.476 | 131 | 3 | 1 |

TABLE 72

Adalimumab 100 mg/mL, pH 5.2 formulated in water, stability after storage

| Testing time point | SEC aggregates monomer fragments | IEC sum of lysin isoforms | visual appearance | subvisible particles (1 mL) >=1 μm | >=10 μm | >=25 μm |
|---|---|---|---|---|---|---|
| T 0 | 0.55 99.40 0.05 | 85.523 | clear, no particular matter | 155 | 3 | 1 |
| T 6 months, −80° C. | 0.47 99.39 0.14 | 82.124 | clear, no particular matter | 210 | 8 | 5 |
| T 6 months, −30° C. | 1.28 98.58 0.14 | 81.61 | clear, no particular matter | 171 | 71 | 51 |

Conclusion

No significant instabilities of Adalimumab formulated in water at 50 and 100 mg/mL after freeze/thaw processing and after storage at −30° C. or −80° C. for up to 6 months have been observed with the analytical methodologies applied.

Example 31

Freezing and Thawing Process of Adalimumab in Low-Ionic Formulation—Process Design Space Including Protein Content Preparation of Solution Adalimumab BDS (Bulk Drug Substance) was thawed in a 23° C. circulating water bath. The solution was up-concentrated to a target concentration of 100 mg/ml for the purpose of volume reduction using a Ultrafiltration/Diafiltration (UF/DF) method (Pellicon "Mini" 2). Two cassettes of Millipore Pellicon 2 tangential flow mini-cassettes with Biomax 10K polyethersulfone were installed in the Pellicon 2 unit. At process start the flow rate was measured at 60 mL/min and feed pressure was 21 psi. The process was stopped at 111.3 mg/ml protein concentration.

Spectra/Por molecularporous membrane tubing was used for dialysis (diameter 48 mm, 18 ml/cm volume, 75 cm length). A volume of 8 L of Adalimumab 100 mg/ml at pH 5.2 were transferred to 8 dialysis tubes. Each tube was filled with 1 L of Adalimumab 100 mg/ml. Four tubes equal to 4 L of solution were placed in a container with 36 L of water for injection, i.e. a solution exchange factor of 1:10 was accomplished. The solution was allowed to reach equilibrium before the volume was exchanged against fresh water for injection. The solution exchange was repeated 5 times until a total solution exchange factor of 1:100,000 was reached.

After the solution was completely exchanged by dialysis it was up-concentrated by the second UF/DF step. The second UF/DF step was performed like the first step. A final concentration of 247.5 mg/ml Adalimumab in low-ionic formulation was achieved. The UF/DF was performed with starting material that already contained polysorbate 80. It could be expected that polysorbate 80 accumulated in the final protein solution resulting in a higher polysorbate content than 0.1%.

The up-concentrated bulk solution of 247.5 mg/ml Adalimumab was diluted with WFI to lower protein concentration levels as needed—200 mg/ml, 175 mg/ml, 150 mg/ml, 140 mg/ml, 130 mg/ml, 120 mg/ml, 100 mg/ml, 80 mg/ml, 50 mg/ml, 40 mg/ml, and 25 mg/ml. The bottle fill volume was 1600 ml for all experiments.

Freezing Procedures

A series of increasing freeze rates was used in this evaluation: Ultra-low temperature freezer bottom shelf<Ultra-low temperature freezer middle shelf<Ultra-low temperature freezer top shelf<<Dry ice.

A <−70° C. freezer was used for the experiments (Capacity: 20.2 Cu. Ft. (572 liters). Three shelves were used. Each was loaded with nine 2 L PETG bottles. The bottles were stored at room temperature before being placed in the freezer. Freezing continues for at least 48 hours. For the design space evaluations, three positions with increasing freeze rates were chosen. A front position on the bottom shelf was used for the slowest freeze rate. Faster freeze rates were accomplished at the center position on the middle shelf. The fastest freeze rate in the freezer setup was performed in the back/right position on the top shelf.

For freezing by dry ice, one bottle was completely surrounded by dry ice for at least 8 hours. In a Styrofoam box, the bottom was covered with a layer of dry ice (approx. 3 to 5 cm thick). One bottle was placed standing on top of the dry ice layer. Consequently, the space between the bottle and the inner walls of the styrofoam box was filled with dry ice until every surface but the cap was covered. After freezing time, the bottle was removed and thawed immediately or placed in a −70° C. freezer for storage.

Thawing Procedures

A series of thawing rates was used in this evaluation: Cooled air at 4° C.<<Water bath 23° C.<Water bath 37° C.

Analytics

The following analytics were performed to characterize the samples:
Osmolality
Conductivity
pH
Density
Protein concentration by direct UV (280 nm)

For the concentration test, samples were diluted with water until an absorbance <1.2 was reached. The absorbance coefficient for the Adalimumab molecule at 280 nm of 1.39 was used.

Characterization of Adalimumab Solutions

Bottle mapping studies revealed a slight tendency towards gradient formation in the bottle volume. Especially for the slower freeze and thaw rates, higher protein concentrations were detected near the bottle bottom. This phenomenon was also reflected in conductivity, density, and osmolality data. The pH appears practically constant in all tested conditions.

In previous investigations regarding the Freeze and Thaw design space for the bottle based system in ultra-low temperature freezers, the appearance of sedimentation was found to be the main failure mode determining the boundaries of the allowable operating range. In this study, this boundary was not observed although the investigated design space covered very wide ranges. The unique behavior of this product is also reflected in the very low tendency to form concentration gradients during this freezing and thawing process. In prior studies it was concluded that the product and process inherent gradient formation is the cause for the appearance of precipitate under certain process conditions. As a result, it was determined that from a process standpoint this system is feasible for Adalimumab in low-ionic formulation pH 5 up to a bulk drug substance concentration of 247.5 mg/ml. The investigated Adalimumab water formulation surprisingly demonstrated superior performance in comparison to other tested Adalimumab formulations.

TABLE 73

Distribution of Protein Concentration, Conductivity, Osmolarity, Density, and pH in the Freshly Thawed (23° C. water bath) 100 mg/ml Adalimumab in Low Ionic Formulation Containing Bottles

| sample name | volume ml | osmolarity mosm/kg | conductivity mS/cm | pH | density g/cm³ | Adalimumab conc mg/ml |
|---|---|---|---|---|---|---|
| Freeze & Thaw Conditions: −70 C. Top/23 C. Thaw |||||||
| 1 | 40 | 11 | 0.61 | 5.43 | 1.021 | 78.0 |
| 2 | 210 | 14 | 0.67 | 5.43 | 1.024 | 92.2 |
| 3 | 225 | 15 | 0.70 | 5.43 | 1.0253 | 98.1 |
| 4 | 200 | 17 | 0.72 | 5.46 | 1.0259 | 103.9 |

TABLE 73-continued

Distribution of Protein Concentration, Conductivity, Osmolarity, Density, and pH in the Freshly Thawed (23° C. water bath) 100 mg/ml Adalimumab in Low Ionic Formulation Containing Bottles

| sample name | volume ml | osmolarity mosm/kg | conductivity mS/cm | pH | density g/cm³ | Adalimumab conc mg/ml |
|---|---|---|---|---|---|---|
| 5 | 175 | 18 | 0.73 | 5.43 | 1.0268 | 100.2 |
| 6 | 180 | 18 | 0.74 | 5.43 | 1.0275 | 100.9 |
| 7 | 230 | 20 | 0.80 | 5.46 | 1.0284 | 109.1 |
| 8 | 180 | 22 | 0.81 | 5.45 | 1.0294 | 111.2 |
| 9 | 150 | 21 | 0.82 | 5.44 | 1.0307 | 118.0 |
| Freeze & Thaw Conditions: −70 C. Middle/23 C. Thaw |||||||
| 1 | 30 | 8 | 0.54 | 5.43 | 1.0174 | 65.3 |
| 2 | 175 | 18 | 0.68 | 5.44 | 1.0235 | 91.3 |
| 3 | 200 | 17 | 0.70 | 5.44 | 1.0245 | 92.1 |
| 4 | 185 | 17 | 0.72 | 5.44 | 1.0249 | 102.9 |
| 5 | 200 | 18 | 0.71 | 5.43 | 1.0248 | 95.6 |
| 6 | 200 | 20 | 0.73 | 5.44 | 1.0262 | 96.6 |
| 7 | 175 | 20 | 0.74 | 5.44 | 1.0283 | 107.5 |
| 8 | 180 | 20 | 0.77 | 5.45 | 1.0306 | 116.1 |
| 9 | 200 | 26 | 0.82 | 5.44 | 1.0346 | 131.1 |
| Freeze & Thaw Conditions: −70 C. Bottom/23 C. Thaw |||||||
| 1 | 35 | 9 | 0.60 | 5.41 | 1.0195 | 73.2 |
| 2 | 200 | 13 | 0.68 | 5.41 | 1.0231 | 89.6 |
| 3 | 225 | 16 | 0.70 | 5.41 | 1.0241 | 93.2 |
| 4 | 180 | 15 | 0.71 | 5.41 | 1.0246 | 96.8 |
| 5 | 200 | 15 | 0.72 | 5.40 | 1.0249 | 95.7 |
| 6 | 200 | 19 | 0.73 | 5.41 | 1.0259 | 96.4 |
| 7 | 185 | 21 | 0.75 | 5.42 | 1.0272 | 102.6 |
| 8 | 200 | 26 | 0.79 | 5.41 | 1.0309 | 116.8 |
| 9 | 175 | 31 | 0.85 | 5.42 | 1.0372 | 141.5 |

TABLE 74

Distribution of Protein Concentration, Conductivity, Osmolarity, Density, and pH in the Freshly Thawed (23° C. water bath) 140 mg/ml Adalimumab in Low Ionic Formulation Containing Bottles

| sample name | volume ml | osmolarity mosm/kg | conductivity mS/cm | pH | density g/cm³ | Adalimumab conc mg/ml |
|---|---|---|---|---|---|---|
| Freeze & Thaw Conditions: −70 C. Top/23 C. Thaw |||||||
| 1 | 50 | 36 | 0.87 | 5.43 | 1.0338 | 130.0 |
| 2 | 215 | 42 | 0.90 | 5.43 | 1.0354 | 139.9 |
| 3 | 170 | 54 | 0.91 | 5.43 | 1.0362 | 144.9 |
| 4 | 210 | 41 | 0.84 | 5.44 | 1.0365 | 141.5 |
| 5 | 200 | 40 | 0.93 | 5.43 | 1.0364 | 157.7 |
| 6 | 200 | 41 | 0.92 | 5.43 | 1.0364 | 140.0 |
| 7 | 190 | 41 | 0.92 | 5.43 | 1.0363 | 143.4 |
| 8 | 180 | 44 | 0.82 | 5.43 | 1.037 | 150.1 |
| 9 | 140 | 45 | 0.95 | 5.41 | 1.038 | 148.3 |
| Freeze & Thaw Conditions: −70 C. Middle/23 C. Thaw |||||||
| 1 | 25 | 32 | 0.81 | 5.45 | 1.0284 | 112.0 |
| 2 | 175 | 34 | 0.84 | 5.44 | 1.0307 | 122.4 |
| 3 | 175 | 36 | 0.88 | 5.44 | 1.033 | 133.9 |
| 4 | 200 | 40 | 0.90 | 5.43 | 1.0342 | 134.6 |
| 5 | 220 | 40 | 0.92 | 5.43 | 1.0351 | 140.9 |
| 6 | 185 | 45 | 0.94 | 5.43 | 1.0369 | 143.6 |
| 7 | 210 | 47 | 0.97 | 5.43 | 1.0384 | 149.8 |
| 8 | 175 | 47 | 0.99 | 5.43 | 1.0399 | 160.3 |
| 9 | 190 | 48 | 1.01 | 5.43 | 1.0435 | 168.3 |
| Freeze & Thaw Condition: −70 C. bottom/23 C. Thaw |||||||
| 1 | 75 | 28 | 0.75 | 5.45 | 1.0257 | 88.7 |
| 2 | 180 | 34 | 0.82 | 5.46 | 1.029 | 111.6 |
| 3 | 175 | 34 | 0.84 | 5.44 | 1.0313 | 123.5 |
| 4 | 220 | 37 | 0.86 | 5.44 | 1.0322 | 118.8 |
| 5 | 165 | 38 | 0.89 | 5.45 | 1.0337 | 126.3 |
| 6 | 215 | 44 | 0.95 | 5.45 | 1.0374 | 137.6 |
| 7 | 210 | 49 | 1.00 | 5.45 | 1.0407 | 149.6 |

TABLE 74-continued

Distribution of Protein Concentration, Conductivity, Osmolarity, Density, and pH in the Freshly Thawed (23° C. water bath) 140 mg/ml Adalimumab in Low Ionic Formulation Containing Bottles

| sample name | volume ml | osmolarity mosm/kg | conductivity mS/cm | pH | density g/cm³ | Adalimumab conc mg/ml |
|---|---|---|---|---|---|---|
| 8 | 150 | 53 | 1.03 | 5.43 | 1.0429 | 154.9 |
| 9 | 180 | 60 | 1.06 | 5.44 | 1.0501 | 183.2 |

TABLE 75

Distribution of Protein Concentration, Conductivity, Osmolarity, Density, and pH in the Freshly Thawed (37° C. water bath) 200 mg/ml Adalimumab in Low Ionic Formulation Containing Bottles

| sample name | volume ml | osmolarity mosm/kg | conductivity mS/cm | pH | density g/cm3 | Adalimumab conc mg/ml |
|---|---|---|---|---|---|---|
| Freeze & Thaw Conditions: −70 C. Top/37 C. Thaw ||||||||
| 1 | 40 | 37 | 0.89 | 5.26 | 1.0573 | 197.5 |
| 2 | 210 | 35 | 0.96 | 5.24 | 1.0573 | 195.3 |
| 3 | 175 | 34 | 0.96 | 5.22 | 1.0578 | 200.3 |
| 4 | 210 | 36 | 0.88 | 5.27 | 1.0579 | 193.9 |
| 5 | 210 | 39 | 0.89 | 5.24 | 1.058 | 210.6 |
| 6 | 190 | 39 | 0.84 | 5.27 | 1.058 | 213.8 |
| 7 | 200 | 41 | 0.88 | 5.27 | 1.058 | 206.7 |
| 8 | 170 | 41 | 0.88 | 5.24 | 1.0581 | 196.6 |
| 9 | 160 | 39 | 0.89 | 5.29 | 1.0595 | 201.9 |
| Freeze & Thaw Conditions: −70 C. Center/37 C. Thaw ||||||||
| 1 | 10 | 31 | 0.85 | 5.29 | 1.0485 | 170.2 |
| 2 | 185 | 35 | 0.89 | 5.31 | 1.0505 | 189.3 |
| 3 | 215 | 37 | 0.90 | 5.33 | 1.0518 | 191.7 |
| 4 | 185 | 38 | 0.89 | 5.27 | 1.0519 | 191.8 |
| 5 | 200 | 36 | 0.90 | 5.32 | 1.0528 | 196.3 |
| 6 | 200 | 48 | 0.90 | 5.28 | 1.0533 | 189.3 |
| 7 | 170 | 37 | 0.90 | 5.23 | 1.0536 | 193.1 |
| 8 | 215 | 39 | 0.91 | 5.33 | 1.0552 | 202.1 |
| 9 | 180 | 48 | 0.92 | 5.31 | 1.0613 | 225.5 |
| Freeze & Thaw Conditions: −70 C. Bottom/37 C. Thaw ||||||||
| 1 | 50 | 22 | 0.96 | 5.27 | 1.0361 | 107.1 |
| 2 | 185 | 29 | 0.83 | 5.26 | 1.0422 | 163.0 |
| 3 | 180 | 38 | 0.88 | 5.27 | 1.0522 | 201.2 |
| 4 | 185 | 41 | 0.90 | 5.24 | 1.0535 | 198.9 |
| 5 | 180 | 44 | 0.92 | 5.28 | 1.0552 | 201.4 |
| 6 | 195 | 40 | 0.91 | 5.32 | 1.0558 | 201.7 |
| 7 | 180 | 40 | 0.91 | 5.32 | 1.0560 | 199.6 |
| 8 | 175 | 41 | 0.85 | 5.26 | 1.0568 | 206.2 |
| 9 | 190 | 48 | 0.91 | 5.3 | 1.0619 | 229.3 |

TABLE 76

Distribution of Protein Concentration, Conductivity, Osmolarity, Density, and pH in the Freshly Thawed (23° C. water bath) 247.5 mg/ml Adalimumab in Low Ionic Formulation Containing Bottles

| sample name | volume ml | osmolarity mosm/kg | conductivity mS/cm | pH | density g/cm³ | Adalimumab conc mg/ml |
|---|---|---|---|---|---|---|
| Freeze & Thaw Conditions: −70 C. Top/23 C. Thaw ||||||||
| 1 | 65 | 46 | 0.98 | 5.28 | 1.0755 | 260.9 |
| 2 | 190 | 72 | 0.97 | 5.28 | 1.0751 | 270.8 |
| 3 | 190 | 56 | 0.97 | 5.28 | 1.0751 | 314.7 |
| 4 | 200 | 49 | 0.96 | 5.27 | 1.0751 | 274.8 |
| 5 | 200 | 58 | 0.96 | 5.27 | 1.0752 | 278.4 |
| 6 | 210 | 57 | 0.97 | 5.28 | 1.0752 | 275.0 |
| 7 | 210 | 76 | 0.96 | 5.28 | 1.0748 | 276.5 |
| 8 | 175 | 75 | 0.96 | 5.27 | 1.0754 | 274.5 |
| 9 | 150 | 62 | 0.97 | 5.28 | 1.0763 | 276.3 |
| Freeze & Thaw Conditions: −70 C. Middle/23 C. Thaw ||||||||
| 1 | 80 | 37 | 0.95 | 5.29 | 1.0671 | 250.0 |
| 2 | 200 | 59 | 0.95 | 5.32 | 1.0704 | 251.3 |
| 3 | 175 | 51 | 0.97 | 5.31 | 1.0722 | 262.7 |
| 4 | 215 | 56 | 0.98 | 5.31 | 1.073 | 327.1 |
| 5 | 200 | 48 | 0.99 | 5.31 | 1.0739 | 267.7 |
| 6 | 200 | 67 | 0.98 | 5.31 | 1.0744 | 270.6 |
| 7 | 230 | 59 | 0.95 | 5.32 | 1.0753 | 273.2 |
| 8 | 175 | 70 | 0.96 | 5.32 | 1.0771 | 273.3 |
| 9 | 175 | 83 | 0.96 | 5.32 | 1.0825 | 289.6 |
| Freeze & Thaw Conditions: −70 C. Bottom/23 C. Thaw ||||||||
| 1 | 50 | 32 | 0.92 | 5.24 | 1.0632 | 215.3 |
| 2 | 220 | 59 | 0.95 | 5.27 | 1.069 | 221.7 |
| 3 | 175 | 72 | 0.96 | 5.27 | 1.0708 | 268.1 |
| 4 | 180 | 58 | 0.96 | 5.27 | 1.0725 | 260.7 |
| 5 | 210 | 63 | 0.96 | 5.27 | 1.0729 | 266.8 |
| 6 | 150 | 69 | 0.96 | 5.28 | 1.0744 | 280.3 |
| 7 | 225 | 50 | 0.96 | 5.29 | 1.0762 | 280.3 |
| 8 | 200 | 68 | 0.95 | 5.28 | 1.0789 | 288.6 |
| 9 | 180 | 70 | 0.95 | 5.29 | 1.0846 | 293.0 |

TABLE 77

Distribution of Protein Concentration, Conductivity, Osmolarity, Density, and pH in the Freshly Thawed (23° C. water bath) 247.5 mg/ml Adalimumab in Low Ionic Formulation Containing Bottles After Dry Ice Freezing

| sample name | volume ml | osmolarity mosm/kg | conductivity mS/cm | pH | density g/cm³ | Adalimumab conc mg/ml |
|---|---|---|---|---|---|---|
| Freeze & Thaw Conditions: Dry Ice Freeze/23 C. Thaw ||||||||
| 1 | 50 | 51 | 0.94 | 5.28 | 1.0643 | 258.9 |
| 2 | 210 | 68 | 0.94 | 5.29 | 1.0683 | 261.9 |
| 3 | 180 | 50 | 0.95 | 5.29 | 1.0702 | 251.7 |
| 4 | 190 | 69 | 0.95 | 5.29 | 1.0732 | 262.2 |
| 5 | 210 | 72 | 0.96 | 5.31 | 1.0738 | 274.4 |
| 6 | 225 | 63 | 0.95 | 5.3 | 1.0746 | 265.7 |
| 7 | 160 | 57 | 0.95 | 5.3 | 1.0747 | 261.9 |
| 8 | 190 | 63 | 0.95 | 5.31 | 1.0749 | 270.9 |
| 9 | 200 | 50 | 0.95 | 5.31 | 1.075 | 271.4 |
| Freeze & Thaw Conditions: Dry Ice Freeze/2-8 C. Thaw ||||||||
| 1 | 50 | 44 | 0.96 | 5.29 | 1.0665 | 263.1 |
| 2 | 190 | 53 | 0.96 | 5.31 | 1.0684 | 258.1 |
| 3 | 200 | 56 | 0.96 | 5.30 | 1.0691 | 247.6 |
| 4 | 200 | 58 | 0.96 | 5.30 | 1.0693 | 262.2 |
| 5 | 190 | 64 | 0.95 | 5.31 | 1.0695 | 243.2 |
| 6 | 200 | 61 | 0.95 | 5.3 | 1.0695 | 266.8 |
| 7 | 175 | 49 | 0.96 | 5.32 | 1.0697 | 256.2 |
| 8 | 200 | 50 | 0.95 | 5.31 | 1.0697 | 261.2 |
| 9 | 175 | 48 | 0.96 | 5.32 | 1.0704 | 247.1 |

APPENDIX A

PCS DATA

| concentration [mg/mL] | concentration [mg/mL] averagne value | z-average [nm] | z-average average value [nm] | peak monomer [nm] | peak monomer average value [nm] |
|---|---|---|---|---|---|
| Adalimumab | | | | | |
| 9.35 | 9.35 | 2.08 | 2.08 | 2.55 | 2.55 |
| 23.40 | 23.27 | 2.30 | 2.47 | 2.81 | 2.87 |
| 22.70 | | 2.77 | | 3.01 | |
| 23.70 | | 2.36 | | 2.78 | |
| 34.80 | 34.20 | 1.56 | 1.55 | 1.85 | 1.87 |
| 35.70 | | 1.54 | | 1.82 | |
| 32.10 | | 1.56 | | 1.93 | |
| 35.40 | 36.10 | 1.61 | 1.63 | 1.92 | 1.92 |
| 36.10 | | 1.64 | | 1.93 | |
| 36.80 | | 1.63 | | 1.92 | |
| 42.10 | 43.00 | 1.75 | 1.75 | 2.12 | 2.12 |
| 45.60 | | 1.78 | | 2.15 | |
| 41.30 | | 1.74 | | 2.10 | |
| 60.20 | 57.40 | 2.06 | 2.02 | 2.27 | 2.37 |
| 55.90 | | 2.04 | | 2.45 | |
| 56.10 | | 1.98 | | 2.39 | |
| 63.20 | 65.87 | 2.11 | 2.24 | 2.52 | 2.67 |
| 71.70 | | 2.49 | | 2.89 | |
| 62.70 | | 2.13 | | 2.61 | |
| 73.40 | 75.13 | 2.38 | 2.41 | 2.83 | 2.89 |
| 75.60 | | 2.51 | | 3.01 | |
| 76.40 | | 2.35 | | 2.82 | |
| 78.60 | 78.07 | 2.53 | 2.55 | 2.99 | 2.99 |
| 78.80 | | 2.62 | | 3.01 | |
| 76.80 | | 2.50 | | 2.96 | |
| 90.40 | 95.73 | 2.80 | 2.85 | 3.35 | 3.41 |
| 107.40 | | 2.99 | | 3.55 | |
| 89.40 | | 2.76 | | 3.33 | |
| 96.20 | 94.77 | 2.88 | 2.86 | 3.50 | 3.50 |
| 96.00 | | 2.91 | | 3.61 | |
| 92.10 | | 2.80 | | 3.38 | |
| 201.00 | 206.63 | 4.52 | 4.82 | 5.22 | 5.74 |
| 227.50 | | 5.04 | | 6.12 | |
| 191.40 | | 4.89 | | 5.89 | |
| J695 | | | | | |
| 9.99 | 9.99 | 2.28 | 2.28 | 1.66 | 1.66 |
| 19.31 | 19.29 | 2.05 | 2.12 | 1.81 | 1.81 |
| 19.26 | | 2.30 | | 1.79 | |
| 19.29 | | 2.02 | | 1.84 | |
| 29.59 | 29.40 | 1.78 | 1.62 | 1.10 | 1.16 |
| 29.7 | | 1.51 | | 1.15 | |
| 28.91 | | 1.56 | | 1.22 | |
| 37.97 | 37.55 | 1.51 | 1.56 | 1.22 | 1.23 |
| 38.02 | | 1.67 | | 1.22 | |
| 36.65 | | 1.49 | | 1.24 | |
| 49.15 | 46.32 | 1.64 | 1.58 | 1.31 | 1.29 |
| 45.95 | | 1.57 | | 1.30 | |
| 43.87 | | 1.53 | | 1.26 | |
| 58.75 | 56.18 | 1.60 | 1.61 | 1.49 | 1.47 |
| 55.02 | | 1.71 | | 1.38 | |
| 54.76 | | 1.53 | | 1.53 | |
| 77.69 | 77.81 | 2.64 | 2.43 | 2.73 | 2.61 |
| 77.62 | | 2.31 | | 2.57 | |
| 78.13 | | 2.35 | | 2.52 | |
| 94.45 | 97.65 | 2.11 | 2.07 | 2.05 | 2.05 |
| 105.06 | | 2.14 | | 2.05 | |
| 93.45 | | 1.97 | | 2.04 | |
| 116.37 | 114.52 | 3.69 | 2.69 | 1.95 | 2.00 |
| 113.92 | | 2.25 | | 2.06 | |
| 113.27 | | 2.13 | | 1.99 | |
| 121.21 | 133.25 | 9.78 | 9.49 | 11.50 | 11.00 |
| 139.8 | | 9.63 | | 11.10 | |
| 138.73 | | 9.06 | | 10.40 | |
| 226.67 | 217.53 | 4.94 | 5.34 | 4.72 | 4.84 |
| 216.1 | | 6.01 | | 5.25 | |
| 209.83 | | 5.06 | | 4.55 | |
| Human Serum Albumin | | | | | |
| 9.88 | 9.88 | 14.90 | 14.90 | 2.32 | 2.32 |
| 22.94 | 22.89 | 8.26 | 8.29 | 1.2 | 1.18 |
| 22.73 | | 8.28 | | 1.18 | |
| 23.00 | | 8.33 | | 1.17 | |
| 36.78 | 36.47 | 7.40 | 7.44 | 1.22 | 1.23 |
| 37.33 | | 7.80 | | 1.24 | |
| 35.29 | | 7.12 | | 1.22 | |
| 45.97 | 46.06 | 7.09 | 6.92 | 1.27 | 1.25 |
| 47.61 | | 6.54 | | 1.24 | |
| 44.61 | | 7.13 | | 1.25 | |
| 58.47 | 58.56 | 5.94 | 6.13 | 1.3 | 1.31 |
| 62.69 | | 6.04 | | 1.31 | |
| 54.52 | | 6.41 | | 1.32 | |
| 61.89 | 60.31 | 5.83 | 6.14 | 1.33 | 1.32 |
| 59.76 | | 6.57 | | 1.34 | |
| 59.28 | | 6.01 | | 1.29 | |
| 75.37 | 76.24 | 5.58 | 5.46 | 1.4 | 1.40 |
| 83.69 | | 5.14 | | 1.45 | |
| 69.67 | | 5.67 | | 1.36 | |
| 92.90 | 85.87 | 5.30 | 5.14 | 1.49 | 1.47 |
| 84.22 | | 5.05 | | 1.49 | |
| 80.50 | | 5.08 | | 1.43 | |
| 115.93 | 112.74 | 4.78 | 4.94 | 1.68 | 1.61 |
| 110.00 | | 5.04 | | 1.58 | |
| 112.30 | | 4.99 | | 1.57 | |
| 182.79 | 177.69 | 9.85 | 9.13 | 2.27 | 2.19 |
| 178.24 | | 9.29 | | 2.21 | |
| 172.05 | | 8.26 | | 2.08 | |

APPENDIX B

SEC DATA

| conc. [mg/mL] | mean conc. [mg/mL] | monomer [%] | mean monomer [%] | aggregate [%] | mean aggregate [%] | fragment [%] | mean fragment [%] |
|---|---|---|---|---|---|---|---|
| Adalimumab | | | | | | | |
| 9.35 | 9.35 | 99.40 | 99.40 | 0.50 | 0.50 | 0.10 | 0.10 |
| 23.40 | 23.27 | 99.60 | 99.57 | 0.40 | 0.40 | 0.10 | 0.10 |
| 22.70 | | 99.50 | | 0.40 | | 0.10 | |
| 23.70 | | 99.60 | | 0.40 | | 0.10 | |
| 34.80 | 34.20 | 99.50 | 99.47 | 0.50 | 0.47 | 0.10 | 0.10 |
| 35.70 | | 99.40 | | 0.50 | | 0.10 | |
| 32.10 | | 99.50 | | 0.40 | | 0.10 | |
| 35.40 | 36.10 | 99.40 | 99.40 | 0.60 | 0.53 | 0.10 | 0.10 |
| 36.10 | | 99.40 | | 0.50 | | 0.10 | |

APPENDIX B-continued

| | | | | | | | |
|---|---|---|---|---|---|---|---|
| 36.80 | | 99.40 | | 0.50 | | 0.10 | |
| 42.10 | 43.00 | 99.40 | 99.33 | 0.50 | 0.57 | 0.10 | 0.10 |
| 45.60 | | 99.30 | | 0.60 | | 0.10 | |
| 41.30 | | 99.30 | | 0.60 | | 0.10 | |
| 60.20 | 57.40 | 99.30 | 99.30 | 0.60 | 0.60 | 0.10 | 0.10 |
| 55.90 | | 99.30 | | 0.60 | | 0.10 | |
| 56.10 | | 99.30 | | 0.60 | | 0.10 | |
| 63.20 | 65.87 | 99.30 | 99.27 | 0.60 | 0.67 | 0.10 | 0.10 |
| 71.70 | | 99.20 | | 0.70 | | 0.10 | |
| 62.70 | | 99.30 | | 0.70 | | 0.10 | |
| 73.40 | 75.13 | 99.20 | 99.23 | 0.70 | 0.70 | 0.10 | 0.10 |
| 75.60 | | 99.20 | | 0.70 | | 0.10 | |
| 76.40 | | 99.30 | | 0.70 | | 0.10 | |
| 78.60 | 78.07 | 99.30 | 99.30 | 0.60 | 0.60 | 0.10 | 0.10 |
| 78.80 | | 99.30 | | 0.60 | | 0.10 | |
| 76.80 | | 99.30 | | 0.60 | | 0.10 | |
| 90.40 | 95.73 | 99.20 | 99.13 | 0.80 | 0.80 | 0.10 | 0.10 |
| 107.40 | | 99.10 | | 0.80 | | 0.10 | |
| 89.40 | | 99.10 | | 0.80 | | 0.10 | |
| 96.20 | 94.77 | 99.10 | 99.03 | 0.80 | 0.87 | 0.10 | 0.10 |
| 96.00 | | 99.00 | | 0.90 | | 0.10 | |
| 92.10 | | 99.00 | | 0.90 | | 0.10 | |
| 201.00 | 206.63 | 98.80 | 98.80 | 1.10 | 1.10 | 0.10 | 0.10 |
| 227.50 | | 98.80 | | 1.10 | | 0.10 | |
| 191.40 | | 98.80 | | 1.10 | | 0.10 | |
| | | | J695 | | | | |
| 9.99 | 9.99 | 99.39 | 99.39 | 0.44 | 0.44 | 0.17 | 0.17 |
| 19.31 | 19.29 | 99.38 | 99.38 | 0.44 | 0.44 | 0.18 | 0.19 |
| 19.26 | | 99.37 | | 0.44 | | 0.20 | |
| 19.29 | | 99.38 | | 0.44 | | 0.18 | |
| 29.59 | 29.40 | 99.31 | 99.33 | 0.51 | 0.50 | 0.18 | 0.18 |
| 29.70 | | 99.32 | | 0.50 | | 0.18 | |
| 28.91 | | 99.35 | | 0.48 | | 0.17 | |
| 37.97 | 37.55 | 99.31 | 99.29 | 0.52 | 0.52 | 0.17 | 0.19 |
| 38.02 | | 99.27 | | 0.52 | | 0.21 | |
| 36.65 | | 99.30 | | 0.51 | | 0.19 | |
| 49.15 | 46.32 | 99.19 | 99.20 | 0.60 | 0.60 | 0.21 | 0.20 |
| 45.95 | | 99.20 | | 0.60 | | 0.20 | |
| 43.87 | | 99.20 | | 0.61 | | 0.19 | |
| 58.75 | 56.18 | 99.16 | 99.16 | 0.64 | 0.64 | 0.21 | 0.21 |
| 55.02 | | 99.17 | | 0.64 | | 0.20 | |
| 54.76 | | 99.15 | | 0.64 | | 0.22 | |
| 77.69 | 77.81 | 99.11 | 99.10 | 0.70 | 0.70 | 0.19 | 0.20 |
| 77.62 | | 99.09 | | 0.69 | | 0.22 | |
| 78.13 | | 99.10 | | 0.70 | | 0.20 | |
| 94.45 | 97.65 | 99.05 | 99.06 | 0.72 | 0.71 | 0.23 | 0.22 |
| 105.06 | | 99.06 | | 0.72 | | 0.21 | |
| 93.45 | | 99.07 | | 0.70 | | 0.23 | |
| 116.37 | 114.52 | 98.94 | 98.91 | 0.85 | 0.88 | 0.21 | 0.22 |
| 113.92 | | 98.91 | | 0.88 | | 0.22 | |
| 113.27 | | 98.89 | | 0.90 | | 0.22 | |
| 121.21 | 133.25 | 98.87 | 98.89 | 0.91 | 0.90 | 0.22 | 0.22 |
| 139.80 | | 98.89 | | 0.89 | | 0.22 | |
| 138.73 | | 98.90 | | 0.89 | | 0.21 | |
| 226.67 | 217.53 | 98.58 | 98.57 | 1.19 | 1.21 | 0.24 | 0.23 |
| 216.10 | | 98.58 | | 1.18 | | 0.24 | |
| 209.83 | | 98.54 | | 1.25 | | 0.21 | |

Human Serum Albumin

| | Peak 1 | | Peak 2 | | Peak 3 | | Peak 4 (HSA) | |
|---|---|---|---|---|---|---|---|---|
| sample | Area [mVs] | Area [%] | Area [mVs] | Area [%] | Area [mVs] | Area [%] | Area [mVs] | Area [%] |
| sample 1<br>c = 9.88 mg/ml | 59.710 | 2.312 | 2.975 | 0.115 | 43.159 | 1.671 | 2477.282 | 95.902 |
| sample 2<br>c = 22.94 mg/ml | 102.785 | 2.685 | 7.859 | 0.205 | 73.588 | 1.923 | 3643.350 | 95.187 |
| sample 3<br>c = 22.73 mg/ml | 124.226 | 3.071 | 11.038 | 0.273 | 83.310 | 2.059 | 3826.908 | 94.597 |
| sample 4<br>c = 23.00 mg/ml | 138.353 | 3.266 | 14.525 | 0.343 | 88.429 | 2.087 | 3994.990 | 94.304 |
| sample 5<br>c = 36.78 mg/ml | 147.465 | 3.459 | 14.537 | 0.341 | 91.304 | 2.141 | 4010.385 | 94.059 |
| sample 6<br>c = 37.33 mg/ml | 153.956 | 3.552 | 14.707 | 0.339 | 94.093 | 2.171 | 4071.680 | 93.938 |
| sample 7<br>c = 35.29 mg/ml | 171.478 | 3.608 | 16.064 | 0.338 | 105.244 | 2.214 | 4459.830 | 93.839 |

APPENDIX B-continued

| sample | | | | | | | | |
|---|---|---|---|---|---|---|---|---|
| sample 8 c = 45.97 mg/ml | 180.027 | 3.675 | 17.392 | 0.355 | 109.717 | 2.239 | 4592.102 | 93.731 |
| sample 9 c = 47.61 mg/ml | 193.325 | 3.719 | 19.206 | 0.370 | 116.474 | 2.241 | 4868.705 | 93.670 |
| sample 10 c = 44.61 mg/ml | 191.512 | 3.799 | 19.167 | 0.380 | 112.261 | 2.227 | 4718.554 | 93.594 |
| sample 11 c = 58.47 mg/ml | 215.044 | 4.026 | 17.870 | 0.335 | 118.481 | 2.218 | 4989.978 | 93.421 |
| sample 12 c = 62.69 mg/ml | 218.072 | 4.037 | 20.088 | 0.372 | 122.251 | 2.263 | 5041.542 | 93.328 |
| sample 13 c = 54.52 mg/ml | 228.014 | 4.053 | 19.957 | 0.355 | 126.583 | 2.250 | 5251.513 | 93.343 |
| sample 14 c = 61.89 mg/ml | 231.235 | 4.085 | 22.518 | 0.398 | 127.330 | 2.250 | 5279.038 | 93.267 |
| sample 15 c = 59.76 mg/ml | 237.894 | 4.100 | 22.939 | 0.395 | 130.352 | 2.246 | 5411.384 | 93.258 |
| sample 16 c = 59.28 mg/ml | 202.103 | 4.139 | 17.178 | 0.352 | 108.780 | 2.228 | 4554.912 | 93.282 |
| sample 17 c = 75.37 mg/ml | 230.552 | 4.196 | 18.565 | 0.338 | 123.207 | 2.242 | 5122.467 | 93.224 |
| sample 18 c = 83.69 mg/ml | 215.365 | 4.162 | 18.136 | 0.351 | 110.152 | 2.129 | 4830.372 | 93.358 |
| sample 21 c = 84.22 mg/ml | 233.866 | 4.316 | 21.951 | 0.405 | 116.325 | 2.147 | 5046.183 | 93.132 |
| sample 22 c = 80.50 mg/ml | 221.816 | 4.461 | 18.940 | 0.381 | 111.006 | 2.232 | 4620.655 | 92.926 |
| sample 23 c = 115.93 mg/ml | 223.187 | 4.783 | 16.684 | 0.358 | 104.116 | 2.231 | 4322.732 | 92.629 |
| sample 24 c = 110.00 mg/ml | 209.281 | 4.718 | 18.745 | 0.423 | 96.430 | 2.174 | 4111.363 | 92.686 |
| sample 25 c = 112.30 mg/ml | 172.657 | 4.537 | 15.457 | 0.406 | 80.850 | 2.125 | 3536.192 | 92.932 |
| sample 26 c = 182.79 mg/ml | 178.208 | 4.950 | 15.254 | 0.424 | 80.906 | 2.247 | 3325.648 | 92.379 |
| sample 27 c = 178.24 mg/ml | 194.516 | 4.814 | 17.323 | 0.429 | 90.433 | 2.238 | 3738.717 | 95.520 |
| sample 28 c = 172.05 mg/ml | 79.605 | 2.103 | 12.876 | 0.340 | 74.965 | 1.981 | 3617.238 | 95.576 |

APPENDIX C

EC DATA

Adalimumab

| conc. [mg/mL] | mean conc. [mg/mL] | sum Lysin [%] | mean sum [%] |
|---|---|---|---|
| 9.35 | 9.35 | 86.09 | 86.09 |
| 23.40 | 23.27 | 86.15 | 86.13 |
| 22.70 | | 86.12 | |
| 23.70 | | 86.13 | |
| 34.80 | 34.20 | 86.15 | 86.11 |
| 35.70 | | 86.11 | |
| 32.10 | | 86.06 | |
| 35.40 | 36.10 | 86.03 | 86.04 |
| 36.10 | | 86.06 | |
| 36.80 | | 86.03 | |
| 42.10 | 43.00 | 85.98 | 85.96 |
| 45.60 | | 85.95 | |
| 41.30 | | 85.95 | |
| 60.20 | 57.40 | 85.97 | 85.96 |
| 55.90 | | 85.94 | |
| 56.10 | | 85.97 | |
| 63.20 | 65.87 | 85.96 | 85.94 |
| 71.70 | | 85.97 | |
| 62.70 | | 85.90 | |
| 73.40 | 75.13 | 85.99 | 85.97 |
| 75.60 | | 85.98 | |
| 76.40 | | 85.95 | |
| 78.60 | 78.07 | 86.00 | 85.97 |
| 78.80 | | 85.97 | |
| 76.80 | | 85.94 | |
| 90.40 | 95.73 | 85.96 | 85.92 |
| 107.40 | | 85.97 | |
| 89.40 | | 85.83 | |
| 96.20 | 94.77 | 85.93 | 85.88 |
| 96.00 | | 85.87 | |

APPENDIX C-continued

EC DATA

| | | | |
|---|---|---|---|
| 92.10 | | 85.84 | |
| 201.00 | 206.63 | 85.88 | 85.90 |
| 227.50 | | 85.97 | |
| 191.40 | | 85.84 | |

J695

| conc. [mg/mL] | mean conc. [mg/mL] | sum peak 1-7 [%] | mean sum peak 1-7 [%] | sum acidic peaks [%] | mean sum acidic peaks [%] | sum basic peaks [%] | mean sum basic peaks [%] |
|---|---|---|---|---|---|---|---|
| 9.99 | 9.99 | 89.24 | 89.24 | 10.24 | 10.24 | 0.52 | 0.52 |
| 19.31 | 19.29 | 89.32 | 89.28 | 10.19 | 10.21 | 0.50 | 0.51 |
| 19.26 | | 89.23 | | 10.26 | | 0.52 | |
| 19.29 | | 89.30 | | 10.19 | | 0.51 | |
| 29.59 | 29.40 | 89.33 | 89.30 | 10.14 | 10.17 | 0.54 | 0.53 |
| 29.70 | | 89.26 | | 10.20 | | 0.54 | |
| 28.91 | | 89.32 | | 10.16 | | 0.52 | |
| 37.97 | 37.55 | 89.32 | 89.30 | 10.13 | 10.15 | 0.56 | 0.55 |
| 38.02 | | 89.27 | | 10.18 | | 0.55 | |
| 36.65 | | 89.31 | | 10.15 | | 0.55 | |
| 49.15 | 46.32 | 89.07 | 89.10 | 10.40 | 10.37 | 0.53 | 0.53 |
| 45.95 | | 89.12 | | 10.34 | | 0.54 | |
| 43.87 | | 89.12 | | 10.36 | | 0.53 | |
| 58.75 | 56.18 | 89.13 | 89.17 | 10.36 | 10.31 | 0.52 | 0.53 |
| 55.02 | | 89.21 | | 10.27 | | 0.52 | |
| 54.76 | | 89.18 | | 10.29 | | 0.54 | |
| 77.69 | 77.81 | 89.22 | 89.17 | 10.25 | 10.29 | 0.53 | 0.54 |
| 77.62 | | 89.09 | | 10.36 | | 0.55 | |
| 78.13 | | 89.20 | | 10.26 | | 0.55 | |
| 94.45 | 97.65 | 89.20 | 89.16 | 10.28 | 10.30 | 0.52 | 0.54 |
| 105.06 | | 89.12 | | 10.33 | | 0.55 | |
| 93.45 | | 89.16 | | 10.29 | | 0.55 | |
| 116.37 | 114.52 | 89.03 | 89.08 | 10.41 | 10.36 | 0.56 | 0.55 |
| 113.92 | | 89.15 | | 10.31 | | 0.54 | |
| 113.27 | | 89.06 | | 10.37 | | 0.56 | |
| 121.21 | 133.25 | 89.26 | 89.13 | 10.20 | 10.33 | 0.54 | 0.55 |
| 139.80 | | 89.07 | | 10.38 | | 0.56 | |
| 138.73 | | 89.05 | | 10.40 | | 0.55 | |
| 226.67 | 217.53 | 88.72 | 88.78 | 10.69 | 10.63 | 0.59 | 0.59 |
| 216.10 | | 88.82 | | 10.60 | | 0.58 | |
| 209.83 | | 88.81 | | 10.60 | | 0.59 | |

APPENDIX D

| Test Item | Component | Duration of Testing | 63 mg/mL 5° C. | 220 mg/mL 5° C. |
|---|---|---|---|---|
| Clarity and opalescence | Turbidity | Initial | 3.6 | 8.0 |
| | | 1 month | 3.5 | 8.0 |
| | | 3 month | 3.5 | 7.4 |
| Degree of coloration of liquids | B scale | Initial | <B9 | =B9 |
| | | 1 month | <B9 | <B8 |
| | | 3 month | <B9 | <B7 |
| pH | Single value | Initial | 5.3 | 5.4 |
| | | 1 month | 5.3 | 5.4 |
| | | 3 month | 5.3 | 5.4 |
| Particulate contamination: visible particles | visual score | Initial | 2.2 | 0.2 |
| | | 1 month | 2.2 | 0.4 |
| | | 3 month | 2.1 | 0.2 |
| Particulate contamination: subvisible particles | Particles >= 10 μm [/Container] | Initial | 181 | 357 |
| | | 1 month | 423 | 290 |
| | | 3 month | 216 | 1762 |
| | Particles >= 25 μm [/Container] | Initial | 15 | 3 |
| | | 1 month | 11 | 18 |
| | | 3 month | 2 | 50 |
| Size exclusion chromatography (SE-HPLC) | Principal peak (aggregate) [%] | Initial | 0.2 | 0.5 |
| | | 1 month | 0.2 | 0.6 |
| | | 3 month | 0.2 | 0.7 |
| | Principal peak (monomer) [%] | Initial | 99.8 | 99.4 |
| | | 1 month | 99.7 | 99.3 |
| | | 3 month | 99.7 | 99.2 |

APPENDIX D-continued

| | | | | |
|---|---|---|---|---|
| Cation exchange HPLC (CEX-HPLC) | Principal peak (fragment) [%] | Initial | 0.1 | 0.1 |
| | | 1 month | 0.1 | 0.1 |
| | | 3 month | 0.0 | 0.0 |
| | 1st acidic region [%] | Initial | 2.2 | 2.2 |
| | | 1 month | 2.2 | 2.2 |
| | | 3 month | 2.1 | 2.0 |
| | 2nd acidic region [%] | Initial | 10.4 | 10.3 |
| | | 1 month | 10.2 | 10.0 |
| | | 3 month | 10.4 | 10.2 |
| | Sum of lysine variants [%] | Initial | 86.0 | 86.1 |
| | | 1 month | 85.9 | 85.9 |
| | | 3 month | 86.2 | 86.1 |
| | Peak between lysine 1 und lysine 2 [%] | Initial | 0.8 | 0.8 |
| | | 1 month | 1.0 | 1.0 |
| | | 3 month | 0.8 | 0.8 |
| | Peaks after Lysin 2 [%] | Initial | 0.5 | 0.6 |
| | | 1 month | 0.7 | 0.9 |
| | | 3 month | 0.5 | 0.8 |

| Test Item | Component | Duration of Testing | 63 mg/mL 25° C./60% R.H. | 220 mg/mL 25° C./60% R.H. |
|---|---|---|---|---|
| Clarity and opalescence | Turbidity | Initial | — | — |
| | | 1 month | 3.51 | 8.55 |
| | | 3 month | 3.70 | 7.56 |
| Degree of coloration of liquids | B scale | Initial | — | — |
| | | 1 month | <B9 | <B8 |
| | | 3 month | <B9 | <B7 |
| pH | Single value | Initial | — | — |
| | | 1 month | 5.4 | 5.4 |
| | | 3 month | 5.3 | 5.4 |
| Particulate contamination: visible particles | visual score | Initial | — | — |
| | | 1 month | 2.5 | 0.7 |
| | | 3 month | 3.4 | 0.0 |
| Particulate contamination: subvisible particles | Particles >= 10 μm [/Container] | Initial | — | — |
| | | 1 month | 412 | 490 |
| | | 3 month | 277 | 4516 |
| | Particles >= 25 μm [/Container] | Initial | — | — |
| | | 1 month | 10 | 14 |
| | | 3 month | 7 | 128 |
| Size exclusion chromatography (SE-HPLC) | Principal peak (aggregate) [%] | Initial | — | — |
| | | 1 month | 0.3 | 0.8 |
| | | 3 month | 0.4 | 1.1 |
| | Principal peak (monomer) [%] | Initial | — | — |
| | | 1 month | 99.6 | 99.0 |
| | | 3 month | 99.4 | 98.6 |
| | Principal peak (fragment) [%] | Initial | — | — |
| | | 1 month | 0.2 | 0.2 |
| | | 3 month | 0.2 | 0.2 |
| Cation exchange HPLC (CEX-HPLC) | 1st acidic region [%] | Initial | — | — |
| | | 1 month | 2.5 | 2.4 |
| | | 3 month | 3.4 | 3.2 |
| | 2nd acidic region [%] | Initial | — | — |
| | | 1 month | 11.7 | 11.4 |
| | | 3 month | 15.3 | 14.9 |
| | Sum of lysine variants [%] | Initial | — | — |
| | | 1 month | 83.6 | 83.8 |
| | | 3 month | 79.2 | 79.2 |
| | Peak between lysine 1 und lysine 2 [%] | Initial | — | — |
| | | 1 month | 1.2 | 1.3 |
| | | 3 month | 1.3 | 1.3 |
| | Peaks after Lysin 2 [%] | Initial | — | — |
| | | 1 month | 0.9 | 1.1 |
| | | 3 month | 0.8 | 1.4 |

| Test Item | Component | Duration of Testing | 63 mg/mL 40° C./75% R.H. | 220 mg/mL 40° C./75% R.H. |
|---|---|---|---|---|
| Clarity and opalescence | Turbidity | Initial | — | — |
| | | 1 month | 3.93 | 7.80 |
| | | 3 month | 3.70 | 8.10 |
| Degree of coloration of liquids | B scale | Initial | — | — |
| | | 1 month | =B9 | =B8 |
| | | 3 month | <B8 | <B7 |
| pH | Single value | Initial | — | — |
| | | 1 month | 5.3 | 5.4 |
| | | 3 month | 5.3 | 5.4 |
| Particulate contamination: visible particles | visual score | Initial | — | — |
| | | 1 month | 6.7 | 0.5 |
| | | 3 month | 17.5 | 0.4 |

APPENDIX D-continued

| | | | | |
|---|---|---|---|---|
| Particulate contamination: subvisible particles | Particles >= 10 μm [/Container] | Initial | — | — |
| | | 1 month | 1088 | 518 |
| | | 3 month | 166 | 612 |
| | Particles >= 25 μm [/Container] | Initial | — | — |
| | | 1 month | 16 | 14 |
| | | 3 month | 11 | 30 |
| Size exclusion chromatography (SE-HPLC) | Principal peak (aggregate) [%] | Initial | — | — |
| | | 1 month | 0.4 | 1.4 |
| | | 3 month | 0.8 | 2.5 |
| | Principal peak (monomer) [%] | Initial | — | — |
| | | 1 month | 99.0 | 98.0 |
| | | 3 month | 97.8 | 96.0 |
| | Principal-peak (fragment) [%] | Initial | — | — |
| | | 1 month | 0.6 | 0.6 |
| | | 3 month | 1.4 | 1.5 |
| Cation exchange HPLC (CEX-HPLC) | 1st acidic region [%] | Initial | — | — |
| | | 1 month | 6.7 | 6.8 |
| | | 3 month | 17.5 | 17.4 |
| | 2nd acidic region [%] | Initial | — | — |
| | | 1 month | 25.1 | 23.6 |
| | | 3 month | 40.9 | 38.6 |
| | Sum of lysine variants [%] | Initial | — | — |
| | | 1 month | 64.5 | 62.0 |
| | | 3 month | 36.0 | 36.0 |
| | Peak between lysine 1 und lysine 2 [%] | Initial | — | — |
| | | 1 month | 2.2 | 2.5 |
| | | 3 month | 2.9 | 3.1 |
| | Peaks after Lysin 2 [%] | Initial | — | — |
| | | 1 month | 1.5 | 5.2 |
| | | 3 month | 1.7 | 4.8 |

APPENDIX E

| Test Item | Component | Duration of Testing | LI 50 01*[2] | LI 50 02*[2] | LI 50 03*[2] | LI 50 04*[2] | LI 50 05*[2] | LI 50 06*[2] | LI 50 07*[2] | LI 50 08*[2] |
|---|---|---|---|---|---|---|---|---|---|---|
| | | | | | 2-8° C. | | | | | |
| Clarity and opalescence | Absorption (340 nm) | Initial | 0.096 | 0.096 | 0.095 | 0.100 | 0.104 | 0.105 | 0.099 | 0.107 |
| | | 1 month | 0.102 | 0.102 | 0.093 | 0.094 | 0.099 | 0.101 | 0.097 | 0.100 |
| Degree of coloration | visual | Initial | | | | clear and colorless | | | | |
| | | 1 month | | | | clear and colorless | | | | |
| pH | Single value | Initial | 5.4 | 5.4 | 5.4 | 5.4 | 5.4 | 5.4 | 5.4 | 5.4 |
| | | 1 month | 5.4 | 5.5 | 5.5 | 5.4 | 5.5 | 5.4 | 5.5 | 5.5 |
| Size exclusion chromatography (SE-HPLC) | Principal peak (aggregat) [%] | Initial | 0.1 | 0.1 | 0.1 | 0.1 | 0.1 | 0.1 | 0.2 | 0.2 |
| | | 1 month | 0.1 | 0.1 | 0.1 | 0.1 | 0.1 | 0.1 | 1.7 | 0.2 |
| | Principal peak (monomer) [%] | Initial | 99.6 | 99.6 | 99.6 | 99.6 | 99.6 | 99.6 | 99.7 | 99.7 |
| | | 1 month | 99.7 | 99.7 | 99.7 | 99.7 | 99.7 | 99.7 | 99.7 | 99.7 |
| | Principal peak (fragment) [%] | Initial | 0.3 | 0.3 | 0.2 | 0.2 | 0.2 | 0.2 | 0.2 | 0.2 |
| | | 1 month | 0.2 | 0.2 | 0.2 | 0.2 | 0.2 | 0.2 | 0.2 | 0.2 |
| Cation exchange HPLC (CEX-HPLC) | 1st acidic region [%] | Initial | 3.8 | 3.7 | 3.7 | 3.7 | 3.7 | 3.9 | 3.8 | 3.8 |
| | | 1 month | 3.4 | 3.4 | 3.4 | 3.4 | 3.4 | 3.5 | 3.4 | 3.4 |
| | 2nd acidic region [%] | Initial | 10.9 | 10.7 | 10.4 | 10.5 | 10.4 | 10.1 | 10.3 | 10.2 |
| | | 1 month | 9.2 | 9.2 | 9.2 | 9.2 | 9.2 | 9.2 | 9.2 | 9.3 |
| | Sum of lysine variants [%] | Initial | 83.8 | 84.2 | 84.4 | 84.3 | 84.4 | 84.6 | 84.4 | 84.6 |
| | | 1 month | 86.0 | 86.0 | 86.0 | 86.0 | 86.0 | 85.9 | 86.1 | 86.0 |
| | Peak between lysine 1 and lysine 2 [%] | Initial | 0.9 | 8.3 | 0.8 | 0.9 | 0.8 | 0.8 | 0.8 | 0.8 |
| | | 1 month | 0.9 | 0.8 | 0.8 | 0.8 | 0.8 | 0.8 | 0.8 | 0.8 |
| | Peaks after Lysin 2 [%[ | Initial | 0.6 | 0.6 | 0.6 | 0.6 | 0.6 | 0.6 | 0.6 | 0.6 |
| | | 1 month | 0.6 | 0.5 | 0.5 | 0.5 | 0.5 | 0.5 | 0.5 | 0.5 |
| | | | | | 25° C. | | | | | |
| Clarity and opalescence | Absorption (340 nm) | Initial | 0.096 | 0.096 | 0.095 | 0.100 | 0.104 | 0.105 | 0.099 | 0.107 |
| | | 1 month | 0.106 | 0.109 | 0.096 | 0.099 | 0.104 | 0.104 | 0.096 | 0.105 |
| Degree of coloration | visual | Initial | | | | clear and colorless | | | | |
| | | 1 month | | | | clear and colorless | | | | |
| pH | Single value | Initial | 5.4 | 5.4 | 5.4 | 5.4 | 5.4 | 5.4 | 5.4 | 5.4 |
| | | 1 month | 5.4 | 5.4 | 5.4 | 5.4 | 5.4 | 5.4 | 5.4 | 5.4 |
| Size exclusion chromatography (SE-HPLC) | Principal peak (aggregat) [%] | Initial | 0.1 | 0.1 | 0.1 | 0.1 | 0.1 | 0.1 | 0.2 | 0.2 |
| | | 1 month | 0.2 | 0.2 | 0.2 | 0.2 | 0.2 | ? | 0.2 | 0.2 |
| | Principal peak (monomer) [%] | Initial | 99.6 | 99.6 | 99.6 | 99.6 | 99.6 | 99.6 | 99.7 | 99.7 |
| | | 1 month | 99.6 | 99.6 | 99.6 | 99.6 | 99.6 | ? | 99.5 | 99.5 |
| | Principal peak (fragment) [%] | Initial | 0.3 | 0.3 | 0.2 | 0.2 | 0.2 | 0.2 | 0.2 | 0.2 |
| | | 1 month | 0.2 | 0.2 | 0.2 | 0.2 | 0.2 | ? | 0.2 | 0.2 |

APPENDIX E-continued

| Test Item | Component | Duration of Testing | | | | | | | |
|---|---|---|---|---|---|---|---|---|---|---|
| Cation exchange HPLC (CEX-HPLC) | 1st acidic region [%] | Initial | 3.8 | 3.7 | 3.7 | 3.7 | 3.7 | 3.9 | 3.8 | 3.8 |
| | | 1 month | 4.1 | 4.2 | 4.1 | 4.1 | 4.2 | 4.2 | 4.1 | 4.2 |
| | 2nd acidic region [%] | Initial | 10.9 | 10.7 | 10.4 | 10.5 | 10.4 | 10.1 | 10.3 | 10.2 |
| | | 1 month | 10.9 | 10.9 | 11.0 | 10.9 | 11.0 | 11.0 | 11.0 | 11.1 |
| | Sum of lysine variants [%] | Initial | 83.8 | 84.2 | 84.4 | 84.3 | 84.4 | 84.6 | 84.4 | 84.6 |
| | | 1 month | 83.3 | 83.4 | 83.3 | 83.3 | 83.2 | 83.2 | 83.3 | 83.1 |
| | Peak between lysine 1 and lysine 2 [%] | Initial | 0.9 | 8.3 | 0.8 | 0.9 | 0.8 | 0.8 | 0.8 | 0.8 |
| | | 1 month | 1.0 | 0.9 | 1.0 | 1.0 | 1.0 | 0.9 | 0.9 | 1.0 |
| | Peaks after Lysin 2 [%] | Initial | 0.6 | 0.6 | 0.6 | 0.6 | 0.6 | 0.6 | 0.6 | 0.6 |
| | | 1 month | 0.7 | 0.6 | 0.7 | 0.7 | 0.7 | 0.6 | 0.6 | 0.6 |

40° C.

| Test Item | Component | Duration of Testing | | | | | | | |
|---|---|---|---|---|---|---|---|---|---|---|
| Clarity and opalescence | Absorption (340 nm) | Initial | 0.096 | 0.096 | 0.095 | 0.100 | 0.104 | 0.105 | 0.099 | 0.107 |
| | | 1 month | 0.100 | 0.110 | 0.099 | 0.101 | 0.111 | 0.116 | 0.105 | 0.113 |
| Degree of coloration | visual | Initial | | | | clear and colorless | | | | |
| | | 1 month | | | | clear and colorless | | | | |
| pH | Single value | Initial | 5.40 | 5.41 | 5.41 | 5.40 | 5.40 | 5.40 | 5.41 | 5.41 |
| | | 1 month | 5.42 | 5.42 | 5.43 | 5.43 | 5.44 | 5.43 | 5.44 | 5.44 |
| Size exclusion chromatography (SE-HPLC) | Principal peak (aggregat) [%] | Initial | 0.106 | 0.104 | 0.119 | 0.136 | 0.139 | 0.145 | 0.158 | 0.159 |
| | | 1 month | 0.324 | 0.336 | 0.322 | 0.334 | 0.347 | 0.349 | 0.411 | 0.444 |
| | Principal peak (monomer) [%] | Initial | 99.605 | 99.629 | 99.632 | 99.626 | 99.619 | 99.626 | 99.653 | 99.655 |
| | | 1 month | 98.924 | 98.914 | 98.931 | 98.914 | 98.895 | 98.894 | 98.845 | 98.782 |
| | Principal peak (fragment) [%] | Initial | 0.289 | 0.267 | 0.249 | 0.238 | 0.242 | 0.229 | 0.189 | 0.186 |
| | | 1 month | 0.752 | 0.751 | 0.747 | 0.752 | 0.758 | 0.757 | 0.744 | 0.773 |
| Cation exchange HPLC (CEX-HPLC) | 1st acidic region [%] | Initial | 3.8 | 3.7 | 3.7 | 3.7 | 3.7 | 3.9 | 3.8 | 3.8 |
| | | 1 month | 5.4 | 5.8 | 5.3 | 5.8 | 5.4 | 5.8 | 5.4 | 5.5 |
| | 2nd acidic region [%] | Initial | 10.9 | 10.7 | 10.4 | 10.5 | 10.4 | 10.1 | 10.3 | 10.2 |
| | | 1 month | 29.8 | 29.8 | 29.7 | 29.7 | 29.8 | 29.8 | 30.2 | 30.7 |
| | Sum of lysine variants [%] | Initial | 83.8 | 84.2 | 84.4 | 84.3 | 84.4 | 84.6 | 84.4 | 84.6 |
| | | 1 month | 61.2 | 61.0 | 61.3 | 61.0 | 61.2 | 60.9 | 60.9 | 60.5 |
| | Peak between lysine 1 and lysine 2 [%] | Initial | 0.9 | 8.3 | 0.8 | 0.9 | 0.8 | 0.8 | 0.8 | 0.8 |
| | | 1 month | 2.3 | 2.1 | 2.3 | 2.2 | 2.2 | 2.2 | 2.1 | 2.0 |
| | Peaks after Lysin 2 [%] | Initial | 0.6 | 0.6 | 0.6 | 0.6 | 0.6 | 0.6 | 0.6 | 0.6 |
| | | 1 month | 1.3 | 1.3 | 1.3 | 1.3 | 1.4 | 1.3 | 1.4 | 1.4 |

| Test Item | Component | Duration of Testing | LI 200 01*2 | LI 200 02*2 | LI 200 03*2 | LI 200 04*2 | LI 200 05*2 | LI 200 06*2 | LI 200 07*2 | LI 200 08*2 |
|---|---|---|---|---|---|---|---|---|---|---|
| 2-8° C. | | | | | | | | | | |
| Clarity and opalescence | Absorption (340 nm) | Initial | 0.181 | 0.187 | 0.182 | 0.192 | 0.184 | 0.197 | 0.191 | 0.199 |
| | | 1 month | 0.181 | 0.185 | 0.189 | 0.181 | 0.190 | 0.180 | 0.192 | 0.192 |
| Degree of coloration | visual | Initial | | | | clear and colorless | | | | |
| | | 1 month | | | | clear and colorless | | | | |
| pH | Single value | Initial | 5.6 | 5.6 | 5.6 | 5.6 | 5.6 | 5.5 | 5.6 | 5.5 |
| | | 1 month | 5.6 | 5.6 | 5.5 | 5.5 | 5.6 | 5.5 | 5.6 | 5.6 |
| Size exclusion chromatography (SE-HPLC) | Principal peak (aggregat) [%] | Initial | 0.5 | 0.5 | 0.5 | 0.5 | 0.5 | 0.5 | 0.5 | 0.6 |
| | | 1 month | 0.6 | 0.6 | 0.6 | 0.6 | 0.6 | 0.6 | 0.7 | 0.7 |
| | Principal peak (monomer) [%] | Initial | 99.3 | 99.3 | 99.3 | 99.3 | 99.3 | 99.3 | 99.3 | 99.3 |
| | | 1 month | 99.3 | 99.3 | 99.2 | 99.3 | 99.3 | 99.2 | 99.2 | 99.2 |
| | Principal peak (fragment) [%] | Initial | 0.2 | 0.2 | 0.2 | 0.2 | 0.2 | 0.2 | 0.2 | 0.1 |
| | | 1 month | 0.2 | 0.2 | 0.2 | 0.2 | 0.2 | 0.2 | 0.2 | 0.2 |
| Cation exchange HPLC (CEX-HPLC) | 1st acidic region [%] | Initial | 3.7 | 3.8 | 3.6 | 4.5 | 3.9 | 2.7 | 2.7 | 2.8 |
| | | 1 month | 3.4 | 3.4 | 3.5 | 3.5 | 3.5 | 3.5 | 3.5 | 3.5 |
| | 2nd acidic region [%] | Initial | 10.4 | 10.2 | 9.8 | 10.1 | 9.5 | 11.6 | 11.5 | 11.3 |
| | | 1 month | 9.1 | 9.0 | 9.1 | 9.1 | 9.0 | 9.1 | 9.1 | 9.1 |
| | Sum of lysine variants [%] | Initial | 84.4 | 84.6 | 85.2 | 83.9 | 85.2 | 84.4 | 84.3 | 84.5 |
| | | 1 month | 86.3 | 86.1 | 86.1 | 86.2 | 86.0 | 86.0 | 86.1 | 86.1 |
| | Peak between lysine 1 and lysine 2 [%] | Initial | 0.8 | 0.8 | 0.8 | 0.8 | 0.8 | 0.8 | 0.8 | 0.8 |
| | | 1 month | 0.6 | 0.8 | 0.6 | 0.6 | 0.8 | 0.7 | 0.6 | 0.6 |
| | Peaks after Lysin 2 [%[ | Initial | 0.6 | 0.6 | 0.6 | 0.7 | 0.6 | 0.6 | 0.6 | 0.6 |
| | | 1 month | 0.7 | 0.7 | 0.7 | 0.7 | 0.7 | 0.7 | 0.8 | 0.7 |
| 25° C. | | | | | | | | | | |
| Clarity and opalescence | Absorption (340 nm) | Initial | 0.181 | 0.187 | 0.182 | 0.192 | 0.184 | 0.197 | 0.191 | 0.199 |
| | | 1 month | 0.178 | 0.177 | 0.198 | 0.189 | 0.200 | 0.194 | 0.194 | 0.172 |
| Degree of coloration | visual | Initial | | | | clear and colorless | | | | |
| | | 1 month | | | | clear and colorless | | | | |
| pH | Single value | Initial | 5.6 | 5.6 | 5.6 | 5.6 | 5.6 | 5.5 | 5.6 | 5.5 |
| | | 1 month | 5.5 | 5.6 | 5.6 | 5.5 | 5.5 | 5.5 | 5.5 | 5.5 |
| Size exclusion chromatography (SE-HPLC) | Principal peak (aggregat) [%] | Initial | 0.5 | 0.5 | 0.5 | 0.5 | 0.5 | 0.5 | 0.5 | 0.6 |
| | | 1 month | 0.8 | 0.8 | 0.8 | 0.8 | 0.8 | 0.8 | 0.9 | 0.9 |
| | Principal peak (monomer) [%] | Initial | 99.3 | 99.3 | 99.3 | 99.3 | 99.3 | 99.3 | 99.3 | 99.3 |
| | | 1 month | 99.0 | 99.0 | 99.0 | 99.0 | 99.0 | 99.0 | 98.9 | 98.9 |
| | Principal peak (fragment) [%] | Initial | 0.2 | 0.2 | 0.2 | 0.2 | 0.2 | 0.2 | 0.2 | 0.1 |
| | | 1 month | 0.2 | 0.2 | 0.2 | 0.2 | 0.2 | 0.2 | 0.2 | 0.2 |
| Cation exchange HPLC | 1st acidic region [%] | Initial | 3.7 | 3.8 | 3.6 | 4.5 | 3.9 | 2.7 | 2.7 | 2.8 |
| | | 1 month | 4.0 | 4.0 | 4.1 | 4.1 | 4.0 | 4.1 | 4.1 | 4.0 |

APPENDIX E-continued

| | | | | | | | | | | |
|---|---|---|---|---|---|---|---|---|---|---|
| (CEX-HPLC) | 2nd acidic region | Initial | 10.4 | 10.2 | 9.8 | 10.1 | 9.5 | 11.6 | 11.5 | 11.3 |
| | [%] | 1 month | 10.6 | 10.7 | 10.7 | 10.7 | 10.7 | 10.7 | 10.7 | 10.9 |
| | Sum of | Initial | 84.4 | 84.6 | 85.2 | 83.9 | 85.2 | 84.4 | 84.3 | 84.5 |
| | lysine variants [%] | 1 month | 83.4 | 83.6 | 83.4 | 83.6 | 83.6 | 83.5 | 83.3 | 83.4 |
| | Peak between lysine 1 | Initial | 0.8 | 0.8 | 0.8 | 0.8 | 0.8 | 0.8 | 0.8 | 0.8 |
| | and lysine 2 [%] | 1 month | 1.0 | 0.8 | 0.8 | 0.7 | 0.7 | 0.8 | 0.9 | 0.8 |
| | Peaks after | Initial | 0.6 | 0.6 | 0.6 | 0.7 | 0.6 | 0.6 | 0.6 | 0.6 |
| | Lysin 2 [%] | 1 month | 0.9 | 0.9 | 0.9 | 0.9 | 0.9 | 0.9 | 0.9 | 0.9 |
| | | 40° C. | | | | | | | | |
| Clarity and | Absorption (340 nm) | Initial | 0.181 | 0.187 | 0.182 | 0.192 | 0.184 | 0.197 | 0.191 | 0.199 |
| opalescence | | 1 month | 0.204 | 0.202 | 0.198 | 0.205 | 0.199 | 0.216 | 0.209 | 0.224 |
| Degree of | visual | Initial | | | | clear and colorless | | | | |
| coloration | | 1 month | | | | clear and colorless | | | | |
| pH | Single value | Initial | 5.57 | 5.56 | 5.55 | 5.56 | 5.55 | 5.54 | 5.55 | 5.52 |
| | | 1 month | 5.54 | 5.55 | 5.55 | 5.55 | 5.55 | 5.55 | 5.53 | 5.54 |
| Size exclusion | Principal peak | Initial | 0.489 | 0.509 | 0.491 | 0.484 | 0.492 | 0.488 | 0.515 | 0.575 |
| chromatography | (aggregat) [%] | 1 month | 1.308 | 1.343 | 1.331 | 1.340 | 1.341 | 1.374 | 1.453 | 1.521 |
| (SE-HPLC) | Principal peak | Initial | 99.294 | 99.296 | 99.348 | 99.333 | 99.313 | 99.349 | 99.320 | 99.290 |
| | (monomer) [%] | 1 month | 97.920 | 97.876 | 97.892 | 97.901 | 97.898 | 97.861 | 97.752 | 97.701 |
| | Principal peak | Initial | 0.218 | 0.196 | 0.161 | 0.183 | 0.195 | 0.163 | 0.165 | 0.135 |
| | (fragment) [%] | 1 month | 0.773 | 0.781 | 0.777 | 0.759 | 0.762 | 0.765 | 0.794 | 0.779 |
| Cation exchange | 1st acidic region | Initial | 3.7 | 3.8 | 3.6 | 4.5 | 3.9 | 2.7 | 2.7 | 2.8 |
| HPLC | [%] | 1 month | 5.3 | 5.6 | 5.3 | 5.6 | 5.3 | 5.6 | 5.3 | 5.4 |
| (CEX-HPLC) | 2nd acidic region | Initial | 10.4 | 10.2 | 9.8 | 10.1 | 9.5 | 11.6 | 11.5 | 11.3 |
| | [%] | 1 month | 28.6 | 28.9 | 28.5 | 28.7 | 28.6 | 28.9 | 29.1 | 29.2 |
| | Sum of | Initial | 84.4 | 84.6 | 85.2 | 83.9 | 85.2 | 84.4 | 84.3 | 84.5 |
| | lysine variants [%] | 1 month | 62.0 | 61.7 | 62.0 | 61.8 | 62.0 | 61.6 | 61.5 | 61.4 |
| | Peak between lysine 1 and | Initial | 0.8 | 0.8 | 0.8 | 0.8 | 0.8 | 0.8 | 0.8 | 0.8 |
| | lysine 2 [%] | 1 month | 2.2 | 2.0 | 2.2 | 2.0 | 2.2 | 2.0 | 2.0 | 2.0 |
| | Peaks after | Initial | 0.6 | 0.6 | 0.6 | 0.7 | 0.6 | 0.6 | 0.6 | 0.6 |
| | Lysin 2 [%] | 1 month | 1.9 | 1.9 | 2.0 | 1.9 | 1.9 | 1.9 | 2.0 | 2.0 |

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference

What is claimed is:

1. An aqueous formulation comprising an antibody, or antigen-binding fragment thereof, at a concentration of at least about 20 mg/mL and water, wherein the formulation has a conductivity of less than about 2.5 mS/cm and the antibody, or antigen-binding fragment thereof, has a molecular weight ($M_w$) greater than about 47 kDa.

2. The formulation of claim 1, wherein the antibody, or antigen-binding fragment thereof, has a $M_w$ greater than about 57 kDa.

3. The formulation of claim 1, wherein the antibody, or antigen-binding fragment thereof, has a $M_w$ greater than about 100 kDa.

4. The formulation of claim 1, wherein the antibody, or antigen-binding fragment thereof, has a $M_w$ greater than about 150 kDa.

5. The formulation of claim 1, wherein the antibody, or antigen-binding fragment thereof, has a $M_w$ greater than about 250 kDa.

6. The formulation of claim 1, wherein the formulation has a conductivity of less than about 2 mS/cm.

7. The formulation of claim 1, wherein the formulation has a conductivity of less than about 1 mS/cm.

8. The formulation of claim 1, wherein the formulation has a conductivity of less than about 0.5 mS/cm.

9. The formulation of claim 1, wherein the concentration of the antibody, or antigen-binding fragment thereof, is at least about 100 mg/mL.

10. The formulation of claim 1, wherein the concentration of the antibody, or antigen-binding fragment thereof, is at least about 150 mg/mL.

11. The formulation of claim 1, wherein the concentration of the antibody, or antigen-binding fragment thereof, is at least about 200 mg/mL.

12. The formulation of claim 1, wherein the concentration of the antibody, or antigen-binding fragment thereof, is greater than 200 mg/mL.

13. An aqueous formulation comprising an antibody, or an antigen-binding fragment thereof, at a concentration of at least about 50 mg/mL, and water, wherein the formulation has an osmolality of no more than about 30 mOsmol/kg and wherein the antibody, or antigen-binding fragment thereof, has a molecular weight ($M_w$) greater than about 47 kDa.

14. The formulation of claim 13, wherein the osmolality of the formulation is no more than about 15 mOsmol/kg.

15. The formulation of claim 13, wherein the concentration of the antibody, or an antigen-binding fragment thereof, is at least about 150 mg/mL.

16. The formulation of claim 13, wherein the concentration of the antibody, or an antigen-binding fragment thereof, is greater than about 200 mg/mL.

17. An aqueous formulation comprising water and at least about 20 mg/mL of an antibody, or an antigen-binding fragment thereof, wherein the antibody, or antigen-binding fragment thereof, has a hydrodynamic diameter ($D_h$) which is at least about 50% less than the $D_h$ of the antibody, or antigen-binding fragment thereof, in a buffered solution at the same concentration, and wherein the antibody, or antigen-binding fragment thereof, has a molecular weight ($M_w$) greater than about 47 kDa.

18. The formulation of claim 17, wherein the $D_h$ of the antibody, or antigen-binding fragment thereof, is at least about 50% less than the $D_h$ of the antibody, or antigen-binding fragment thereof, in phosphate buffered saline (PBS) at the same concentration.

19. The formulation of claim 18, wherein the $D_h$ of the protein is at least about 60% less than the $D_h$ of the antibody, or antigen-binding fragment thereof, in PBS at the same concentration.

20. The formulation of claim 18, wherein the $D_h$ of the antibody, or antigen-binding fragment thereof, is at least about 70% less than the $D_h$ of the antibody, or antigen-binding fragment thereof, in PBS at the same concentration.

21. The formulation of any one of claims 1, 13, and 17, wherein the antibody, or antigen-binding fragment thereof, is selected from the group consisting of a chimeric antibody, a human antibody, a humanized antibody, and a domain antibody (dAb).

22. The formulation of any one of claims 1, 13, and 17, wherein the antibody, or antigen-binding fragment thereof, is an anti-tumor necrosis factor alpha (TNFα) or an anti-interleukin-12 (IL-12) antibody, or antigen-binding fragment thereof.

23. The formulation of claim 22, wherein the anti-IL-12 antibody, or antigen-binding fragment thereof, is ustekinumab.

24. The formulation of claim 22, wherein the anti-TNFα antibody, or antigen-binding fragment thereof, is selected from the group consisting of infliximab, golimumab, and certolizumab pegol.

25. The formulation of claim 22, wherein the anti-TNFα antibody, or antigen-binding fragment thereof, is adalimumab.

26. The formulation of claim 13 or 17, wherein the antibody, or antigen-binding fragment thereof, is selected from the group consisting of, alemtuzumab, arcitumomab, cetuximab, trastuzumab, imciromab pentetate, capromab pendetide, infliximab, abciximab, rituximab, basiliximab, palivizumab, nofetumomab, omalizumab, daclizumab, ibritumomab tiuxetan, muromonab-CD3, edrecolomab gemtuzumab ozogamicin, golimumab, certolizumab pegol, eculizumab, ustekinumab, panitumumab, tositumomab, $I^{131}$ tositumomab, and bevacizumab.

27. The formulation of claim 13 or 17, wherein the antibody, or antigen-binding fragment thereof, is adalimumab.

28. An aqueous formulation comprising an antibody, or an antigen-binding fragment, at a concentration of at least about 20 mg/mL, and water, wherein the antibody, or antigen-binding fragment, has a hydrodynamic diameter ($D_h$) of less than about 4 nm, and wherein the antibody, or antigen-binding fragment thereof, has a molecular weight ($M_w$) greater than about 47 kDa.

29. The formulation of claim 28, wherein the antibody has a $D_h$ of less than about 3 nm.

30. The formulation of claim 28, wherein the antibody, or antigen-binding fragment thereof, is selected from the group consisting of a chimeric antibody, a human antibody, a humanized antibody, and a domain antibody (dAb).

31. The formulation of claim 28, wherein the antibody, or antigen-binding fragment thereof, is an anti-TNF-alpha or an anti-IL-12 antibody, or antigen-binding fragment thereof.

32. The formulation of claim 28, wherein the antibody, or antigen-binding fragment thereof, is selected from the group consisting of, alemtuzumab, arcitumomab, cetuximab, trastuzumab, imciromab pentetate, capromab pendetide, infliximab, abciximab, rituximab, basiliximab, palivizumab, nofetumomab, omalizumab, daclizumab, ibritumomab tiuxetan, muromonab-CD3, edrecolomab gemtuzumab ozogamicin, golimumab, certolizumab pegol, eculizumab, ustekinumab, panitumumab, tositumomab, $I^{131}$ tositumomab, and bevacizumab.

33. The formulation of claim 28, wherein the antibody, or antigen-binding fragment thereof, is adalimumab.

34. The formulation of any one of claims 1, 13, 17, and 28, further comprising a non-ionizable excipient.

35. The formulation of claim 34, wherein the non-ionizable excipient is selected from the group consisting of a polyol, a non-ionic surfactant, sucrose, trehalose, raffinose, and maltose.

36. The formulation of claim 35, wherein the polyol is mannitol or sorbitol.

37. The formulation of claim 35, wherein the non-ionic surfactant is polysorbate 20, polysorbate 40, polysorbate 60 or polysorbate 80.

38. The formulation of any one of claims 1, 13, 17, and 28, wherein the formulation is stable in a liquid form for at least about 3 months or at least about 12 months.

39. The formulation of any one of claims 1, 13, 17, and 28, wherein the formulation does not comprise an agent selected from the group consisting of a tonicity modifier, a stabilizing agent, a surfactant, an anti-oxidant, a cryoprotectant, a bulking agent, a lyroprotectant, a basic component, and an acidic component.

40. The formulation of any one of claims 1, 13, 17, and 28, wherein the formulation is suitable for in vitro or in vivo use.

41. The formulation of claim 40, wherein the formulation is suitable for administration to a subject via a mode of administration selected from the group consisting of subcutaneous, intravenous, inhalation, intradermal, transdermal, intraperitoneal, and intramuscular.

42. A device comprising the formulation of any one claims 1, 13, 17, and 28.

43. An article of manufacture comprising the formulation of any one of claims 1, 13, 17, and 28.

44. An aqueous formulation comprising an antibody, or an antigen-binding fragment thereof, at a concentration of at least about 20 mg/ml, the antibody, or antigen-binding fragment thereof, prepared by
  a) providing the antibody, or antigen-binding fragment thereof, in a first solution; and
  b) subjecting the first solution to diafiltration using water as a diafiltration medium until at least a five-fold volume exchange with the water has been achieved;
  wherein the antibody, or antigen-binding fragment thereof, has a molecular weight ($M_w$) greater than about 47 kDa.

45. An aqueous formulation comprising water and at least about 50 mg/ml of an antibody, or an antigen-binding fragment thereof, wherein the antibody, or antigen-binding fragment thereof, has a hydrodynamic diameter ($D_h$) which is at least about 50% less than the $D_h$ of the antibody, or antigen-binding fragment thereof, in a buffered solution at the same concentration, and wherein the antibody, or antigen-binding fragment thereof, has a molecular weight ($M_w$) greater than about 47 kDa.

46. The formulation of claim 45, wherein the concentration of the antibody, or antigen-binding fragment thereof, is at least about 150 mg/mL.

47. The formulation of claim 45, wherein the concentration of the antibody, or antigen-binding fragment thereof, is greater than 200 mg/mL.

48. The formulation of claim 45, further comprising a non-ionizable excipient.

49. The formulation of claim 48, wherein the non-ionizable excipient is selected from the group consisting of a polyol, a non-ionic surfactant, sucrose, trehalose, raffinose, and maltose.

50. The formulation of claim 49, wherein the non-ionic surfactant is polysorbate 20, polysorbate 40, polysorbate 60 or polysorbate 80.

51. The formulation of claim 45, wherein the formulation is stable in a liquid form for at least about 3 months or at least about 12 months.

52. The formulation of claim 45, wherein the formulation does not comprise an agent selected from the group consisting of a tonicity modifier, a stabilizing agent, a surfactant, an anti-oxidant, a cryoprotectant, a bulking agent, a lyroprotectant, a basic component, and an acidic component.

53. The formulation of claim 45, wherein the formulation is suitable for in vitro or in vivo use.

54. The formulation of claim 53, wherein the formulation is suitable for administration to a subject via a mode of administration selected from the group consisting of subcutaneous, intravenous, inhalation, intradermal, transdermal, intraperitoneal, and intramuscular.

55. A device comprising the formulation of claim 45.

56. An article of manufacture comprising the formulation of claim 45.

57. An aqueous formulation comprising water and an antibody, or antigen-binding fragment thereof, at a concentration of at least about 50 mg/mL,
wherein the formulation has a conductivity of less than about 2.5 mS/cm, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

58. The formulation of claim 57, wherein the concentration of the antibody, or antigen-binding fragment thereof, is at least about 75 mg/mL.

59. The formulation of claim 57, wherein the formulation has a conductivity of less than about 2 mS/cm.

60. The formulation of claim 57, further comprising a non-ionizable excipient.

61. The formulation of claim 60, wherein the non-ionizable excipient is a polyol.

62. The formulation of claim 61, wherein the polyol is mannitol.

63. The formulation of claim 60, wherein the non-ionizable excipient is a non-ionic surfactant.

64. The formulation of claim 63, wherein the non-ionic surfactant is polysorbate 80.

65. The formulation of claim 60, wherein the non-ionizable excipient is sucrose.

66. The formulation of claim 57, wherein the antibody, or antigen-binding portion thereof, has an LCVR comprising the amino acid sequence set forth in SEQ ID NO: 1, and an HCVR comprising the amino acid sequence set forth in SEQ ID NO: 2.

67. The formulation of claim 57, wherein the antibody, or antigen-binding portion thereof, is adalimumab.

68. An aqueous formulation comprising water and an antibody, or an antigen-binding fragment thereof, at a concentration of at least about 50 mg/mL,
wherein the antibody, or an antigen-binding fragment thereof, has a hydrodynamic diameter ($D_h$) which is at least about 50% less than the $D_h$ of the antibody, or antigen-binding fragment thereof, in a buffered solution at the same concentration, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

69. The formulation of claim 68, wherein the $D_h$ of the antibody, or antigen-binding fragment thereof, is at least about 50% less than the $D_h$ of the antibody, or antigen-binding fragment thereof, in phosphate buffered saline (PBS) at the same concentration.

70. The formulation of claim 69, wherein the $D_h$ of the antibody, or antigen-binding fragment thereof, is at least about 60% less than the $D_h$ of the antibody, or antigen-binding fragment thereof, in PBS at the same concentration.

71. The formulation of claim 70, wherein the $D_h$ of the antibody, or antigen-binding fragment thereof, is at least about 70% less than the $D_h$ of the antibody, or antigen-binding fragment thereof, in PBS at the same concentration.

72. The formulation of claim 68, wherein the antibody, or antigen-binding portion thereof, has an LCVR comprising the amino acid sequence set forth in SEQ ID NO: 1, and an HCVR comprising the amino acid sequence set forth in SEQ ID NO: 2.

73. The formulation of claim 68, wherein the antibody, or antigen-binding portion thereof, is adalimumab.

74. The formulation of claim 68, further comprising a non-ionizable excipient.

75. The formulation of claim 74, wherein the non-ionizable excipient is a polyol.

76. The formulation of claim 75, wherein the polyol is mannitol.

77. The formulation of claim 74, wherein the non-ionizable excipient is a non-ionic surfactant.

78. The formulation of claim 77, wherein the non-ionic surfactant is polysorbate 80.

79. The formulation of claim 74, wherein the non-ionizable excipient is sucrose.

80. The formulation of claim 68, further comprising mannitol and polysorbate 80.

81. The formulation of claim 68, further comprising sucrose and polysorbate 80.

82. The formulation of claim 80 or 81, wherein the antibody, or antigen-binding portion thereof, has an LCVR comprising the amino acid sequence set forth in SEQ ID NO: 1, and an HCVR comprising the amino acid sequence set forth in SEQ ID NO: 2.

83. The formulation of claim 80 or 81, wherein the antibody, or antigen-binding portion thereof, is adalimumab.

84. An aqueous formulation comprising water and an antibody, or an antigen-binding fragment, at a concentration of at least about 50 mg/mL,
wherein the antibody, or antigen-binding fragment, has a hydrodynamic diameter ($D_h$) of less than about 4 nm, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

85. The formulation of claim 84, wherein the antibody, or antigen-binding portion thereof, has a $D_h$ of less than about 3 nm.

86. The formulation of claim 84, wherein the antibody, or antigen-binding portion thereof, has an LCVR comprising the amino acid sequence set forth in SEQ ID NO: 1, and an HCVR comprising the amino acid sequence set forth in SEQ ID NO: 2.

87. The formulation of claim 84, wherein the antibody, or antigen-binding portion thereof, is adalimumab.

88. The formulation of claim 84, further comprising a non-ionizable excipient.

89. The formulation of claim 88, wherein the non-ionizable excipient is a polyol.

90. The formulation of claim 89, wherein the polyol is mannitol.

91. The formulation of claim 88, wherein the non-ionizable excipient is a non-ionic surfactant.

92. The formulation of claim 91, wherein the non-ionic surfactant is polysorbate 80.

93. The formulation of claim 88, wherein the non-ionizable excipient is sucrose.

94. The formulation of claim 84, further comprising mannitol and polysorbate 80.

95. The formulation of claim 84, further comprising sucrose and polysorbate 80.

96. The formulation of claim 94 or 95 wherein the antibody, or antigen-binding portion thereof, has an LCVR comprising the amino acid sequence set forth in SEQ ID NO: 1, and an HCVR comprising the amino acid sequence set forth in SEQ ID NO: 2.

97. The formulation of claim 94 or 95, wherein the antibody, or antigen-binding portion thereof, is adalimumab.

98. A device comprising the formulation of any one of claims 57, 68, or 84.

99. An article of manufacture comprising the formulation of any one of claims 57, 68, or 84.

100. An aqueous formulation comprising
mannitol,
polysorbate 80,
an antibody, or antigen-binding fragment thereof, at a concentration of at least about 20 mg/mL, and
water,
wherein the formulation has a conductivity of less than about 2.5 mS/cm, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

101. The formulation of claim 100, wherein the formulation has a conductivity of less than about 1.0 mS/cm.

102. The formulation of claim 100, wherein the formulation has a conductivity of less than about 0.5 mS/cm.

103. The formulation of claim 100, wherein the antibody concentration is at least about 50 mg/mL.

104. The formulation of claim 100, wherein the antibody, or antigen-binding portion thereof, has an LCVR comprising the amino acid sequence set forth in SEQ ID NO: 1, and an HCVR comprising the amino acid sequence set forth in SEQ ID NO: 2.

105. The formulation of claim 100, wherein the antibody, or antigen-binding portion thereof, is adalimumab.

106. An aqueous formulation comprising
mannitol,
polysorbate 80,
an antibody, or antigen-binding fragment thereof, at a concentration of at least about 20 mg/mL, and
water,
wherein the antibody, or an antigen-binding fragment thereof, has a hydrodynamic diameter ($D_h$) which is at least about 50% less than the $D_h$ of the antibody, or antigen-binding fragment thereof, in a buffered solution at the same concentration, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

107. The formulation of claim 106, wherein the $D_h$ of the antibody, or antigen-binding fragment thereof, is at least about 50% less than the $D_h$ of the antibody, or antigen-binding fragment thereof, in phosphate buffered saline (PBS) at the same concentration.

108. The formulation of claim 107, wherein the $D_h$ of the antibody, or antigen-binding fragment thereof, is at least about 60% less than the $D_h$ of the antibody, or antigen-binding fragment thereof, in PBS at the same concentration.

109. The formulation of claim 107, wherein the $D_h$ of the antibody, or antigen-binding fragment thereof, is at least about 70% less than the $D_h$ of the antibody, or antigen-binding fragment thereof, in PBS at the same concentration.

110. The formulation of claim 106, wherein the antibody, or antigen-binding portion thereof, has an LCVR comprising the amino acid sequence set forth in SEQ ID NO: 1, and an HCVR comprising the amino acid sequence set forth in SEQ ID NO: 2.

111. The formulation of claim 106, wherein the antibody, or antigen-binding portion thereof, is adalimumab.

112. The formulation of claim 106, wherein the antibody concentration is at least about 50 mg/mL.

113. An aqueous formulation comprising
mannitol,
polysorbate 80,
an antibody, or antigen-binding fragment thereof, at a concentration of at least about 20 mg/mL, and
water,
wherein the antibody, or antigen-binding fragment, has a hydrodynamic diameter ($D_h$) of less than about 4 nm, and
wherein the antibody, or antigen-binding fragment thereof, has a light chain variable region (LCVR) having a CDR3 domain comprising the amino acid sequence of SEQ ID NO:3, or modified from SEQ ID NO:3 by a single alanine substitution at position 1, 4, 5, 7 or 8, a CDR2 domain comprising the amino acid sequence of SEQ ID NO:5, and a CDR1 domain comprising the amino acid sequence of SEQ ID NO: 7, and a heavy chain variable region (HCVR) having a CDR3 domain comprising the amino acid sequence of SEQ ID NO:4, or modified from SEQ ID NO:4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO:8.

114. The formulation of claim 113, wherein the antibody, or antigen-binding portion thereof, has a $D_h$ of less than about 3 nm.

115. The formulation of claim 113, wherein the antibody, or antigen-binding portion thereof, has an LCVR comprising the amino acid sequence set forth in SEQ ID NO: 1, and an HCVR comprising the amino acid sequence set forth in SEQ ID NO: 2.

116. The formulation of claim 113, wherein the antibody, or antigen-binding portion thereof, is adalimumab.

117. The formulation of claim 113, wherein the antibody concentration is at least about 50 mg/mL.

118. A device comprising the formulation of any one of claims 100, 106, and 113.

119. An article of manufacture comprising the formulation of any one of claims 100, 106, and 113.

120. A method of preparing an aqueous formulation comprising an antibody, or antigen-binding fragment thereof, at a concentration of at least about 20 mg/ml and water, the method comprising:
a) providing the antibody, or antigen-binding fragment thereof, in a first solution; and
b) subjecting the first solution to diafiltration using water as a diafiltration medium until at least five-fold volume exchange with the water has been achieved to thereby prepare the aqueous formulation;
wherein the antibody or antigen-binding fragment thereof, has a molecular weight ($M_w$) greater than about 47 kDa.

121. A method of preparing an aqueous formulation of an antibody, or antigen-binding fragment thereof, at a concentration of at least about 20 mg/ml, the method comprising:
a) providing the antibody, or an antigen-binding fragment thereof, in a first solution;
b) subjecting the first solution to diafiltration using water as a diafiltration medium until at least a five-fold volume exchange with the water has been achieved to thereby prepare a diafiltered antibody, or antigen-binding fragment thereof, solution; and
c) concentrating the diafiltered antibody, or antigen-binding fragment thereof, solution to thereby prepare the aqueous formulation of the antibody, or antigen-binding fragment thereof;
wherein the antibody, or antigen-binding fragment thereof, has a molecular weight ($M_w$) greater than about 47 kDa.

122. The method of claim 121, wherein the concentration of the diafiltered antibody, or antigen-binding fragment thereof, solution is achieved via centrifugation.

123. The method of claim 120 or 121, wherein the diafiltration medium consists of water.

124. The method of claim 120 or 121, wherein the first solution is subjected to diafiltration with water until at least about a six-fold volume exchange or at least about a seven-fold volume exchange is achieved.

125. The method of claim 120 or 121, wherein the aqueous formulation has a final concentration of excipients which is at least about 95% less or 99% less than the first solution.

126. The method of claim 120 or 121, wherein the first antibody, or antigen-binding fragment thereof, solution is obtained from a mammalian cell expression system and has been purified to remove host cell proteins (HCPs).

127. The method of claim 120 or 121, wherein the antibody, or antigen-binding fragment thereof, has a molecular weight ($M_w$) selected from the group consisting of greater than about 57 kDa, greater than about 100 kDa, greater than about 150 kDa, greater than about 200 kDa, and greater than about 250 kDa.

128. The method of claim 120 or 121, further comprising adding an excipient to the aqueous formulation.

129. The method of claim 128, wherein the aqueous formulation is a pharmaceutical formulation.

130. The method of claim 120 or 121, wherein the aqueous formulation is a pharmaceutical formulation.

131. The method of claim 130, further comprising loading the aqueous formulation into a device suitable for administering the aqueous formulation to a subject.

132. The method of claim 120 or 121, wherein the antibody, or antigen-binding fragment thereof, is selected from the group consisting of a chimeric antibody, a human antibody, a humanized antibody, and a domain antibody (dAb).

133. The method of claim 120 or 121, wherein the antibody, or antigen-binding fragment thereof, is an anti-TNFα or an anti-IL-12 antibody.

134. The method of claim 120 or 121, wherein the antibody, or antigen-binding fragment thereof, is selected from the group consisting of, alemtuzumab, arcitumomab, cetuximab, trastuzumab, imciromab pentetate, capromab pendetide, infliximab, abciximab, rituximab, basiliximab, palivizumab, nofetumomab, omalizumab, daclizumab, ibritumomab tiuxetan, muromonab-CD3, edrecolomab gemtuzumab ozogamicin, golimumab, certolizumab pegol, eculizumab, ustekinumab, panitumumab, tositumomab, $I^{131}$ tositumomab, and bevacizumab.

135. The formulation of claim 120 or 121, wherein the antibody, or antigen-binding fragment thereof, is adalimumab.

* * * * *

```
SEQUENCE LISTING

<160> NUMBER OF SEQ ID NOS: 8

<210> SEQ ID NO 1
<211> LENGTH: 107
<212> TYPE: PRT
<213> ORGANISM: Artificial Sequence
<220> FEATURE:
<223> OTHER INFORMATION: Variable light chain

<400> SEQUENCE: 1

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75

Pro Glu Asp Val Ala Thr Tyr Tyr Cys Gln Arg Tyr Asn Arg Ala Pro
80                  85                  90                  95

Tyr Thr Phe Gly Gln Gly Thr Lys Val Glu Ile Lys
                100                 105
```

```
<210> SEQ ID NO 2
<211> LENGTH: 121
<212> TYPE: PRT
<213> ORGANISM: Artificial Sequence
<220> FEATURE:
<223> OTHER INFORMATION: Variable heavy chain

<400> SEQUENCE: 2

Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asp Asp
                20                  25                  30

Tyr Ala Met His Trp Val Arg Gln Ala Pro Gly Lys Gly Leu Glu Trp
            35                  40                  45

Val Ser Ala Ile Thr Trp Asn Ser Gly His Ile Asp Tyr Ala Asp Ser
        50                  55                  60

Val Glu Gly Arg Phe Thr Ile Ser Arg Asp Asn Ala Lys Asn Ser Leu
65                  70                  75

Tyr Leu Gln Met Asn Ser Leu Arg Ala Glu Asp Thr Ala Val Tyr Tyr
80                  85                  90                  95

Cys Ala Lys Val Ser Tyr Leu Ser Thr Ala Ser Ser Leu Asp Tyr Trp
                100                 105                 110

Gly Gln Gly Thr Leu Val Thr Val Ser Ser
            115                 120

<210> SEQ ID NO 3
<211> LENGTH: 9
<212> TYPE: PRT
<213> ORGANISM: Artificial Sequence
<220> FEATURE:
<221> NAME/KEY: VARIANT
<222> LOCATION: 9
<223> OTHER INFORMATION: Xaa = Thr or Ala
<223> OTHER INFORMATION: Variable light chain CDR3

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<221> NAME/KEY: VARIANT
<222> LOCATION: 12
<223> OTHER INFORMATION: Xaa = Tyr or Asn
<223> OTHER INFORMATION: Variable heavy chain CDR3

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Variable light chain CDR2

<400> SEQUENCE: 5

Ala Ala Ser Thr Leu Gln Ser
1               5

<210> SEQ ID NO 6
```

```
<211> LENGTH: 17
<212> TYPE: PRT
<213> ORGANISM: Artificial Sequence
<220> FEATURE:
<223> OTHER INFORMATION: Variable heavy chain CDR2

<400> SEQUENCE: 6

Ala Ile Thr Trp Asn Ser Gly His Ile Asp Tyr Ala Asp Ser Val
  1               5                  10                  15

Glu Gly

<210> SEQ ID NO 7
<211> LENGTH: 11
<212> TYPE: PRT
<213> ORGANISM: Artificial Sequence
<220> FEATURE:
<223> OTHER INFORMATION: Variable light chain CDR1

<400> SEQUENCE: 7

Arg Ala Ser Gln Gly Ile Arg Asn Tyr Leu Ala
  1               5                  10

<210> SEQ ID NO 8
<211> LENGTH: 5
<212> TYPE: PRT
<213> ORGANISM: Artificial Sequence
<220> FEATURE:
<223> OTHER INFORMATION: Variable heavy chain CDR1

<400> SEQUENCE: 8

Asp Tyr Ala Met His
  1               5
```